US011685740B2

(12) United States Patent
Masuda et al.

(10) Patent No.: US 11,685,740 B2
(45) Date of Patent: *Jun. 27, 2023

(54) BICYCLIC NITROGEN-CONTAINING HETEROCYCLIC DERIVATIVES AND PHARMACEUTICAL COMPOSITION COMPRISING THE SAME

(71) Applicant: Shionogi & Co., Ltd., Osaka (JP)

(72) Inventors: Koji Masuda, Osaka (JP); Shuichi Sugiyama, Osaka (JP); Toru Yamada, Osaka (JP); Eiichi Kojima, Osaka (JP); Tomoyuki Ogawa, Osaka (JP); Naotake Kobayashi, Osaka (JP); Hiroyuki Kai, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/349,042

(22) Filed: Jun. 16, 2021

(65) Prior Publication Data

US 2021/0317125 A1 Oct. 14, 2021

Related U.S. Application Data

(63) Continuation of application No. 16/340,467, filed as application No. PCT/JP2017/037300 on Oct. 16, 2017, now Pat. No. 11,066,409.

(30) Foreign Application Priority Data

Oct. 17, 2016 (JP) .............................. JP2016-203289
Jul. 7, 2017 (JP) .............................. JP2017-133192

(51) Int. Cl.
*C07D 487/04* (2006.01)
*C07D 471/04* (2006.01)
(Continued)

(52) U.S. Cl.
CPC ............ *C07D 487/04* (2013.01); *A61P 25/04* (2018.01); *A61P 25/28* (2018.01); *C07D 471/04* (2013.01); *C07D 473/18* (2013.01); *C07D 498/04* (2013.01)

(58) Field of Classification Search
CPC .. C07D 471/04; C07D 487/04; C07D 498/04; C07D 473/18; A61K 31/5383; A61P 43/00
(Continued)

(56) References Cited

U.S. PATENT DOCUMENTS

2009/0281107 A1 11/2009 Congy et al.
2011/0319400 A1 12/2011 Flores et al.
(Continued)

FOREIGN PATENT DOCUMENTS

EP 2 399 910 12/2011
EP 3 287 443 2/2018
(Continued)

OTHER PUBLICATIONS

Geoffrey Burnstock, "Purinergic mechanosensory transduction and visceral pain", BioMed Central, Molecular Pain 2009, 5:69.
Baroja-Mazo et al., "The participation of plasma membrane hemichannels to purinergic signaling", Biochimica et Bioplysica Acta 1828 (2013) pp. 79-93.
MacKenzie et al., "Rapid Secretion of Interleukin-iß by Microvesicle Shedding", Immunity, vol. 8, pp. 825-835, Nov. 2001.
Chessell et al., "Disruption of the P2X7 purinoceptor gene abolishes chronic inflammatory and neuropathic pain", Pain 114 (2005) pp. 386-396.
Serge et al., "Genetically determined P2X7 receptor pore formation regulates variability in chronic pain sensitivity", Nature Medicine, vol. 18, No. 4, Apr. 2012, pp. 595-599.
(Continued)

*Primary Examiner* — Susanna Moore
(74) *Attorney, Agent, or Firm* — Wenderoth, Lind & Ponack, L.L.P.

(57) ABSTRACT

Provided are a novel compound having an antagonistic activity for the $P2X_7$ receptor, and a pharmaceutical composition having an antagonistic activity for the $P2X_7$ receptor. A compound represented by Formula (I):

[Chemical Formula 1]

(I)

wherein $Z^1$ is $C(R^4)$ or the like; $R^4$ is a hydrogen atom or the like; $Z^2$ is $C(R^{5a})(R^{5a'})$ or the like; the dashed line represents the presence or absence of a bond; when the dashed line represents the presence of a bond, then $R^{5a'}$ is absent; $R^{5a}$ and $R^{5a'}$ are each independently a hydrogen atom or the like; Ring Q is a substituted or unsubstituted 5-membered non-aromatic heterocycle or the like; $Y^1$ is O or the like; $R^{2a}$ is a group represented by the formula: $—(C(R^{2a'})(R^{2b'}))_n—R^1$; $R^{2b}$ is a hydrogen atom or the like; $R^{2a'}$ and $R^{2b'}$ is each independently a hydrogen atom or the like; $R^1$ is substituted or unsubstituted aromatic carbocyclyl or the like; X is $N(R^{7a})$ or the like; $R^{7a}$ is a hydrogen atom or the like; $R^3$ is substituted or unsubstituted aromatic carbocyclyl or the like; n is an integer from 0 to 4; and m is an integer from 0 to 4, or a pharmaceutically acceptable salt thereof.

8 Claims, No Drawings

(51) Int. Cl.

| | |
|---|---|
| C07D 473/18 | (2006.01) |
| C07D 498/04 | (2006.01) |
| A61P 25/24 | (2006.01) |
| A61P 25/28 | (2006.01) |
| A61P 25/04 | (2006.01) |

(58) Field of Classification Search
USPC .......................................... 544/180; 514/245
See application file for complete search history.

(56) References Cited

U.S. PATENT DOCUMENTS

| | | |
|---|---|---|
| 2011/0319418 A1 | 12/2011 | Flores et al. |
| 2013/0172317 A1 | 7/2013 | Kai et al. |
| 2013/0225596 A1 | 8/2013 | Kai et al. |
| 2016/0024072 A1 | 1/2016 | Kai et al. |
| 2016/0052892 A1 | 2/2016 | Kai et al. |
| 2016/0115151 A1 | 4/2016 | Kai |
| 2016/0318916 A1 | 11/2016 | Tanaka et al. |

FOREIGN PATENT DOCUMENTS

| | | |
|---|---|---|
| KR | 10-2012-0089074 | 8/2012 |
| WO | 03/042190 | 5/2003 |
| WO | 03/042191 | 5/2003 |
| WO | 2004/058270 | 7/2004 |
| WO | 2004/058731 | 7/2004 |
| WO | 2004/099146 | 11/2004 |
| WO | 2006/003500 | 1/2006 |
| WO | 2006/003513 | 1/2006 |
| WO | 2006/003517 | 1/2006 |
| WO | 2006/086229 | 8/2006 |
| WO | 2006/102112 | 9/2006 |
| WO | 2006/104713 | 10/2006 |
| WO | 2006/104715 | 10/2006 |
| WO | 2007/079163 | 7/2007 |
| WO | 2007/079214 | 7/2007 |
| WO | 2008/066789 | 6/2008 |
| WO | 2008/124153 | 10/2008 |
| WO | 2009/002423 | 12/2008 |
| WO | 2009/057827 | 5/2009 |
| WO | 2009/058653 | 5/2009 |
| WO | 2010/072597 | 7/2010 |
| WO | 2010/072599 | 7/2010 |
| WO | 2010/072605 | 7/2010 |
| WO | 2010/072607 | 7/2010 |
| WO | 2010/072647 | 7/2010 |
| WO | 2010/125101 | 11/2010 |
| WO | 2010/125102 | 11/2010 |
| WO | 2010/126104 | 11/2010 |
| WO | 2010/133973 | 11/2010 |
| WO | 2011/012592 | 2/2011 |
| WO | 2011/033055 | 3/2011 |
| WO | 2011/047323 | 4/2011 |
| WO | 2011/079000 | 6/2011 |
| WO | 2011/109254 | 9/2011 |
| WO | 2012/036193 | 3/2012 |
| WO | 2013/089212 | 6/2013 |
| WO | 2014/152537 | 9/2014 |
| WO | 2014/152604 | 9/2014 |
| WO | 2014/152621 | 9/2014 |
| WO | 2014/154896 | 10/2014 |
| WO | 2015/099107 | 7/2015 |
| WO | 2016/019228 | 2/2016 |
| WO | 2016/039983 | 3/2016 |
| WO | 2016/084922 | 6/2016 |
| WO | 2016/088838 | 6/2016 |
| WO | 2017/204316 | 11/2017 |
| WO | 2017/204318 | 11/2017 |
| WO | 2017/209265 | 12/2017 |
| WO | 2017/209267 | 12/2017 |
| WO | 2018/074390 | 4/2018 |
| WO | 2018/074565 | 4/2018 |

OTHER PUBLICATIONS

Skaper et al., "The P2X7 purinergic receptor: from physiology to neurological disorders", The FASEB Journal, vol. 24, No. 2, pp. 337-345, Aug. 2017.
Takenouchi et al., "P2X7 Receptor Signaling Pathway as a Therapeutic Target for Neurodegenerative Diseases", Arch. Immunol. Ther. Exp. (Warsz). Apr. 2010; 58:91-96.
Friedle et al., "Recent Patents on Novel P2X7 Receptor Antagonists and their Potential for Reducing Central Nervous System Inflammation", Recent Pat CNS Drug Discovery, Jan. 2010; 5(1):35-45.
Registry, US: American Chemical Society, CAS RN 872552-91-5, 872495-92-6.
Azaroual et al., "NMR studies of interactions of new $CB_2$ cannabinoid receptor ligands with cyclodextrins hosts. Corrrelation with micellar electrokinetic chromatography and reversed phase high performance liquid chromatography", Journal of Inclusion Phenomena and Macrocyclic Chemishy (2014), 78(1-4), pp. 265-274.
Bakali et al., "4-Oxo-1,4-dihydropyridines as Selective $CB_2$ Cannabinoid Receptor Ligands: Structural Insights into the Design of a Novel Inverse Agonist Series", Journal of Medicinal Chemistry 2010, 53(22), pp. 7918-7931.
Duplantier et al., Optimization of the physicochemical and pharmacokinetic attributes in a 6-azauracil series of P2X7 receptor antagonists leading to the discovery of the clinical candidate CE-224,535, Bioorganic & Medicinal Chemistry Letters 21 (2011)pp. 3708-3711.
Subramanyam et al., "Discovery, synthesis and SAR of azinyl- and azolylbenzamides antagonists of the P2X7 receptor", Bioorganic & Medicinal Chemistry Letters 21 (2011) pp. 5475-5479.
Lopez-Tapia et al., "Novel Series of Dihydropyridinone P2X7 Receptor Antagonists", J. Med. Chem. 2015, 58, pp. 8413-8426.
Jin-Hee Park et al., "P2X7 receptor antagonists: a patent review (2010-2015)", Expert Opinion on Therapeutic Patents, 27:3, pp. 257-267. (2016).
Chen et al., "Discovery of 2-chloro-N-((4,4-difluoro-1-hydroxycyclohexyl)methyl)-5-(5-fluoropyrimidin-2-yl)benzamide as apotent and CNS penetrable P2X7 receptor antagonist", Bioorganic & Medicinal Chemishy Letters (2010), 20(10), pp. 3107-3111.
Xiaohai Wang et al., "P2X7 receptor inhibition improves recovery after spinal cord injury", Nature Medicine 2004, 10, 8, pp. 821-827.
Letavic et al., "Synthesis and Pharmacological Characterization of Two Novel, Brain Penetrating P2X7 Antagonists", ACS. Med. Chem. Lett. 2013, 4, pp. 419-422.
Nelson et al., "Structure—Activity Relationship Studies on a Series of Novel, Substituted 1-Benzyl-5-phenyltetrazole P2X7 Antagonists", J. Med. Chem. 2006, 49, pp. 3659-3666.
Swanson et al., "Identification of (R)-(2-Chloro-3-(trifluoromethyl)phenyl)(1-(5-fluoropyridin-2-yl)-4-methyl-6,7-dihydro-1H-imidazo[4,5-c]pyridin-5(H)-yl)methanone (JNJ 541660060), a Small Molecule Antagonist of the P2X7 receptor", J. Med. Chem. 2016, 59, pp. 8535-8548.
Letavic et al., "4-Methyl-6,7-dihydro-4H-triazolo[4,5-c]pyridine-Based P2X7 Receptor Antagonists: Optimization of Pharmacokinetic Properties Leading to the Identification of a Clinical Candidate", J. Med. Chem. 2017, 60, pp. 4559-4572.
Chrovian et al., "A Dipolar Cycloaddition Reaction to Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", J. Med. Chem. 2018, 61, pp. 207-223.
Savaii et al., "Synthesis, SAR, and Pharmacological Characterization of Brain Penetrant P2X7 Receptor Antagonists", Med. Chem. Lett. 2015, 6, pp. 671-676.
Bhattacharya et al., "Neuropsychopharmacology of JNJ-55308942: evaluation of a clinical candidate targeting P2X7 ion channels in animal models of neuroinflammation and anhedonia", Neuropsychopharmacologyvolume 43, pp. 2586-2596(2018).
International Search Report dated Jan. 16, 2018 in International Application No. PCT/JP2017/037300.
International Preliminary Report on Patentability dated May 2, 2019 in International Application No. PCT/JP2017/037300.

(56) References Cited

OTHER PUBLICATIONS

Extended European Search Report dated Feb. 13, 2020 in European Patent Application No. 17863024.0.
Bartlett et al., "The P2X7 Receptor Channel: Recent Developments and the Use of P2X7 Antagonists in Models of Disease", Pharmacological Reviews, 66:638-675, Jul. 2014.
Burnstock, G., "Purinergic Signalling and Neurological Diseases: Update", Autonomic Neuroscience Centre, CNS & Neurological Disorders Drug Targets, 16(3):257-265, Jan. 1, 2017.
STN Search Results-1: Compounds-RN 1327184-63-3, RN 1327174-36-6, RN 1327171-54-9, STN entered date.Sep. 2, 2011.
STN Search Results-2: Compounds- RN 872496-05-4, RN 872496-03-2, RN 872496-02-1, RN 872496-01-0, RN 663922-25-6, STN entered date.Jan. 24, 2006.
Cecil Textbook of Medicine, edited by Bennet, J.C., and Plum F., 20th edition, vol. 1, 1004-101 O, 1996.
Freshney et al., Culture of Animal Cells, A Manual of Basic Technique, Alan R. Liss, Inc., 1983, New York, p. 4.
Dermer et al., Bio/Technology, 1994, 12:320.

BICYCLIC NITROGEN-CONTAINING HETEROCYCLIC DERIVATIVES AND PHARMACEUTICAL COMPOSITION COMPRISING THE SAME

TECHNICAL FIELD

The invention relates to a compound useful for the treatment of diseases or conditions associated with the $P2X_7$ receptor and a pharmaceutical composition containing thereof.

BACKGROUND ART

Adenosine triphosphate (ATP) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. (Non-Patent Document 1) ATP thus released mediates various extracellular signal transductions through an ATP receptor.

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel.

The $P2X_7$ receptor, a non-selective cation channel, belongs to the P2X family, and forms a homo-trimeric structure. Activation of $P2X_7$ by extracellular ATP allows for the passage of cations across the plasma membrane. Prolonged or repeated ATP stimulation leads to the pore formation of pannexin hemichannel, and induces the cellular activation following the release of small molecule such as ATP. (Non-Patent Document 2) It is reported that the activation of $P2X_7$ is involved in inflammation, immune and pain by the maturation and secretion of proinflammatory cytokines such as interleukin-1 beta and interleukin-18. (Non-Patent, Document 3) Thus, it is known that the $P2X_7$ receptor is involved in pain, central nervous system disease, immune disease and inflammatory disease. (Non-Patent Document 7-8, and Patent Document 1)

$P2X_7$ is distributed in macrophages, mast cells, microglia, and astrocytes. It is known that disruption of the $P2X_7$ receptor gene abolishes chronic inflammatory and neuropathic pain. (Non-Patent, Document 4) It is reported that the P451L mutation of the mouse P2X7 gene has impaired pore formation and shows less mechanical sensitivity of neuropathic pain model mice. (Non-Patent Document 5) Additionally, an association between lower pain intensity in chronic pain patients and the hypofunctional allele of $P2X_7$ has been reported, suggesting that $P2X_7$ antagonist is useful in the treatment of chronic pain such as rheumatoid arthritis, osteoarthritis and neuropathic pain.

Additionally, it has been reported that $P2X_7$ may be involved in multiple sclerosis, spinal cord injury, stroke, Alzheimer's disease, and depression (Non-Patent Document 6), suggesting that $P2X_7$ antagonist is useful in the treatment of these central nervous system disease.

The compounds having an analgesic effect are described in Patent Documents 2 and 3. However, the compounds have different chemical structures from the compounds of the present invention, and there is neither disclosure nor suggestion about an antagonistic activity for the $P2X_7$ receptor.

The compounds having an antagonistic activity for the $P2X_7$ receptor are described in Patent Documents 4 and 5. However, the compounds have different chemical structures from the compounds of the present invention.

PRIOR ART REFERENCES

Patent Document

[Patent Document 1] International Publication WO 2012/036193A
[Patent Document 2] International Publication WO 2013/118855A
[Patent Document 3] International Publication WO 2012/020742A
[Patent Document 4] International Publication WO 2015/099107A
[Patent Document 5] International Publication WO 2016/171249A

Non-Patent Document

[Non-patent Document 1] Burnstock G., Mol Pain. 2009. 5. 69
[Non-patent, Document 2] Baroja-Mazo A et, al., Biochim Biophys Acta. 2013. 1828. 79-93
[Non-patent Document 3] MacKenzie A et al., Immunity. 2001. 15. 825-835
[Non-patent Document 4] Chessell I P et al., Pain. 2005. 114. 386-396
[Non-patent Document 5] Sorge R E et al., Nature Med. 2012. 18. 595-599
[Non-patent Document 6] Skaper S D et al., FASEB J. 2010. 24. 337-345
[Non-patent Document 7] Takenouchi T et al., Arch Immunol Ther Exp (Warsz). 2010 April; 58(2): 91-6
[Non-patent Document 8] Friedle S A et al., Recent Pat CNS Drug Discov. 2010 January; 5(1): 35-45

SUMMARY OF THE INVENTION

Problems to be Solved by the Invention

The objective of the present invention is to provide novel compounds having an antagonistic activity for the $P2X_7$ receptor and a pharmaceutical composition having an antagonistic activity for the $P2X_7$ receptor.

Means for Solving the Problem

The present invention relates to the following (1'), (1) to (44) and (1001) to (1007):
(1")
A compound represented by Formula (I):

[Chemical Formula 1]

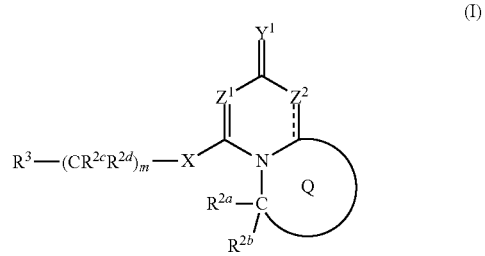

wherein $Z^1$ is $C(R^4)$ or N;

$R^4$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino;

$Z^2$ is $C(R^{5a})(R^{5a'})$ or $N(R^{5b})$;

the dashed line represents the presence or absence of a bond;

when the dashed line represents the presence of a bond, then $R^{5a'}$ and $R^{5b}$ are absent;

$R^{5a}$ and $R^{5a'}$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkonylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic hetorocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{5b}$ is a hydrogen atom, carboxy, carbamoyl, sulfamoyl, sulfo, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl;

Ring Q is a substituted or unsubstituted 5-membered non-aromatic heterocycle or a substituted or unsubstituted 6-membered non-aromatic heterocycle;

$Y^1$ is $N(R^6)$, O, or S;

$R^6$ is a hydrogen atom, hydroxy, cyano, carboxy, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{2a}$ is a group represented by the formula: $-C(R^{2a'})(R^{2b'}))_n-R^1$;

$R^{2b}$ is a hydrogen atom, halogen, hydroxy, substituted or unsubstituted alkyl, or substituted or unsubstituted alkyloxy;

$R^{2a'}$ is each independently a hydrogen atom, halogen, hydroxy, substituted or unsubstituted alkyl, or substituted or unsubstituted alkyloxy;

$R^{2b'}$ is each independently a hydrogen atom, halogen, hydroxy, substituted or unsubstituted alkyl, or substituted or unsubstituted alkyloxy;

$R^{2a'}$ and $R^{2b'}$ which are attached to the same carbon atom may be taken together to form oxo;

$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

X is $N(R^{7a})$, $C(R^{8a})(R^{8b})$, O or S;

$R^{7a}$ is a hydrogen atom, substituted or unsubstituted alkyl, or substituted or unsubstituted alkylcarbonyl;

$R^{8a}$ and $R^{8b}$ are each independently a hydrogen atom, halogen, hydroxy, substituted or unsubstituted alkyl, or substituted or unsubstituted alkyloxy;

$R^{2c}$ is each independently a hydrogen atom, halogen, hydroxy, substituted or unsubstituted alkyl, or substituted or unsubstituted alkyloxy;

$R^{2d}$ is each independently a hydrogen atom, halogen, hydroxy, substituted or unsubstituted alkyl, or substituted or unsubstituted alkyloxy;

$R^{2c}$ and $R^{2d}$ which are attached to the same carbon atom may be taken together to form a substituted or unsubstituted non-aromatic carbocycle, or two $R^{2c}$ may be taken together to form a substituted or unsubstituted non-aromatic carbocycle;

$R^3$ is substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;

n is an integer from 0 to 4; and m is an integer from 0 to 4, provided that the following compounds are excluded:

[Chemical Formula 2]

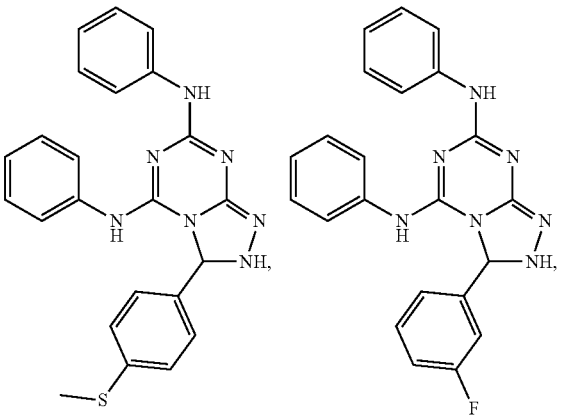

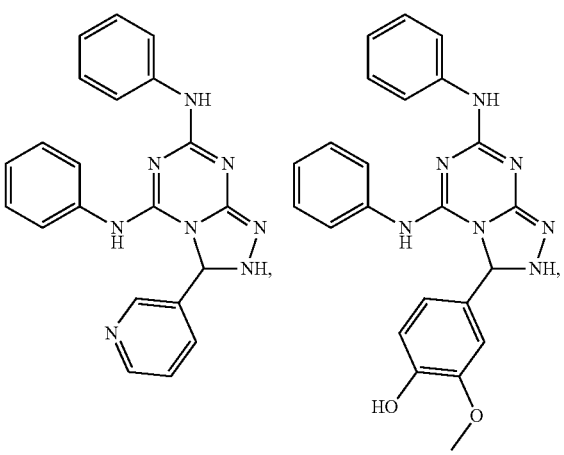

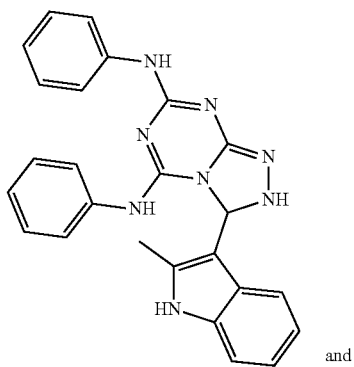

and

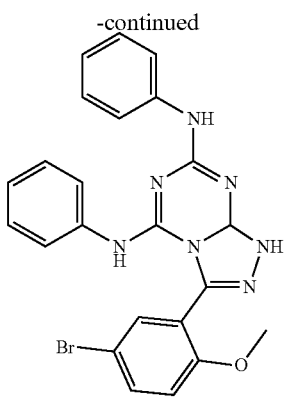

or a pharmaceutically acceptable salt thereof.

(1') A compound represented by Formula (I):

[Chemical Formula 3]

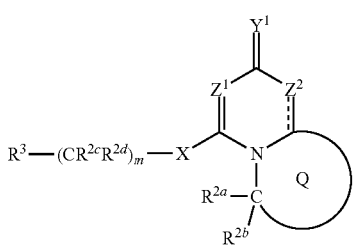

(I)

wherein $Z^1$ is $C(R^4)$ or N;

$R^4$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino;

$Z^2$ is $C(R^{5a})(R^{5a'})$ or $N(R^{5b})$;

the dashed line represents the presence or absence of a bond;

when the dashed line represents the presence of a bond, then $R^{5a'}$ and $R^{5b}$ are absent;

$R^{5a}$ and $R^{5a'}$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonyl amino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonyl amino;

$R^{5b}$ is a hydrogen atom, carboxy, carbamoyl, sulfamoyl, sulfo, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl;

Ring Q is a substituted or unsubstituted 5-membered non-aromatic heterocycle, a substituted or unsubstituted 5-membered aromatic heterocycle, or a substituted or unsubstituted 6-membered non-aromatic heterocycle;

$Y^1$ is $N(R^6)$, O, or S;

$R^6$ is a hydrogen atom, hydroxy, cyano, carboxy, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{2a}$ is a group represented by the formula: $-(C(R^{2a'})(R^{2b'}))_n-R^1$;

$R^{2b}$ is a hydrogen atom, halogen, hydroxy, substituted or unsubstituted alkyl, or substituted or unsubstituted alkyloxy;

$R^{2a'}$ is each independently a hydrogen atom, halogen, hydroxy, substituted or unsubstituted alkyl, or substituted or unsubstituted alkyloxy;

$R^{2b'}$ is each independently a hydrogen atom, halogen, hydroxy, substituted or unsubstituted alkyl, or substituted or unsubstituted alkyloxy;

$R^{2a'}$ and $R^{2b'}$ which are attached to the same carbon atom may be taken together to form oxo;

$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

X is $N(R^{7a})$, $C(R^{8a})(R^{8b})$, O or S;

$R^{7a}$ is a hydrogen atom, substituted or unsubstituted alkyl, or substituted or unsubstituted alkylcarbonyl;

$R^{8a}$ and $R^{8b}$ are each independently a hydrogen atom, halogen, hydroxy, substituted or unsubstituted alkyl, or substituted or unsubstituted alkyloxy;

$R^{2c}$ is each independently a hydrogen atom, halogen, hydroxy, substituted or unsubstituted alkyl, or substituted or unsubstituted alkyloxy;

$R^{2d}$ is each independently a hydrogen atom, halogen, hydroxy, substituted or unsubstituted alkyl, or substituted or unsubstituted alkyloxy;

$R^{2c}$ and $R^{2d}$ which are attached to the same carbon atom may be taken together to form a substituted or unsubstituted non-aromatic carbocycle, or two $R^{2c}$ may be taken together to form a substituted or unsubstituted non-aromatic carbocycle;

$R^3$ is substituted or unsubstituted aromatic carbocyclyl, substituted or unsubstituted aromatic heterocyclyl, substituted or unsubstituted non-aromatic carbocyclyl, or substituted or unsubstituted non-aromatic carbocyclyl;

n is an integer from 0 to 4; and m is an integer from 0 to 4, provided that the following compounds are excluded:

[Chemical Formula 4]

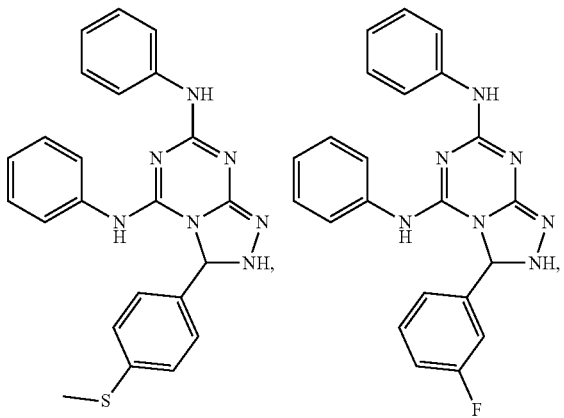

-continued

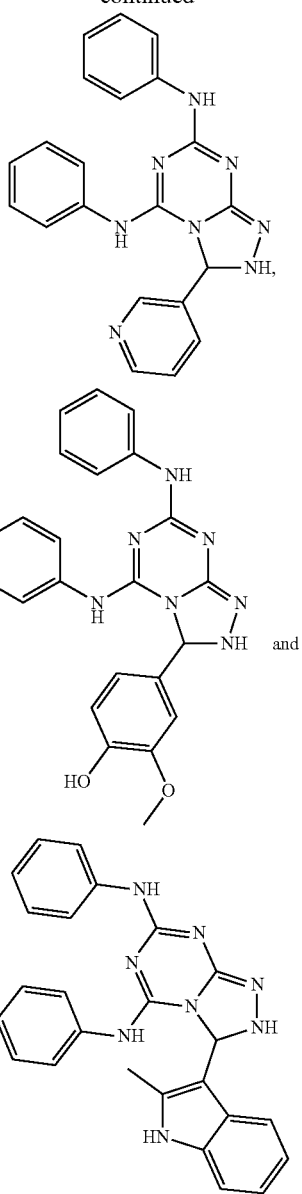

or a pharmaceutically acceptable salt thereof.

(1) A compound represented by Formula (I):

[Chemical Formula 5]

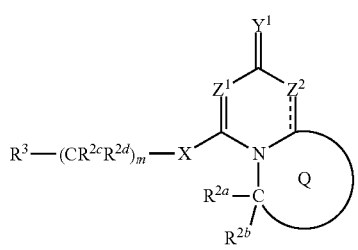

(I)

wherein
$Z^1$ is $C(R^4)$ or N;
$R^4$ is a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino;
$Z^2$ is $C(R^{5a})(R^{5a'})$ or $N(R^{5b})$;
the dashed line represents the presence or absence of a bond;
when the dashed line represents the presence of a bond, then $R^{5a'}$ and $R^{5b}$ are absent;
$R^{5a}$ and $R^{5a'}$ are each independently a hydrogen atom, halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted alkyloxycarbonylamino, substituted or unsubstituted alkenyloxycarbonylamino, substituted or unsubstituted alkynyloxycarbonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonyl amino;

$R^{5b}$ is a hydrogen atom, carboxy, carbamoyl, sulfamoyl, sulfo, cyano, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbamoyl, substituted or unsubstituted alkenylcarbamoyl, substituted or unsubstituted alkynylcarbamoyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, or substituted or unsubstituted non-aromatic heterocyclylcarbamoyl;

Ring Q is a substituted or unsubstituted 5-membered non-aromatic heterocycle or a substituted or unsubstituted 6-membered non-aromatic heterocycle;

$Y^1$ is $N(R^6)$, O, or S;

$R^6$ is a hydrogen atom, hydroxy, cyano, carboxy, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

$R^{2a}$ is a group represented by the formula: $-(C(R^{2a'})(R^{2b'}))_n-R^1$;

$R^{2b}$ is a hydrogen atom, halogen, hydroxy, substituted or unsubstituted alkyl, or substituted or unsubstituted alkyloxy;

$R^{2a'}$ is each independently a hydrogen atom, halogen, hydroxy, substituted or unsubstituted alkyl, or substituted or unsubstituted alkyloxy;

$R^{2b'}$ is each independently a hydrogen atom, halogen, hydroxy, substituted or unsubstituted alkyl, or substituted or unsubstituted alkyloxy;

$R^{2a'}$ and $R^{2b'}$ which are attached to the same carbon atom may be taken together to form oxo;

$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;

X is $N(R^{7a})$, $C(R^{8a})(R^{8b})$, O, or S;

$R^{7a}$ is a hydrogen atom, substituted or unsubstituted alkyl, or substituted or unsubstituted alkylcarbonyl;

$R^{8a}$ and $R^{8b}$ are each independently a hydrogen atom, halogen, hydroxy, substituted or unsubstituted alkyl, or substituted or unsubstituted alkyloxy;

$R^{2c}$ is each independently a hydrogen atom, halogen, hydroxy, substituted or unsubstituted alkyl, or substituted or unsubstituted alkyloxy;

$R^{2d}$ is each independently a hydrogen atom, halogen, hydroxy, substituted or unsubstituted alkyl, or substituted or unsubstituted alkyloxy;

$R^{2c}$ and $R^{2d}$ which are attached to the same carbon atom may be taken together to form a substituted or unsubstituted non-aromatic carbocycle, or two $R^{2c}$ may be taken together to form a substituted or unsubstituted non-aromatic carbocycle;

$R^3$ is substituted or unsubstituted aromatic carbocyclyl, substituted or unsubstituted aromatic heterocyclyl, substituted or unsubstituted non-aromatic carbocyclyl, or substituted or unsubstituted non-aromatic carbocyclyl;

n is an integer from 0 to 4; and m is an integer from 0 to 4, provided that the following compounds are excluded:

[Chemical Formula 6]

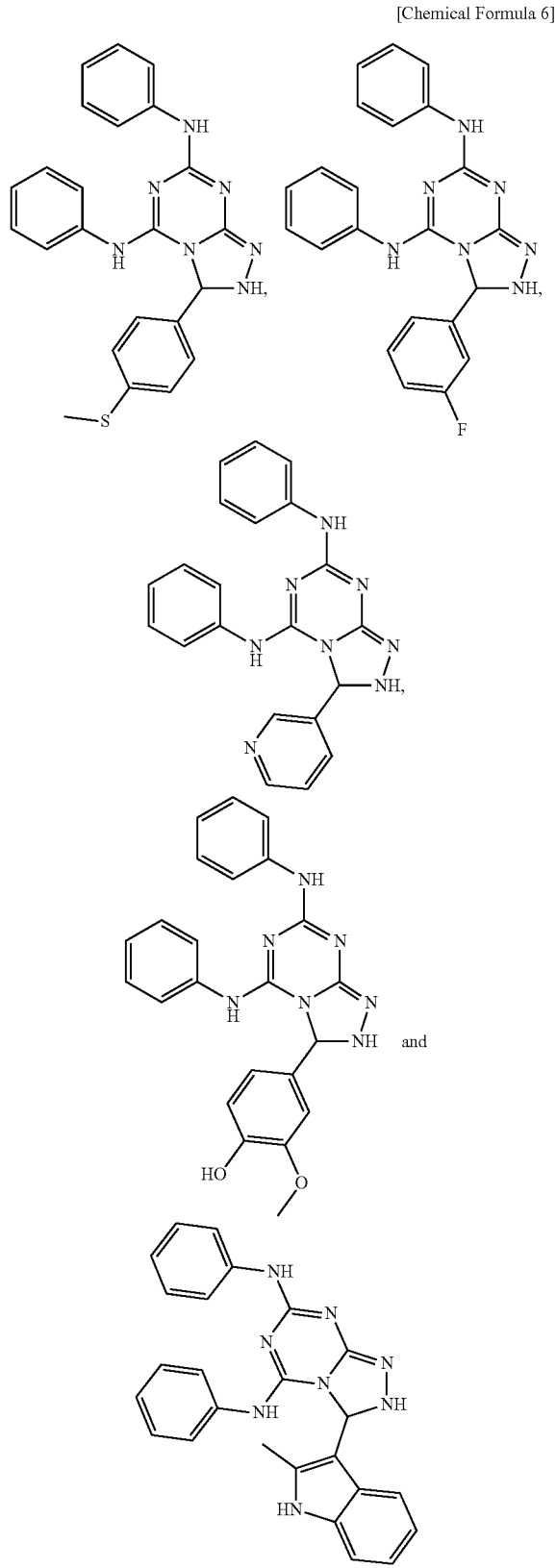

or a pharmaceutically acceptable salt thereof.

(2)
The compound according to any one of the above (1″), (1′), and (1), wherein
the dashed line represents the presence of a bond, or a pharmaceutically acceptable salt thereof.

(3)
The compound according to any one of the above (1″), (1′), and (1), wherein

[Chemical Formula 7]

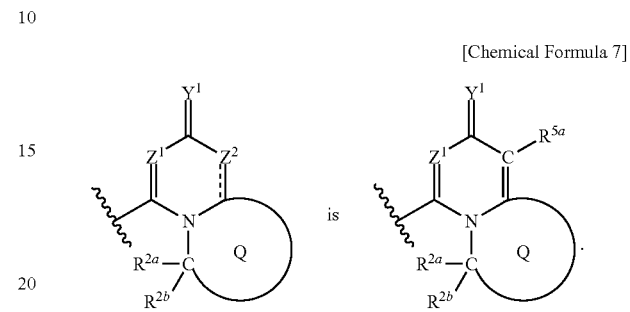

or a pharmaceutically acceptable salt thereof.

(4)
The compound according to the above (2) or (3), wherein
Ring Q is a substituted or unsubstituted 5-membered saturated heterocycle or a substituted or unsubstituted 6-membered saturated heterocycle, or a pharmaceutically acceptable salt thereof.

(5)
The compound according to any one of the above (1″), (1′), and (1), wherein
the dashed line represents the absence of a bond, or a pharmaceutically acceptable salt thereof.

(6)
The compound according to any one of the above (1″), (1′), and (1), wherein

[Chemical Formula 8]

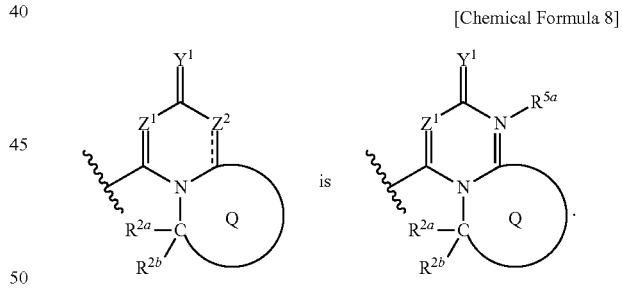

or a pharmaceutically acceptable salt thereof.

(7)
The compound according to the above (5) or (6), wherein
Ring Q is a substituted or unsubstituted 5-membered non-aromatic heterocycle, or a pharmaceutically acceptable salt thereof.

(8)
The compound according to any one of the above (1″), (1′), and (1) to (7), wherein
$Z^1$ is N,
or a pharmaceutically acceptable salt thereof.

(9)
The compound according to any one of the above (1″), (1′), and (1) to (8), wherein
$Y^1$ is O,
or a pharmaceutically acceptable salt thereof.

(10)
The compound according to any one of the above (1"), (1'), and (1) to (9), wherein
X is N($R^{7a}$),
or a pharmaceutically acceptable salt thereof.
(11)
The compound according to any one of the above (1"), (1'), and (1) to (10), wherein
$R^{7a}$ is a hydrogen atom,
or a pharmaceutically acceptable salt thereof.
(12)
The compound according to any one of the above (1"), (1'), and (1) to (11), wherein
$R^1$ is substituted or unsubstituted 6-membered aromatic carbocyclyl, or substituted or unsubstituted 5- to 6-membered aromatic heterocyclyl, or a pharmaceutically acceptable salt thereof.
(13)
The compound according to any one of the above (1"), (1'), and (1) to (11), wherein
$R^1$ is substituted or unsubstituted 6-membered aromatic carbocyclyl, or a pharmaceutically acceptable salt thereof.
(14)
The compound according to any one of the above (1"), (1'), and (1) to (11), wherein
$R^1$ is 6-membered aromatic carbocyclyl substituted with one or more halogen atom(s) and optionally substituted with one or more and same or different substituent(s), or 5- to 6-membered aromatic heterocyclyl substituted with one or more halogen atom(s) and optionally substituted with one or more and same or different substituent(s), or a pharmaceutically acceptable salt thereof.
(15)
The compound according to any one of the above (1"), (1'), and (1) to (11), wherein
$R^1$ is 6-membered aromatic carbocyclyl substituted with one or more halogen atom(s) and optionally substituted with one or more and same or different substituent(s),
or a pharmaceutically acceptable salt thereof.
(16)
The compound according to any one of the above (1"), (1'), and (1) to (15), wherein
$R^{2a'}$ and $R^{2b'}$ are each a hydrogen atom, or a pharmaceutically acceptable salt thereof.
(17)
The compound according to any one of the above (1"), (1'), and (1) to (16), wherein
$R^{2b}$ is a hydrogen atom,
or a pharmaceutically acceptable salt thereof.
(18)
The compound according to any one of the above (1"), (1'), and (1) to (17), wherein
$R^{5a}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, or substituted or unsubstituted aromatic heterocyclyl, or a pharmaceutically acceptable salt thereof.
(19)
The compound according to any one of the above (1"), (1'), and (1) to (17), wherein
$R^{5a}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, or substituted or unsubstituted aromatic heterocyclyl, or a pharmaceutically acceptable salt thereof.
(20)
The compound according to any one of the above (1"), (1'), and (1) to (19), wherein
$R^{5a'}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, or substituted or unsubstituted aromatic heterocyclyl,
or a pharmaceutically acceptable salt thereof.
(21)
The compound according to any one of the above (1"), (1'), and (1) to (19), wherein
$R^{5a'}$ is a hydrogen atom,
or a pharmaceutically acceptable salt thereof.
(22)
The compound according to any one of the above (1"), (1'), and (1) to (21), wherein
$R^{5b}$ is a hydrogen atom, substituted or unsubstituted alkyl, substituted or unsubstituted alkenyl, or substituted or unsubstituted alkynyl, or a pharmaceutically acceptable salt thereof.
(23)
The compound according to any one of the above (1"), (1'), and (1) to (22), wherein
$R^{5b}$ is a hydrogen atom, or substituted or unsubstituted alkyl, or a pharmaceutically acceptable salt thereof.
(24)
The compound according to any one of the above (1"), (1'), and (1) to (23), wherein
$R^3$ is substituted or unsubstituted 6-membered aromatic carbocyclyl, or substituted or unsubstituted 6- to 10-membered aromatic heterocyclyl, or a pharmaceutically acceptable salt thereof.
(25)
The compound of any one of the above (1"), (1'), and (1) to (23), wherein
$R^3$ is a group represented by the Formula:

[Chemical Formula 9]

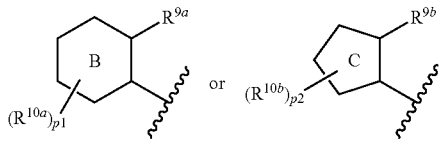

wherein
Ring B is a 6-membered aromatic carbocycle or a 6-membered aromatic heterocycle;
Ring C is a 5-membered aromatic heterocycle;
$R^{9a}$ and $R^{9b}$ are halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonyl amino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclyl amino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{10a}$ and $R^{10b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{9a}$, $R^{9b}$, $R^{10a}$ and $R^{10b}$ may be any of the following a) to c):

a) $R^{9a}$ and $R^{10a}$, or $R^{9b}$ and $R^{10b}$ are taken together to form a (C1-C3) bridge, wherein one of the carbon atoms constituting the bridge may be replaced with an oxygen atom or a nitrogen atom;

b) $R^{9a}$ and $R^{10a}$ which are attached to the adjacent ring-constituting atoms, or $R^{9b}$ and $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and c) two $R^{10a}$ which are attached to the adjacent ring-constituting atoms, or two $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle; and p1 is an integer from 0 to 3;
p2 is an integer from 0 to 2,
or a pharmaceutically acceptable salt thereof.

(26)
The compound according to the above (25), wherein
$R^3$ is a group represented by:

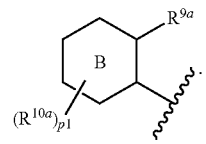

[Chemical Formula 10]

or a pharmaceutically acceptable salt thereof.

(27)
The compound according to the above (25) or (26), wherein
$R^{9a}$ and $R^{9b}$ are each halogen, substituted or unsubstituted alkyl, substituted or unsubstituted alkenyl, or substituted or unsubstituted alkynyl, or a pharmaceutically acceptable salt thereof.

(28)
The compound according to the above (25) or (26), wherein
$R^{9a}$ and $R^{9b}$ are each substituted or unsubstituted alkyl, or a pharmaceutically acceptable salt thereof.

(29)
The compound according to any one of the above (25) to (28), wherein
$R^{10a}$ and $R^{10b}$ are each independently halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy,
or a pharmaceutically acceptable salt thereof.

(30)
The compound according to any one of the above (25) to (28), wherein
$R^{10a}$ and $R^{10b}$ are each independently halogen, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or a pharmaceutically acceptable salt thereof.

(31)
The compound according to any one of the above (25) to (30), wherein
$R^{9a}$ and $R^{10a}$ which are attached to the adjacent ring-constituting atoms or $R^{9b}$ and $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle, or
two $R^{10a}$ which are attached to the adjacent ring-constituting atoms or two $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle,
or a pharmaceutically acceptable salt thereof.

(32)
The compound according to any one of the above (25) to (30), wherein
$R^{9a}$ and $R^{10a}$ which are attached to the adjacent ring-constituting atoms or $R^{9b}$ and $R^{10b}$ which are attached to the adjacent ring-constituting atoms are taken together to form a substituted or unsubstituted aromatic heterocycle, or
two $R^{10a}$ which are attached to the adjacent ring-constituting atoms or two $R^{10b}$ which are attached to the adjacent ring-constituting atoms are taken together to form a substituted or unsubstituted aromatic heterocycle, or a substituted or unsubstituted non-aromatic heterocycle,
or a pharmaceutically acceptable salt thereof.

(33)
The compound according to any one of the above (1"), (1'), and (1) to (32), wherein
n is 0,
or a pharmaceutically acceptable salt thereof.

(34)
The compound according to any one of the above (1"), (1'), and (1) to (33), wherein
m is 0,
or a pharmaceutically acceptable salt thereof.

(35)
The compound according to any one of the above (1"), (1'), and (1) to (34), wherein
$R^{2c}$ and $R^{2d}$ are each independently a hydrogen atom or halogen,
or a pharmaceutically acceptable salt thereof.

(36)
The compound according to any one of the above (1"), (1'), and (1) to (34), wherein
$R^{2c}$ and $R^{2d}$ are each a hydrogen atom,
or a pharmaceutically acceptable salt thereof.

(37)
The compound according to any one of the above (1"), (1'), and (1) to (36), wherein
$R^4$ is a hydrogen atom, halogen, or substituted or unsubstituted alkyl,
or a pharmaceutically acceptable salt thereof.

(38)
The compound according to any one of the above (1"), (1'), and (1) to (36), wherein
$R^4$ is a hydrogen atom,
or a pharmaceutically acceptable salt thereof.

(39)
The compound according to the above (1"), (1'), and (1), wherein
the compound is selected from the group consisting of Examples I-0059, I-0102, I-0135, I-0142, I-0145, I-0147, I-0149, I-0154, I-0158, I-0161, I-0162, I-0164, I-0168, I-0171, I-0176, I-0188, I-0192, and I-0201,
or a pharmaceutically acceptable salt thereof.

(40)
A P2X$_7$ receptor inhibitor comprising:
the compound according to any one of the above (1"), (1'), and (1) to (39), or a pharmaceutically acceptable salt thereof.

(41)
A pharmaceutical composition comprising:
the compound according to any one of the above (1"), (1'), and (1) to (39), or a pharmaceutically acceptable salt thereof.

(42)
The pharmaceutical composition according to the above (41), having an antagonistic activity for the P2X$_7$ receptor.

(43)
The compound according to any one of the above (1"), (1'), and (1) to (39), or a pharmaceutically acceptable salt thereof for use in treating and/or preventing a disease associated with the P2X$_7$ receptor.

(44)
A method for treating and/or preventing a disease associated with the P2X$_7$ receptor characterized by administering the compound according to any one of the above (1"), (1'), and (1) to (39), or a pharmaceutically acceptable salt thereof.

(1001) A pharmaceutical composition comprising the compound according to any one of the above (1) to (39), or a pharmaceutically acceptable salt thereof, for oral administration.

(1002) The pharmaceutical composition according to the above (1001), which is a tablet, powder, granule, capsule, pill, film, suspension, emulsion, elixir, syrup, lemonade, spirit, aromatic water, extract, decoction or tincture.

(1003) The pharmaceutical composition according to the above (1002), which is a sugar-coated tablet, film-coated tablet, enteric-coated tablet, sustained-release tablet, troche tablet, sublingual tablet, buccal tablet, chewable tablet, orally dispersing tablet, dry syrup, soft capsule, micro capsule or sustained-release capsule.

(1004) A pharmaceutical composition comprising the compound according to any one of the above (1) to (39), or a pharmaceutically acceptable salt thereof, for parenteral administration.

(1005) The pharmaceutical composition according to the above (1004), for dermal, subcutaneous, intravenous, intraarterial, intramuscular, intraperitoneal, transmucosal, inhalation, transnasal, ophthalmic, inner ear or vaginal administration.
(1006) The pharmaceutical composition according to the above (1004) or (1005), which is injection, infusion, eye drop, nose drop, ear drop, aerosol, inhalation, lotion, impregnation, liniment, mouthwash, enema, ointment, plaster, jelly, cream, patch, cataplasm, external powder or suppository.
(1007) A pharmaceutical composition comprising the compound according to any one of the above (1) to (39), or a pharmaceutically acceptable salt thereof, for a pediatric or geriatric patient.

Effect of the Invention

The compounds of the present invention have an antagonistic activity for the P2X$_7$ receptor, and are useful as a therapeutic and/or preventive agent for diseases or conditions associated with the P2X$_7$ receptor.

MODE FOR CARRYING OUT THE INVENTION

Terms used in this description are explained below. Each term, unless otherwise indicated, has the same meaning when it is used alone or together with other terms.

The term "consist of" means having only a component.

The term "comprise" means that an element that is not described is not excluded without limitations to a component.

"Halogen" includes a fluorine atom, a chlorine atom, a bromine atom and an iodine atom. A fluorine atom and a chlorine atom are preferable.

"Alkyl" includes a C1 to C15, preferably C1 to C10, more preferably C1 to C6 and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably C2 to C10, more preferably C2 to C6 and further preferably C2 to Cd linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

"Alkynyl" includes a C2 to C10, preferably C2 to C8, more preferably C2 to C6 and further preferably C2 to C4 linear or branched hydrocarbon group having one or more triple bond(s) at any position(s). For example, it includes ethynyl, propynyl, butynyl, pentynyl, hexynyl, heptynyl, octynyl, nonynyl, decynyl and the like. Furthermore, it may have double bond(s) at any position(s).

A preferred embodiment of "alkynyl" is ethynyl, propynyl, butynyl or pentynyl.

"Aromatic carbocycle" means a cyclic aromatic hydrocarbon ring which is monocyclic or polycyclic having two or more rings. For example, it includes benzene, naphthalene, anthracene, phenanthrene and the like.

A preferred embodiment of "aromatic carbocycle" is benzene.

"Aromatic carbocyclyl" means a cyclic aromatic hydrocarbon group which is monocyclic or polycyclic having two or more rings. For example, it includes phenyl, naphthyl, anthryl, phenanthryl and the like.

A preferred embodiment of "aromatic carbocyclyl" is phenyl.

"Non-aromatic carbocycle" means a cyclic saturated hydrocarbon ring or a cyclic unsaturated non-aromatic hydrocarbon ring, which is monocyclic or polycyclic having two or more rings. "Non-aromatic carbocycle", which is polycyclic having two or more rings, includes a fused ring wherein a non-aromatic carbocycle, which is monocyclic or polycyclic having two or more rings, is fused with a ring of the above "aromatic carbocycle".

In addition, the "non-aromatic carbocycle" also includes a ring having a bridge or a ring to form a spiro ring as follows.

[Chemical Formula 11]

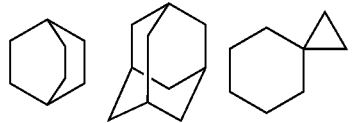

A non-aromatic carbocycle which is monocyclic is preferably C3 to C16, more preferably C3 to C12 and further preferably C4 to C8 carbocycle. For example, it includes cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclohexadiene and the like.

A non-aromatic carbocycle which is polycyclic having two or more rings includes, for example, indane, indene, acenaphthalene, tetrahydronaphthalene, fluorene and the like.

"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocyclyl, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

[Chemical Formula 12]

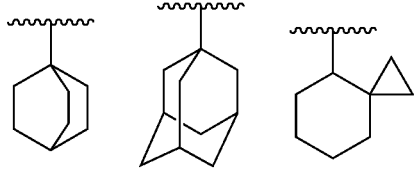

A non-aromatic carbocyclyl which is monocyclic is preferably C3 to C10, more preferably C3 to C12 and further preferably C4 to C8 carbocyclyl. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings includes, for example, indanyl, indenyl, acenaphthyl, tetrahydronaphthyl, fluorenyl and the like.

"Aromatic heterocycle" means an aromatic ring, which is monocyclic or polycyclic having two or more rings, containing one or more and same or different of heteroatom(s) selected independently from O, S and N.

"Aromatic heterocycle", which is polycyclic having two or more rings, includes a fused ring wherein an aromatic heterocycle, which is monocyclic or polycyclic having two or more rings, is fused with a ring of the above "aromatic carbocycle".

An aromatic heterocycle which is monocyclic is preferably a 5- to 8-membered and more preferably 5- to 6-membered ring. For example, it includes pyrrole, imidazole, pyrazole, pyridine, pyridazine, pyrimidine, pyrazine, triazole, triazine, tetrazole, furan, thiophene, isoxazole, oxazole, oxadiazole, isothiazole, thiazole, thiadiazole and the like.

An aromatic heterocycle which is bicyclic includes, for example, indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzoxadiazole, benzisothiazole, benzothiazole, benzothiadiazole, benzofuran, isobenzofuran, benzothiophene, benzotriazole, imidazopyridine, triazolopyridine, imidazothiazole, pyrazinopyridazine, oxazolopyridine, thiazolopyridine and the like.

An aromatic heterocycle which is polycyclic having three or more rings includes, for example, carbazole, acridine, xanthene, phenothiazine, phenoxathiine, phenoxazine, dibenzofuran and the like.

"Aromatic heterocyclyl" means an aromatic cyclyl, which is monocyclic or polycyclic having two or more rings, containing one or more and same or different of heteroatom(s) selected independently from O, S and N.

"Aromatic heterocyclyl", which is polycyclic having two or more rings, includes a fused ring group wherein an aromatic heterocyclyl, which is monocyclic or polycyclic having two or more rings, is fused with a ring of the above "aromatic carbocyclyl".

An aromatic heterocyclyl which is monocyclic is preferably a 5- to 6-membered ring. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic includes, for example, indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocycle" means a non-aromatic ring, which is monocyclic or polycyclic having two or more rings, containing one or more and same or different of heteroatom(s) selected independently from O, S and N.

"Non-aromatic heterocycle", which is polycyclic having two or more rings, includes a fused ring wherein a non-aromatic heterocycle, which is monocyclic or polycyclic having two or more ring(s), is fused with a ring of the above "aromatic carbocyclo", "non-aromatic carbocycle" and/or "aromatic heterocycle". The non-aromatic heterocycle, which is polycyclic having two or more rings, further includes a fused ring wherein an aromatic heterocycle, which is monocyclic or polycyclic having two or more rings, is fused with a ring of the above "non-aromatic carbocycle".

In addition, the "non-aromatic heterocycle" also includes a ring having a bridge or a ring to form a spiro ring as follows.

[Chemical Formula 13]

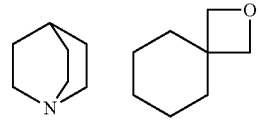

A non-aromatic heterocycle which is monocyclic is preferably a 3- to 8-membered and more preferably 5- to 6-membered ring. For example, it includes dioxane, thiirane, oxirane, oxetane, oxathiolane, azetidine, thiane, thiazolidine, pyrrolidine, pyrroline, imidazolidine, imidazoline, pyrazolidine, pyrazoline, piperidine, piperazine, morpholine, thiomorpholine, dihydropyridine, tetrahydropyridine, tetrahydrofuran, tetrahydropyrane, dihydrothiazole, tetrahydrothiazole, tetrahydroisothiazole, dihydrooxazine, hexahydroazepine, tetrahydrodiazepine, tetrahydropyridazine, hexahydropyrimidine, dioxolane, dioxazine, aziridine, dioxoline, oxepane, thiolane, thiine, thiazine and the like.

A non-aromatic heterocycle which is polycyclic having two or more rings includes, for example, indoline, isoindolinel, chromane, isochromane and the like.

"Non-aromatic heterocyclyl" means a non-aromatic cyclyl, which is monocyclic or polycyclic having two or more rings, containing one or more and same or different of heteroatom(s) selected independently from O, S and N.

"Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl". The non-aromatic heterocyclyl, which is polycyclic having two or more rings, further includes a fused ring wherein an aromatic heterocyclyl, which is monocyclic or polycyclic having two or more rings, is fused with a ring of the above "non-aromatic carbocyclyl".

In addition, the "non-aromatic heterocyclyl" also includes a group having a bridge or a group to form a spiro ring as follows:

[Chemical Formula 14]

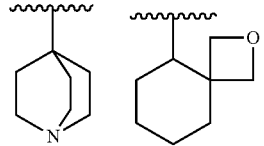

A non-aromatic heterocyclyl which is monocyclic is preferably a 3- to 8-membered and more preferably 5- to 6-membered ring. For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidinyl, piperazinyl, morpholinyl, morpholino, thiomorpholinyl, thiomorpholino, dihydropyridinyl, tetrahydropyridinyl, tetrahydrofuryl, tetrahydropyranyl, dihydrothiazolinyl, tetrahydrothiazolinyl, tetrahydroisothiazolinyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings includes, for example, indolinyl, isoindolinyl, chromanyl, isochromanyl and the like.

"Alkyloxy" means a group wherein the above "alkyl" is bonded to an oxygen atom. For example, it includes methyloxy, ethyloxy, n-propyloxy, isopropyloxy, n-butyloxy, tert-butyloxy, isobutyloxy, secbutyloxy, pentyloxy, isopentyloxy, hexyloxy and the like.

A preferred embodiment of "alkyloxy" is methyloxy, ethyloxy, n-propyloxy, isopropyloxy or tert-butyloxy.

"Alkenyloxy" means a group wherein the above "alkenyl" is bonded to an oxygen atom. For example, it includes vinyloxy, allyloxy, 1-propenyloxy, 2-butenyloxy, 2-pentenyloxy, 2-hexenyloxy, 2-heptenyloxy, 2-octenyloxy and the like.

"Alkynyloxy" means a group wherein the above "alkynyl" is bonded to an oxygen atom. For example, it includes ethynyloxy, 1-propynyloxy, 2-propynyloxy, 2-butynyloxy, 2-pentynyloxy, 2-hexynyloxy, 2-heptynyloxy, 2-octynyloxy and the like.

"Alkylsulfanyl" means a group wherein a hydrogen atom bonded to a sulfur atom of a sulfanyl group is replaced with the above "alkyl". For example, it includes methylsulfanyl, ethylsulfanyl, n-propylsulfanyl, isopropylsulfanyl and the like.

"Alkenylsulfanyl" means a group wherein a hydrogen atom bonded to a sulfur atom of a sulfanyl group is replaced with the above "alkenyl". For example, it includes ethylenylsulfanyl, propenylsulfanyl and the like.

"Alkynylsulfanyl" means a group wherein a hydrogen atom bonded to a sulfur atom of a sulfanyl group is replaced with the above "alkynyl". For example, it includes ethynylsulfanyl, propynylsulfanyl and the like.

"Alkylamino" means a group wherein a hydrogen atom attached to a nitrogen atom of an amino group is replaced with the above "alkyl". For example, it includes methylamino, ethylamino, isopropylamino and the like. Another hydrogen atom attached to the nitrogen atom of the amino group may be replaced with the above "alkyl".

A preferred embodiment of "alkylamino" is methylamino or ethylamino.

"Alkenylamino" means a group wherein a hydrogen atom attached to a nitrogen atom of an amino group is replaced with the above "alkenyl". For example, it includes ethylenylamino, propenylamino and the like. Another hydrogen atom attached to the nitrogen atom of the amino group may be replaced with the above "alkyl".

"Alkynylamino" means a group wherein a hydrogen atom attached to a nitrogen atom of an amino group is replaced with the above "alkynyl". For example, it includes ethynylamino, propynylamino and the like. Another hydrogen atom attached to the nitrogen atom of the amino group may be replaced with the above "alkyl".

"Alkylcarbonyl" means a group wherein the above "alkyl" is bonded to a carbonyl group. For example, it includes methylcarbonyl, ethylcarbonyl, propylcarbonyl, isopropylcarbonyl, tert-butylcarbonyl, isobutylcarbonyl, sec-butylcarbonyl, penthylcarbonyl, isopenthylcarbonyl, hexylcarbonyl and the like.

A preferred embodiment of "alkylcarbonyl" is methylcarbonyl, ethylcarbonyl or n-propylcarbonyl.

"Alkenylcarbonyl" means a group wherein the above "alkenyl" is bonded to a carbonyl group. For example, it includes ethylenylcarbonyl, propenylcarbonyl and the like.

"Alkynylcarbonyl" means a group wherein the above "alkynyl" is bonded to a carbonyl group. For example, it includes ethynylcarbonyl, propynylcarbonyl and the like.

"Alkylsulfonyl" means a group wherein the above "alkyl" is bonded to a sulfonyl group. For example, it includes methylsulfonyl, ethylsulfonyl, propylsulfonyl, isopropylsulfonyl, tert-butylsulfonyl, isobutylsulfonyl, sec-butylsulfonyl and the like.

A preferred embodiment of "alkylsulfonyl" is methylsulfonyl or ethylsulfonyl.

"Alkenylsulfonyl" means a group wherein the above "alkenyl" is bonded to a sulfonyl group. For example, it includes ethylenylsulfonyl, propenylsulfonyl and the like.

"Alkynylsulfonyl" means a group wherein the above "alkynyl" is bonded to a sulfonyl group. For example, it includes ethynylsulfonyl, propynylsulfonyl and the like.

"Alkylcarbonyloxy" means a group wherein the above "alkylcarbonyl" is bonded to an oxygen atom. For example, it includes methylcarbonyloxy, ethylcarbonyloxy, propylcarbonyloxy, isopropylcarbonyloxy, tert-butylcarbonyloxy, isobutylcarbonyloxy, secbutylcarbonyloxy and the like.

A preferred embodiment of "alkylcarbonyloxy" is methylcarbonyloxy or ethylcarbonyloxy.

"Alkenylcarbonyloxy" means a group wherein the above "alkenylcarbonyl" is bonded to an oxygen atom. For example, it includes ethylenylcarbonyloxy, propenylcarbonyloxy and the like.

"Alkynylcarbonyloxy" means a group wherein the above "alkynylcarbonyl" is bonded to an oxygen atom. For example, it includes ethynylcarbonyloxy, propynylcarbonyloxy and the like.

"Alkyloxycarbonyl" means a group wherein the above "alkyloxy" is bonded to a carbonyl group. For example, it includes methyloxycarbonyl, ethyloxycarbonyl, propyloxycarbonyl, isopropyloxycarbonyl, tert-butyloxycarbonyl, isobutyloxycarbonyl, secbutyloxycarbonyl, penthyloxycarbonyl, isopenthyloxycarbonyl, hexyloxycarbonyl and the like.

A preferred embodiment of "alkyloxycarbonyl" is methyloxycarbonyl, ethyloxycarbonyl or propyloxycarbonyl.

"Alkenyloxycarbonyl" means a group wherein the above "alkenyloxy" is bonded to a carbonyl group. For example, it includes ethylenyloxycarbonyl, propenyloxycarbonyl and the like.

"Alkynyloxycarbonyl" means a group wherein the above "alkynyloxy" is bonded to a carbonyl group. For example, it includes ethynyloxycarbonyl, propynyloxycarbonyl and the like.

"Alkylsulfonyloxy" means a group wherein the above "alkylsulfonyl" is bonded to an oxygen atom. For example, it includes methylsulfonyloxy, ethylsulfonyloxy, propylsulfonyloxy, isopropylsulfonyloxy, tert-butylsulfonyloxy, isobutylsulfonyloxy, secbutylsulfonyloxy and the like.

A preferred embodiment of "alkylsulfonyloxy" is methylsulfonyloxy or ethylsulfonyloxy.

"Alkenylsulfonyloxy" means a group wherein the above "alkenylsulfonyl" is bonded to an oxygen atom. For example, it includes ethylenylsulfonyloxy, propenylsulfonyloxy and the like.

"Alkynylsulfonyloxy" means a group wherein the above "alkynylsulfonyl" is bonded to an oxygen atom. For example, it includes ethynylsulfonyloxy, propynylsulfonyloxy and the like.

"Alkyloxysulfonyl" means a group wherein the above "alkyloxy" is bonded to a sulfonyl group. For example, it includes methyloxysulfonyl, ethyloxysulfonyl, propyloxysulfonyl, isopropyloxysulfonyl, tert-butyloxysulfonyl, isobutyloxysulfonyl, secbutyloxysulfonyl, pentyloxysulfonyl, isopentyloxysulfonyl, hexyloxysulfonyl and the like.

A preferred embodiment of "alkyloxysulfonyl" is methyloxysulfonyl, ethyloxysulfonyl, or propyloxysulfonyl.

"Alkenyloxysulfonyl" means a group wherein the above "alkenyloxy" is bonded to a sulfonyl group. For example, it includes ethylenyloxysulfonyl, propenyloxysulfonyl and the like.

"Alkynyloxysulfonyl" means a group wherein the above "alkynyloxy" is bonded to a sulfonyl group. For example, it includes ethynyloxysulfonyl, propynyloxysulfonyl and the like.

"Alkylcarbamoyl" means a group wherein a hydrogen atom bonded to a nitrogen atom of a carbamoyl group is replaced with the above "alkyl". For example, it includes methylcarbamoyl, ethylcarbamoyl and the like. Another hydrogen atom bonded to the nitrogen atom of the carbamoyl group may be replaced with the above "alkyl".

"Alkenylcarbamoyl" means a group wherein a hydrogen atom bonded to a nitrogen atom of a carbamoyl group is replaced with the above "alkenyl". For example, it includes ethylenylcarbamoyl, propenylcarbamoyl and the like. Another hydrogen atom bonded to the nitrogen atom of the carbamoyl group may be replaced with the above "alkyl".

"Alkynylcarbamoyl" means a group wherein a hydrogen atom bonded to a nitrogen atom of a carbamoyl group is replaced with the above "alkynyl". For example, it includes ethynylcarbamoyl, propynylcarbamoyl and the like. Another hydrogen atom bonded to the nitrogen atom of the carbamoyl group may be replaced with the above "alkyl".

"Alkylsulfamoyl" means a group wherein a hydrogen atom bonded to a nitrogen atom of a sulfamoyl group is replaced with the above "alkyl". For example, it includes methylsulfamoyl, dimethylsulfamoyl and the like. Another hydrogen atom bonded to the nitrogen atom of the sulfamoyl group may be replaced with the above "alkyl".

"Alkenylsulfamoyl" means a group wherein a hydrogen atom bonded to a nitrogen atom of a sulfamoyl group is replaced with the above "alkenyl". For example, it includes ethylenylsulfamoyl, propenylsulfamoyl and the like. Another hydrogen atom bonded to the nitrogen atom of the carbamoyl group may be replaced with the above "alkyl".

"Alkynylsulfamoyl" means a group wherein a hydrogen atom bonded to a nitrogen atom of a sulfamoyl group is replaced with the above "alkynyl". For example, it includes ethynylsulfamoyl, propynylsulfamoyl and the like. Another hydrogen atom bonded to the nitrogen atom of the carbamoyl group may be replaced with the above "alkyl".

"Alkylcarbonylamino" means a group wherein a hydrogen atom bonded to a nitrogen atom of an amino group is replaced with the above "alkylcarbonyl". For example, it includes methylcarbonylamino, ethylcarbonylamino, propylcarbonylamino, isopropylcarbonylamino, tert-butylcarbonylamino, isobutylcarbonylamino, sec-butylcarbonylamino and the like. Another hydrogen atom bonded to the nitrogen atom of the amino group may be replaced with the above "alkyl".

A preferred embodiment of "alkylcarbonylamino" is methylcarbonylamino or ethylcarbonylamino.

"Alkenylcarbonylamino" means a group wherein a hydrogen atom bonded to a nitrogen atom of an amino group is replaced with the above "alkenylcarbonyl". For example, it includes ethylenylcarbonylamino, propenylcarbonylamino and the like. Another hydrogen atom bonded to the nitrogen atom of the amino group may be replaced with the above "alkyl".

"Alkynylcarbonylamino" means a group wherein a hydrogen atom bonded to a nitrogen atom of an amino group is replaced with the above "alkynylcarbonyl". For example, it includes ethynylcarbonylamino, propynylcarbonylamino and the like. Another hydrogen atom bonded to the nitrogen atom of the amino group may be replaced with the above "alkyl".

"Alkylsulfonylamino" means a group wherein a hydrogen atom bonded to a nitrogen atom of an amino group is replaced with the above "alkylsulfonyl". For example, it includes methylsulfonylamino, ethylsulfonylamino, propylsulfonylamino, isopropylsulfonylamino, tert-butylsulfonylamino, isobutylsulfonylamino, sec butylsulfonylamino and the like. Another hydrogen atom bonded to the nitrogen atom of the amino group may be replaced with the above "alkyl".

A preferred embodiment of "alkylsulfonylamino" is methylsulfonylamino or ethylsulfonylamino.

"Alkenylsulfonylamino" means a group wherein a hydrogen atom bonded to a nitrogen atom of an amino group is replaced with the above "alkenylsulfonyl". For example, it includes ethylenylsulfonylamino, propenylsulfonylamino and the like. Another hydrogen atom bonded to the nitrogen atom of the amino group may be replaced with the above "alkyl".

"Alkynylsulfonylamino" means a group wherein a hydrogen atom bonded to a nitrogen atom of an amino group is replaced with the above "alkynylsulfonyl". For example, it includes ethynylsulfonylamino, propynylsulfonylamino and the like. Another hydrogen atom bonded to the nitrogen atom of the amino group may be replaced with the above "alkyl".

"Alkyloxycarbonylamino" means a group wherein a hydrogen atom bonded to a nitrogen atom of an amino group is replaced with the above "alkyloxycarbonyl". For example, it includes methyloxycarbonylamino, ethyloxycarbonylamino, propyloxycarbonylamino, isopropyloxycarbonylamino, tert-butyloxyearbonylamino, isobutyloxycarbonylamino, sec-butyloxyearbonylamino, pentyloxycarbonylamino, isopentyloxycarbonylamino, hexyloxycarbonylamino and the like. Another hydrogen atom bonded to the nitrogen atom of the amino group may be replaced with the above "alkyl".

A preferred embodiment of "alkyloxycarbonyl" is methyloxycarbonylamino, ethyloxycarbonylamino, propyloxycarbonylamino and the like.

"Alkenyloxycarbonylamino" means a group wherein a hydrogen atom bonded to a nitrogen atom of an amino group is replaced with the above "alkenyloxycarbonyl". For example, it includes ethylenyloxycarbonylamino, propenyloxycarbonylamino and the like. Another hydrogen atom bonded to the nitrogen atom of the amino group may be replaced with the above "alkyl".

"Alkynyloxycarbonylamino" means a group wherein a hydrogen atom bonded to a nitrogen atom of an amino group is replaced with the above "alkynyloxycarbonyl". For example, it includes ethynyloxycarbonylamino, propynyloxycarbonylamino and the like. Another hydrogen atom bonded to the nitrogen atom of the amino group may be replaced with the above "alkyl".

"Alkylimino" means a group wherein a hydrogen atom bonded to a nitrogen atom of an imino group is replaced with the above "alkyl". For example, it includes methylimino, ethylimino, n-propylimino, isopropylimino and the like.

"Alkyloxyimino" means a group wherein a hydrogen atom bonded to a nitrogen atom of an imino group is replaced with the above "alkyloxy". For example, it includes methyloxyimino, ethyloxyimino, n-propyloxyimino, isopropyloxyimino and the like.

The "aromatic carbocycle" part of "aromatic carbocyclyloxy", "aromatic carbocyclylamino", "aromatic carbocyclylsulfanyl", "aromatic carbocyclylcarbonyl", "aromatic carbocyclylsulfonyl", "aromatic carbocyclylcarbonyloxy", "aromatic carbocyclylsulfonyloxy", "aromatic carbocyclyloxycarbonyl", "aromatic carbocyclyloxysulfonyl", "aromatic carbocyclylcarbamoyl", "aromatic carbocyclylsulfamoyl", "aromatic carbocyclylcarbonylamino", "aromatic carbocyclylsulfonylamino", and "aromatic carbocyclyloxycarbonylamino" is the same as the above "aromatic carbocyclyl".

"Aromatic carbocyclyloxy" means a group wherein "aromatic carbocycle" is bonded to an oxygen atom. For example, it includes phenyloxy, naphthyloxy and the like.

"Aromatic carbocyclylamino" means a group wherein a hydrogen atom attached to a nitrogen atom of an amino group is replaced with the "aromatic carbocycle". For example, it includes phenylamino, naphthylamino and the like. Another hydrogen atom bonded to the nitrogen atom of the amino group may be replaced with the above "alkyl".

"Aromatic carbocyclylsulfanyl" means a group wherein a hydrogen atom bonded to a sulfur atom of a sulfanyl group is replaced with "aromatic carbocycle". For example, it includes phenylsulfanyl, naphthylsulfanyl and the like.

"Aromatic carbocyclylcarbonyl" means a group wherein "aromatic carbocycle" is bonded to a carbonyl group. For example, it includes phenylcarbonyl, naphthylcarbonyl and the like.

"Aromatic carbocyclylsulfonyl" means a group wherein "aromatic carbocycle" is bonded to a sulfonyl group. For example, it includes phenylsulfonyl, naphthylsulfonyl and the like.

"Aromatic carbocyclylcarbonyloxy" means a group wherein the above "aromatic carbocyclylcarbonyl" is bonded to an oxygen atom. For example, it includes phenylcarbonyloxy, naphthylcarbonyloxy and the like.

"Aromatic carbocyclylsulfonyloxy" moans a group wherein the above "aromatic carbocyclylsulfonyl" is bonded to an oxygen atom. For example, it includes phenylsulfonyloxy, naphthylsulfonyloxy and the like.

"Aromatic carbocyclyloxycarbonyl" means a group wherein the above "aromatic carbocyclyloxy" is bonded to a carbonyl group. For example, it includes phenyloxycarbonyl, naphthyloxycarbonyl and the like.

"Aromatic carbocyclyloxysulfonyl" means a group wherein the above "aromatic carbocyclyloxy" is bonded to a sulfonyl group. For example, it includes phenyloxysulfonyl, naphthyloxysulfonyl and the like.

"Aromatic carbocyclylcarbamoyl" means a group wherein a hydrogen atom bonded to a nitrogen atom of a carbamoyl group is replaced with the "aromatic carbocycle". For example, it includes phenylcarbamoyl, naphthylcarbamoyl and the like. Another hydrogen atom bonded to the nitrogen atom of the carbamoyl group may be replaced with the above "alkyl".

"Aromatic carbocyclylsulfamoyl" means a group wherein a hydrogen atom bonded to a nitrogen atom of a sulfamoyl group is replaced with the "aromatic carbocycle". For example, it includes phenylsulfamoyl, naphthylsulfamoyl and the like. Another hydrogen atom bonded to the nitrogen atom of the sulfamoyl group may be replaced with the above "alkyl".

"Aromatic carbocyclylcarbonylamino" means a group wherein a hydrogen atom attached to a nitrogen atom of an amino group is replaced with the above "aromatic carbocyclylcarbonyl". For example, it includes phenylcarbonylamino, naphthylcarbonylamino and the like. Another hydrogen atom bonded to the nitrogen atom of the amino group may be replaced with the above "alkyl".

"Aromatic carbocyclylsulfonylamino" means a group wherein a hydrogen atom bonded to a nitrogen atom of an amino group is replaced with the above "aromatic carbocyclylsulfonyl". For example, it includes phenylsulfonylamino, naphthylsulfonylamino and the like. Another hydrogen atom bonded to the nitrogen atom of the amino group may be replaced with the above "alkyl".

"Aromatic carbocyclyloxycarbonylamino" means a group wherein a hydrogen atom attached to a nitrogen atom of an amino group is replaced with the above "aromatic carbocyclyloxycarbonyl". For example, it includes phenyloxycarbonylamino, naphthyloxycarbonylamino and the like. Another hydrogen atom bonded to the nitrogen atom of the amino group may be replaced with the above "alkyl".

The "non-aromatic carbocycle" part of "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocyclyloxysulfonyl", "non-aromatic carbocyclylcarbamoyl", "non-aromatic carbocyclylsulfamoyl", "non-aromatic carbocyclylcarbonylamino", "non-aromatic carbocyclylsulfonylamino", and "non-aromatic carbocyclyloxycarbonylamino" is the same as the above "non-aromatic carbocyclyl".

"Non-aromatic carbocyclyloxy" means a group wherein "non-aromatic carbocycle" is bonded to an oxygen atom. For example, it includes cyclopropyloxy, cyclohexyloxy, cyclohexenyloxy and the like.

"Non-aromatic carbocyclylamino" means a group wherein a hydrogen atom attached to a nitrogen atom of an amino group is replaced with the "non-aromatic carbocycle". For example, it includes cyclopropylamino, cyclohexylamino, cyclohexenylamino and the like. Another hydrogen atom bonded to the nitrogen atom of the amino group may be replaced with the above "alkyl".

"Non-aromatic carbocyclylsulfanyl" means a group wherein a hydrogen atom bonded to a sulfur atom of a sulfanyl group is replaced with "non-aromatic carbocycle". For example, it includes cyclopropylsulfanyl, cyclohexylsulfanyl, cyclohexenylsulfanyl and the like.

"Non-aromatic carbocyclylcarbonyl" means a group wherein "non-aromatic carbocycle" is bonded to a carbonyl group. For example, it includes cyclopropylcarbonyl, cyclohexylcarbonyl, cyclohexenylcarbonyl and the like.

"Non-aromatic carbocyclylsulfonyl" means a group wherein "non-aromatic carbocycle" is bonded to a sulfonyl group. For example, it includes cyclopropylsulfonyl, cyclohexylsulfonyl, cyclohexenylsulfonyl and the like.

"Non-aromatic carbocyclylcarbonyloxy" means a group wherein the above "non-aromatic carbocyclylcarbonyl" is bonded to an oxygen atom. For example, it includes cyclopropylcarbonyloxy, cyclohexylcarbonyloxy, cyclohexenylcarbonyloxy and the like.

"Non-aromatic carbocyclylsulfonyloxy" means a group wherein the above "non-aromatic carbocyclylsulfonyl" is bonded to an oxygen atom. For example, it includes cyclopropylsulfonyloxy, cyclohexylsulfonyloxy, cyclohexenylsulfonyloxy and the like.

"Non-aromatic carbocyclyloxycarbonyl" means a group wherein the above "non-aromatic carbocyclyloxy" is bonded to a carbonyl group. For example, it includes cyclopropyloxycarbonyl, cyclohexyloxycarbonyl, cyclohexenyloxycarbonyl and the like.

"Non-aromatic carbocyclyloxysulfonyl" means a group wherein the above "non-aromatic carbocyclyloxy" is bonded to a sulfonyl group. For example, it includes cyclopropyloxysulfonyl, cyclohexyloxysulfonyl, cyclohexenyloxysulfonyl and the like.

"Non-aromatic carbocyclylcarbamoyl" means a group wherein a hydrogen atom bonded to a nitrogen atom of a carbamoyl group is replaced with the "non-aromatic carbocycle". For example, it includes cyclopropylcarbamoyl, cyclohexylcarbamoyl, cyclohexenylcarbamoyl and the like. Another hydrogen atom bonded to the nitrogen atom of the carbamoyl group may be replaced with the above "alkyl".

"Non-aromatic carbocyclylsulfamoyl" means a group wherein a hydrogen atom bonded to a nitrogen atom of a sulfamoyl group is replaced with the "non-aromatic carbocycle". For example, it includes cyclopropylsulfamoyl, cyclohexylsulfamoyl, cyclohexenylsulfamoyl and the like. Another hydrogen atom bonded to the nitrogen atom of the sulfamoyl group may be replaced with the above "alkyl".

"Non-aromatic carbocyclylcarbonylamino" means a group wherein a hydrogen atom attached to a nitrogen atom of an amino group is replaced with the above "non-aromatic carbocyclylcarbonyl". For example, it includes cyclopropylcarbonylamino, cyclohexylcarbonylamino, cyclohexenylcarbonylamino and the like. Another hydrogen atom bonded to the nitrogen atom of the amino group may be replaced with the above "alkyl".

"Non-aromatic carbocyclylsulfonylamino" means a group wherein a hydrogen atom bonded to a nitrogen atom of an amino group is replaced with the above "non-aromatic carbocyclylsulfonyl". For example, it includes cyclopropylsulfonylamino, cyclohexylsulfonylamino, cyclohexenylsulfonylamino and the like. Another hydrogen atom bonded to the nitrogen atom of the amino group may be replaced with the above "alkyl".

"Non-aromatic carbocyclyloxycarbonylamino" means a group wherein a hydrogen atom attached to a nitrogen atom of an amino group is replaced with the above "non-aromatic carbocyclyloxycarbonyl". For example, it includes cyclopropyloxycarbonyl amino, cyclobexyloxycarbonyl amino, cyclohexenyloxycarbonylamino and the like. Another hydrogen atom bonded to the nitrogen atom of the amino group may be replaced with the above "alkyl".

The "aromatic heterocycle" part of "aromatic heterocyclyloxy", "aromatic heterocyclylamino", "aromatic heterocyclylsulfanyl", "aromatic heterocyclylcarbonyl", "aromatic heterocyclylsulfonyl", "aromatic heterocyclylcarbonyloxy", "aromatic heterocyclylsulfonyloxy", "aromatic heterocyclyloxycarbonyl", "aromatic heterocyclyloxysulfonyl", "aromatic heterocyclylcarbamoyl", "aromatic heterocyclylsulfamoyl", "aromatic heterocyclylcarbonylamino", "aromatic heterocyclylsulfonylamino", and "aromatic heterocyclyloxycarbonylamino" is the same as the above "aromatic heterocyclyl".

"Aromatic heterocyclyloxy" means a group wherein "aromatic heterocycle" is bonded to an oxygen atom. For example, it includes pyridyloxy, oxazolyloxy and the like.

"Aromatic heterocyclylamino" means a group wherein a hydrogen atom attached to a nitrogen atom of an amino group is replaced with the "aromatic heterocycle". For example, it includes pyridylamino, oxazolylamino and the like. Another hydrogen atom bonded to the nitrogen atom of the amino group may be replaced with the above "alkyl".

"Aromatic heterocyclylsulfanyl" means a group wherein a hydrogen atom bonded to a sulfur atom of a sulfanyl group is replaced with "aromatic heterocycle". For example, it includes pyridylsulfanyl, oxazolylsulfanyl and the like.

"Aromatic heterocyclylcarbonyl" means a group wherein "aromatic heterocycle" is bonded to a carbonyl group. For example, it includes pyridylcarbonyl, oxazolylcarbonyl and the like.

"Aromatic heterocyclylsulfonyl" means a group wherein "aromatic heterocycle" is bonded to a sulfonyl group. For example, it includes pyridylsulfonyl, oxazolylsulfonyl and the like.

"Aromatic heterocyclylcarbonyloxy" means a group wherein the above "aromatic heterocyclylcarbonyl" is bonded to an oxygen atom. For example, it includes pyridylcarbonyloxy, oxazolylcarbonyloxy and the like.

"Aromatic heterocyclylsulfonyloxy" means a group wherein the above "aromatic heterocyclylsulfonyl" is bonded to an oxygen atom. For example, it includes pyridylsulfonyloxy, oxazolylsulfonyloxy and the like.

"Aromatic heterocyclyloxycarbonyl" means a group wherein the above "aromatic heterocyclyloxy" is bonded to a carbonyl group. For example, it includes pyridyloxycarbonyl, oxazolyloxycarbonyl and the like.

"Aromatic heterocyclyloxysulfonyl" means a group wherein the above "aromatic heterocyclyloxy" is bonded to a sulfonyl group. For example, it includes pyridyloxysulfonyl, oxazolyloxysulfonyl and the like.

"Aromatic heterocyclylcarbamoyl" means a group wherein a hydrogen atom bonded to a nitrogen atom of a carbamoyl group is replaced with the "aromatic heterocycle". For example, it includes pyridylcarbamoyl, oxazolylcarbamoyl and the like. Another hydrogen atom bonded to the nitrogen atom of the carbamoyl group may be replaced with the above "alkyl".

"Aromatic heterocyclylsulfamoyl" means a group wherein a hydrogen atom bonded to a nitrogen atom of a sulfamoyl group is replaced with the "aromatic heterocycle". For example, it includes pyridylsulfamoyl, oxazolylsulfamoyl and the like. Another hydrogen atom bonded to the nitrogen atom of the sulfamoyl group may be replaced with the above "alkyl".

"Aromatic heterocyclylcarbonylamino" means a group wherein a hydrogen atom attached to a nitrogen atom of an amino group is replaced with the above "aromatic heterocyclylcarbonyl". For example, it includes pyridylcarbonylamino, oxazolylcarbonylamino and the like. Another hydrogen atom bonded to the nitrogen atom of the amino group may be replaced with the above "alkyl".

"Aromatic heterocyclylsulfonyl amino" means a group wherein a hydrogen atom bonded to a nitrogen atom of an amino group is replaced with the above "aromatic heterocyclylsulfonyl". For example, it includes pyridylsulfonylamino, oxazolylsulfonylamino and the like. Another hydrogen atom bonded to the nitrogen atom of the amino group may be replaced with the above "alkyl".

"Aromatic heterocyclyloxycarbonylamino" means a group wherein a hydrogen atom attached to a nitrogen atom of an amino group is replaced with the above "aromatic heterocyclyloxycarbonyl". For example, it includes pyridyloxycarbonylamino, oxazolyloxycarbonylamino and the like. Another hydrogen atom bonded to the nitrogen atom of the amino group may be replaced with the above "alkyl".

The "non-aromatic heterocycle" part of "non-aromatic heterocyclyloxy", "non-aromatic heterocyclylamino", "non-aromatic heterocyclylsulfanyl", "non-aromatic heterocyclylcarbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non-aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" is the same as the above "non-aromatic heterocyclyl".

"Non-aromatic heterocyclyloxy" means a group wherein "non-aromatic heterocycle" is bonded to an oxygen atom. For example, it includes piperidinyloxy, tetrahydrofuryloxy and the like.

"Non-aromatic heterocyclylamino" means a group wherein a hydrogen atom attached to a nitrogen atom of an amino group is replaced with the "non-aromatic heterocycle". For example, it includes piperidinylamino, tetrahydrofurylamino and the like. Another hydrogen atom bonded to the nitrogen atom of the amino group may be replaced with the above "alkyl".

"Non-aromatic heterocyclylsulfanyl" means a group wherein a hydrogen atom bonded to a sulfur atom of a sulfanyl group is replaced with "non-aromatic heterocycle". For example, it includes piperidinylsulfanyl, tetrahydrofurylsulfanyl and the like.

"Non-aromatic heterocyclylcarbonyl" means a group wherein "non-aromatic heterocycle" is bonded to a carbonyl group. For example, it includes piperidinylcarbonyl, tetrahydrofurylcarbonyl and the like.

"Non-aromatic heterocyclylsulfonyl" means a group wherein "non-aromatic heterocycle" is bonded to a sulfonyl group. For example, it includes piperidinylsulfonyl, tetrahydrofurylsulfonyl and the like.

"Non-aromatic heterocyclylcarbonyloxy" means a group wherein the above "non-aromatic heterocyclylcarbonyl" is bonded to an oxygen atom. For example, it includes piperidinylcarbonyloxy, tetrahydrofurylcarbonyloxy and the like.

"Non-aromatic heterocyclylsulfonyloxy" means a group wherein the above "non-aromatic heterocyclylsulfonyl" is bonded to an oxygen atom. For example, it includes piperidinylsulfonyloxy, tetrahydrofurylsulfonyloxy and the like.

"Non-aromatic heterocyclyloxycarbonyl" means a group wherein the above "non-aromatic heterocyclyloxy" is bonded to a carbonyl group. For example, it includes piperidinyloxycarbonyl, tetrahydrofuryloxycarbonyl and the like.

"Non-aromatic heterocyclyloxysulfonyl" means a group wherein the above "non-aromatic heterocyclyloxy" is bonded to a sulfonyl group. For example, it includes piperidinyloxysulfonyl, tetrahydrofuryloxysulfonyl and the like.

"Non-aromatic heterocyclylcarbamoyl" means a group wherein a hydrogen atom bonded to a nitrogen atom of a carbamoyl group is replaced with the "non-aromatic heterocycle". For example, it includes piperidinylcarbamoyl, tetrahydrofurylcarbamoyl and the like. Another hydrogen atom bonded to the nitrogen atom of the carbamoyl group may be replaced with the above "alkyl".

"Non-aromatic heterocyclylsulfamoyl" means a group wherein a hydrogen atom bonded to a nitrogen atom of a sulfamoyl group is replaced with the "non-aromatic heterocycle". For example, it includes piperidinylsulfamoyl, tetrahydrofurylsulfamoyl and the like. Another hydrogen atom bonded to the nitrogen atom of the sulfamoyl group may be replaced with the above "alkyl".

"Non-aromatic heterocyclylcarbonylamino" means a group wherein a hydrogen atom attached to a nitrogen atom of an amino group is replaced with the above "non-aromatic heterocyclylcarbonyl". For example, it includes piperidinylcarbonylamino, tetrahydrofurylcarbonylamino and the like. Another hydrogen atom bonded to the nitrogen atom of the amino group may be replaced with the above "alkyl".

"Non-aromatic heterocyclylsulfonylamino" means a group wherein a hydrogen atom bonded to a nitrogen atom of an amino group is replaced with the above "non-aromatic heterocyclylsulfonyl". For example, it includes piperidinylsulfonylamino, tetrahydrofurylsulfonylamino and the like. Another hydrogen atom bonded to the nitrogen atom of the amino group may be replaced with the above "alkyl".

"Non-aromatic heterocyclyloxycarbonylamino" means a group wherein a hydrogen atom attached to a nitrogen atom of an amino group is replaced with the above "non-aromatic heterocyclyloxycarbonyl". For example, it includes piperidinyloxycarbonylamino, tetrahydrofuryloxycarbonylamino and the like. Another hydrogen atom bonded to the nitrogen atom of the amino group may be replaced with the above "alkyl".

"Haloalkyl" means a group wherein one or more "halogen" described above is bonded to the above "alkyl". For example, it includes monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl, 1,1,1-trifluoropropan-2-yl and the like.

A preferred embodiment of "haloalkyl" is trifluoromethyl or trichloromethyl.

"Haloalkyloxy" means a group wherein the above "haloalkyl" is bonded to an oxygen atom. For example, it includes monofluoromethoxy, monofluoroethoxy, trifluoromethoxy, trichloromethoxy, trilluoroethoxy, trichloroethoxy and the like.

A preferred embodiment of "haloalkyloxy" is trifluoromethoxy or trichloromethoxy.

"Haloalkylamino" means a group wherein a hydrogen atom bonded to a nitrogen atom of an amino group is replaced with the above "haloalkyl". For example, it includes monofluoromethylamino, monofluoroethylamino, trifluoromethyl amino, trichloromethyl amino, trifluoroethylamino, trichloroethylamino and the like. Another hydrogen atom bonded to the nitrogen atom of the amino group may be replaced with the above "alkyl" or the above "haloalkyl".

A preferred embodiment of "haloalkylamino" is trifluoromethylamino or trichloromethyl amino.

"Haloalkylsulfanyl" means a group wherein the above "haloalkyl" is bonded to a sulfanyl group. For example, it includes monofluoromethylsulfanyl, monofluoroethylsulfanyl, trifluoromethylsulfanyl, trichloromethylsulfanyl, trifluoroethylsulfanyl, trichloroethylsulfanyl and the like.

A preferred embodiment of "haloalkylsulfanyl" is trifluoromethylsulfanyl or trichloromethylsulfanyl.

"Haloalkylcarbonyl" means a group wherein the above "haloalkyl" is bonded to a carbonyl group. For example, it includes monofluorometliylcarbonyl, monofluoroethylcarbonyl, trifluoromethylcarbonyl, trichloromethylcarbonyl, trifluoroethylcarbonyl, trichloroethylcarbonyl and the like.

A preferred embodiment of "haloalkylcarbonyl" is trifluoromethylcarbonyl or trichloromethylcarbonyl.

"Haloalkylsulfonyl" means a group wherein the above "haloalkyl" is bonded to a sulfonyl group. For example, it includes monofluoromethylsulfonyl, monofluoroethylsulfonyl, trifluoromethylsulfonyl, trichloromethylsulfonyl, trifluoroethylsulfonyl, trichloroethylsulfonyl and the like.

A preferred embodiment of "haloalkylsulfonyl" is trifluoromethylsulfonyl or trichloromethylsulfonyl.

"Haloalkylcarbamoyl" means a group wherein a hydrogen atom bonded to a nitrogen atom of a carbamoyl group is replaced with the above "haloalkyl". For example, it includes monofluoromethylcarbamoyl, monofluoroethylcarbamoyl, trifluoromethylcarbamoyl, trichloromethylcarbamoyl, trifluoroethylcarbamoyl, trichloroethylcarbamoyl and the like. Another hydrogen atom bonded to the nitrogen atom of the carbamoyl group may be replaced with the above "alkyl" or the above "haloalkyl".

A preferred embodiment of "haloalkylcarbamoyl" is trifluoromethylcarbamoyl or trichloromethylcarbamoyl.

"Haloalkylsulfamoyl" means a group wherein a hydrogen atom bonded to a nitrogen atom of a sulfamoyl group is replaced with the above "haloalkyl". For example, it includes monofluoromethylsulfamoyl, monofluoroethylsulfamoyl, trifluoromethylsulfamoyl, trichloromethylsulfamoyl, trifluoroethylsulfamoyl, trichloroethylsulfamoyl and the like. Another hydrogen atom bonded to the nitrogen atom of the sulfamoyl group may be replaced with the above "alkyl" or the above "haloalkyl".

A preferred embodiment of "haloalkylsulfamoyl" is trifluoromethylsulfamoyl or trichloromethylsulfamoyl.

"Haloalkylcarbonylamino" means a group wherein a hydrogen atom bonded to a nitrogen atom of an amino group is replaced with the above "haloalkylcarbonyl". For example, it includes monofluoromethylcarbonylamino, monofluoroethylcarbonyl amino, trifluoromethylcarbonyl amino, trichloromethylcarbonylamino, trifluoroethylcarbonylamino, trichloroethylcarbonyl amino and the like. Another hydrogen atom bonded to the nitrogen atom of the amino group may be replaced with the above "alkyl" or the above "haloalkyl".

A preferred embodiment of "haloalkylcarbonylamino" is trifluoromethylcarbonylamino or trichloromethylcarbonylamino.

"Haloalkylsulfonylamino" means a group wherein a hydrogen atom bonded to a nitrogen atom of an amino group is replaced with the above "haloalkylsulfonyl". For example, it includes monofluoromethylsulfonylamino, monofluoroethylsulfonylamino, trifluoromethylsulfonylamino, trichloromethylsulfonylamino, trifluoroethylsulfonylamino, trichloroethylsulfonylamino and the like. Another hydrogen atom bonded to the nitrogen atom of the amino group may be replaced with the above "alkyl" or the above "haloalkyl".

A preferred embodiment of "haloalkylsulfonylamino" is trifluoromethylsulfonylamino or trichloromethylsulfonylamino.

"Haloalkylcarbonyloxy" means a group wherein the above "haloalkylcarbonyl" is bonded to an oxygen atom. For example, it includes monofluoromethylcarbonyloxy, monofluoroethylcarbonyloxy, trifluoromethylcarbonyloxy, trichloromethylcarbonyloxy, trifluoroethylcarbonyloxy, trichloroethylcarbonyloxy and the like.

A preferred embodiment of "haloalkylcarbonyloxy" is trifluoromethylcarbonyloxy or trichloromethylcarbonyloxy.

"Haloalkylsulfonyloxy" means a group wherein the above "haloalkylsulfonyl" is bonded to an oxygen atom. For example, it includes monofluoromethylsulfonyloxy, monofluoroethylsulfonyloxy, trifluoromethylsulfonyloxy, trichloromethylsulfonyloxy, trifluoroethylsulfonyloxy, trichloroethylsulfonyloxy and the like.

A preferred embodiment of "haloalkylsulfonyloxy" is trifluoromethylsulfonyloxy or trichloromethylsulfonyloxy.

"Haloalkyloxycarbonyl" means a group wherein the above "haloalkyloxy" is bonded to a carbonyl group. For example, it includes monofluoromethyloxycarbonyl, monofluoroethyloxycarbonyl, trifluoromethyloxycarbonyl, trichloromethyloxycarbonyl, trifluoroethyloxycarbonyl, trichloroethyloxycarbonyl and the like.

A preferred embodiment of "haloalkyloxycarbonyl" is trifluoromethyloxycarbonyl or trichloromethyloxycarbonyl.

"Haloalkyloxysulfonyl" means a group wherein the above "haloalkyloxy" is bonded to a sulfonyl group. For example, it includes monofluoromethyloxysulfonyl, monofluoroethyloxysulfonyl, trifluoromethyloxysulfonyl, trichloromethyloxysulfonyl, trifluoroethyloxysulfonyl, trichloroethyloxysulfonyl and the like.

A preferred embodiment of "haloalkyloxysulfonyl" is trifluoromethyloxysulfonyl or trichloromethyloxysulfonyl.

The substituents of "substituted or unsubstituted alkyl" include the substituent group A. A carbon atom at any position(s) may be bonded to one or more group(s) selected from the substituent group A.

The substituent group A: halogen, hydroxy, carboxy, amino, carbamoyl, sulfamoyl, sulfo, cyano, formyl, imino, hydroxyimino, cyanoimino, alkyloxy optionally substituted with one or more group(s) selected from the substituent group C2, alkylamino optionally substituted with one or more group(s) selected from the substituent group C2, alkylsulfanyl optionally substituted with one or more group (s) selected from the substituent group C2, alkylimino optionally substituted with one or more group(s) selected from the substituent group C2, alkyloxyimino optionally substituted with one or more group(s) selected from the substituent group C2, alkylcarbonyl optionally substituted with one or more group(s) selected from the substituent group C2, alkylsulfonyl optionally substituted with one or more group(s) selected from the substituent group C2, alkylcarbonylamino optionally substituted with one or more group(s) selected from the substituent group C2, alkylsulfonylamino optionally substituted with one or more group(s) selected from the substituent group C2, alkylcarbamoyl optionally substituted with one or more group(s) selected from the substituent group C2, alkylsulfamoyl optionally substituted with one or more group(s) selected from the substituent group C2, alkylcarbonyloxy optionally substituted with one or more group(s) selected from the substituent, group C2, alkyloxycarbonyl optionally substituted with one or more group(s) selected from the substituent group C2, alkylsulfonyloxy optionally substituted with one or more group(s) selected from the substituent group C2, alkyloxysulfonyl optionally substituted with one or more group(s) selected from the substituent group C2, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group(s) selected from the substituent group E, non-aromatic heterocyclyl optionally substituted with one or more group(s) selected from the substituent group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group(s) selected from the substituent group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E, aromatic carbocyclylcarbonyl optionally substituted with one or more group (s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclylsulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group (s) selected from the substituent group E, non-aromatic heterocyclylsulfonyl optionally substituted with one or more group(s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent, group E, non-aromatic heterocyclylsulfonylamino optionally substituted with one or more group(s) selected from the substituent group E, aromatic carbocyclylcarbamoyl optionally substituted with one or more group(s) selected from the substituent group E, non-aromatic carbocyclylcarbamoyl optionally substituted with one or more group(s) selected from the substituent group E, aromatic heterocyclylcarbamoyl optionally substituted with one or more group(s) selected from the substituent group E, non-aromatic heterocyclylcarbamoyl optionally substituted with one or more group(s) selected from the substituent group E, aromatic carbocyclylsulfamoyl optionally substituted with one or more group(s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent group E, non-aromatic heterocyclylsulfamoyl optionally substituted with one or more group(s) selected from the substituent group E, aromatic carbocyclyloxycarbonyl optionally substituted with one or more group(s) selected from the substituent group E, non-aromatic carbocyclyloxycarbonyl optionally substituted with one or more group(s) selected from the substituent group E, aromatic heterocyclyloxycarbonyl optionally substituted with one or more group(s) selected from the substituent group E, non-aromatic heterocyclyloxycarbonyl optionally substituted with one or more group(s) selected from the substituent group E, aromatic carbocyclyloxysulfonyl optionally substituted with one or more group(s) selected from the substituent group E, non-aromatic carbocyclyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent, group E, non-aromatic carbocyclylcarbonyloxy optionally substituted with one or more group(s) selected from the substituent group E, aromatic heterocyclylcarbonyloxy optionally substituted with one or more group(s) selected from the substituent group E, non-aromatic heterocyclylcarbonyloxy optionally substituted with one or more group(s) selected from the substituent group E, aromatic carbocyclylsulfonyloxy optionally substituted with one or more group(s) selected from the substituent group E, non-aromatic carbocyclylsulfonyloxy optionally substituted with one or more group(s) selected from the substituent group E, aromatic heterocyclylsulfonyloxy optionally substituted with one or more group(s) selected from the substituent group E, and non-aromatic heterocyclylsulfonyloxy optionally substituted with one or more group(s) selected from the substituent group E.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" include the substituent group B. A carbon atom at any position(s) may be bonded to one or more group(s) selected from the substituent group B.

The substituent group B: halogen, hydroxy, carboxy, amino, carbamoyl, sulfamoyl, sulfo, cyano, formyl, imino, hydroxyimino, cyanoimino, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylimino optionally substituted with one or more group(s) selected from the substituent group D, alkyloxyimino optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, alkyloxysulfonyl optionally substituted with one or more group(s) selected from the substituent group D, aromatic carbocyclyl optionally substituted with one or more group(s) selected from the substituent group B, non-aromatic carbocyclyl optionally substituted with one or more group(s) selected from the substituent group E, aromatic heterocyclyl optionally substituted with one or more group (s) selected from the substituent group E, non-aromatic heterocyclyl optionally substituted with one or more group(s) selected from the substituent group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group(s) selected from the substituent group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E, aromatic carbocyclylcarbonyl optionally substituted with one or more group (s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclylsulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group (s) selected from the substituent group E, non-aromatic heterocyclylsulfonyl optionally substituted with one or more group(s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent group E, non-aromatic carbocyclylcarbamoyl optionally substituted with one or more group(s) selected from the substituent group E, aromatic heterocyclylcarbamoyl optionally substituted with one or more group(s) selected from the substituent group E, non-aromatic heterocyclylcarbamoyl optionally substituted with one or more group(s) selected from the substituent group E, aromatic carbocyclylsulfamoyl optionally substituted with one or more group(s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent group E, non-aromatic heterocyclylsulfamoyl optionally substituted with one or more group(s) selected from the substituent group E, aromatic carbocyclyloxycarbonyl optionally substituted with one or more group(s) selected from the substituent group E, non-aromatic carbocyclyloxycarbonyl optionally substituted with one or more group(s) selected from the substituent group E, aromatic heterocyclyloxycarbonyl optionally substituted with one or more group(s) selected from the substituent group E, non-aromatic heterocyclyloxycarbonyl optionally substituted with one or more group(s) selected from the substituent group E, aromatic carbocyclyloxysulfonyl optionally substituted with one or more group(s) selected from the substituent group E, non-aromatic carbocyclyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent group E, non-aromatic carbocyclylcarbonyloxy optionally substituted with one or more group(s) selected from the substituent group E, aromatic heterocyclylcarbonyloxy optionally substituted with one or more group(s) selected from the substituent group E, non-aromatic heterocyclylcarbonyloxy optionally substituted with one or more group(s) selected from the substituent group E, aromatic carbocyclylsulfonyloxy optionally substituted with one or more group(s) selected from the substituent group E, non-aromatic carbocyclylsulfonyloxy optionally substituted with one or more group(s) selected from the substituent group E, aromatic heterocyclylsulfonyloxy optionally substituted with one or more group(s) selected from the substituent group E, and non-aromatic heterocyclylsulfonyloxy optionally substituted with one or more group(s) selected from the substituent group E.

The substituents on the rings of "aromatic carbocycle", "non-aromatic carbocycle", "aromatic heterocycle", and "non-aromatic heterocycle" of "substituted or unsubstituted 5-membered non-aromatic heterocycle" and "substituted or unsubstituted 6-membered non-aromatic heterocycle", "substituted or unsubstituted aromatic carbocycle", "substituted or unsubstituted non-aromatic carbocycle", "substituted or unsubstituted aromatic heterocycle", and "substituted or unsubstituted non-aromatic heterocycle", "substituted or unsubstituted 6-membered aromatic carbocycle", "substituted or unsubstituted 5- to 6-membered non-aromatic carbocycle", "substituted or unsubstituted 5- to 6-membered aromatic heterocycle", and "substituted or unsubstituted 5- to 6-membered non-aromatic heterocycle", "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted 6-membered aromatic carbocyclyl", "substituted or unsubstituted 3- to 6-membered non-aromatic carbocyclyl", "substituted or unsubstituted 5- to 6-membered aromatic heterocyclyl", and "substituted or unsubstituted 5- to 6-membered non-aromatic heterocyclyl", "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclyl amino", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" include the substituent group C1. An atom at any position(s) on the ring may be bonded to one or more group(s) selected from the substituent group C1.

The substituent group C1: halogen, hydroxy, carboxy, amino, carbamoyl, sulfamoyl, sulfo, cyano, alkyl optionally substituted with one or more group(s) selected from the substituent group D, alkenyl optionally substituted with one or more group(s) selected from the substituent group D, alkynyl optionally substituted with one or more group(s) selected from the substituent group D, alkyloxy optionally substituted with one or more group(s) selected from the substituent group D, alkenyloxy optionally substituted with one or more group(s) selected from the substituent group D, alkynyloxy optionally substituted with one or more group(s) selected from the substituent group D, alkylamino optionally substituted with one or more group(s) selected from the substituent group D, alkenylamino optionally substituted with one or more group(s) selected from the substituent group D, alkynylamino optionally substituted with one or more group(s) selected from the substituent group D, alkylsulfanyl optionally substituted with one or more group(s) selected from the substituent group D, alkenylsulfanyl optionally substituted with one or more group(s) selected from the substituent group D, alkynylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, alkyloxysulfonyl optionally substituted with one or more group(s) selected from the substituent group D, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group (s) selected from the substituent group E, non-aromatic heterocyclyl optionally substituted with one or more group(s) selected from the substituent group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group(s) selected from the substituent, group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E, aromatic carbocyclylcarbonyl optionally substituted with one or more group (s) selected from the substituent group E, non-aromatic carbocyclylcarbonyl optionally substituted with one or more group(s) selected from the substituent group E, aromatic heterocyclylcarbonyl optionally substituted with one or more group(s) selected from the substituent group E, non-aromatic heterocyclylcarbonyl optionally substituted with one or more group(s) selected from the substituent group E, aromatic carbocyclylsulfonyl optionally substituted with one or more group(s) selected from the substituent group E, non-aromatic carbocyclylsulfonyl optionally substituted with one or more group(s) selected from the substituent group E, aromatic heterocyclylsulfonyl optionally substituted with one or more group (s) selected from the substituent group E, non-aromatic heterocyclylsulfonyl optionally substituted with one or more group(s) selected from the substituent group E, aromatic carbocyclylcarbonylamino optionally substituted with one or more group(s) selected from the substituent group E, non-aromatic carbocyclylcarbonylamino optionally substituted with one or more group(s) selected from the substituent group E, aromatic heterocyclylcarbonylamino optionally substituted with one or more group(s) selected from the substituent group E, non-aromatic heterocyclylcarbonylamino optionally substituted with one or more group(s) selected from the substituent, group E, aromatic carbocyclylsulfonylamino optionally substituted with one or more group(s) selected from the substituent group E, non-aromatic carbocyclylsulfonylamino optionally substituted with one or more group(s) selected from the substituent group E, aromatic heterocyclylsulfonylamino optionally substituted with one or more group(s) selected from the substituent group E, non-aromatic heterocyclylsulfonylamino optionally substituted with one or more group(s) selected from the substituent group E, aromatic carbocyclylcarbamoyl optionally substituted with one or more group(s) selected from the substituent, group E, non-aromatic carbocyclylcarbamoyl optionally substituted with one or more group(s) selected from the substituent group E, aromatic heterocyclylcarbamoyl optionally substituted with one or more group(s) selected from the substituent group E, non-aromatic heterocyclylcarbamoyl optionally substituted with one or more group(s) selected from the substituent group E, aromatic carbocyclylsulfamoyl optionally substituted with one or more group(s) selected from the substituent group E, non-aromatic carbocyclylsulfamoyl optionally substituted with one or more group(s) selected from the substituent group E, aromatic heterocyclylsulfamoyl optionally substituted with one or more group(s) selected from the substituent group E, non-aromatic heterocyclylsulfamoyl optionally substituted with one or more group(s) selected from the substituent group E, aromatic carbocyclyloxycarbonyl optionally substituted with one or more group(s) selected from the substituent group E, non-aromatic carbocyclyloxycarbonyl optionally substituted with one or more group(s) selected from the substituent group E, aromatic heterocyclyloxycarbonyl optionally substituted with one or more group(s) selected from the substituent, group E, non-aromatic heterocyclyloxycarbonyl optionally substituted with one or more group(s) selected from the substituent group E, aromatic carbocyclyloxysulfonyl optionally substituted with one or more group(s) selected from the substituent group E, non-aromatic carbocyclyloxysulfonyl optionally substituted with one or more group(s) selected from the substituent group E, aromatic heterocyclyloxysulfonyl optionally substituted with one or more group(s) selected from the substituent group E, non-aromatic heterocyclyloxysulfonyl optionally substituted with one or more group(s) selected from the substituent group E, aromatic carbocyclylcarbonyloxy optionally substituted with one or more group(s) selected from the substituent group E, non-aromatic carbocyclylcarbonyloxy optionally substituted with one or more group(s) selected from the substituent group E, aromatic heterocyclylcarbonyloxy optionally substituted with one or more group(s) selected from the substituent group E, non-aromatic heterocyclylcarbonyloxy optionally substituted with one or more group(s) selected from the substituent group E, aromatic carbocyclylsulfonyloxy optionally substituted with one or more group(s) selected from the substituent group E, non-aromatic carbocyclylsulfonyloxy optionally substituted with one or more group(s) selected from the substituent group E, aromatic heterocyclylsulfonyloxy optionally substituted with one or more group(s) selected from the substituent group E, and non-aromatic heterocyclylsulfonyloxy optionally substituted with one or more group(s) selected from the substituent group E.

The substituent group C2: halogen, hydroxy, carboxy, amino, carbamoyl, sulfamoyl, sulfo, cyano, alkyloxy, haloalkyloxy, alkylamino, haloalkylamino, alkylsulfanyl, haloalkylsulfanyl, and
aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, and non-aromatic heterocyclyl optionally substituted with one or more group(s) selected from the substituent group F.

The substituent group D: halogen, hydroxy, carboxy, amino, carbamoyl, sulfamoyl, sulfo, cyano, alkyloxy, non-aromatic carbocyclyl, and alkylsulfonyl.

The substituent group E: halogen, hydroxy, carboxy, amino, carbamoyl, sulfamoyl, sulfo, and cyano, and
alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, alkylcarbonyloxy optionally substituted with one or more group(s) selected from the substituent group D, alkyloxycarbonyl optionally substituted with one or more group(s) selected from the substituent group D, alkylsulfonyloxy optionally substituted with one or more group(s) selected from the substituent group D, and alkyloxysulfonyl optionally substituted with one or more group(s) selected from the substituent group D.

The substituent group F: halogen, hydroxy, carboxy, amino, carbamoyl, sulfamoyl, sulfo, cyano, alkyl, haloalkyl, alkyloxy, haloalkyloxy, alkylamino, haloalkylamino, alkylsulfanyl, haloalkylsulfanyl, alkylcarbonyl, haloalkylcarbonyl, alkylsulfonyl, haloalkylsulfonyl, alkylcarbonylamino, haloalkylcarbonylamino, alkylsulfonylamino, haloalkylsulfonylamino, alkylcarbamoyl, haloalkylcarbamoyl, alkylsulfamoyl, and haloalkylsulfamoyl.

"Substituted or unsubstituted non-aromatic carbocyclyl" and "substituted or unsubstituted non-aromatic heterocyclyl" may be optionally substituted with one or more "oxo". In this case, it means a group wherein two hydrogen atoms on a carbon atom are replaced as below.

[Chemical Formula 15]

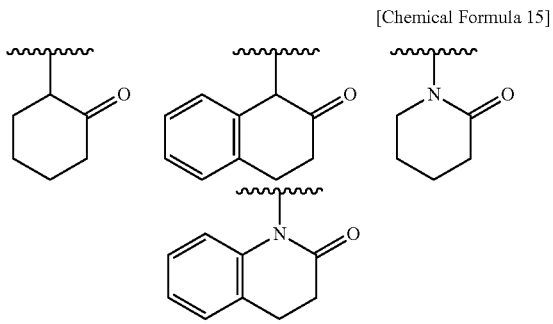

The non-aromatic carbocycle or non-aromatic heterocycle part of the above "non-aromatic carbocyclyloxy", "non-aromatic carbocyclylamino", "non-aromatic carbocyclylsulfanyl", "non-aromatic carbocyclylcarbonyl", "non-aromatic carbocyclylsulfonyl", "non-aromatic carbocyclylcarbonyloxy", "non-aromatic carbocyclylsulfonyloxy", "non-aromatic carbocyclyloxycarbonyl", "non-aromatic carbocyclyloxysulfonyl", "non-aromatic carbocyclylcarbamoyl", "non-aromatic carbocyclylsulfamoyl", "non-aromatic carbocyclylcarbonylamino", "non-aromatic carbocyclylsulfonylamino", "non-aromatic carbocyclyloxycarbonylamino", "non-aromatic heterocyclyloxy", "non-aromatic heterocyclylamino", "non-aromatic heterocyclylsulfanyl", "non-aromatic heterocyclylcarbonyl", "non-aromatic heterocyclylsulfonyl", "non-aromatic heterocyclylcarbonyloxy", "non-aromatic heterocyclylsulfonyloxy", "non-aromatic heterocyclyloxycarbonyl", "non-aromatic heterocyclyloxysulfonyl", "non-aromatic heterocyclylcarbamoyl", "non-aromatic heterocyclylsulfamoyl", "non-aromatic heterocyclylcarbonylamino", "non-aromatic heterocyclylsulfonylamino", and "non-aromatic heterocyclyloxycarbonylamino" may be optionally substituted with one or more "oxo" as above.

The substituents on the rings of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted 6-membered aromatic carbocyclyl", "substituted or unsubstituted 3- to 6-membered non-aromatic carbocyclyl", "substituted or unsubstituted 5- to 6-membered aromatic heterocyclyl", and "substituted or unsubstituted 5- to 6-membered non-aromatic heterocyclyl" in $R^1$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D or the like.

One embodiment is, for example, halogen, alkyl, haloalkyl or the like.

One embodiment is, for example, halogen, alkyl or the like.

One embodiment is, for example, halogen or the like.

The substituents of "substituted or unsubstituted alkyl", and "substituted or unsubstituted alkyloxy" in $R^{2a'}$, $R^{2b'}$, $R^{2b}$, $R^{2c}$, $R^{2d}$, $R^{8a}$ and $R^{8b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent, group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group (s) selected from the substituent group F, non-aromatic heterocyclyl optionally substituted with one or more group(s) selected from the substituent group F and the like.

One embodiment is, for example, halogen, hydroxy, cyano or the like.

One embodiment is, for example, halogen or the like.

The substituents of "substituted or unsubstituted alkyl", and "substituted or unsubstituted alkylcarbonyl" in $R^{7a}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, cyano or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", and "substituted or unsubstituted alkynylamino" in $R^4$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent, group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent, group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, cyano or the like.

One embodiment is, for example, halogen or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", and "substituted or unsubstituted alkynyloxy" in $R^6$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, cyano or the like.

One embodiment is, for example, halogen or the like.

The substituents on the rings of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl" in $R^6$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynyl amino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{5a}$, $R^{5a'}$ and $R^{5b}$ include halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group(s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclylamino optionally substituted with one or more group(s) selected from the substituent group F, non-aromatic carbocyclylamino optionally substituted with one or more group(s) selected from the substituent group F, aromatic heterocyclylamino optionally substituted with one or more group(s) selected from the substituent group F, and non-aromatic heterocyclylamino optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, hydroxy, cyano, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, hydroxy, cyano or the like.

One embodiment is, for example, halogen or the like.

One embodiment is, for example, hydroxy or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", "substituted or unsubstituted non-aromatic heterocyclyl amino", "substituted or unsubstituted aromatic carbocyclylsulfanyl", "substituted or unsubstituted non-aromatic carbocyclylsulfanyl", "substituted or unsubstituted aromatic heterocyclylsulfanyl", "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", "substituted or unsubstituted non-aromatic heterocyclylsulfamoyl", "substituted or unsubstituted aromatic carbocyclylcarbonyl amino", "substituted or unsubstituted non-aromatic carbocyclylcarbonylamino", "substituted or unsubstituted aromatic heterocyclylcarbonylamino", "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", "substituted or unsubstituted non-aromatic heterocyclylsulfonylamino", "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{5a}$, $R^{5a'}$, and $R^{5b}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

The substituents on the rings of "substituted or unsubstituted 5-membered non-aromatic heterocycle", "substituted or unsubstituted 5-membered aromatic heterocycle", and "substituted or unsubstituted 6-membered non-aromatic heterocycle" in Ring Q include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, alkyl or the like.

The substituents on the rings of "substituted or unsubstituted aromatic carbocyclyl", "substituted or unsubstituted aromatic heterocyclyl", "substituted or unsubstituted non-aromatic carbocyclyl", and "substituted or unsubstituted non-aromatic heterocyclyl" in $R^3$ include, for example, halogen, hydroxy, carboxy, amino, carbamoyl, sulfamoyl, sulfo, cyano, formyl, oxo, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group E, non-aromatic carbocyclyl optionally substituted with one or more group(s) selected from the substituent group E, aromatic heterocyclyl optionally substituted with one or more group(s) selected from the substituent group E, non-aromatic heterocyclyl optionally substituted with one or more group(s) selected from the substituent group E, aromatic carbocyclyloxy optionally substituted with one or more group(s) selected from the substituent group E, non-aromatic carbocyclyloxy optionally substituted with one or more group(s) selected from the substituent group E, aromatic heterocyclyloxy optionally substituted with one or more group(s) selected from the substituent group E, non-aromatic heterocyclyloxy optionally substituted with one or more group(s) selected from the substituent group E, aromatic carbocyclylsulfanyl optionally substituted with one or more group(s) selected from the substituent group E, non-aromatic carbocyclylsulfanyl optionally substituted with one or more group(s) selected from the substituent group E, aromatic heterocyclylsulfanyl optionally substituted with one or more group(s) selected from the substituent group E, non-aromatic heterocyclylsulfanyl optionally substituted with one or more group(s) selected from the substituent group E, aromatic carbocyclylamino optionally substituted with one or more group(s) selected from the substituent group E, non-aromatic carbocyclylamino optionally substituted with one or more group(s) selected from the substituent group E, aromatic heterocyclylamino optionally substituted with one or more group(s) selected from the substituent group E, non-aromatic heterocyclylamino optionally substituted with one or more group(s) selected from the substituent group E and the like.

One embodiment is, for example, halogen, hydroxy, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, cyano, alkyl optionally substituted with one or more group(s) selected from the substituent group D, alkyloxy optionally substituted with one or more group(s) selected from the substituent group D or the like.

One embodiment is, for example, halogen, cyano, alkyl, haloalkyl, alkyloxy, haloalkyloxy or the like.

One embodiment is, for example, halogen, cyano, substituted or unsubstituted alkyl (the substituent is hydroxy, halogen or alkyloxy), substituted or unsubstituted alkyloxy (the substituent is hydroxy, alkyloxy or halogen) or the like.

One embodiment is, for example, alkyl, cyano, halogen, hydroxyalkyl or hydroxy alkyloxy or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonyl amino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{9a}$ and $R^{9b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent, group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group (s) selected from the substituent group F, non-aromatic heterocyclyl optionally substituted with one or more group(s) selected from the substituent group F or the like.

One embodiment is, for example, halogen or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclyl amino", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclyl carbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{9a}$ and $R^{9b}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{10a}$ and $R^{10b}$ include, for example, halogen, hydroxy, carboxy, amino, carbamoyl, sulfamoyl, sulfo, cyano, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F, aromatic carbocyclyloxy optionally substituted with one or more group(s) selected from the substituent group F, non-aromatic carbocyclyloxy optionally substituted with one or more group(s) selected from the substituent group F, aromatic heterocyclyloxy optionally substituted with one or more group(s) selected from the substituent group F, non-aromatic heterocyclyloxy optionally substituted with one or more group(s) selected from the substituent group F, aromatic carbocyclylsulfanyl optionally substituted with one or more group(s) selected from the substituent group F, non-aromatic carbocyclylsulfanyl optionally substituted with one or more group(s) selected from the substituent group F, aromatic heterocyclylsulfanyl optionally substituted with one or more group(s) selected from the substituent group F, non-aromatic heterocyclylsulfanyl optionally substituted with one or more group(s) selected from the substituent group F, aromatic carbocyclylamino optionally substituted with one or more group(s) selected from the substituent group F, non-aromatic carbocyclylamino optionally substituted with one or more group(s) selected from the substituent group F, aromatic heterocyclyl amino optionally substituted with one or more group(s) selected from the substituent group F, and non-aromatic heterocyclylamino optionally substituted with one or more group(s) selected from the substituent group F and the like.

One embodiment is, for example, halogen, hydroxy, cyano, alkyloxy optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F or the like.

One embodiment is, for example, halogen, hydroxy, cyano or the like.

One embodiment is, for example, halogen or the like.

One embodiment is, for example, hydroxy or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl",
"substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclyl amino",
"substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl",
"substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl",
"substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl",
"substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy",
"substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl",
"substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy",
"substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl",
"substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl",
"substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl",
"substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino",
"substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and
"substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{10a}$ and $R^{10b}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent, group D, alkyloxy optionally substituted with one or more group(s) selected from the substituent group D or the like.

The substituents on the rings of "substituted or unsubstituted aromatic carbocycle", "substituted or unsubstituted non-aromatic carbocycle", "substituted or unsubstituted aromatic heterocycle", and "substituted or unsubstituted non-aromatic heterocycle" when "$R^{9a}$ and $R^{10a}$ which are attached to the adjacent ring-constituting atoms, or $R^{9b}$ and $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", and the substituents on the rings of "substituted or unsubstituted 5-membered non-aromatic carbocycle", "substituted or unsubstituted 5-membered aromatic heterocycle", "substituted or unsubstituted 5-membered non-aromatic heterocycle", "substituted or unsubstituted 6-membered aromatic carbocycle", "substituted or unsubstituted 6-membered non-aromatic carbocycle", "substituted or unsubstituted 6-membered aromatic heterocycle" and "substituted or unsubstituted 6-membered non-aromatic heterocycle" in Ring F3 and Ring G3 include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

The substituents on the rings of "substituted or unsubstituted aromatic carbocycle", "substituted or unsubstituted non-aromatic carbocycle", "substituted or unsubstituted aromatic heterocycle", and "substituted or unsubstituted non-aromatic heterocycle" when "two $R^{10a}$ which are attached to the adjacent ring-constituting atoms, or two $R^{10b}$ which are attached to the adjacent ring-constituting atoms are taken together to form a substituted or unsubstituted aromatic carbocycle, a substituted or unsubstituted non-aromatic carbocycle, a substituted or unsubstituted aromatic heterocycle, or a substituted or unsubstituted non-aromatic heterocycle", and the substituents on the rings of "substituted or unsubstituted 5-membered non-aromatic carbocycle", "substituted or unsubstituted 5-membered aromatic heterocycle", "substituted or unsubstituted 5-membered non-aromatic heterocycle", "substituted or unsubstituted 6-membered aromatic carbocycle", "substituted or unsubstituted 6-membered non-aromatic carbocycle", "substituted or unsubstituted 6-membered aromatic heterocycle" and "substituted or unsubstituted 6-membered non-aromatic heterocycle" in Ring F1 and Ring G1 include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One embodiment is, for example, alkyl or the like.

The substituents of "substituted or unsubstituted alkyl", "substituted or unsubstituted alkenyl", "substituted or unsubstituted alkynyl", "substituted or unsubstituted alkyloxy", "substituted or unsubstituted alkenyloxy", "substituted or unsubstituted alkynyloxy", "substituted or unsubstituted alkylsulfanyl", "substituted or unsubstituted alkenylsulfanyl", "substituted or unsubstituted alkynylsulfanyl", "substituted or unsubstituted alkylamino", "substituted or unsubstituted alkenylamino", "substituted or unsubstituted alkynylamino", "substituted or unsubstituted alkylcarbonyl", "substituted or unsubstituted alkenylcarbonyl", "substituted or unsubstituted alkynylcarbonyl", "substituted or unsubstituted alkylsulfonyl", "substituted or unsubstituted alkenylsulfonyl", "substituted or unsubstituted alkynylsulfonyl", "substituted or unsubstituted alkylcarbonyloxy", "substituted or unsubstituted alkenylcarbonyloxy", "substituted or unsubstituted alkynylcarbonyloxy", "substituted or unsubstituted alkyloxycarbonyl", "substituted or unsubstituted alkenyloxycarbonyl", "substituted or unsubstituted alkynyloxycarbonyl", "substituted or unsubstituted alkylsulfonyloxy", "substituted or unsubstituted alkenylsulfonyloxy", "substituted or unsubstituted alkynylsulfonyloxy", "substituted or unsubstituted alkyloxysulfonyl", "substituted or unsubstituted alkenyloxysulfonyl", "substituted or unsubstituted alkynyloxysulfonyl", "substituted or unsubstituted alkylcarbamoyl", "substituted or unsubstituted alkenylcarbamoyl", "substituted or unsubstituted alkynylcarbamoyl", "substituted or unsubstituted alkylsulfamoyl", "substituted or unsubstituted alkenylsulfamoyl", "substituted or unsubstituted alkynylsulfamoyl", "substituted or unsubstituted alkylcarbonylamino", "substituted or unsubstituted alkenylcarbonylamino", "substituted or unsubstituted alkynylcarbonylamino", "substituted or unsubstituted alkylsulfonylamino", "substituted or unsubstituted alkenylsulfonylamino", "substituted or unsubstituted alkyloxycarbonylamino", "substituted or unsubstituted alkenyloxycarbonylamino", and "substituted or unsubstituted alkynyloxycarbonylamino" in $R^{10a1}$ and $R^{10a2}$ include, for example, halogen, hydroxy, carboxy, amino, carbamoyl, sulfamoyl, sulfo, cyano, alkyloxy optionally substituted with one or more group(s) selected from the substituent group D, alkyl amino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, aromatic carbocyclyl optionally substituted with one or more group(s) selected from the substituent group F, non-aromatic carbocyclyl optionally substituted with one or more group(s) selected from the substituent group F, aromatic heterocyclyl optionally substituted with one or more group(s) selected from the substituent group F, non-aromatic heterocyclyl optionally substituted with one or more group(s) selected from the substituent group F and the like.

One embodiment is, for example, halogen, hydroxy, cyano or the like.

One embodiment is, for example, halogen or the like.

The substituents on the rings of "aromatic carbocycle", "non-aromatic carbocycle", "aromatic heterocycle", and "non-aromatic heterocycle" of "substituted or unsubstituted aromatic carbocyclyl", "substituted or unsubstituted non-aromatic carbocyclyl", "substituted or unsubstituted aromatic heterocyclyl", and "substituted or unsubstituted non-aromatic heterocyclyl", "substituted or unsubstituted aromatic carbocyclyloxy", "substituted or unsubstituted non-aromatic carbocyclyloxy", "substituted or unsubstituted aromatic heterocyclyloxy", and "substituted or unsubstituted non-aromatic heterocyclyloxy", "substituted or unsubstituted aromatic carbocyclylamino", "substituted or unsubstituted non-aromatic carbocyclylamino", "substituted or unsubstituted aromatic heterocyclylamino", and "substituted or unsubstituted non-aromatic heterocyclyl amino", "substituted or unsubstituted aromatic carbocyclylsulfanyl", "substituted or unsubstituted non-aromatic carbocyclylsulfanyl", "substituted or unsubstituted aromatic heterocyclylsulfanyl", and "substituted or unsubstituted non-aromatic heterocyclylsulfanyl", "substituted or unsubstituted aromatic carbocyclylcarbonyl", "substituted or unsubstituted non-aromatic carbocyclylcarbonyl", "substituted or unsubstituted aromatic heterocyclylcarbonyl", and "substituted or unsubstituted non-aromatic heterocyclylcarbonyl", "substituted or unsubstituted aromatic carbocyclylsulfonyl", "substituted or unsubstituted non-aromatic carbocyclylsulfonyl", "substituted or unsubstituted aromatic heterocyclylsulfonyl", and "substituted or unsubstituted non-aromatic heterocyclylsulfonyl", "substituted or unsubstituted aromatic carbocyclylcarbonyloxy", "substituted or unsubstituted non-aromatic carbocyclylcarbonyloxy", "substituted or unsubstituted aromatic heterocyclylcarbonyloxy", and "substituted or unsubstituted non-aromatic heterocyclylcarbonyloxy", "substituted or unsubstituted aromatic carbocyclyloxycarbonyl", "substituted or unsubstituted non-aromatic carbocyclyloxycarbonyl", "substituted or unsubstituted aromatic heterocyclyloxycarbonyl", and "substituted or unsubstituted non-aromatic heterocyclyloxycarbonyl", "substituted or unsubstituted aromatic carbocyclylsulfonyloxy", "substituted or unsubstituted non-aromatic carbocyclylsulfonyloxy", "substituted or unsubstituted aromatic heterocyclylsulfonyloxy", and "substituted or unsubstituted non-aromatic heterocyclylsulfonyloxy", "substituted or unsubstituted aromatic carbocyclyloxysulfonyl", "substituted or unsubstituted non-aromatic carbocyclyloxysulfonyl", "substituted or unsubstituted aromatic heterocyclyloxysulfonyl", and "substituted or unsubstituted non-aromatic heterocyclyloxysulfonyl", "substituted or unsubstituted aromatic carbocyclylcarbamoyl", "substituted or unsubstituted non-aromatic carbocyclylcarbamoyl", "substituted or unsubstituted aromatic heterocyclylcarbamoyl", and "substituted or unsubstituted non-aromatic heterocyclylcarbamoyl", "substituted or unsubstituted aromatic carbocyclylsulfamoyl", "substituted or unsubstituted non-aromatic carbocyclylsulfamoyl", "substituted or unsubstituted aromatic heterocyclylsulfamoyl", and "substituted or unsubstituted non-aromatic heterocyclylsulfamoyl", "substituted or unsubstituted aromatic carbocyclylcarbonylamino", "substituted or unsubstituted non-aromatic carbocyclylcarbonylamino", "substituted or unsubstituted aromatic heterocyclylcarbonylamino", and "substituted or unsubstituted non-aromatic heterocyclylcarbonylamino", "substituted or unsubstituted aromatic carbocyclylsulfonylamino", "substituted or unsubstituted non-aromatic carbocyclylsulfonylamino", "substituted or unsubstituted aromatic heterocyclylsulfonylamino", and "substituted or unsubstituted non-aromatic heterocyclylsulfonylamino", and "substituted or unsubstituted aromatic carbocyclyloxycarbonylamino", "substituted or unsubstituted non-aromatic carbocyclyloxycarbonylamino", "substituted or unsubstituted aromatic heterocyclyloxycarbonylamino", and "substituted or unsubstituted non-aromatic heterocyclyloxycarbonylamino" in $R^{10a1}$ and $R^{10a2}$ include, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D, alkylcarbonyl optionally substituted with one or more group(s) selected from the substituent group D, alkylsulfonyl optionally substituted with one or more group(s) selected from the substituent group D, alkylcarbonylamino optionally substituted with one or more group(s) selected from the substituent group D, alkylsulfonylamino optionally substituted with one or more group(s) selected from the substituent group D, alkylcarbamoyl optionally substituted with one or more group(s) selected from the substituent group D, alkylsulfamoyl optionally substituted with one or more group(s) selected from the substituent group D and the like.

One embodiment is, for example, halogen, hydroxy, carboxy, amino, carbamoyl, sulfamoyl, sulfo, cyano, alkyl optionally substituted with one or more group(s) selected from the substituent group D, alkyloxy optionally substituted with one or more group(s) selected from the substituent group D, alkylamino optionally substituted with one or more group(s) selected from the substituent group D, alkylsulfanyl optionally substituted with one or more group(s) selected from the substituent group D or the like.

One embodiment is, for example, halogen, alkyl optionally substituted with one or more group(s) selected from the substituent group D, alkyloxy optionally substituted with one or more group(s) selected from the substituent group D or the like.

One aspect of the present invention is illustrated below.

Specific examples of each substituent in the compound represented by Formula
(1) or pharmaceutically acceptable salt thereof are shown below. All combinations each selected from (a) to (v) are illustrated for the compounds represented by Formula (I).
(a) A compound according to the following (ad) or a pharmaceutically acceptable salt thereof.
(a-1) The compound represented by formula (I) wherein X is $N(R^{7a})$, or pharmaceutically acceptable salt thereof.
(b) A compound according to any one of the following (b-1) or (b-2) or a pharmaceutically acceptable salt thereof.
(b-1) The compound of formula (I) or the above (a), wherein $R^{7a}$ is a hydrogen atom, or substituted or unsubstituted alkyl, or pharmaceutically acceptable salt thereof.
(b-2) The compound of formula (I) or the above (a), wherein $R^{7a}$ is a hydrogen atom, or pharmaceutically acceptable salt thereof.
(c) A compound according to any one of the following (c1) to (c3) or a pharmaceutically acceptable salt thereof.
(c1) The compound of formula (I) or the above (a) or (b), wherein $R^{8a}$ and $R^{8b}$ are each independently a hydrogen atom, halogen or substituted or unsubstituted alkyl, or pharmaceutically acceptable salt thereof.
(c2) The compound of formula (I) or the above (a) or (b) wherein $R^{8a}$ and $R^{8b}$ are each independently a hydrogen atom, or halogen, or pharmaceutically acceptable salt thereof.
(c3) The compound of formula (I) or the above (a) or (b) wherein each of $R^{8a}$ and $R^{8b}$ is a hydrogen atom, or pharmaceutically acceptable salt thereof.
(d) A compound according to the following (d-1) or (d-2) or a pharmaceutically acceptable salt thereof.
(d-1) The compound of any one of formula (I) and the above (a) to (c), wherein n is 0, or pharmaceutically acceptable salt thereof.
(d-2) The compound of any one of formula (I) and the above (a) to (c) and (d-1), wherein m is 0,
or pharmaceutically acceptable salt thereof.
(e) A compound according to any one of the following (e-1) to (e-3),
or a pharmaceutically acceptable salt thereof.
(e-1) The compound of any one of Formula (I) and the above (a) to (d), wherein
$R^{2a'}$ is a hydrogen atom, halogen, or substituted or unsubstituted alkyl, or
$R^{2a}$ and $R^{2b}$ which are attached to the same carbon atom are taken together to form oxo,
or pharmaceutically acceptable salt thereof.
(e-2) The compound of any one of Formula (I) and the above (a) to (d), wherein
$R^{2a'}$ is a hydrogen atom or halogen,
or pharmaceutically acceptable salt thereof.
(e-3) The compound of any one of Formula (I) and the above (a) to (d), wherein
$R^{2a'}$ is a hydrogen atom,
or pharmaceutically acceptable salt thereof.
(f) A compound according to any one of the following (f-1) to (f-3),
or a pharmaceutically acceptable salt thereof.
(f-1) The compound of any one of Formula (I) and the above (a) to (e), wherein
$R^{2b'}$ is a hydrogen atom, halogen, or substituted or unsubstituted alkyl, or
$R^{2a}$ and $R^{2b}$ which are attached to the same carbon atom are taken together to form oxo,
or a pharmaceutically acceptable salt thereof.
(f-2) The compound of any one of Formula (I) and the above (a) to (e), wherein
$R^{2b'}$ is a hydrogen atom or halogen,
or a pharmaceutically acceptable salt thereof.
(f-3) The compound of any one of Formula (I) and the above (a) to (e), wherein
$R^{2b'}$ is a hydrogen atom,
or a pharmaceutically acceptable salt thereof.
(g) A compound according to any one of the following (g-1) to (g-3),
or a pharmaceutically acceptable salt thereof.
(g-1) The compound of any one of Formula (I) and the above (a) to (f), wherein
$R^{2b}$ is a hydrogen atom, halogen, or substituted or unsubstituted alkyl, or
$R^{2a}$ and $R^{2b}$ which are attached to the same carbon atom are taken together to form oxo,
or a pharmaceutically acceptable salt thereof.
(g-2) The compound of any one of Formula (I) and the above (a) to (f), wherein
$R^{2b}$ is a hydrogen atom or halogen,
or a pharmaceutically acceptable salt thereof.
(g-3) The compound of any one of Formula (I) and the above (a) to (f), wherein
$R^{2b}$ is a hydrogen atom,
or a pharmaceutically acceptable salt thereof.

(h) A compound according to any one of the following (h-1) to (h-3),
or a pharmaceutically acceptable salt thereof.
(h-1) The compound of any one of Formula (I) and the above (a) to (g), wherein
$R^{2c}$ is a hydrogen atom, halogen, or substituted or unsubstituted alkyl,
or a pharmaceutically acceptable salt thereof.
(h-2) The compound of any one of Formula (I) and the above (a) to (g), wherein
$R^{2c}$ is a hydrogen atom or halogen,
or a pharmaceutically acceptable salt thereof.
(h-3) The compound of any one of Formula (I) and the above (a) to (g), wherein
$R^{2c}$ is a hydrogen atom,
or a pharmaceutically acceptable salt thereof.
(i) A compound according to any one of the following (i-1) to (i-3),
or a pharmaceutically acceptable salt thereof.
(i-1) The compound of any one of Formula (I) and the above (a) to (h), wherein
$R^{2d}$ is a hydrogen atom, halogen, or substituted or unsubstituted alkyl,
or a pharmaceutically acceptable salt thereof.
(i-2) The compound of any one of Formula (I) and the above (a) to (h), wherein
$R^{2d}$ is a hydrogen atom or halogen,
or a pharmaceutically acceptable salt thereof.
(i-3) The compound of any one of Formula (I) and the above (a) to (h), wherein
$R^{2d}$ is a hydrogen atom,
or a pharmaceutically acceptable salt thereof.
(j) A compound according to the following (j-1),
or a pharmaceutically acceptable salt thereof.
(j-1) The compound of any one of Formula (I) and the above (a) to (i), wherein
$Y^1$ is O,
or a pharmaceutically acceptable salt thereof.
(k) A compound according to any one of the following (k-1) to (k-3),
or a pharmaceutically acceptable salt thereof.
(k-1) The compound of any one of Formula (I) and the above (a) to (j), wherein
$R^4$ is a hydrogen atom, halogen, or substituted or unsubstituted alkyl,
or a pharmaceutically acceptable salt thereof.
(k-2) The compound of any one of Formula (I) and the above (a) to (j), wherein
$R^4$ is a hydrogen atom or halogen,
or a pharmaceutically acceptable salt thereof.
(k-3) The compound of any one of Formula (I) and the above (a) to (j), wherein
$R^4$ is a hydrogen atom,
or a pharmaceutically acceptable salt thereof.
(l) A compound according to the following (l-1) or (l-2),
or a pharmaceutically acceptable salt thereof.
(l-1) The compound of any one of Formula (I) and the above (a) to (k), wherein
$R^6$ is a hydrogen atom, hydroxy, cyano, substituted or unsubstituted alkyl, or substituted or unsubstituted alkyloxy,
or a pharmaceutically acceptable salt thereof.
(l-2) The compound of any one of Formula (I) and the above (a) to (k), wherein
$R^6$ is a hydrogen atom,
or a pharmaceutically acceptable salt thereof.

(m) A compound according to any one of the following (m-1) to (m-17),
or a pharmaceutically acceptable salt thereof.
(m-1) The compound of any one of Formula (I) and the above (a) to (l), wherein
$R^1$ is substituted or unsubstituted 6-membered aromatic carbocyclyl, substituted or unsubstituted 3 to 6-membered non-aromatic carbocyclyl, substituted or unsubstituted 5- to 6-membered aromatic heterocyclyl, or substituted or unsubstituted 5- to 6-membered non-aromatic heterocyclyl,
or a pharmaceutically acceptable salt thereof.
(m-2) The compound of any one of Formula (I) and the above (a) to (l), wherein
$R^1$ is substituted or unsubstituted 6-membered aromatic carbocyclyl, or substituted or unsubstituted 5- to 6-membered aromatic heterocyclyl,
or a pharmaceutically acceptable salt thereof.
(m-3) The compound of any one of Formula (I) and the above (a) to (l), wherein
$R^1$ is substituted or unsubstituted phenyl,
or a pharmaceutically acceptable salt thereof.
(m-4) The compound of any one of Formula (I) and the above (a) to (l), wherein
$R^1$ is phenyl substituted with one or more group(s) selected from halogen and alkyl, or unsubstituted phenyl,
or a pharmaceutically acceptable salt thereof.
(m-5) The compound of any one of Formula (I) and the above (a) to (l), wherein
$R^1$ is 6-membered aromatic carbocyclyl substituted with one or more halogen atom(s) and optionally substituted with one or more and same or different substituent(s), or 5- to 6-membered aromatic heterocyclyl substituted with one or more halogen atom(s) and optionally substituted with one or more and same or different substituent(s),
or a pharmaceutically acceptable salt thereof.
(m-6) The compound of any one of Formula (I) and the above (a) to (l), wherein
$R^1$ is phenyl substituted with one or more halogen atom(s) and optionally substituted with one or more and same or different substituent(s),
or a pharmaceutically acceptable salt thereof.
(m-7) The compound of any one of Formula (I) and the above (a) to (l), wherein
$R^1$ is phenyl substituted with one or more halogen atom(s),
or a pharmaceutically acceptable salt thereof.
(m-8) The compound of any one of Formula (I) and the above (a) to (l), wherein
$R^1$ is a group represented by the formula:

[Chemical Formula 16]

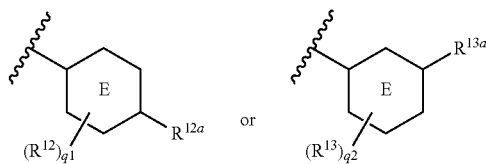

wherein
Ring E is a 6-membered aromatic carbocycle, a 6-membered non-aromatic carbocycle, a 6-membered aromatic heterocycle, or a 6-membered non-aromatic heterocycle;
$R^{12a}$ and $R^{13a}$ are each independently halogen;

$R^{12}$ and $R^{13}$ are each independently a group selected from the substituent group C1;
q1 is an integer from 0 to 2; and
q2 is an integer from 0 to 2,
or a pharmaceutically acceptable salt thereof.
(m-9) The compound of the above (m-8), wherein
$R^{12}$ and $R^{13}$ are each independently halogen, alkyl optionally substituted with one or more group(s) selected from the substituent group D, or alkyloxy optionally substituted with one or more group(s) selected from the substituent group D,
or a pharmaceutically acceptable salt thereof.
(m-10) The compound of the above (m-8), wherein
$R^{12}$ and $R^{13}$ are each independently halogen, alkyl, or haloalkyl,
or a pharmaceutically acceptable salt thereof.
(m-11) The compound of the above (m-8), wherein
$R^{12}$ and $R^{13}$ are each independently halogen,
or a pharmaceutically acceptable salt thereof.
(m-12) The compound of any one of Formula (I) and the above (a) to (1), wherein
$R^1$ is a group represented by the formula:

[Chemical Formula 17]

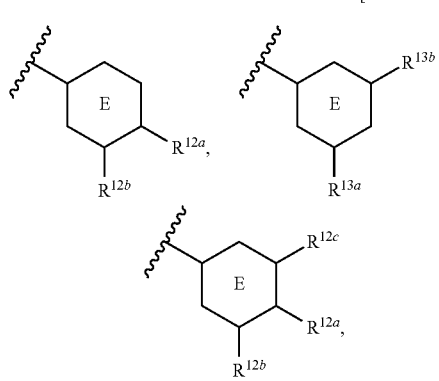

wherein
$R^{12a}$ and $R^{13a}$ are each independently halogen; and
$R^{12b}$, $R^{12c}$, and $R^{13b}$ are each independently halogen, alkyl optionally substituted with one or more group(s) selected from the substituent group D, or alkyloxy optionally substituted with one or more group(s) selected from the substituent group D,
or a pharmaceutically acceptable salt thereof.
(m-13) The compound of the above (m-12), wherein
$R^{12b}$, $R^{12c}$, and $R^{13b}$ are each independently halogen, or alkyl optionally substituted with one or more group(s) selected from the substituent group D,
or a pharmaceutically acceptable salt thereof.
(m-14) The compound of the above (m-12), wherein
$R^{12b}$, $R^{12c}$, and $R^{13b}$ are each independently halogen, alkyl, or haloalkyl,
or a pharmaceutically acceptable salt thereof.
(m-15) The compound of the above (m-12), wherein
$R^{12b}$, $R^{12c}$, and $R^{13b}$ are each independently halogen,
or a pharmaceutically acceptable salt thereof.
(m-16) The compound of any one of the above (m-7) to (m-15), wherein
Ring E is benzene or a 6-membered aromatic heterocycle,
or a pharmaceutically acceptable salt thereof.
(m-17) The compound of any one of the above (m-7) to (m-15), wherein Ring E is benzene,
or a pharmaceutically acceptable salt thereof.

(m-18) The compound of the above (m-17), wherein
$R^{12a}$, $R^{12b}$, and $R^{12c}$ are each independently halogen,
or a pharmaceutically acceptable salt thereof.
(n) A compound according to any one of the following (n-1) to (n-14),
or a pharmaceutically acceptable salt thereof.
(n-1) The compound according to any one of Formula (I) and the above (a) to (m),
wherein
$Z^1$ is N,
or a pharmaceutically acceptable salt thereof.
(n-2) The compound according to any one of Formula (I) and the above (a) to (m),
wherein
$Z^1$ is $C(R^4)$,
or a pharmaceutically acceptable salt thereof.
(n-3) The compound of any one of Formula (I), the above (a) to (m), (n-f), and (n-2), wherein
the dashed line represents the presence of a bond,
or a pharmaceutically acceptable salt thereof.
(n-4) The compound of the above (n-3), wherein

[Chemical Formula 18]

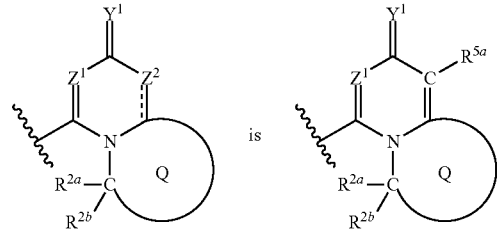

or a pharmaceutically acceptable salt thereof.
(n-5) The compound according to the above (n-3) or (n-4), wherein
Ring Q is a substituted or unsubstituted 5-membered saturated heterocycle or a substituted or unsubstituted 6-membered saturated heterocycle,
or a pharmaceutically acceptable salt thereof.
(n-6) The compound according to the above (n-3) or (n-4), wherein
Ring Q is substituted or unsubstituted pyrrolidine, substituted or unsubstituted imidazolidine, substituted or unsubstituted oxazolidine, substituted or unsubstituted piperidine, substituted or unsubstituted oxadian, substituted or unsubstituted hexahydropyrimidine, substituted or unsubstituted morpholine, or substituted or unsubstituted piperazine,
or a pharmaceutically acceptable salt thereof.
(n-7) The compound according to the above (n-3) or (n-4), wherein
Ring Q is substituted or unsubstituted pyrrolidine, substituted or unsubstituted imidazolidine, substituted or unsubstituted oxazolidine, substituted or unsubstituted piperidine, substituted or unsubstituted oxadian, or substituted or unsubstituted morpholine,
or a pharmaceutically acceptable salt thereof.
(n-8) The compound according to the above (n-3) or (n-4), wherein
Ring Q is unsubstituted pyrrolidine; imidazolidine substituted with one or more group(s) selected from alkyl; unsubstituted imidazolidine; unsubstituted oxazolidine; unsubstituted piperidine; unsubstituted oxadian; or unsubstituted morpholine,
or a pharmaceutically acceptable salt thereof.

(n-9) The compound of any one of Formula (I), the above (a) to (m), (n-1) and (n-2), wherein
the dashed line represents the absence of a bond,
or a pharmaceutically acceptable salt thereof.
(n-10) The compound of the above (n-9), wherein

[Chemical Formula 19]

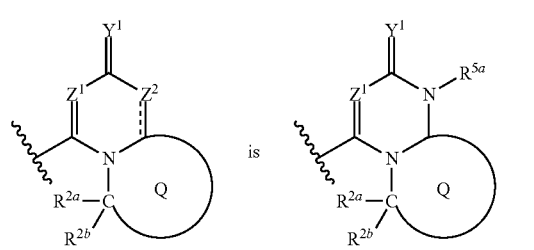

or a pharmaceutically acceptable salt thereof.
(n-11) The compound according to the above (n-9) or (n-10), wherein
Ring Q is substituted or unsubstituted dihydropyrrole, substituted or unsubstituted dihydroimidazole, substituted or unsubstituted tetrahydropyrimidine, or substituted or unsubstituted tetrahydropyrazine,
or a pharmaceutically acceptable salt thereof.
(n-12) The compound according to the above (n-9) or (n-10), wherein
Ring Q is substituted or unsubstituted dihydroimidazole,
or a pharmaceutically acceptable salt thereof.
(n-13) The compound according to the above (n-9) or (n-10), wherein
Ring Q is unsubstituted dihydroimidazole,
or a pharmaceutically acceptable salt thereof.
(n-14) The compound according to any one of the above Formula (I), the above (a) to (m), (n-1), and (n-13), wherein

[Chemical Formula 20]

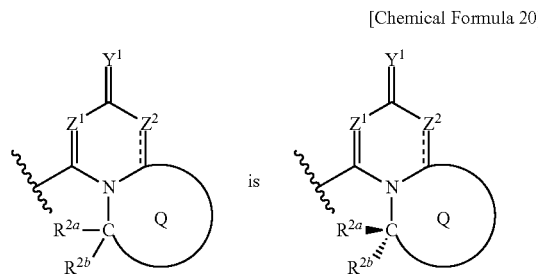

or a pharmaceutically acceptable salt thereof.
(o) A compound according to any one of the following (o-1) to (o-10),
or a pharmaceutically acceptable salt thereof.
(o-1) The compound of any one of Formula (I) and the above (a) to (n), wherein
$R^{5a}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
or a pharmaceutically acceptable salt thereof.
(o-2) The compound of any one of Formula (I) and the above (a) to (n), wherein
$R^{5a}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, or substituted or unsubstituted aromatic heterocyclyl,
or a pharmaceutically acceptable salt thereof.
(o-3) The compound of any one of Formula (I) and the above (a) to (n), wherein
$R^{5a}$ is each independently halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted aromatic carbocyclyl, or substituted or unsubstituted aromatic heterocyclyl,
or a pharmaceutically acceptable salt thereof.
(o-4) The compound of any one of Formula (I) and the above (a) to (n), wherein
$R^{5a}$ is halogen, substituted or unsubstituted alkyl, substituted or unsubstituted alkenyl, substituted or unsubstituted alkyloxy, or substituted or unsubstituted aromatic carbocyclyl,
or a pharmaceutically acceptable salt thereof.
(o-5) The compound of any one of Formula (I) and the above (a) to (n), wherein
$R^{5a}$ is halogen; unsubstituted alkyl; unsubstituted alkenyl; unsubstituted alkyloxy; or unsubstituted aromatic carbocyclyl,
or a pharmaceutically acceptable salt thereof.
(o-6) The compound of any one of Formula (I), the above (a) to (n), and the above (o-1) to (o-5), wherein
$R^{5a'}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, or substituted or unsubstituted aromatic heterocyclyl,
or a pharmaceutically acceptable salt thereof.
(o-7) The compound according to any one of Formula (I), the above (a) to (n), and the above (o-1) to (o-5), wherein
$R^{5a'}$ is a hydrogen atom,
or a pharmaceutically acceptable salt thereof.
(o-8) The compound according to any one of Formula (I), the above (a) to (n), and the above (o-1) to (o-7), wherein
$R^{5b}$ is a hydrogen atom, substituted or unsubstituted alkyl, substituted or unsubstituted alkenyl, or substituted or unsubstituted alkynyl,
or a pharmaceutically acceptable salt thereof.
(o-9) The compound according to any one of Formula (I), the above (a) to (n), and the above (o-1) to (o-7), wherein
$R^{5b}$ is a hydrogen atom, or substituted or unsubstituted alkyl,
or a pharmaceutically acceptable salt thereof.

(o-10) The compound according to any one of Formula (I), the above (a) to (n), and the above (o-1) to (o-7), wherein $R^{5b}$ is unsubstituted alkyl,
or a pharmaceutically acceptable salt thereof.
(p) A compound according to any one of the following (p-1) to (p-3),
or a pharmaceutically acceptable salt thereof.
(p-1) The compound according to any one of Formula (I) and the above (a) to (o), wherein
$R^3$ is substituted or unsubstituted 6-membered aromatic carbocyclyl, or substituted or unsubstituted 6- to 10-membered aromatic heterocyclyl,
or a pharmaceutically acceptable salt thereof.
(p-2) The compound according to any one of Formula (I) and the above (a) to (o), wherein
$R^3$ is substituted or unsubstituted 6-membered aromatic carbocyclyl, substituted or unsubstituted 6-membered aromatic heterocyclyl, or substituted or unsubstituted 9 to 10-membered aromatic heterocyclyl,
or a pharmaceutically acceptable salt thereof.
(p-3) The compound according to any one of Formula (I) and the above (a) to (o), wherein
$R^3$ is substituted or unsubstituted phenyl, substituted or unsubstituted pyridyl, substituted or unsubstituted pyrimidyl, substituted or unsubstituted pyrazyl, substituted or unsubstituted benzothiazolyl, substituted or unsubstituted dihydroisobenzofuranyl, or substituted or unsubstituted indolyl,
or a pharmaceutically acceptable salt thereof.
(q) A compound according to any one of the following (q-1) to (q-12) or a pharmaceutically acceptable salt thereof.
(q-1) The compound of any one of formula (I) and the above (a) to (p), wherein $R^3$ is a group represented by the Formula:

[Chemical Formula 21]

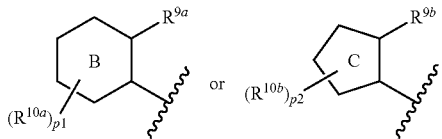

wherein
Ring B is a 6-membered aromatic carbocycle, a 6-membered aromatic heterocycle, or a 6-membered non-aromatic heterocycle, Ring C is a 5-membered aromatic heterocycle, $R^{9a}$ and $R^{9b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

$R^{10a}$ and $R^{10b}$ are each independently halogen, hydroxy, carboxy, amino, carbamoyl, sulfamoyl, sulfo, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkylcarbonyloxy, substituted or unsubstituted alkenylcarbonyloxy, substituted or unsubstituted alkynylcarbonyloxy, substituted or unsubstituted alkyloxycarbonyl, substituted or unsubstituted alkenyloxycarbonyl, substituted or unsubstituted alkynyloxycarbonyl, substituted or unsubstituted alkylsulfonyloxy, substituted or unsubstituted alkenylsulfonyloxy, substituted or unsubstituted alkynylsulfonyloxy, substituted or unsubstituted alkyloxysulfonyl, substituted or unsubstituted alkenyloxysulfonyl, substituted or unsubstituted alkynyloxysulfonyl, substituted or unsubstituted alkylcarbamoyl, substituted or unsubstituted alkenylcarbamoyl, substituted or unsubstituted alkynylcarbamoyl, substituted or unsubstituted alkylsulfamoyl, substituted or unsubstituted alkenylsulfamoyl, substituted or unsubstituted alkynylsulfamoyl, substituted or unsubstituted alkylcarbonylamino, substituted or unsubstituted alkenylcarbonylamino, substituted or unsubstituted alkynylcarbonylamino, substituted or unsubstituted alkylsulfonylamino, substituted or unsubstituted alkenylsulfonylamino, substituted or unsubstituted alkynylsulfonylamino, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylamino, substituted or unsubstituted non-aromatic carbocyclylamino, substituted or unsubstituted aromatic heterocyclylamino, substituted or unsubstituted non-aromatic heterocyclylamino, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyloxy, substituted or unsubstituted non-aromatic carbocyclylsulfonyloxy, substituted or unsubstituted aromatic heterocyclylsulfonyloxy, substituted or unsubstituted non-aromatic heterocyclylsulfonyloxy, substituted or unsubstituted aromatic carbocyclyloxysulfonyl, substituted or unsubstituted non-aromatic carbocyclyloxysulfonyl, substituted or unsubstituted aromatic heterocyclyloxysulfonyl, substituted or unsubstituted non-aromatic heterocyclyloxysulfonyl, substituted or unsubstituted aromatic carbocyclylcarbamoyl, substituted or unsubstituted non-aromatic carbocyclylcarbamoyl, substituted or unsubstituted aromatic heterocyclylcarbamoyl, substituted or unsubstituted non-aromatic heterocyclylcarbamoyl, substituted or unsubstituted aromatic carbocyclylsulfamoyl, substituted or unsubstituted non-aromatic carbocyclylsulfamoyl, substituted or unsubstituted aromatic heterocyclylsulfamoyl, substituted or unsubstituted non-aromatic heterocyclylsulfamoyl, substituted or unsubstituted aromatic carbocyclylcarbonylamino, substituted or unsubstituted non-aromatic carbocyclylcarbonylamino, substituted or unsubstituted aromatic heterocyclylcarbonylamino, substituted or unsubstituted non-aromatic heterocyclylcarbonylamino, substituted or unsubstituted aromatic carbocyclylsulfonylamino, substituted or unsubstituted non-aromatic carbocyclylsulfonylamino, substituted or unsubstituted aromatic heterocyclylsulfonylamino, substituted or unsubstituted non-aromatic heterocyclylsulfonylamino, substituted or unsubstituted aromatic carbocyclyloxycarbonylamino, substituted or unsubstituted non-aromatic carbocyclyloxycarbonylamino, substituted or unsubstituted aromatic heterocyclyloxycarbonylamino, or substituted or unsubstituted non-aromatic heterocyclyloxycarbonylamino;

p1 is an integer from 0 to 3; and p2 is an integer from 0 to 2, or pharmaceutically acceptable salt thereof.

(q-2) The compound of the above (q-1), wherein $R^3$ is a group represented by the formula:

[Chemical Formula 22]

or a pharmaceutically acceptable salt thereof.

(q-3) The compound of any one of the above (q-1) or (q-2), wherein $R^{10a}$ and $R^{10b}$ are each independently halogen, hydroxy, amino, carbamoyl, cyano, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, substituted or unsubstituted alkynylamino, substituted or unsubstituted alkylcarbonyl, substituted or unsubstituted alkenylcarbonyl, substituted or unsubstituted alkynylcarbonyl, substituted or unsubstituted alkylsulfonyl, substituted or unsubstituted alkenylsulfonyl, substituted or unsubstituted alkynylsulfonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy, or pharmaceutically acceptable salt thereof.

(q-4) The compound of the above (q-1) or (q-2), wherein $R^{10a}$ and $R^{10b}$ are each independently halogen, cyano, substituted or unsubstituted alkyl, substituted or unsubstituted alkenyl, substituted or unsubstituted alkynyl, substituted or unsubstituted alkyloxy, substituted or unsubstituted alkenyloxy, or substituted or unsubstituted alkynyloxy,
or a pharmaceutically acceptable salt thereof.

(q-5) The compound of the above (q-1) or (q-2), wherein $R^{10a}$ and $R^{10b}$ are each independently halogen, cyano, substituted or unsubstituted alkyl, or substituted or unsubstituted alkyloxy,
or a pharmaceutically acceptable salt thereof.

(q-6) The compound of the above (q-1) or (q-2), wherein $R^{10a}$ and $R^{10b}$ are each independently halogen; cyano; alkyl; haloalkyl; alkyloxy; haloalkyloxy, hydroxyalkyl, or hydroxyalkyloxy,
or a pharmaceutically acceptable salt thereof.

(q-7) The compound of any one of the above (q-1) to (q-6), wherein
p1 is 1 or 2,
or a pharmaceutically acceptable salt thereof.

(q-8) The compound of any one of the above (q-1) to (q-6), wherein
p1 is 2,
or a pharmaceutically acceptable salt thereof.

(q-9) The compound of any one of the above (q-1) to (q-6), wherein
p1 is 1,
or a pharmaceutically acceptable salt thereof.

(q-10) The compound of any one of the above (q-1) to (q-6), wherein
p1 is 0,
or a pharmaceutically acceptable salt thereof.

(q-11) The compound of any one of the above (q-1) to (q-10), wherein
p2 is 1,
or a pharmaceutically acceptable salt thereof.

(q-12) The compound of any one of the above (q-1) to (q-10), wherein
p2 is 0,
or a pharmaceutically acceptable salt thereof.

(q-13) The compound of the above (q-1), wherein $R^{10a}$ and $R^{10b}$ are each independently halogen; cyano; hydroxyalkyl; or hydroxyalkyloxy,
or a pharmaceutically acceptable salt thereof.

(q-14) The compound of the above (q-2), wherein $R^{10a}$ is each independently alkyloxy; cyano; halogen; alkyloxyalkyloxy; hydroxyalkyl; hydroxyalkyloxy; haloalkyloxy; or alkyloxyalkyl,
or a pharmaceutically acceptable salt thereof.

(q-15) The compound of the above (q-2), wherein $R^{10a}$ is each independently halogen; cyano; hydroxyalkyl; or hydroxyalkyloxy,
or a pharmaceutically acceptable salt thereof.

(r) A compound according to any one of the following (r-1) to (r-11),
or a pharmaceutically acceptable salt thereof.

(r-1) The compound of any one of Formula (I) and the above (a) to (p), wherein
$R^3$ is a group represented by the formula:

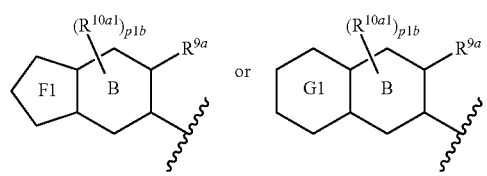

[Chemical Formula 23]

wherein
Ring F1 is a substituted or unsubstituted 5-membered non-aromatic carbocycle, a substituted or unsubstituted 5-membered aromatic heterocycle, or a substituted or unsubstituted 5-membered non-aromatic heterocycle,
Ring G1 is a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted 6-membered non-aromatic heterocycle,
Ring B is a 6-membered aromatic carbocycle or a 6-membered aromatic heterocycle,
p1b is 0 or 1,
$R^{9a}$ and $R^{9b}$ are the same as the above (q-1); and
$R^{10a1}$ is the same as $R^{10a}$ of the above (q-1),
or a pharmaceutically acceptable salt thereof.
The above definition of $R^3$ means that $R^{10a1}$ is a substituent on Ring B.

(r-2) The compound of any one of Formula (I) and the above (a) to (p), wherein
$R^3$ is a group represented by the formula:

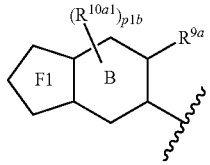

[Chemical Formula 24]

or a pharmaceutically acceptable salt thereof.

(r-3) The compound of the above (r-1) or (r-2), wherein
Ring F1 is substituted or unsubstituted cyclopentene, substituted or unsubstituted furan, substituted or unsubstituted thiophene, substituted or unsubstituted pyrrole, substituted or unsubstituted pyrazole, substituted or unsubstituted imidazole, substituted or unsubstituted thiazole, substituted or unsubstituted oxazole, substituted or unsubstituted dihydrofuran, substituted or unsubstituted dihydrothiophene, substituted or unsubstituted dihydropyrrole, or substituted or unsubstituted dioxole,
or a pharmaceutically acceptable salt thereof.
(r-4) The compound of the above (r-1) or (r-2), wherein
Ring F1 is substituted or unsubstituted dihydrofuran, or substituted or unsubstituted thiazole,
or a pharmaceutically acceptable salt thereof.
(r-5) The compound of the above (r-1) or (r-2), wherein
Ring F1 is unsubstituted dihydrofuran; or thiazole substituted with one or more group(s) selected from alkyl,
or a pharmaceutically acceptable salt thereof.
(r-6) The compound of any one of the above (r-1) to (r-5), wherein Ring G1 is substituted or unsubstituted benzene, substituted or unsubstituted cyclohexane, substituted or unsubstituted pyridine, substituted or unsubstituted pyrazine, substituted or unsubstituted pyrimidine, substituted or unsubstituted pyran, substituted or unsubstituted dihydropyran, substituted or unsubstituted dihydropyridine, substituted or unsubstituted tetrahydropyridine, substituted or unsubstituted dihydropyrazine, substituted or unsubstituted tetrahydropyrazine, substituted or unsubstituted oxazine, substituted or unsubstituted dihydrooxazine, substituted or unsubstituted dioxin, or substituted or unsubstituted dihydrodioxin, or pharmaceutically acceptable salt thereof.
(r-7) The compound of any one of the above (r-1) to (r-6), wherein p1b is 0, or pharmaceutically acceptable salt thereof.
(r-8) The compound of any one of the above (r-1) to (r-6), wherein p1b is 1, or pharmaceutically acceptable salt thereof.
(r-9) The compound of any one of the above (r-1) to (r-8), wherein $R^{10a1}$ is halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynyl amino, or pharmaceutically acceptable salt thereof.
(r-10) The compound of any one of the above (r-1) to (r-8), wherein $R^{10a1}$ is halogen, substituted or unsubstituted alkyl, or substituted or unsubstituted alkyloxy, or pharmaceutically acceptable salt thereof.
(r-11) The compound of any one of the above (r-1) to (r-8), wherein $R^{10a1}$ is halogen, or pharmaceutically acceptable salt thereof.
(s) A compound according to any one of the following (s-1) to (s-6) or a pharmaceutically acceptable salt thereof.
(s-1) The compound of any one of Formula (I) and the above (a) to (r), wherein $R^{9a}$ and $R^{9b}$ are each independently halogen, hydroxy, amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.
(s-2) The compound according to any one of Formula (I) and the above (a) to (r), wherein
$R^{9a}$ and $R^{9b}$ are each independently halogen, substituted or unsubstituted alkyl, substituted or unsubstituted alkyloxy, substituted or unsubstituted alkylsulfanyl, or substituted or unsubstituted alkylamino,
or a pharmaceutically acceptable salt thereof.
(s-3) The compound of any one of Formula (I) and the above (a) to (r), wherein $R^{9a}$ and $R^{9b}$ are each independently halogen, substituted or unsubstituted alkyl, substituted or unsubstituted alkenyl, or substituted or unsubstituted alkynyl, or pharmaceutically acceptable salt thereof.
(s-4) The compound of any one of Formula (I) and the above (a) to (r), wherein $R^{9a}$ and $R^{9b}$ are each independently substituted or unsubstituted alkyl, or pharmaceutically acceptable salt thereof.
(s-5) The compound of any one of Formula (I) and the above (a) to (r), wherein $R^{9a}$ and $R^{9b}$ are each independently unsubstituted alkyl, or pharmaceutically acceptable salt thereof.
(s-6) The compound of any one of Formula (I) and the above (a) to (r), wherein $R^{9a}$ and $R^{9b}$ are each independently unsubstituted methyl or unsubstituted ethyl, or pharmaceutically acceptable salt thereof.
(s-7) The compound according to any one of Formula (I) and the above (a) to (r), wherein
$R^{9a}$ and $R^{9b}$ are each independently unsubstituted methyl,
or a pharmaceutically acceptable salt thereof.
(s-8) The compound according to any one of Formula (I) and the above (a) to (r),
wherein
$R^{9a}$ is unsubstituted methyl,
or a pharmaceutically acceptable salt thereof.
(t) A compound according to any one of the following (t-1) to (t-10) or a pharmaceutically acceptable salt thereof.
(t-1) The compound of any one of Formula (I) and the above (a) to (p), wherein $R^3$ is a group represented by the Formula:

[Chemical Formula 25]

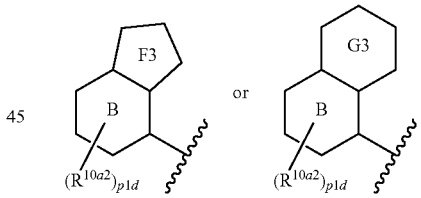

wherein Ring F3 is a substituted or unsubstituted 5-membered non-aromatic carbocycle, a substituted or unsubstituted 5-membered aromatic heterocycle, or a substituted or unsubstituted 5-membered non-aromatic heterocycle;
Ring G3 is a substituted or unsubstituted 6-membered aromatic carbocycle, a substituted or unsubstituted 6-membered non-aromatic carbocycle, a substituted or unsubstituted 6-membered aromatic heterocycle, or a substituted or unsubstituted 6-membered non-aromatic heterocycle;
Ring B is a 6-membered aromatic carbocycle or a 6-membered aromatic heterocycle,
p1d is 0 or 1; and
$R^{10a2}$ is the same as $R^{10a}$ of the above (q-1), or pharmaceutically acceptable salt thereof.
The above definition of $R^3$ means that $R^{10a1}$ is a substituent on Ring B.
(t-2) The compound of the above (t-1), wherein Ring F3 is substituted or unsubstituted cyclopentene, substituted or unsubstituted furan, substituted or unsubstituted thiophene, substituted or unsubstituted pyrrole, substituted or unsubstituted pyrazolo, substituted or unsubstituted imidazole, substituted or unsubstituted thiazole, substituted or unsubstituted oxazole, substituted or unsubstituted dihydrofuran, substituted or unsubstituted dihydrothiophene, substituted or unsubstituted dihydropyrrole, or substituted or unsubstituted dioxole, or pharmaceutically acceptable salt thereof.

(t-3) The compound of the above (t-1) or (t-2), wherein Ring G3 is substituted or unsubstituted benzene, substituted or unsubstituted cyclohexene, substituted or unsubstituted pyridine, substituted or unsubstituted pyrazino, substituted or unsubstituted pyrimidine, substituted or unsubstituted pyran, substituted or unsubstituted dihydropyran, substituted or unsubstituted dihydropyridine, substituted or unsubstituted tetrahydropyridine, substituted or unsubstituted dihydropyrazine, substituted or unsubstituted tetrahydropyrazine, substituted or unsubstituted oxazine, substituted or unsubstituted dihydrooxazine, substituted or unsubstituted dioxin, or substituted or unsubstituted dihydrodioxin, or pharmaceutically acceptable salt thereof.

(t-4) The compound of the above (t-1) or (t-2), wherein
Ring G3 is substituted or unsubstituted pyridine,
or a pharmaceutically acceptable salt thereof.

(t-5) The compound of any one of the above (t-1) or (t-2), wherein
Ring G3 is unsubstituted pyridine,
or a pharmaceutically acceptable salt thereof.

(t-6) The compound of any one of the above (t-1) to (t-5), wherein p1d is 0, or pharmaceutically acceptable salt thereof.

(t-7) The compound of any one of the above (t-1) to (t-5), wherein p1d is 1, or pharmaceutically acceptable salt thereof.

(t-8) The compound of any one of the above (t-1) to (t-7), wherein $R^{10a2}$ is halogen, hydroxy, amino, carbamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfanyl, substituted or unsubstituted alkenylsulfanyl, substituted or unsubstituted alkynylsulfanyl, substituted or unsubstituted alkylamino, substituted or unsubstituted alkenylamino, or substituted or unsubstituted alkynylamino, or pharmaceutically acceptable salt thereof.

(t-9) The compound of any one of the above (t-1) to (t-7), wherein $R^{10a2}$ is halogen, substituted or unsubstituted alkyl, or substituted or unsubstituted alkyloxy, or pharmaceutically acceptable salt thereof.

(t-10) The compound of any one of the above (t-1) to (t-7), wherein $R^{10a2}$ is halogen,
or a pharmaceutically acceptable salt thereof.

(u) A compound according to any one of the following (u-1) to (u-5),
or a pharmaceutically acceptable salt thereof.

(u-1) The compound of any one of Formula (I) and the above (a) to (t), wherein Ring B is benzene, cyclohexene, or a 6-membered aromatic heterocycle, or pharmaceutically acceptable salt thereof.

(u-2) The compound of any one of Formula (I) and the above (a) to (t), wherein Ring B is benzene, or a 6-membered aromatic heterocycle, or pharmaceutically acceptable salt thereof.

(u-3) The compound of any one of Formula (I) and the above (a) to (t), wherein Ring B is benzene, pyridine, pyrimidine, or pyrazine, or pharmaceutically acceptable salt thereof.

(u-4) The compound of any one of Formula (I) and the above (a) to (t), wherein Ring B is benzene, or pyridine, or pharmaceutically acceptable salt thereof.

(u-5) The compound of any one of Formula (I) and the above (a) to (t), wherein Ring B is benzene, or pharmaceutically acceptable salt thereof.

(v) A compound according to any one of the following (v-1) to (v-4) or a pharmaceutically acceptable salt thereof.

(v-1) The compound of any one of Formula (I) and the above (a) to (u), wherein Ring C is cyclopentane, or a 5-membered aromatic heterocycle, or pharmaceutically acceptable salt thereof.

(v-2) The compound of any one of Formula (I) and the above (a) to (u), wherein Ring C is a 5-membered aromatic heterocycle, or pharmaceutically acceptable salt thereof.

(v3) The compound of any one of Formula (I) and the above (a) to (u), wherein Ring C is pyrrole, pyrazole, or imidazole, or a pharmaceutically acceptable salt thereof.

(v4) The compound of any one of Formula (I) and the above (a) to (u), wherein
Ring C is pyrazole,
or a pharmaceutically acceptable salt thereof.

The compounds represented by Formula (I) are not limited to specific isomers but include all possible isomers (e.g., keto-enol isomers, imine-enamine isomers, diastereoisomers, enantiomers, rotamers or the like), racemates or mixtures thereof.

For example, a compound represented by Formula (I) wherein $R^{7a}$ is a hydrogen atom includes the following tautomer.

[Chemical Formula 26]

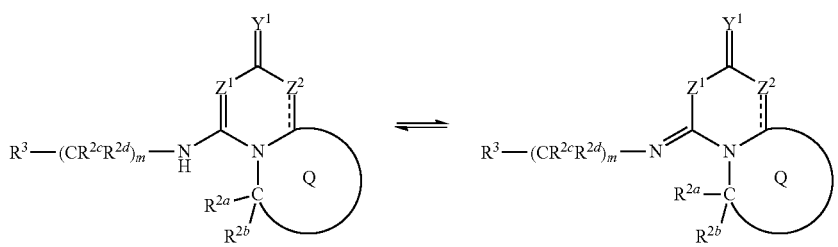

When the dashed line represents the absence of a bond in the compound represented by Formula (I), then a double bond is formed between carbon atoms adjacent to $Z^2$ and N and ring-constituting atoms of Ring Q to which the carbon atoms are adjacent.

In the present specification, in a group represented by the Formula:

[Chemical Formula 27]

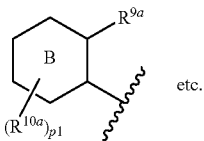

p1 hydrogen atom(s) which is attached to a ring-constituting atom on Ring B can be replaced with $R^{10a}$.

In the present specification, in a group represented by the Formula:

[Chemical Formula 28]

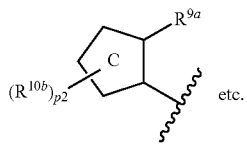

p2 hydrogen atom(s) which is attached to a ring-constituting atom on Ring C can be replaced with $R^{10b}$.

In the present specification, in a group represented by the Formula:

[Chemical Formula 29]

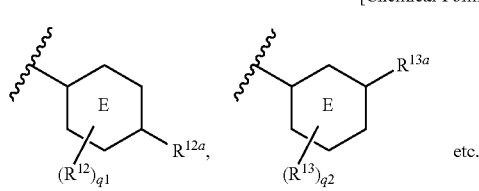

q1 hydrogen atom(s) which is attached to a ring-constituting atom on Ring E can be replaced with $R^{12}$. q2 hydrogen atom(s) which is attached to a ring-constituting atom on Ring E can be replaced with $R^{13}$.

In the present specification, in a group represented by the Formula:

[Chemical Formula 30]

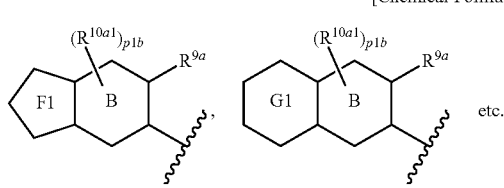

p1b hydrogen atom(s) which is attached to a ring-constituting atom on Ring B can be replaced with $R^{10a1}$.

In the present specification, in a group represented by the Formula:

[Chemical Formula 31]

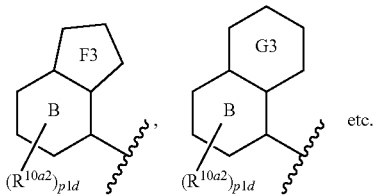

p1d hydrogen atom(s) which is attached to a ring-constituting atom on Ring B can be replaced with $R^{10a2}$.

One or more hydrogen, carbon and/or other atoms in the compounds represented by Formula (I) may be replaced with isotopes of hydrogen, carbon and/or other atoms respectively. Example s of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by Formula (I) include the compounds replaced with these isotopes. The compounds replaced with the above isotopes are useful as medicines and include all of radiolabeled compounds of the compound of Formula (I). A "method of radiolabeling" in the manufacture of the "radiolabeled compounds" is encompassed by the present invention, and the "radiolabeled compounds" are useful for studies on metabolized drug pharmacokinetics, studies on binding assay and/or diagnostic tools.

A radiolabeled compound of the compounds represented by Formula (I) can be prepared using well-known methods in the art. For example, a tritium-labeled compound represented by Formula (I) can be prepared by introducing a tritium to a certain compound represented by Formula (I), through a catalytic dehalogenation reaction using a tritium. This method comprises reacting with an appropriately-halogenated precursor of the compound represented by Formula (I) with tritium gas in the presence of an appropriate catalyst, such as Pd/C, and in the presence or absent of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by Formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by Formula (I) of the present invention or pharmaceutically acceptable salts thereof may form solvates (e.g., hydrates or the like) and/or crystal polymorphs. The present invention encompasses those various solvates and crystal polymorphs. "Solvates" may be those wherein any numbers of solvent molecules (e.g., water molecules or the like) are coordinated with the compounds represented by Formula (I). When the compounds represented by Formula (I) or pharmaceutically acceptable salts thereof are allowed to stand in the atmosphere, the compounds may absorb water, resulting in attachment of adsorbed water or formation of hydrates. Recrystallization of the compounds represented by Formula (I) or pharmaceutically acceptable salts thereof may produce crystal polymorphs.

The compounds represented by Formula (T) of the present invention or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions in vivo. Prodrugs include compounds that are converted to the compounds represented by Formula (I) through enzymatic oxidation, reduction, hydrolysis or the like under physiological conditions in vivo, compounds that are converted to the compounds represented by Formula (I) through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by Formula (I) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-Ph$SO_3-$, Ph$SO_3-$ and p-$CH_3$Ph$SO_3$.

The compounds of the present invention have an antagonistic activity for the $P2X_7$ receptor, and therefore, are useful as a therapeutic and/or preventive agent for diseases associated with the $P2X_7$ receptor. As the diseases associated with the $P2X_7$ receptor, pain, central nervous system diseases, immune diseases and inflammatory diseases and the like, preferably pain are exemplified (Non-patent Document 7-8 and Patent Document 1 etc.).

As pain, pain associated with zoster, postherpetic neuralgia, trigeminal neuralgia, thalamic pain, cancer pain, postoperative pain, menstrual pain, labor pain, chest pain, abdominal pain, colic pain, lumbar backache, headache, migraine, sciatica, sore muscle, orofacial pain, toothache, glossagra, shoulder pain, nociceptive pain, pain associated with deafferentation, psychogenic pain and the like; pain associated with the disease such as entrapment neuropathy, carpal canal syndrome, diabetes, Guillain-Barre syndrome, myofascial pain syndrome, fibromyalgia syndrome, complex regional pain syndrome, causalgia, Hansen's disease, spinal cord injury, stroke, multiple sclerosis, Parkinson's disease, endometriosis, hernia of intervertebral disk, arthritis, rheumatoid arthritis, osteoarthritis, cervical spondylosis deformans, spinal canal stenosis, thoracic outlet syndrome, traumatic brachial plexus injury syndrome, shoulder-hand syndrome, whiplash injury, cholelithiasis, pancreatitis, cystitis, urethritis, urinary calculosis, prostatitis, ulcerative colitis, Crohn's disease, irritable bowel syndrome, bone fracture, osteoporosis, gout, cauda equina syndrome, ankylosing spondylitis, painful spasm, ABC syndrome, skin disease, arteriosclerosis obliterans, Buerger's disease, Raynaud's phenomenon, gangrene, temporomandibular arthrosis, somatoform disorder, somatization disorder, depression and the like;

pain associated with drug therapy, and pain associated with radiation therapy are exemplified. Additionally, effects for opioid tolerance can be expected.

Preferably, as pain, pain associated with zoster, postherpetic neuralgia, trigeminal neuralgia, thalamic pain, cancer pain, postoperative pain, sciatica, pain associated with deafferentation and the like;

pain associated with the disease such as entrapment neuropathy, carpal canal syndrome, diabetes, Guillain-Barre syndrome, myofascial pain syndrome, fibromyalgia syndrome, complex regional pain syndrome, causalgia, spinal cord injury, stroke, multiple sclerosis, Parkinson's disease, hernia of intervertebral disk, arthritis, rheumatoid arthritis, osteoarthritis, cervical spondylosis deformans, spinal canal stenosis, traumatic brachial plexus injury syndrome, shoulder-hand syndrome, cystitis, ulcerative colitis, Crohn's disease, irritable bowel syndrome, gout, depression and the like;

pain associated with drug therapy, and pain associated with radiation therapy are exemplified. Additionally, effects for opioid tolerance can be expected.

As central nervous system diseases, Alzheimer's disease, Cerebral amyloid angiopathy, Parkinson's disease, Creutzfeldt-Jakob disease, Huntington's chorea, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

Preferably, as central nervous system diseases, Alzheimer's disease, Cerebral amyloid angiopathy, Parkinson's disease, depression, schizophrenia, attention deficit hyperactivity disorder, sleep disorder, autism spectrum disorder, epilepsy, stroke, multiple sclerosis, spinal cord injury, amyotrophic lateral sclerosis, opioid dependence, cocaine dependence, nicotine dependence and the like are exemplified.

As immune diseases and inflammatory diseases, rheumatoid arthritis, osteoarthritis, asthma, bronchitis, chronic obstructive pulmonary disease, pulmonary emphysema, septic shock, hepatitis, hepatic fibrosis, hepatic cirrhosis, cholecystitis, glomerulonephritis, nephrotic syndrome, pancreatitis, cystitis, urethritis, prostatitis, ulcerative colitis, Crohn's disease, irritable bowel syndrome, psoriasis, atopic dermatitis, contact dermatitis, eczematous dermatitis, delayed-type hypersensitivity reaction, conjunctivitis, uveitis, growth and metastasis of malignant cell (prostate cancer, breast cancer, lung cancer, uterine cancer, pancreatic cancer, colorectal cancer etc.), leukemia, meningitis, burn injury, glossitis, gingivitis, periodontal disease, esophagitis and the like are exemplified. It is possible that rejection associated with allograft or blood transfusion is involved in the P2X7 receptor. As the other diseases associated with the P2X7 receptor, circulatory diseases such as atherosclerosis, ischemic heart disease, diabetes and the like, bone diseases such as osteoporosis, bone Paget's disease, osteonecrosis, temporomandibular arthrosis and the like, and urologic diseases such as overactive bladder, stress urinary incontinence, prostatomegaly and the like are exemplified.

Preferably, as immune diseases and inflammatory diseases, rheumatoid arthritis, arthritis, osteoarthritis, asthma, bronchitis, chronic obstructive pulmonary disease, cystitis, ulcerative colitis, Crohn's disease and the like are exemplified.

(Synthetic Procedures for the Compound of the Present Invention)

For example, the compounds represented by Formula (I) of the present invention can be prepared by the general procedures described below. The starting materials and reaction reagents used in such synthesis are commercially available or can be synthesized according to methods well known in the art using the compounds commercially available. The methods for extraction, purification and the like may be carried out by using the usual method for the experiments of organic chemistry.

The compounds of the present invention can be synthesized by referring to the known methods in the art.

In all the following steps, when a substituent which interferes with the reaction, e.g. hydroxy, mercapto, amino, formyl, carbonyl, carboxy, is possessed, the substituent is protected by the method such as those described in Protective Groups in Organic Synthesis, Theodora W Greene (John Wiley & Sons) in advance, and the protective group may be removed at a desirable step.

During all the following steps, the order of the steps to be performed may be appropriately changed. In each step, an intermediate may be isolated and then used in the next step.

In this description, meanings of each abbreviation are as follows:

BINAP: 2,2'-bis(Diphenylphosphino)-1,1'-binaphthyl
Boc: tert-Butoxycarbonyl
Cbz: Benzyloxycarbonyl
DEAD: Diethyl azodicarboxylate
D1AD: Diisopropyl azodicarboxylate
DIBAL: Diisobutylaluminum hydride
DIEA: N,N-Diisopropylethylamine
DMA: N,N-Dimethylacetamide
DMAP: 4-Dimethylaminopyridine
DMF: N,N-Dimethylformamide
DMSO: Dimethylsulfoxide
DPPF: 1,1'-bis(Diphenylphosphino)ferrocene
EDC: 1-Ethyl-3-(3-dimethylaminopropyl)carbodiimide
HATU: O-(7-Azabenzotriazol-1-yl)-1,1,3,3-tetramethyluronium hexafluorophosphate
Me: Methyl
NBS: N-Bromosuccinimide
NCS: N-Chlorosuccinimide
NIS: N-Iodosuccinimide
NMP: N-Methylpyrrolidone
Pd$_2$(dba)$_3$: bis(Dibenzylideneacetone)palladium
Pd(OAc)$_2$: Palladium acetate
Pd(PPh$_3$)$_4$: Tetrakis(triphenylphosphine)palladium
Pd$_2$(dba)$_3$: tris(Dibenzylideneacetone)bispalladium
PdCl$_2$(dppf): [1,1'-bis(Diphenylphosphino)ferrocene]palladium(II) dichloride
Ph: Phenyl
PMB: para-Methoxybenzyl
TBAF: Tetrabutylammonium fluoride
TBDPS: tert-Butyldiphenylsilyl
TBS: tert-Butyldimethylsilyl
TFA: Trifluoroacetic acid
t-Bu: tert-Butyl Xantphos: 4,5'-bis(Diphenylphosphino)-9,9'-dimethylxanthene
X-Phos: 2,4,6-Triisopropyl-2'-(dicyclohexylphosphino)biphenyl

[Method A]

[Chemical Formula 32]

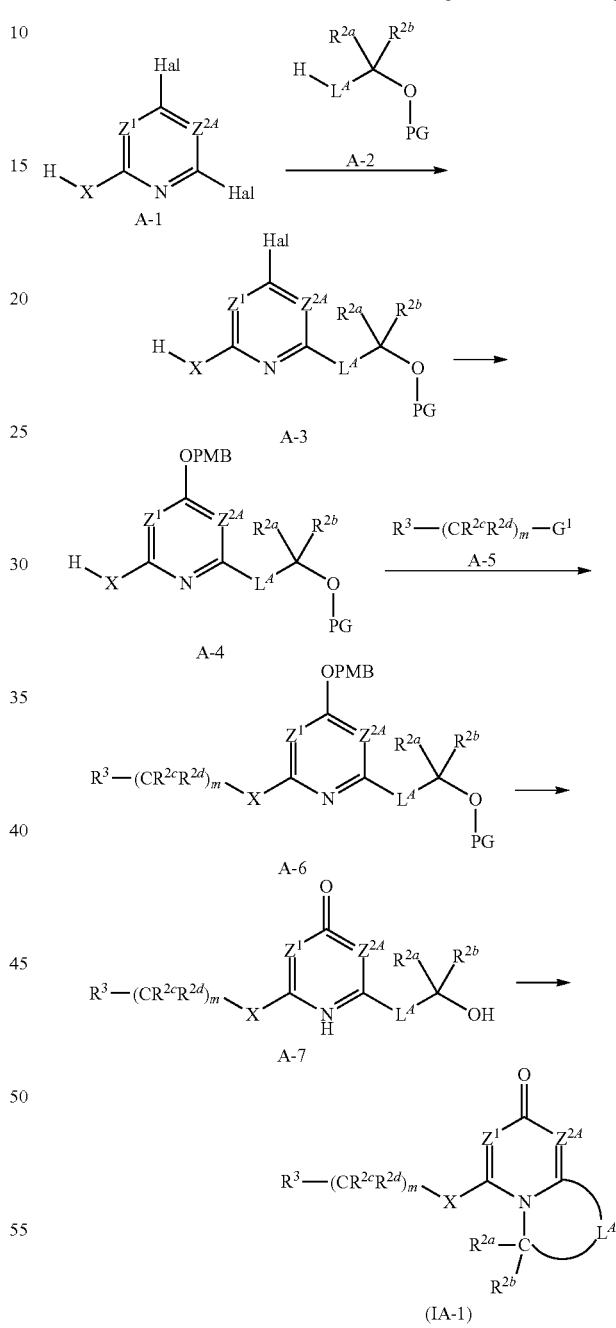

wherein
Hal is each independently halogen;
PG is an appropriate protecting group of a hydroxy group;
G$^1$ is a leaving group such as halogen, substituted or unsubstituted alkylsulfanyl, substituted or unsubstituted alkylsulfinyl, or substituted or unsubstituted alkylsulfonyl;

-$L^A$- is an appropriate group forming Ring Q and represented by -$L^{A'}$-C($R^{41}$)($R^{42}$)—, -$L^{A'}$-(C($R^{41}$)($R^{42}$))$_2$— or the like;

-$L^{A'}$ is N($R^{43}$), O, S or the like; $R^{41}$, $R^{42}$, and $R^{43}$ are each independently a hydrogen atom or a group selected from the substituent group C1;

$Z^{2A}$ is C($R^{5a}$) or N; and the other symbols are the same as the above (1).

Step 1

A compound (A-3) can be synthesized by the reaction of the compound (A-1) with a compound (A-2) in the presence of abase in the appropriate solvent.

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 2.0 mole equivalent(s) can be used per an equivalent of the compound (A-2).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine and the like are exemplified. The reaction solvent may be used alone or in combination.

The reaction temperature is 0° C. to 80° C., preferably 0° C. to 40° C.

The reaction time is 0.5 hours to 48 hours, preferably 1 hour to 16 hours.

The obtained desired compound (A-3) can be purified as necessary by the methods which are usually used (e.g., column chromatography, recrystallization etc.).

Step 2

A compound (A-4) can be synthesized by the reaction of the compound (A-3) with para-methoxybenzyl alcohol in the presence of a base in the appropriate solvent.

In this reaction, 1.0 or more mole equivalent(s) of the para-methoxybenzyl alcohol, preferably 1.0 to 3.0 mole equivalent(s) can be used per an equivalent of the compound (A-3).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.) and the like are exemplified. 1.0 or more mole equivalent(s), preferably 1.0 to 2.0 mole equivalent(s) can be used per an equivalent of the compound (A-3).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), NMP, acetonitrile, DMA and the like are exemplified. The reaction solvent may be used alone or in combination.

The reaction temperature is 0° C. to 100° C., preferably 0° C. to 80° C.

The reaction time is 0.5 hours to 24 hours, preferably 1 hour to 8 hours.

The obtained desired compound (A-4) can be purified as necessary by the methods which are usually used (e.g., column chromatography, recrystallization etc.).

Step 3

A compound (A-6) can be synthesized by the reaction of the compound (A-4) with the compound (A-5) in the presence of a metal catalyst and a ligand, or a base or an acid without any solvent or in the appropriate solvent as necessary.

In this reaction, 1.0 or more mole equivalent(s) of the compound (A-5), preferably 1.0 to 5.0 mole equivalent(s) can be used per an equivalent of the compound (A-4).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (A-4).

As the acid, for example, acetic acid, propionic acid and the like are exemplified. 1.0 or more mole equivalent(s), preferably 1.0 to 5.0 mole equivalent(s) can be used per an equivalent of the compound (A-4).

As the metal catalyst, Pd(OAc)$_2$, Pd$_2$(dba)$_3$, Pd(PPh$_3$)$_4$, bis(triphenylphosphine)palladium(II) dichloride, bis(tri-tert-hutylphosphine) palladium, PdCl$_2$(dppf) and the like are exemplified. 0.001 to 0.5 mole equivalent(s) can be used per an equivalent of the compound (A-4).

As the ligand, DPPF, BINAP, Xantphos, X-Phos and the like are exemplified. 0.001 to 0.5 mole equivalent(s) can be used per an equivalent of the compound (A-4).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), halogenated hydrocarbons (e.g., chloroform, dichloromethane etc.), DMF, DMSO, NMP, acetonitrile, pyridine, water and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 hours to 18 hours.

The obtained desired compound (A-6) can be purified as necessary by the methods which are usually used (e.g., column chromatography, recrystallization etc.).

Step 4

A compound (A-7) can be synthesized by the reaction of the compound (A-6) in the presence of an acid without any solvent or in the appropriate solvent.

As the acid, for example, hydrochloric acid, sulfuric acid, hydrobromic acid, TFA, acetic acid and the like are exemplified. 1.0 or more mole equivalent(s), preferably 1.0 to 5.0 mole equivalent(s) can be used per an equivalent of the compound (A-6).

As the reaction solvent, alcohols (e.g., tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), hydrocarbon halides (e.g., chloroform, dichloromethane etc.), acetonitrile, water and the like are exemplified. The reaction solvent may be used alone or in combination.

The reaction temperature is 0 to 150° C., under microwave irradiation as necessary, preferably 0 to 100° C.

The reaction time is 0.1 to 24 hours, preferably 0.5 hours to 8 hours.

The obtained desired compound (A-7) can be purified as necessary by the methods which are usually used (e.g., column chromatography, recrystallization etc.).

Step 5

A compound (IA-1) can be synthesized by the reaction of the compound (A-7) in the presence of triphenylphosphine and a condensing agent or in the presence of a base in the appropriate solvent.

As the condensing agent, DEAD, DIAD, iodine and the like are exemplified. 1.0 or more mole equivalent(s), preferably 1.0 to 5.0 mole equivalent(s) can be used per an equivalent of the compound A-7.

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium bicarbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 2.0 or more mole equivalent(s), preferably 2.0 to 5.0 mole equivalent(s) can be used per an equivalent of the compound (A-7).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), hydrocarbon halides (e.g., chloroform, dichloromethane etc.), ethyl acetate, acetonitrile and the like are exemplified. The reaction solvent may be used alone or in combination.

The reaction temperature is 0° C. to 80° C., preferably 10° C. to 40° C.

The reaction time is 0.1 hours to 12 hours, preferably 0.2 hours to 6 hours.

The obtained desired compound (IA-1) can be purified by the methods which are usually used (e.g., column chromatography, recrystallization etc.) and can be optically resolved by preparative SFC (liquid carbon dioxide-methanol) using a chiral column, as necessary.

[Method B]

[Chemical Formula 33]

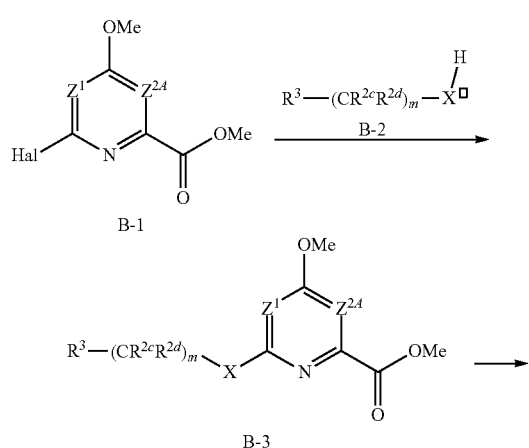

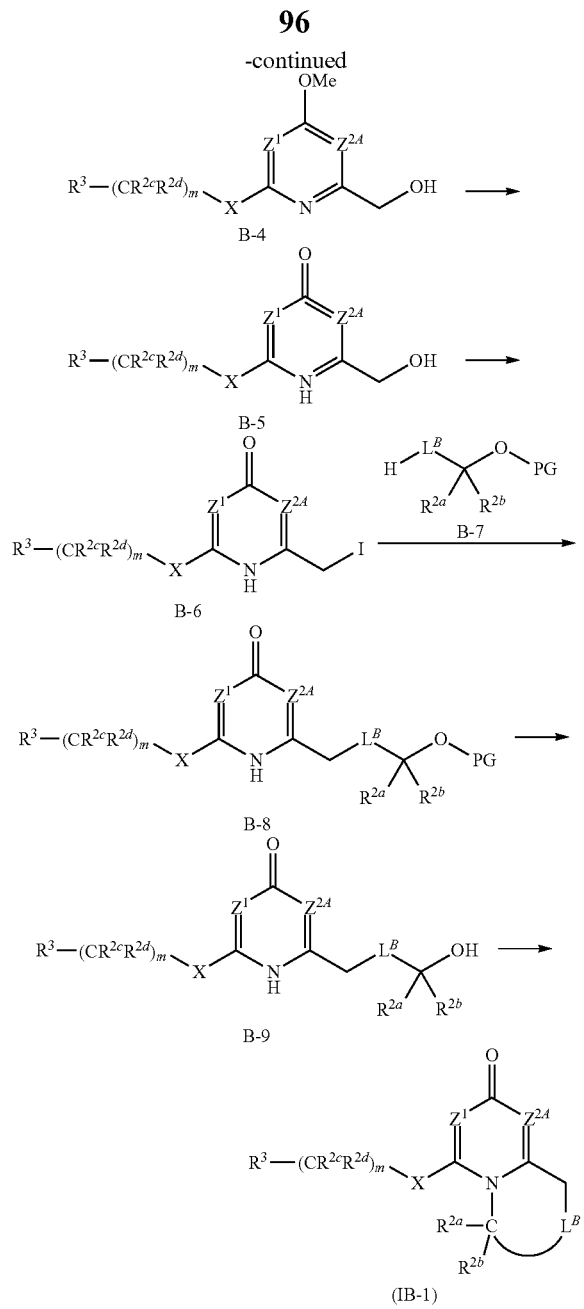

wherein

Hal is each independently halogen;

PG is an appropriate protecting group of a hydroxy group;

-$L^B$- is an appropriate group forming Ring Q and represented by -$L^{B'}$—C($R^{A1}$)($R^{A2}$)— or the like;

-$L^{B'}$ is N($R^{A3}$), O, S or the like;

$R^{A1}$, $R^{A2}$, $R^{A3}$, and $Z^{2A}$ are the same as the method A; and the other symbols are the same as the above (1).

Step 1

A compound (B-3) can be synthesized by the reaction of the compound (B-1) with the compound (B-2) in the presence of a palladium catalyst and a ligand or in the presence of a base without any solvent or in the appropriate solvent as necessary.

In this reaction, 1.0 or more mole equivalent(s) of the compound (B-2), preferably 1.0 to 3.0 mole equivalent(s) can be used per an equivalent of the compound (B-1).

As the palladium catalyst, Pd(OAc)$_2$, Pd$_2$(dba)$_3$, Pd(PPh$_3$)$_4$, bis(triphenylphosphine)palladium(II) dichloride, bis(tri-tert-butylphosphine)palladium, PdCl$_2$(dppf) and the like are exemplified. 0.001 to 0.5 mole equivalent(s) can be used per an equivalent of the compound (B-1).

As the ligand, for example, triphenylphosphine, DPPF, BINAP, Xantphos, X-Phos and the like are exemplified. 0.001 to 0.5 mole equivalent(s) can be used per an equivalent of the compound (B-1).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 1.0 or more mole equivalent(s), preferably 1.0 to 5.0 mole equivalent(s) can be used per an equivalent of the compound (B-1).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), hydrocarbon halides (e.g., chloroform, dichloromethane etc.), DMF, DMSO, NMP, acetonitrile, pyridine and the like are exemplified. The reaction solvent may be used alone or in combination.

The reaction temperature is 0 to 200° C., under microwave irradiation as necessary, preferably 0 to 150° C.

The reaction time is 0.1 to 72 hours, preferably 0.5 hours to 18 hours. The obtained desired compound (B-3) can be purified as necessary by the methods which are usually used (e.g., column chromatography, recrystallization etc.).

Step 2

A compound (B-4) can be synthesized by the reaction of the compound (B-3) with a reducing agent in the appropriate solvent.

As the reducing agent, sodium borohydride, lithium borohydride, lithium aluminum hydride, DIBAL and the like are exemplified. 1.0 or more mole equivalent(s), preferably 1.0 to 10.0 mole equivalent(s) can be used per an equivalent of the compound (B-3).

As the reaction solvent, alcohols (e.g., methanol, ethanol, tert-butanol, isopropanol etc.), aromatic hydrocarbons (e.g., toluene, benzene, xylene etc.), ethers (e.g., tetrahydrofuran, diethylether, dioxane, dimethoxyethane etc.), hydrocarbon halides (e.g., chloroform, dichloromethane etc.), DMF, NMP, acetonitrile, water and the like are exemplified. The reaction solvent may be used alone or in combination.

The reaction temperature is 0 to 150° C., preferably 20 to 150° C.

The reaction time is 0.1 to 48 hours, preferably 1 hour to 24 hours.

The obtained desired compound (B-4) can be purified as necessary by the methods which are usually used (e.g., column chromatography, recrystallization etc.).

Step 3

A compound (B-5) can be synthesized by the reaction of the compound (B-4) according to the synthetic procedures described in the step 4 of the method A.

The obtained desired compound (B-5) can be purified as necessary by the methods which are usually used (e.g., column chromatography, recrystallization etc.).

Step 4

A compound (B-6) can be synthesized by the reaction of the compound (B-5) in the presence of triphenylphosphine, imidazole, and iodine in the appropriate solvent.

In this reaction, 1.0 or more mole equivalent(s) of triphenylphosphine, preferably 1.0 to 3.0 mole equivalent(s) can be used per an equivalent of the compound (B-5).

In this reaction, 1.0 or more mole equivalent(s) of imidazole, preferably 1.0 to 5.0 mole equivalent(s) can be used per an equivalent of the compound (B-5).

In this reaction, 1.0 or more mole equivalent(s) of iodine, preferably 1.0 to 3.0 mole equivalent(s) can be used per an equivalent of the compound (B-5).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), hydrocarbon halides (e.g., chloroform, dichloromethane etc.), ethyl acetate, acetonitrile and the like are exemplified. The reaction solvent may be used alone or in combination.

The reaction temperature is 0° C. to 80° C., preferably 10° C. to 40° C.

The reaction time is 0.1 hours to 12 hours, preferably 0.2 hours to 6 hours.

The obtained desired compound (B-6) can be purified as necessary by the methods which are usually used (e.g., column chromatography, recrystallization etc.).

Step 5

A compound (B-8) can be synthesized by the reaction of the compound (B-6) with the compound (B-7) according to the synthetic procedures described in the step 1 of the method A.

The obtained desired compound (B-8) can be purified as necessary by the methods which are usually used (e.g., column chromatography, recrystallization etc.).

Step 6

A compound (B-9) can be synthesized by the reaction of the compound (B-8) according to the synthetic procedures described in the step 4 of the method A.

The obtained desired compound (B-9) can be purified as necessary by the methods which are usually used (e.g., column chromatography, recrystallization etc.).

Step 7

A compound (IB-1) can be synthesized by the reaction of the compound (B-9) according to the synthetic procedures described in the step 5 of the method A.

The obtained desired compound (IB-1) can be purified by the methods which are usually used (e.g., column chromatography, recrystallization etc.) and can be optically resolved by preparative SFC (liquid carbon dioxide-methanol) using a chiral column, as necessary.

[Method C1]

[Chemical Formula 34]

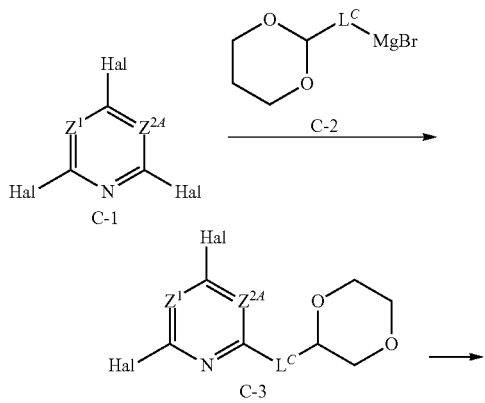

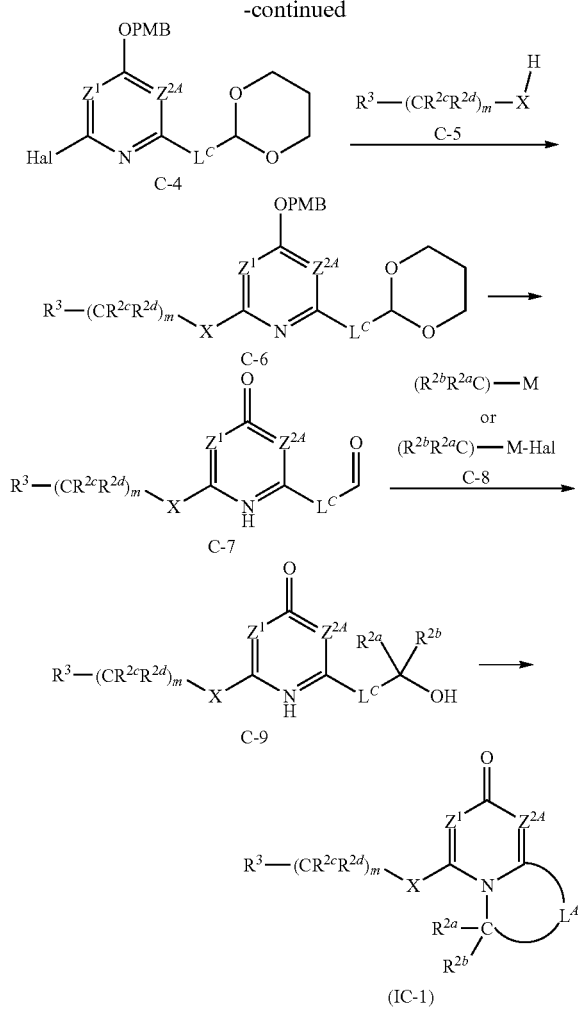

wherein
M is alkaline metal or alkaline earth metal;
Hal is each independently halogen;
-$L^C$- is an appropriate group forming Ring Q and represented by —(C($R^{A1}$)($R^{A2}$))$_2$—, —(C($R^{A1}$)($R^{A2}$))$_3$— or the like;
$R^{A1}$, $R^{A2}$, and $Z^{2A}$ are the same as the method A; and
the other symbols are the same as the above (1).

Step 1

A compound (C-3) can be synthesized by the reaction of the compound (C-4) with the compound (C-2) in the presence of a metal catalyst in the appropriate solvent.

In this reaction, 1.0 or more mole equivalent(s) of the compound (C-2), preferably 1.0 to 3.0 mole equivalent(s) can be used per an equivalent of the compound (C-1).

As the metal catalyst, for example, trisacetylacetonato iron and the like are exemplified. 0.001 to 0.5 mole equivalent(s) can be used per an equivalent of the compound (C-1).

As the reaction solvent, aromatic hydrocarbons (e.g., toluene, benzene, xylene etc.), ethers (e.g., tetrahydrofuran, diethylether, dioxane, dimethoxyethane etc.) and the like are exemplified. The reaction solvent may be used alone or in combination.

The reaction temperature is −78 to 100° C., preferably −78 to 40° C.

The reaction time is 0.1 to 8 hours, preferably 0.2 hours to 4 hours.

The obtained desired compound (C-3) can be purified as necessary by the methods which are usually used (e.g., column chromatography, recrystallization etc.).

Step 2

A compound (C-4) can be synthesized by the reaction of the compound (C-3) according to the synthetic procedures described in the step 2 of the method A.

The obtained desired compound (C-4) can be purified as necessary by the methods which are usually used (e.g., column chromatography, recrystallization etc.).

Step 3

A compound (C-6) can be synthesized by the reaction of the compound (C-4) with the compound (C-5) according to the synthetic procedures described in the step 1 of the method B.

The obtained desired compound (C-6) can be purified as necessary by the methods which are usually used (e.g., column chromatography, recrystallization etc.).

Step 4

A compound (C-7) can be synthesized by the reaction of the compound (C-6) according to the synthetic procedures described in the step 4 of the method A.

The obtained desired compound (C-7) can be purified as necessary by the methods which are usually used (e.g., column chromatography, recrystallization etc.).

Step 5

A compound (C-9) can be synthesized by the reaction of the compound (C-7) with a nucleophile (C-8) in the appropriate solvent.

As the nucleophile (C-8), organic lithium reagents (alkyl lithium, allyl lithium etc.), Grignard reagents (alkylmagnesium bromide, allylmagnesium bromide etc.), and mixed reagents of these with metal salts are exemplified. 1.0 or more mole equivalent(s), preferably 1.0 to 5.0 mole equivalent(s) can be used per an equivalent of the compound (C-7).

As the reaction solvent, aromatic hydrocarbons (e.g., toluene, benzene, xylene etc.), ethers (e.g., tetrahydrofuran, diethylether, dioxane, dimethoxyethane etc.) and the like are exemplified. The reaction solvent may be used alone or in combination.

The reaction temperature is −78 to the reflux temperature of the solvent, preferably −40 to 0° C.

The reaction time is 0.5 to 24 hours, preferably 1 hour to 8 hours. The obtained desired compound (C-9) can be purified as necessary by the methods which are usually used (e.g., column chromatography, recrystallization etc.).

The nucleophile (C-8) can be adjusted by the lithiation of a halide represented by ($R^{2c}R^{2d}$C)—X using an alkyl lithium such as n-butyllithium.

As the reaction solvent, tetrahydrofuran, dioxane and the like are exemplified. The reaction solvent is not specifically limited as long as it is a solvent that does not react with alkyl lithium. The temperature of the lithiation reaction is preferably about −78° C. to 0° C.

Step 6

A compound (IC-1) can be synthesized by the cyclization of the compound (C-9) according to the synthetic procedures described in the step 5 of the method A.

The obtained desired compound (IC-1) can be purified by the methods which are usually used (e.g., column chromatography, recrystallization etc.) and can be optically resolved by preparative SFC (liquid carbon dioxide-methanol) using a chiral column, as necessary.

[Method D]

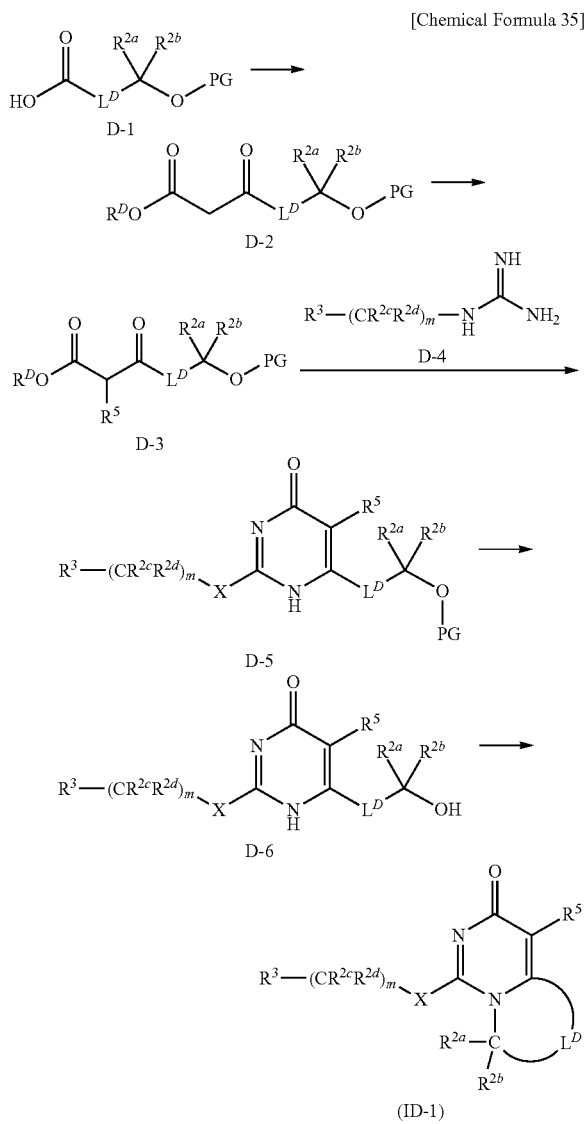

wherein
PG is an appropriate protecting group of a hydroxy group;
$R^D$ is substituted or unsubstituted alkyl;
-$L^D$- is an appropriate group forming Ring Q and represented by —(C($R^{41}$)($R^{42}$))$_2$—, —(C($R^{41}$)($R^{42}$))$_3$— or the like;
$R^{41}$ and $R^{42}$ are the same as the method A; and
the other symbols are the same as the above (1).

Step 1
A compound (D-2) can be synthesized by the reaction of the compound (D-1) with Meldrum's acid in the presence of a condensing agent and a base in the appropriate solvent.

In this reaction, 1.0 or more mole equivalent(s) of the Meldrum's acid, preferably 1.0 to 3.0 mole equivalent(s) can be used per an equivalent of the compound (D-1).

As the condensing agent, dicyclohexylcarbodiimide, carbonyl diimidazole, dicyclohexylcarbodiimide-N-hydroxybenzotriazole, EDC, 4-(4,6-dimethoxy-1,3,5,-triazin-2-yl)-4-methylmorpholinium chloride, HATU and the like are exemplified. 1 to 5 mole equivalent(s) can be used per an equivalent of a compound i1.

As the base, for example, metal carbonate (e.g., sodium carbonate, potassium carbonate, cesium carbonate etc.), pyridine, triethylamine, DIEA and the like are exemplified. 1.0 or more mole equivalent(s), preferably 1.0 to 5.0 mole equivalent(s) can be used per an equivalent of the compound (D-1).

As the reaction solvent, ethers (e.g., tetrahydrofuran, diethylether, dioxane, dimethoxyethane etc.), hydrocarbon halides (e.g., chloroform, dichloromethane etc.), DMA, DMF, DMSO, NMP, acetonitrile and the like are exemplified. The reaction solvent may be used alone or in combination.

The reaction temperature is −20° C. to 60° C., preferably 0° C. to 30° C.

The reaction time is 0.1 to 24 hours, preferably 1 hour to 12 hours.

The obtained desired compound (D-2) can be purified as necessary by the methods which are usually used (e.g., column chromatography, recrystallization etc.).

Step 2
A compound (D-3) can be synthesized by the reaction of the compound (D-2) with an oxidizing agent in the appropriate solvent.

As the oxidizing agent, for example, 1-chloromethyl-4-fluoro-1,4-diazoniabicyclo[2,2,2]octane bis(tetrafluoroborate), iodobenzene diacetate and the like are exemplified. 1.0 or more mole equivalent(s), preferably 1.0 to 3.0 mole equivalent(s) can be used per an equivalent of the compound (D-2).

As the reaction solvent, alcohols (e.g., methanol, ethanol, tert-butanol, isopropanol etc.), aromatic hydrocarbons (e.g., toluene, benzene, xylene etc.), ethers (e.g., tetrahydrofuran, diethylether, dioxane, dimethoxyethane etc.), acetonitrile and the like are exemplified. The reaction solvent may be used alone or in combination.

The reaction temperature is 0 to 60° C., preferably 0 to 40° C.

The reaction time is 0.1 to 144 hours, preferably 1 hour to 24 hours.

The obtained desired compound (D-3) can be purified as necessary by the methods which are usually used (e.g., column chromatography, recrystallization etc.).

Step 3
A compound (D-5) can be synthesized by the cyclization of the compound (D-3) with the compound (D-4) in the presence of a base in the appropriate solvent.

In this reaction, 1.0 or more mole equivalent(s) of the compound (D-4), preferably 1.0 to 2.0 mole equivalent(s) can be used per an equivalent of the compound (D-3).

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 2.0 or more mole equivalent(s), preferably 2.0 to 5.0 mole equivalent(s) can be used per an equivalent of the compound (D-4).

As the reaction solvent, alcohols (e.g., methanol, ethanol, tert-butanol, isopropanol etc.), aromatic hydrocarbons (e.g., toluene, benzene, xylene etc.), ethers (e.g., tetrahydrofuran, diethylether, dioxane, dimethoxyethane etc.), hydrocarbon halides (e.g., chloroform, dichloromethane etc.), acetonitrile and the like are exemplified. The reaction solvent may be used alone or in combination.

The reaction temperature is 0° C. to the reflux temperature of the solvent, preferably 20 to 80° C.

The reaction time is 0.1 to 24 hours, preferably 1 hour to 8 hours.

The obtained desired compound (D-5) can be purified as necessary by the methods which are usually used (e.g., column chromatography, recrystallization etc.).

Step 4

A compound (D-6) can be synthesized by the reaction of the compound (D-5) according to the synthetic procedures described in the step 4 of the method A.

The obtained desired compound (D-6) can be purified as necessary by the methods which are usually used (e.g., column chromatography, recrystallization etc.).

Step 5

A compound (ID-1) can be synthesized by the cyclization of the compound (D-6) according to the synthetic procedures described in the step 5 of the method A.

The obtained desired compound (ID-1) can be purified by the methods which are usually used (e.g., column chromatography, recrystallization etc.) and can be optically resolved by preparative SFC (liquid carbon dioxide-methanol) using a chiral column, as necessary.

[Method E]

[Chemical Formula 36]

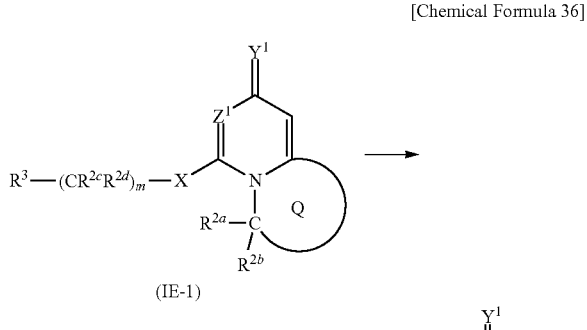

(IE-1)

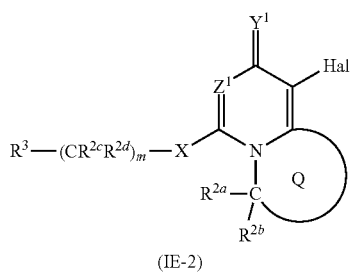

(IE-2)

wherein

Hal is halogen; and the other symbols are the same as the above (1).

Step 1

A compound (IE-2) can be synthesized by the reaction of the compound (IE-1) with a halide reagent in the appropriate solvent.

As the halide reagent, NCS, NBS, NIS, bromine and the like are exemplified.

In this reaction, 1.0 or more mole equivalent(s) of the halide reagent, preferably 1.0 to 3.0 mole equivalent(s) can be used per an equivalent of the compound (IE-1).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), hydrocarbon halides (e.g., chloroform, dichloromethane etc.), DMF, DMSO, NMP, acetonitrile and the like are exemplified. The reaction solvent, may be used alone or in combination.

The reaction temperature is 0 to 120° C., preferably 0 to 80° C.

The reaction time is 0.1 to 72 hours, preferably 0.5 hours to 18 hours.

The obtained desired compound (IE-2) can be purified as necessary by the methods which are usually used (e.g., column chromatography, recrystallization etc.).

As a reaction following the method E, the Suzuki coupling reaction is exemplified below, but there is no limitation to the Suzuki coupling reaction, and a substituent can be introduced using a known method in this field.

[Method F]

[Chemical Formula 37]

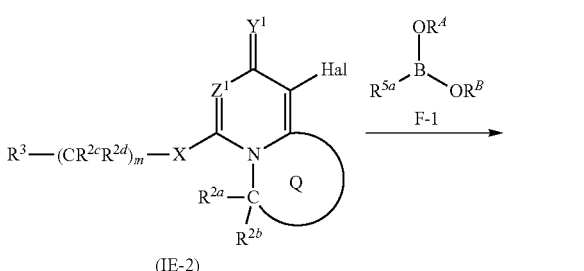

(IE-2)

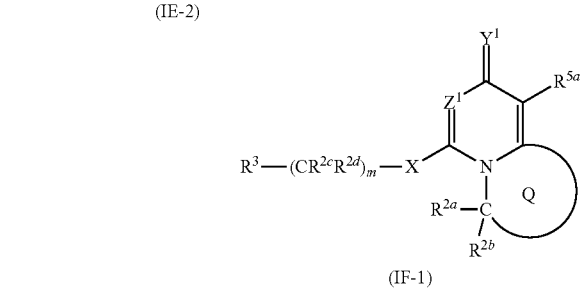

(IF-1)

wherein $R^A$ and $R^B$ are each independently hydrogen, or substituted or unsubstituted alkyl, or are taken together to form a substituted or unsubstituted non-aromatic heterocycle;

Hal is halogen; and the other symbols are the same as the above (1).

A compound (IF-1) can be synthesized by the reaction of the compound (IE-2) obtained in the method E with boronic acid or boronic acid ester (F-1) in the presence of a metal catalyst and a base in the appropriate solvent.

In this reaction, 1.0 or more mole equivalent(s) of the boronic acid or boronic acid ester (F-1), preferably 1.0 to 5.0 mole equivalent(s) can be used per an equivalent of the compound (IE-2).

As the metal catalyst, Pd(OAc)$_2$, Pd$_2$(dba)$_3$, Pd(PPh$_3$)$_4$, bis(triphenylphosphine)palladium(II) dichloride, bis(tri-tert-butylphosphine)palladium, PdCl$_2$(dppf) and the like are exemplified. 0.001 to 0.5 mole equivalent(s) can be used per an equivalent of the compound (IE-2).

As the base, lithium hydroxide, sodium hydroxide, potassium hydroxide, potassium tert-butoxide, sodium tert-butoxide, sodium carbonate, cesium carbonate, potassium bicarbonate, sodium hydrogen carbonate, sodium phosphate, sodium hydrogen phosphate, potassium phosphate, potassium hydrogen phosphate and the like can be exemplified. 1.0 to 10.0 mole equivalent(s) can be used per an equivalent of the compound (IE-2).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, DMA, NMP, DMSO, water and a mixed solvent thereof and the like are exemplified.

The reaction temperature is 20 to 250° C., under microwave irradiation as necessary, preferably 0 to 200° C.

The reaction time is 0.1 to 48 hours, preferably 0.5 to 12 hours.

The obtained desired compound (IF-1) can be purified as necessary by the methods which are usually used (e.g., column chromatography, recrystallization etc.).

[Method G]

[Chemical Formula 38]

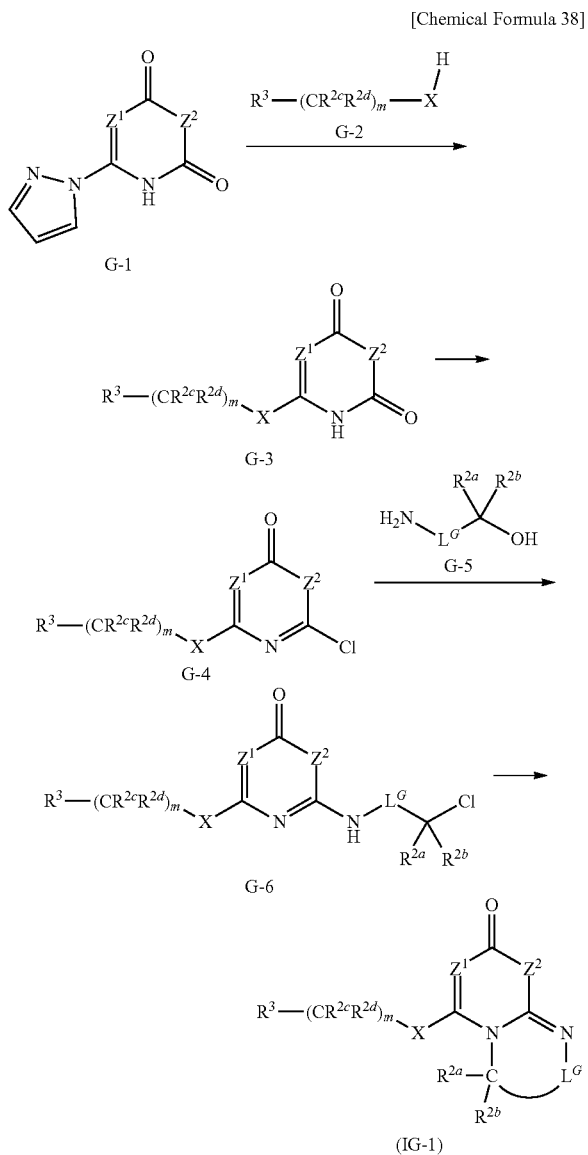

wherein

-L$^G$- is an appropriate group forming Ring Q and represented by —C(R$^{A1}$)(R$^{A2}$)—, —(C(R$^{A1}$)(R$^{A2}$))$_2$— or the like;

R$^{A1}$ and R$^{A2}$ are the same as the method A; and the other symbols are the same as the above (1).

Step 1

A compound (G-3) can be synthesized by the reaction of a compound (G-1) with a compound (G-2) that are obtained according to the synthetic procedures described in the step 1 of the method B according to the synthesis method described in International Publication WO 2012/020749A.

The obtained desired compound (G-3) can be purified as necessary by the methods which are usually used (e.g., column chromatography, recrystallization etc.).

Step 2

A compound (G-4) can be synthesized by the reaction of the compound (G-3) with phosphorus oxychloride without any solvent or in the appropriate solvent.

In this reaction, 1.0 or more mole equivalent(s) of the phosphorus oxychloride, preferably 1.0 to 10.0 mole equivalent(s) can be used per the compound (G-3).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), mixed solvents thereof and the like are exemplified.

The reaction temperature is 0 to 100° C., preferably 20 to 80° C.

The reaction time is 0.1 to 24 hours, preferably 0.5 hours to 12 hours.

The obtained desired compound (G-4) can be purified as necessary by the methods which are usually used (e.g., column chromatography, recrystallization etc.).

Step 3

A compound (G-6) can be synthesized by the reaction of the compound (G-4) with a compound (G-5) in the appropriate solvent.

In this reaction, 1.0 or more mole equivalent(s) of the compound (G-5), preferably 1.0 to 10.0 mole equivalent(s) can be used per the compound (G-6).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), DMF, DMA, NMP, DMSO water, mixed solvents thereof and the like are exemplified.

The reaction temperature is 20 to 250° C., under microwave irradiation as necessary, preferably 0 to 200° C.

The reaction time is 0.1 to 48 hours, preferably 0.5 hours to 12 hours.

The obtained desired compound (G-6) can be purified as necessary by the methods which are usually used (e.g., column chromatography, recrystallization etc.).

Step 4

A compound (IG-1) can be synthesized by the reaction of the compound (G-6) in the presence of a base in the appropriate solvent.

As the base, for example, metal hydroxide (e.g., sodium hydroxide, potassium hydroxide, tripotassium phosphate etc.), metal hydride (e.g., sodium hydride, lithium hydride etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 2.0 or more mole equivalent(s), preferably 2.0 to 6.0 mole equivalent(s) can be used per an equivalent of the compound (G-6).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), DMF, DMA, NMP, DMSO, mixed solvents thereof and the like are exemplified.

The reaction temperature is 20 to 250° C., under microwave irradiation as necessary, preferably 0 to 150° C.

The reaction time is 0.1 to 48 hours, preferably 0.5 hours to 12 hours.

The obtained desired compound (IG-1) can be purified by the methods which are usually used (e.g., column chromatography, recrystallization etc.) and can be optically resolved by preparative SFC (liquid carbon dioxide-methanol) using a chiral column, as necessary.

[Method H]

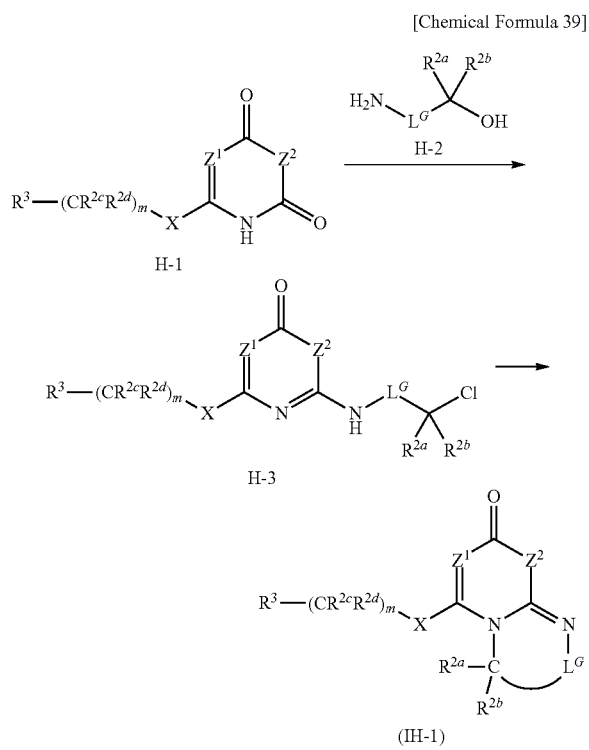

[Chemical Formula 39]

wherein

-$L^G$- is an appropriate group forming Ring Q and represented by —C($R^{A1}$)($R^{A2}$)—, —(C($R^{A1}$)($R^{A2}$))$_2$— or the like;

$R^{A1}$ and $R^{A2}$ are the same as the method A; and the other symbols are the same as the above (1).

Step 1

A compound (H-3) can be synthesized by the reaction of a compound (H-1) obtained according to the synthetic procedures described in the step 1 of the method G with a compound (H-2) in the presence of a base and a phosphonitrilic chloride trimer.

The obtained desired compound (H-3) can be purified as necessary by the methods which are usually used (e.g., column chromatography, recrystallization etc.).

Step 2

A compound (IH-1) can be synthesized by the reaction of the compound (H-3) with trimethylamine hydrochloride and methanesulfonyl chloride in the presence of a base in the appropriate solvent.

As the base, for example, metal hydroxide (e.g., sodium hydroxide, potassium hydroxide, tripotassium phosphate etc.), metal carbonate (e.g., sodium carbonate, potassium carbonate, cesium carbonate etc.), metal alkoxide (e.g., sodium methoxide, sodium ethoxide, potassium tert-butoxide etc.), metal alkyl (e.g., butyllithium etc.), pyridine, triethylamine, DIEA and the like are exemplified. 2.0 or more mole equivalent(s), preferably 2.0 to 6.0 mole equivalent(s) can be used per an equivalent of the compound (H-3).

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethylether, dioxane, dimethoxyethane etc.), DMF, DMA, NMP, DMSO, mixed solvents thereof and the like are exemplified.

The reaction temperature is −10 to 50° C., preferably 0 to 20° C.

The reaction time is 0.1 to 24 hours, preferably 0.5 hours to 12 hours.

The obtained desired compound (IH-1) can be purified by the methods which are usually used (e.g., column chromatography, recrystallization etc.) and can be optically resolved by preparative SFC (liquid carbon dioxide-methanol) using a chiral column, as necessary.

In the synthesis of the compound of the present invention, C=O can be appropriately converted to C=S at a desirable step on the basis of the synthesis method of method α shown below.

[Method α]

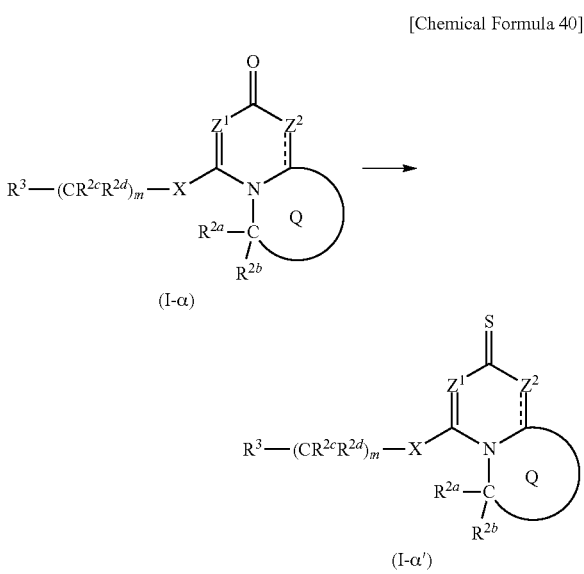

[Chemical Formula 40]

wherein each symbol is the same as the above (1).

A compound (Iα') can be synthesized by the reaction of the compound (Iα) with 2,4-bis(4-methoxyphenyl)-1,3,2,4-dithiadiphosphethane-2,4-disulfide in the appropriate solvent.

As the reaction solvent, aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), acetonitrile and the like are exemplified. The reaction solvent can be used alone or in combination.

The reaction temperature is −10 to 110° C., preferably 0 to 80° C.

The reaction time is 0.1 to 72 hours, preferably 0.5 hours to 18 hours.

The obtained desired compound (Iα') can be purified as necessary by the methods which are usually used (e.g., column chromatography, recrystallization etc.).

In the synthesis of the compound of the present invention, C=S can be appropriately converted to C=N($R^6$) at a desirable step on the basis of the synthesis method of method β shown below.

[Method β]

[Chemical Formula 41]

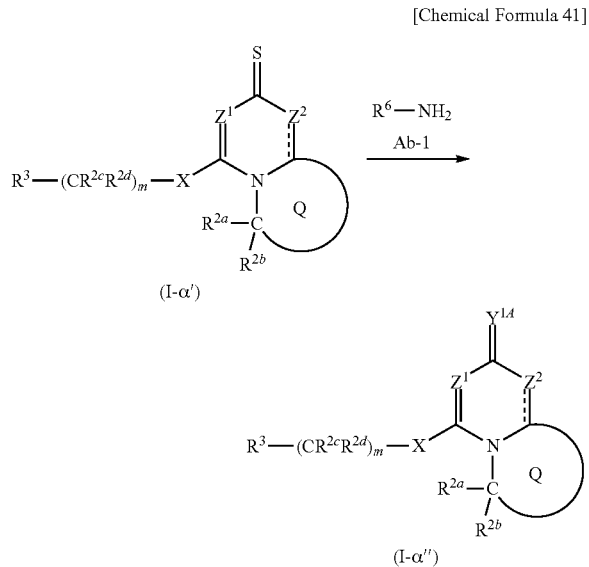

wherein $Y^{1A}$ is N($R^6$); and the other symbols are the same as the above (1).

A compound (Iα") can be synthesized by the reaction of the compound (Iα') obtained by the method α with a compound (Ab-1) in the presence of an acid or a base in the appropriate solvent.

In this reaction, 1.0 or more mole equivalent(s) of the compound (Ab-1), preferably 1.0 to 5.0 mole equivalent(s) can be used per an equivalent of the compound (Iα').

As the acid, for example, acetic acid, trifluoroacetic acid, p-toluenesulfonic acid and the like are exemplified. 0.05 or more mole equivalents, preferably 0.1 to 2.0 mole equivalents can be used per an equivalent of the compound (Iα').

As the base, for example, pyridine, triethylamine, DIEA and the like are exemplified. 1.0 or more mole equivalent(s), preferably 1.0 to 20.0 mole equivalent(s) can be used per an equivalent of the compound (Iα').

As the reaction solvent, alcohols (e.g., methanol, ethanol, tert-butanol, isopropanol etc.), aromatic hydrocarbons (e.g., toluene, benzene, xylene etc.), saturated hydrocarbons (e.g., cyclohexane, hexane etc.), ethers (e.g., tetrahydrofuran, diethyl ether, dioxane, dimethoxyethane etc.), DMF, NMP, acetonitrile, DMA and the like are exemplified. The reaction solvent can be used alone or in combination.

The reaction temperature is 0 to 150° C., preferably 0 to 80° C.

The reaction time is 0.1 to 72 hours, preferably 0.5 hours to 18 hours.

The obtained desired compound (Iα") can be purified as necessary by the methods which are usually used (e.g., column chromatography, recrystallization etc.).

An optically active form of the compound represented by Formula (I) can be produced by using an optically active starting material, synthesizing an optically active intermediate by asymmetric synthesis at an appropriate step, or optically resolving racemic intermediates or final products at an appropriate step. The approach for the optical resolution includes a method of resolving optical isomers using an optically active column, kinetic optical resolution using enzymatic reaction or the like, crystallization and resolution of diastereomers by salt formation using a chiral acid or a chiral base, preferential crystallization and the like.

The preferred compound of the present invention not only has an antagonistic activity for the $P2X_7$ receptor but also is useful as a medicine and has any or all of the following superior characteristics:

a) The inhibitory activity for CYP enzymes (e.g., CYP1A2, CYP2C9, CYP2C19, CYP2D6, CYP3A4 and the like) is weak.

b) The compound demonstrates good pharmacokinetics, such as a high bioavailability, moderate clearance and the like.

c) The compound has a high metabolic stability.

d) The compound has no irreversible inhibitory effect against CYP enzymes (e.g., CYP3A4) when the concentration is within the range described in the present description as the measurement conditions.

e) The compound has no mutagenicity.

f) The compound is associated with a low cardiovascular risk.

g) The compound has a high solubility.

h) The compound has a high selectivity for the $P2X_7$ receptor (e.g., high selectivity in the other receptors of the P2X family).

i) The compound has a high brain distribution.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may prepared according to the usual method and administered. The tablets can be sugar-coated tablets, film-coated tablets, enteric-coating tablets, sustained-release tablets, troche tablets, sublingual tablets, buccal tablets, chewable tablets or orally dispersing tablets. Powders and granules can be dry syrups. Capsules can be soft capsules, micro capsules or sustained-release capsules.

In case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered, injections can be emulsions whose type is O/W, W/O, O/W/O, W/O/W or the like.

The pharmaceutical composition may be manufactured by mixing an effective amount of the compound of the present invention with various pharmaceutical additives suitable for the formulation, such as excipients, binders, moistening agents, disintegrants, lubricants, diluents and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 300 and preferably 0.1 to 100 mg/man/day. For parenteral administration, although the dosage highly varies with administration routes, a usual dosage is 0.005 to 10 and preferably 0.01 to 1 mg/man/day. The dosage may be administered in one to several divisions per day.

The present invention will be described in more detail with reference to, but not limited to, the following Examples, Reference Examples and Test Examples.

NMR analysis of each example was performed by 400 MHz using DMSO-$d_6$ or CDCl$_3$.

"RT" in tables means retention time in LC/MS: liquid column chromatography/mass analysis and these are measured under the conditions as below:

Condition [1]
Column: Shim-pack XR-ODS (2.2 μm, i.d. 50×3.0 mm) (Shimadzu)
Flow rate: 1.6 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

Condition [2]
Column: ACQUITY UPLC (registered trademark) BEH C18 (1.7 μm i.d. 2. 1×50 mm)(Waters)
Flow rate: 0.8 mL/min
UV detection wavelength: 254 nm
Mobile phases: [A] is 10 mmol/L Ammonium Carbonate solution, and [B] is acetonitrile.
Gradient: linear gradient of 5% to 100% solvent [B] for 3.5 minutes was performed, and 100% solvent [B] was maintained for 0.5 minute.

Condition[3]
Column: ACQUITY UPLC (registered trademark) BEH C18 (1.7 μm i.d. 2. 1×50 mm)(Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3.5 minutes was performed, and 100% solvent [B] was maintained for 0.5 minute.

Condition [4]
Column: ACQUITY UPLC (registered trademark) BEH C18 (1.7 μm i.d. 2.1×50 mm) (Waters)
Flow rate: 0.55 mL/minute
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3 minutes was performed, and 100% solvent [B] was maintained for 0.5 minute.

The optical resolution was performed under the following Preparative conditions using a semi-preparative SFC system, available from JASCO Corporation.

Preparative condition 1
Column: Two columns, CHIRALPAK ID/SFC (5 μm i.d. 250×20 mm) (DAICEL), were used in series.
Flow rate: 30 mL/min
UV detection wavelength: 220 nm
Back pressure: 8 MPa
Mobile phases: [A] is liquid carbon dioxide, and [B] is isopropanol. 35% solvent [B] was maintained, and the solution was sent for 40 minutes.

Preparative condition 2
Column: Two columns, CHIRALPAK IC/SFC (5 μm i.d. 250×20 mm) (DAICEL), were used in series.
Flow rate: 40 mL/min
UV detection wavelength: 220 nm
Back pressure: 8 MPa
Mobile phases: [A] is liquid carbon dioxide, and [B] is methanol. 30% solvent [B] was maintained, and the solution was sent for 40 minutes.

Preparative condition 3
Column: Two columns, CHIRALPAK IC/SFC (5 μm i.d. 250×20 mm) (DAICEL), were used in series.
Flow rate: 40 mL/min
UV detection wavelength: 220 nm
Back pressure: 10 MPa
Mobile phases: [A] is liquid carbon dioxide, and [B] is methanol. 25% solvent [B] was maintained, and the solution was sent for 35 minutes.

Preparative condition 4
Column: CHIRALPAK IC/SFC (5 μm i.d. 250×20 mm) (DAICEL) was used. Flow rate: 40 mL/min
UV detection wavelength: 220 nm
Back pressure: 15 MPa
Mobile phases: [A] is liquid carbon dioxide, and [B] is methanol. 25% solvent [B] was maintained, and the solution was sent for 15 minutes.

Example 1

Synthesis of Compound I-0002

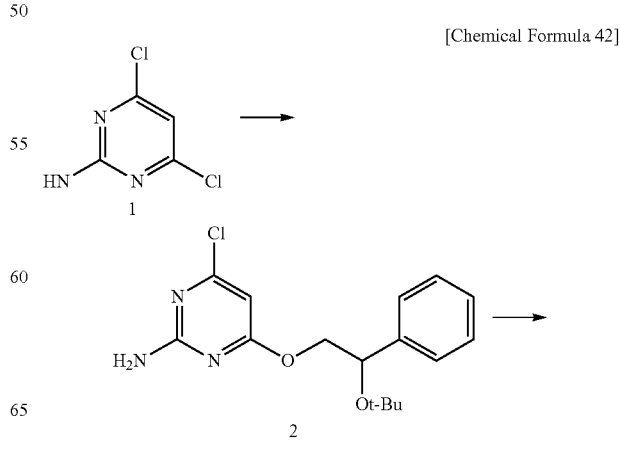

[Chemical Formula 42]

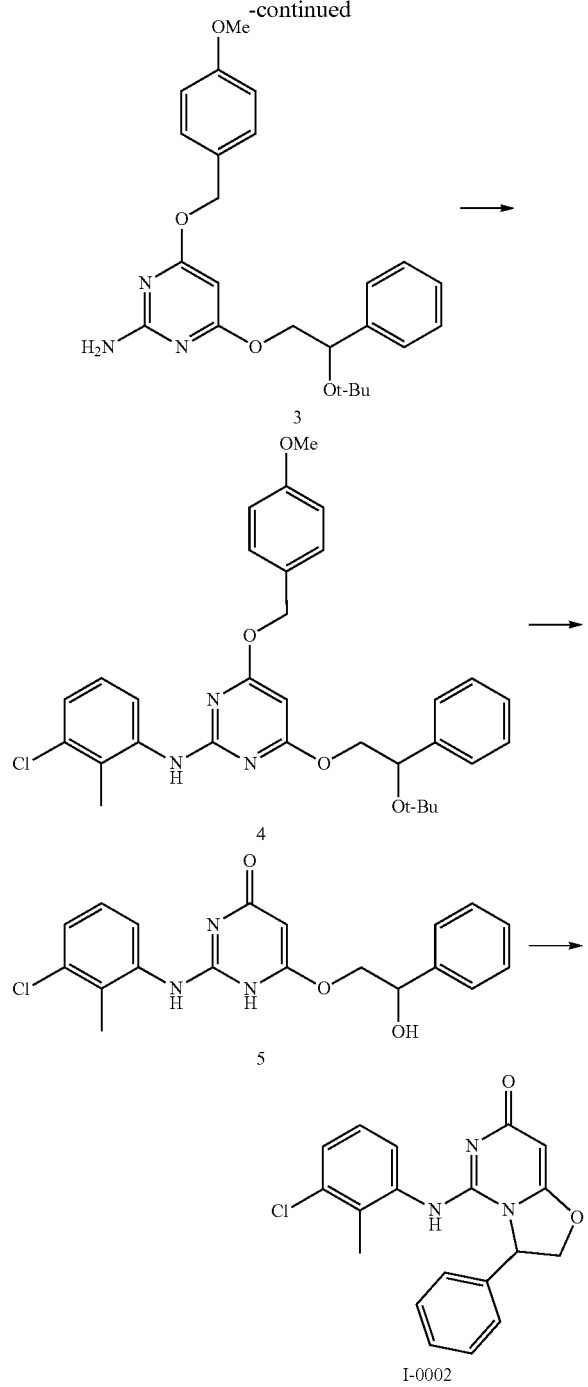

The obtained residue was purified by silica-gel column chromatography (hexane-ethyl acetate) to give Compound 2 (1150 mg, yield 49%).

$^1$H-NMR (CDCl$_3$) δ: 1.15 (s, 9H), 4.20-4.31 (m, 2H), 4.84 (dd, J=8.2, 4.0 Hz, 1H), 5.02 (brs, 2H), 7.25-7.29 (m, 2H), 7.34 (t, J=7.3 Hz, 2H), 7.41 (d, J=7.7 Hz, 2H).

Step 2

Under nitrogen atmosphere, 4-methoxybenzyl alcohol (623 mg, 4.51 mmol) was added to a suspension of sodium hydride (60 wt %, 159 mg, 3.97 mmol) in tetrahydrofuran (7 mL) at 0° C. The mixture was stirred at room temperature for 30 minutes. A tetrahydrofuran (7 mL) solution of Compound 2 (580 mg, 1.80 mmol) was added thereto. The mixture was stirred at 70° C. for 1 hour. Water was added to the reaction mixture. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give Compound 3 (304 mg, yield 40%).

1H-NMR (CDCl3) δ: 1.14 (s, 9H), 3.81 (s, 3H), 4.11-4.18 (m, 1H), 4.26 (dd, J=10.8, 3.8 Hz, 1H), 4.79 (brs, 2H), 4.84 (dd, J=7.8, 4.0 Hz, 1H), 5.20 (s, 2H), 5.51 (s, 1H), 6.89 (d, J=7.5 Hz, 2H), 7.23-7.42 (m, 7H).

Step 3

Under nitrogen atmosphere, Compound 3 (135 mg, 0.319 mmol) was dissolved in toluene (1.5 mL), and 1-bromo-3-chloro-2-methyl benzene (65.5 mg, 0.319 mmol), sodium-tert-butoxide (61.3 mg, 0.638 mmol), BINAP (39.7 mg, 0.064 mmol), and Pd$_2$(dba)$_3$ (29.2 mg, 0.032 mmol) were added thereto. The mixture was stirred at 100° C. for 40 minutes under microwave irradiation. Water was added to the reaction mixture. The mixture was extracted with ethyl acetate. The organic layer was washed by water and brine, and dried over anhydrous sodium sulfate. The solvent, was evaporated under reduced pressure. The obtained residue was purified by silica-gel column chromatography (hexane-ethyl acetate) to give Compound 4 (165 mg, yield 94%).

1H-NMR (CDCl3) δ: 1.11 (s, 9H), 2.38 (s, 3H), 3.81 (s, 3H), 4.15 (t, J=9.7 Hz, 1H), 4.31 (dd, J=11.0, 3.5 Hz, 1H), 4.80 (dd, J=8.3, 3.8 Hz, 1H), 5.23 (s, 2H), 5.61 (s, 1H), 6.63 (s, 1H), 6.89 (d, J=7.5 Hz, 2H), 7.10-7.19 (m, 2H), 7.24-7.32 (m, 7H), 7.82 (d, J=7.8 Hz, 1H).

Step 4

A 4 mol/L hydrochloric acid solution (dioxane solution, 5 mL, 20 mmol) was added to Compound 4 (165 mg, 0.301 mmol). The mixture was stirred at room temperature for 2 hours. Water was added to the reaction mixture. The mixture was neutralized with the aqueous solution of sodium hydroxide and extracted with a dichloromethane-methanol mixed solvent. The organic layer was washed by brine, and dried over anhydrous sodium sulfate. The solvent was evaporated under reduced pressure to give Compound 5 (102 mg, yield 91%).

[M+H]=372: Condition [2]: Retention time=1.76 (minutes)

Step 5

DIAD (0.282 mL, 1.45 mmol) was added to a suspension of Compound 5 (60 mg, 0.161 mmol) and triphenylphosphine (423 mg, 1.61 mmol) in dichloromethane (4 mL). The mixture was stirred at room temperature for 30 minutes. Water was added to the reaction mixture. The mixture was extracted with ethyl acetate. The organic layer was washed by brine, and dried over anhydrous sodium sulfate. The solvent was evaporated under reduced pressure. The Step 1

Under nitrogen atmosphere, 2-(tert-butoxy)-2-phenylethanol (1.43 g, 7.36 mmol) was added to a suspension of sodium hydride (60 wt %, 324 mg, 8.10 mmol) in tetrahydrofuran (10 mL) and DMF (5 mL) at 0° C. The mixture was stirred at room temperature for 35 minutes. 2-amino-4,6-dichloropyrimidine (1.33 g, 8.10 mmol) was added thereto, and the mixture was stirred at 100° C. for 30 minutes. Water was added to the reaction mixture. The mixture was extracted with ethyl acetate. The organic layer was washed by water and brine, and dried over anhydrous sodium sulfate. The solvent was evaporated under reduced pressure.

obtained residue was purified by silica-gel column chromatography (hexane-ethyl acetate) to give Compound I-0002 (20 mg, yield 35%).

1H-NMR (DMSO-d6) δ: 1.56 (s, 3H), 4.58 (d, J=8.7 Hz, 1H), 4.93 (s, 1H), 5.06 (t, J=8.4 Hz, 1H), 5.66 (br, 1H), 6.53 (br, 1H), 6.96-7.04 (m, 2H), 7.30-7.44 (m, 5H), 9.58 (brs, 1H).

Example 2

Synthesis of Compound I-Q003

[Chemical Formula 43]

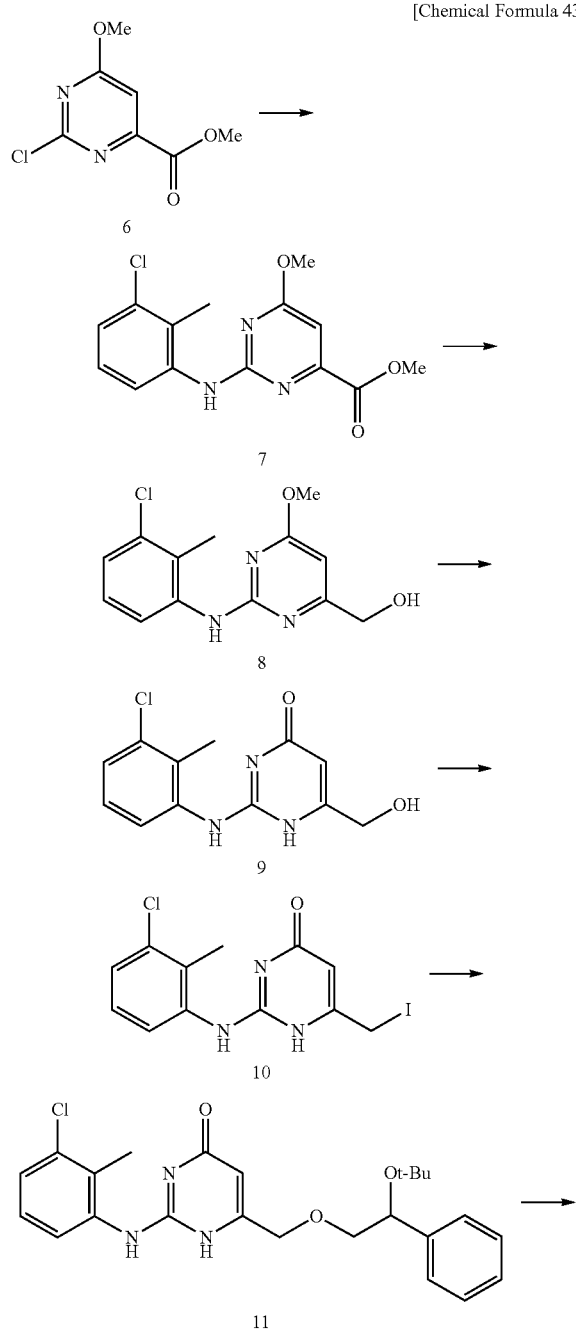

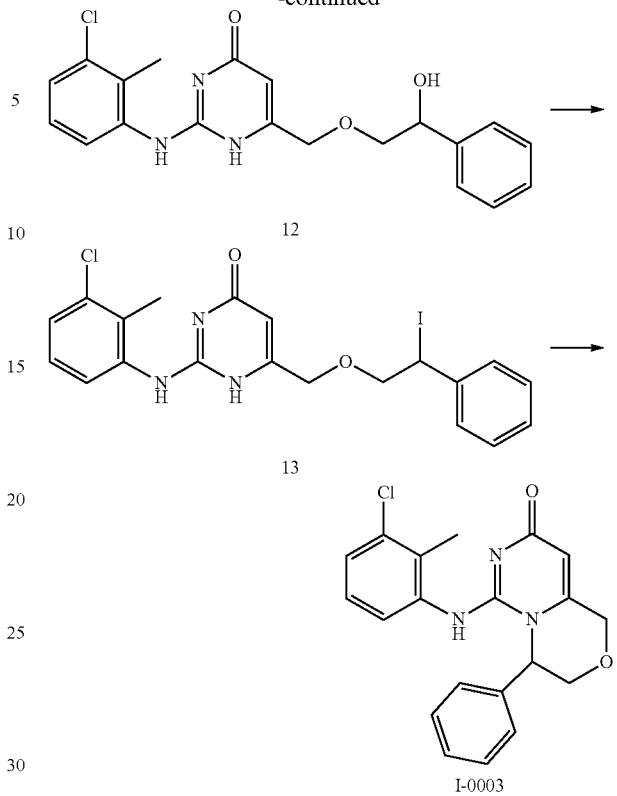

Step 1

Under nitrogen atmosphere, 3-chloro-2-methylaniline (105 mg, 0.740 mmol) was added to a suspension of Compound 6 (50 mg, 0.247 mmol) in dioxane (1 mL). The mixture was refluxed by heating for 22 hours. The aqueous solution of saturated ammonium chloride was added to the reaction mixture. The mixture was extracted with chloroform. The organic layer was dried over anhydrous sodium sulfate. The solvent was evaporated under reduced pressure. The obtained residue was purified by silica-gel column chromatography (hexane-ethyl acetate) to give Compound 7 (27 mg, yield 36%).

1H-NMR (CDCl3) δ: 2.38 (s, 3H), 3.91 (s, 3H), 3.98 (s, 3H), 6.89 (s, 1H), 7.03 (s, 1H), 7.12-7.19 (m, 2H), 7.84 (d, J=7.8 Hz, 1H).

Step 2

Under nitrogen atmosphere, a 1.03 mol/L DIBAL solution (13.9 mL, 14.3 mmol) was added to a tetrahydrofuran (10 mL) solution of Compound 7 (1.0 g, 3.25 mmol). The mixture was stirred at 0° C. for 3 hours. Methanol and a saturated Rochelle salt solution were added to the reaction mixture. The mixture was stirred at room temperature for 1 hour. The mixture was extracted with ethyl acetate. The organic layer was washed by water, and dried over anhydrous sodium sulfate. The solvent was evaporated under reduced pressure. The obtained residue was purified by silica-gel column chromatography (hexane-ethyl acetate) to give Compound 8 (830 mg, yield 91%).

1H-NMR (CDCl3) δ: 2.39 (s, 3H), 3.16 (br, 1H), 3.91 (s, 3H), 4.55 (s, 2H), 6.14 (s, 1H), 6.77 (br, 1H), 7.12-7.18 (m, 2H), 7.84 (d, J=7.8 Hz, 1H).

Step 3

Concentrated hydrochloric acid (20 mL) was added to Compound 8 (650 mg, 2.32 mmol). The mixture was stirred at 100° C. for 1.5 hours. The reaction mixture was neutralized with saturated sodium bicarbonate water to be a pH of 5. The mixture was extracted with ethyl acetate. The organic layer was dried over anhydrous sodium sulfate. The solvent was evaporated under reduced pressure to give Compound 9 (535 mg, yield 87%).

[M+H]=266: Condition [2]: Retention time=1.15 (minutes)

Step 4

Compound 9 (485 mg, 1.83 mmol) was dissolved in dichloromethane (15 mL). Under ice cooling, imidazole (373 mg, 5.48 mmol), triphenylphosphine (622 mg, 2.37 mmol), and iodine (602 mg, 2.37 mmol) were added thereto. The mixture was stirred at room temperature for 30 minutes. The aqueous solution of saturated ammonium chloride was added to the reaction mixture. The mixture was extracted with ethyl acetate. The organic layer was washed by water, and dried over anhydrous sodium sulfate. The solvent was evaporated under reduced pressure. The obtained residue was washed by toluene to give Compound 10 (380 mg, yield 55%).

1H-NMR (DMSO-d6) δ: 2.28 (s, 3H), 4.11 (s, 2H), 5.91 (s, 1H), 7.18-7.27 (m, 2H), 7.68 (d, J=6.5 Hz, 1H).

Step 5

Under nitrogen atmosphere, 2-(tert-butoxy)-2-phenylethanol (786 mg, 4.05 mmol) was added to a suspension of sodium hydride (60 wt %, 158 mg, 3.95 mmol) in DMF (3 mL) at 0° C. Subsequently, a DMF (3 mL) solution of Compound 10 (380 mg, 1.01 mmol) was added thereto. The mixture was stirred at 0° C. for 10 minutes. The aqueous solution of saturated ammonium chloride was added to the reaction mixture. The mixture was extracted with ethyl acetate. The organic layer was washed by water, and dried over anhydrous sodium sulfate. The solvent was evaporated under reduced pressure. The obtained residue was purified by silica-gel column chromatography (hexane-ethyl acetate) to give Compound 11 (280 mg, yield 63%).

[M+H]=442: Condition [2]: Retention time=2.40 (minutes)

Step 6

A 4 mol/L hydrochloric acid solution (dioxane solution, 3 ml, 12 mmol) was added to Compound 11 (270 mg, 0.611 mmol). The mixture was stirred at room temperature for 30 minutes. Saturated sodium bicarbonate water and the aqueous solution of saturated ammonium chloride were added to the reaction mixture. The mixture was extracted with chloroform. The organic layer was dried over anhydrous sodium sulfate. The solvent was evaporated under reduced pressure. The obtained residue was purified by silica-gel column chromatography (hexane-ethyl acetate) to give Compound 12 (180 mg, yield 76%).

[M+H]=386: Condition [2]: Retention time=1.73 (minutes)

Step 7

Under nitrogen atmosphere, imidazole (48.2 mg, 0.708 mmol) and triphenylphosphine (74.2 mg, 0.283 mmol) were added to a suspension of Compound 12 (91 mg, 0.236 mmol) in dichloromethane (2 mL). Iodine (71.8 mg, 0.283 mmol) was added thereto at 0° C. The mixture was stirred at room temperature for 2 hours. The aqueous solution of saturated ammonium chloride was added to the reaction mixture. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate) to give the crude product of Compound 13.

Step 8

Under nitrogen atmosphere, the crude product of Compound 13 obtained in the step 7 was dissolved in DMF (5 mL). Potassium carbonate (81 mg, 0.59 mmol) was added thereto. The mixture was stirred at 60° C. for 30 minutes. Water was added to the reaction mixture. The mixture was adjusted to pH 6 with a 10% aqueous solution of citric acid. The mixture was extracted with ethyl acetate. The organic layer was washed by water and brine, and dried over anhydrous sodium sulfate. The solvent was evaporated under reduced pressure. The obtained residue was purified by silica-gel column chromatography (hexane-ethyl acetate). An optically active form was separated by preparative SFC (Preparative condition 4) to give Compound I-0003.

1H-NMR (DMSO-d6) δ: 1.45 (s, 3H), 4.04 (d, J=12.0 Hz, 1H), 4.23 (d, J=10.2 Hz, 1H), 4.61 (d, J=16.2 Hz, 1H), 4.75 (d, J=16.2 Hz, 1H), 5.33 (s, 1H), 5.47 (s, 1H), 6.47 (br, 1H), 6.95-7.03 (m, 2H), 7.23-7.29 (m, 3H), 7.34-7.38 (m, 2H), 9.74 (br, 1H).

Reference Example 1

Synthesis of Compound 15

[Chemical Formula 44]

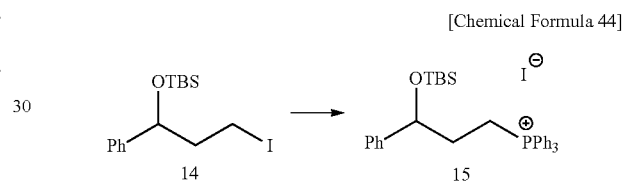

tert-Butyl(3-iodine-phenylpropoxy)dimethylsilane (3.24 g, 8.61 mmol) (the synthesis method is described in Journal of the American Chemical Society, 135(14), 5242-5245; 2013) was dissolved in toluene (30 mL). Triphenylphosphine (2.71 g, 10.33 mmol) was added thereto. The mixture was stirred for 10 hours under reflux by heating. After cooling, the precipitated solids were filtered, washed by diisopropyl ether, and dried under reduced pressure to give Compound 15 (6.32 g, quant.).

Condition [1]: Retention time=2.11 (minutes): [M+H]=511.3

Example 3

Synthesis of Compound I-Q005

[Chemical Formula 45]

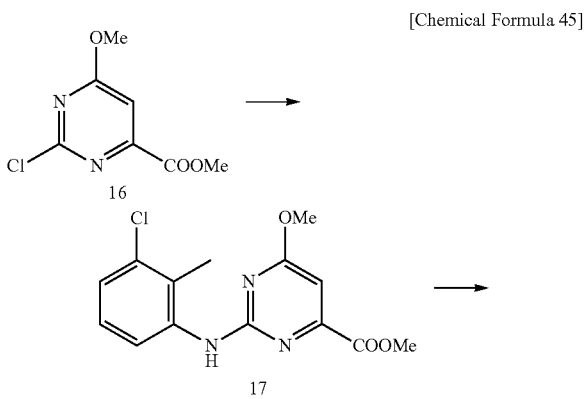

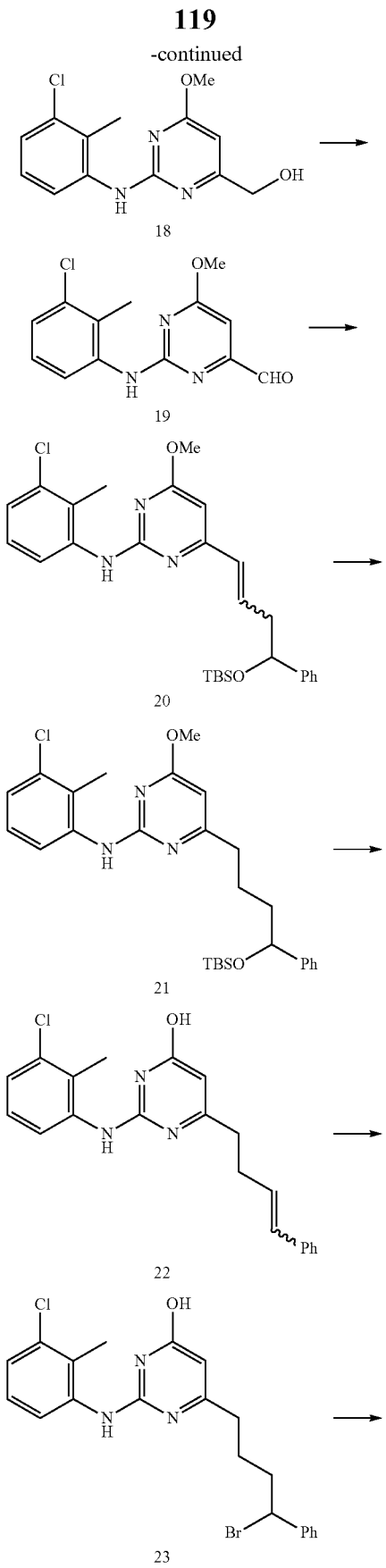

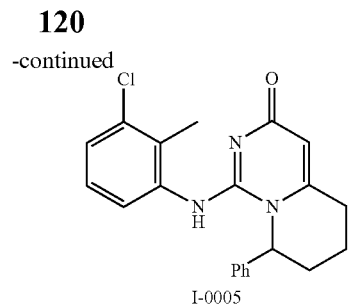

I-0005

Step 1

Under nitrogen atmosphere, 2-chloro-6-methoxy-4-methylpyrimidinecarboxylate (6.9 g, 34.1 mmol) and 3-chloro-2-methylaniline (16.28 mL, 136 mmol) were mixed. The mixture was stirred for 10 hours under reflux by heating. After cooling, the aqueous solution of saturated ammonium chloride was added thereto. The aqueous layer was extracted with chloroform. The organic layer was dried over anhydrous sodium sulfate. The solvent was evaporated under reduced pressure. The obtained residue was purified by silica-gel column chromatography (hexane-ethyl acetate) to give Compound 17 (6.9 g, yield 66%).

Condition [3]: Retention time=4.25 (minutes): [M+H]=308.3

Step 2

Under nitrogen atmosphere, Compound 17 (3 g, 9.75 mmol) was dissolved in tetrahydrofuran (30 ml). Under ice cooling, DIBAL (31.2 ml, 32.2 mmol) was added thereto. The mixture was stirred for 1 hour. Methanol and a Rochelle salt solution were added thereto. The mixture was stirred at room temperature. The mixture was extracted with ethyl acetate. The organic layer was washed by water, and dried over anhydrous sodium sulfate. The solvent was evaporated under reduced pressure. The obtained residue was purified by silica-gel column chromatography (hexane-ethyl acetate) to give Compound 18 (2.0 g, yield 73%).

Condition [3]: Retention time=2.53 (minutes): [M+H]=280.4

Step 3

Under nitrogen atmosphere, Compound 18 (600 mg, 2.14 mmol) was dissolved in dichloromethane. Under water cooling, Dess-Martin periodinane (1319 mg, 3.11 mmol) was added thereto. The mixture was stirred for 2.5 hours. A 10% aqueous solution of sodium thiosulfate was added thereto. The mixture was stirred for 30 minutes. The reaction mixture was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give Compound 19 (264.6 mg, yield 44%).

Condition [1]: Retention time=2.17 (minutes): [M+H]=278.0

Step 4

Under nitrogen atmosphere, Compound 15 (747 mg, 1.17 mmol) was dissolved in tetrahydrofuran (1 mL), and cooled to −78° C. A 1.67 mol/L n-butyllithium-hexane solution (0.701 mL, 1.17 mmol) was added dropwise thereto. The mixture was stirred at −78° C. for 30 minutes. A tetrahydrofuran (1 mL) solution of the compound 19 (50 mg, 0.18 mmol) was added dropwise thereto. The mixture was stirred at −78° C. for 1 hour. The aqueous solution of saturated ammonium chloride was added thereto. The mixture was heated to room temperature. The aqueous layer was extracted with dichloromethane. The solvent was evaporated under reduced pressure. The obtained residue was purified by silica-gel column chromatography (hexane-ethyl acetate) to give Compound 20 (89.2 mg, yield 97%).

Condition [1]: Retention time=3.51 (minutes): [M+H]=510.3

Step 5

Compound 20 (105 mg, 0.206 mmol) was dissolved in methanol (2 mL). Palladium/carbon (palladium 10%) (about 55% water-moist products) (20 mg) was added thereto. The mixture was stirred for 19 hours under hydrogen atmosphere. The reaction mixture was filtered through Celite. The filtrate was concentrated to give the crude product of Compound 21 (112 mg).

Condition [1]: Retention time=3.53 (minutes): [M+H]=512.2

Step 6

Sodium iodide (97 mg, 0.644 mmol) was suspended in acetonitrile (2 mL). Chlorotrimethylsilane (70 mg, 0.644 mmol) was added thereto. The mixture was stirred for 0.5 hours to prepare an iodotrimethylsilane solution. The crude product of Compound 21 (110 mg) obtained in the step 5 was dissolved in acetonitrile (3 mL). The prepared iodotrimethylsilane solution was added thereto. The mixture was stirred for 18 hours under reflux by heating. After cooling, the saturated aqueous solution of sodium hydrogen carbonate and a 10% aqueous solution of sodium thiosulfate were added thereto. The mixture was stirred. The aqueous layer was extracted with chloroform. The solvent was evaporated under reduced pressure. The obtained residue was purified by silica-gel column chromatography (hexane-ethyl acetate) to give Compound 22 (14.6 mg, yield 19%).

Condition [1]: Retention time=2.22 (minutes): [M+H]=366.0

Step 7

Compound 22 was dissolved in a 25% hydrogen bromide solution (acetic acid solution) (0.5 ml). The mixture was stirred at room temperature for 0.5 hours. The saturated aqueous solution of sodium hydrogen carbonate was added thereto. The aqueous layer was extracted with dichloromethane. The solvent was evaporated under reduced pressure to give the crude product of Compound 23 (14.2 mg).

Condition [1]: Retention time=2.27 (minutes): [M+H]=446.0

Step 8

The crude product of Compound 23 (14.2 mg) obtained in the step 7 and potassium carbonate (13.18 mg, 0.095 mmol) were dissolved in DMF (1 mL). The mixture was stirred at 70° C. for 0.5 hours. After cooling, the mixture was diluted with water, and extracted with ethyl acetate. The organic layer was dried over anhydrous magnesium sulfate. The solvent was evaporated under reduced pressure. The obtained residue was purified by preparative thin-layer chromatography (hexane-ethyl acetate) to give Compound I-0005 (5.2 mg, yield 45%).

$^1$H-NMR (CDCl$_3$) δ: 1.53 (s, 3H), 1.65-1.78 (m, 2H), 2.17-2.34 (m, 2H), 2.69-2.84 (m, 2H), 5.34 (s, 1H), 6.00 (dd, J=5.0, 2.3 Hz, 1H), 6.49 (dd, J=6.9, 2.6 Hz, 1H), 6.97-7.03 (m, 2H), 7.15 (d, J=7.3 Hz, 2H), 7.28 (d, J=7.3 Hz, 1H), 7.35 (t, J=7.5 Hz, 3H).

Example 4

Synthesis of Compound I-0006

[Chemical Formula 46]

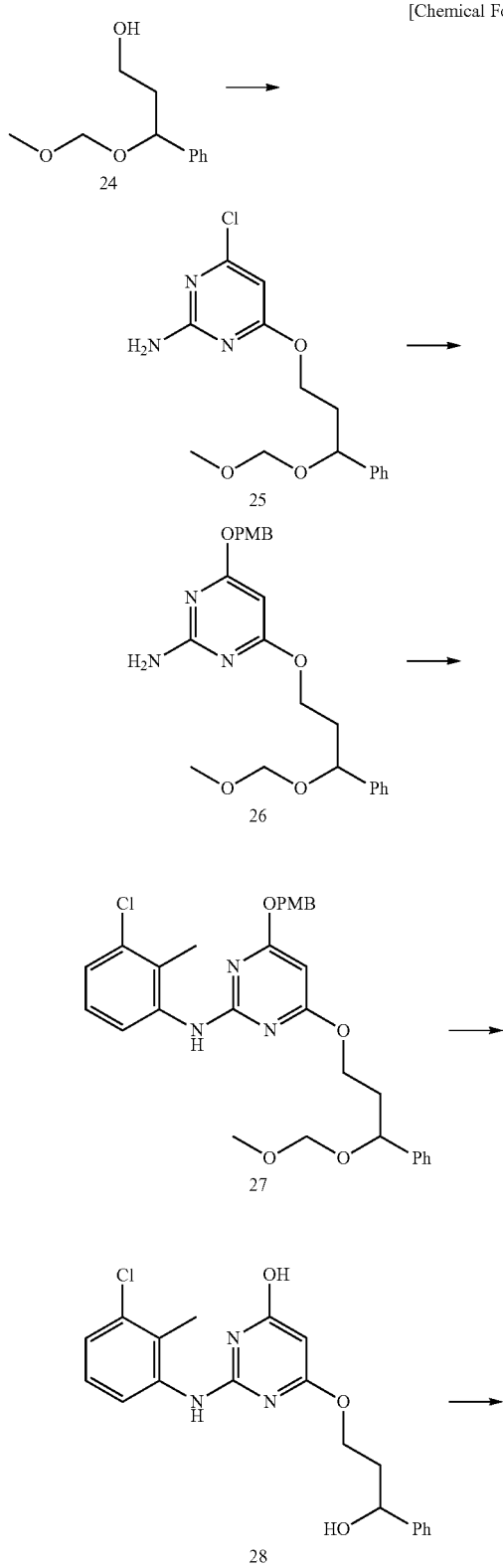

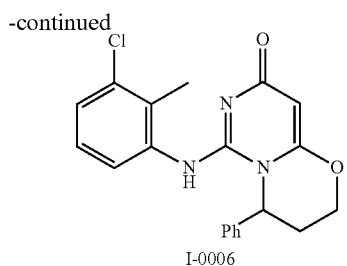

I-0006

Step 1

Under nitrogen atmosphere, Compound 24 (2 g, 10.19 mmol) (the synthesis method is described in Zhurnal Obshchei Khimii (1963), 5(4), 1446-51) was dissolved in tetrahydrofuran (20 mL). Under ice cooling, sodium hydride (0.448 g, 11.21 mmol) was added thereto. The mixture was stirred for 0.5 hours. 4,6-dichloropyrimidin-2-amine (1.671 g, 10.19 mmol) was added thereto. The mixture was heated to room temperature, and stirred at room temperature for 3 hours and then stirred at 60° C. for 4 hours. After cooling, the aqueous solution of saturated ammonium chloride was added thereto. The mixture was extracted with chloroform. The organic layer was dried over anhydrous magnesium sulfate. The solvent was evaporated under reduced pressure. The obtained residue was purified by silica-gel column chromatography (hexane-ethyl acetate) to give Compound 25 (2.58 g, yield 78%).

Condition [1]: Retention time=2.03 (minutes): [M+H]=324.0

Step 2

Under nitrogen atmosphere, Compound 25 (2.52 g, 7.78 mmol) was dissolved in tetrahydrofuran (20 mL). Under ice cooling, sodium hydride (0.623 g, 15.57 mmol) was added thereto. The mixture was heated to room temperature, and stirred for 0.5 hours. Under ice cooling, para-methoxybenzyl alcohol (2.151 g, 15.57 mmol) was added thereto, and the mixture was heated to 80° C. The mixture was stirred for 2 hours, cooled to room temperature, and diluted with water. The aqueous layer was extracted with ethyl acetate. The organic layer was dried over anhydrous magnesium sulfate. The residue was purified by silica-gel column chromatography (hexane-ethyl acetate) to give Compound 26 (3.12 g, yield 68%).

Condition [1]: Retention time=2.24 (minutes): [M+H]=426.2

Step 3

Under nitrogen atmosphere, Compound 26 (1.5 g, 3.53 mmol), 1-bromo-3-chloro-2-methyl benzene (1.087 g, 5.29 mmol), Pd$_2$(dba)$_3$ (0.646 g, 0.705 mmol), BINAP (0.878 g, 1.41 mmol), and sodium tert-butoxide (0.678 g, 7.05 mmol) were suspended in toluene (15 mL). The mixture was stirred at 100° C. for 2 hours. After cooling, the mixture was neutralized with a 5% aqueous solution of citric acid. The aqueous layer was extracted with chloroform. The organic layer was dried over anhydrous magnesium sulfate. The solvent was evaporated under reduced pressure. The obtained residue was purified by silica-gel column chromatography (hexane-ethyl acetate) to give Compound 27 (1.6 g, yield 64%).

Condition [1]: Retention time=3.07 (minutes): [M+H]=550.2

Step 4

Compound 27 (1.08 g, 1.531 mmol) was dissolved in a 4 mol/L hydrochloric acid-dioxane solution. The mixture was stirred for 3 hours. The saturated aqueous solution of sodium hydrogen carbonate was added thereto for neutralization. The aqueous layer was extracted with chloroform. The mixture was dried over anhydrous magnesium sulfate. The solvent was evaporated under reduced pressure to give the crude product of Compound 28 (1.13 g, yield 96%).

Condition [1]: Retention time=1.74 (minutes): [M+H]=386.1

Step 5

The crude product of Compound 28 (1 g) obtained in the step 4 and triphenylphosphine (1.36 g, 5.18 mmol) were dissolved in tetrahydrofuran (200 mL). Under ice cooling, a 1.9 mol/L DIAD-toluene solution (2.73 mL, 5.18 mmol) was added thereto. The mixture was heated to room temperature, and stirred for 5 minutes. The mixture was diluted with water. The aqueous layer was extracted with chloroform. The mixture was dried over anhydrous magnesium sulfate. The solvent was evaporated under reduced pressure. The residue was purified by preparative thin-layer chromatography (hexane-ethyl acetate) to give Compound I-0006 (5.2 mg, yield 1%).

$^1$H-NMR (CDCl$_3$) δ: 1.60 (s, 3H), 2.24 (dd, J=14.3, 2.8 Hz, 1H), 2.62-2.71 (m, 1H), 3.72-3.79 (m, 1H), 4.16 (dt, J=16.6, 6.1 Hz, 1H), 4.32-4.36 (m, 1H), 4.99 (d, J=2.0 Hz, 1H), 6.00 (d, J=3.3 Hz, 1H), 6.53 (dd, J=7.0, 2.3 Hz, 1H), 6.98-7.04 (m, 2H), 7.22 (d, J=6.3 Hz, 2H), 7.33 (t, J=7.5 Hz, 1H), 7.41 (t, J=7.0 Hz, 2H).

Example 5

Synthesis of Compound I-0007

[Chemical Formula 47]

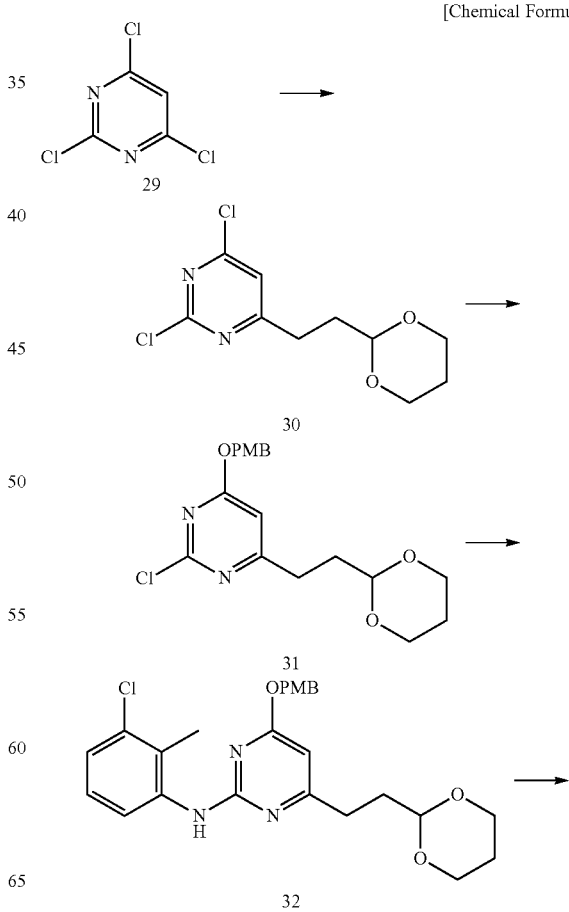

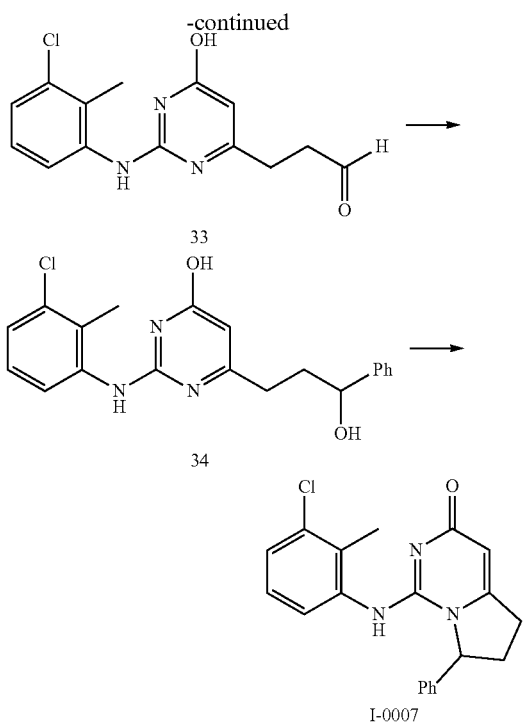

Step 1

Under nitrogen atmosphere, magnesium (1.59 g, 65.4 mmol) was suspended in tetrahydrofuran (30 mL). 2-(2-bromo ethyl)-1,3-dioxane (1 mL, 7.39 mmol) and iodine (8.8 mg, 0.035 mmol) were added thereto. The mixture was stirred. Under water cooling, 2-(2-bromo ethyl)-1,3-dioxane (7.12 mL, 52.6 mmol) was slowly added dropwise thereto. The mixture was stirred at room temperature for 3.5 hours to prepare a Grignard reagent. 2,4,6-Trichloropyrimidine was dissolved in tetrahydrofuran (40 mL), and cooled to −78° C. The prepared Grignard reagent was added dropwise thereto. A tetrahydrofuran (10 mL) solution of trisacetylacetonatoiron (0.963 g, 2.73 mmol) was added dropwise thereto. The mixture was stirred at −78° C. for 20 minutes. The aqueous solution of ammonium chloride was added thereto. The mixture was heated to room temperature. The aqueous layer was extracted with ethyl acetate. The organic layer was dried over anhydrous magnesium sulfate. The solvent was evaporated under reduced pressure. The obtained residue was purified by silica-gel column chromatography (hexane-ethyl acetate) to give Compound 30 (5.37 g, yield 37%).

Condition [1]: Retention time=1.76 (minutes): [M+H]=263.1

Step 2

Under nitrogen atmosphere, para-methoxybenzyl alcohol (62.3 g, 451 mmol) and Compound 30 (113 g, 429 mmol) were dissolved in tetrahydrofuran (1130 mL). Under ice cooling, sodium hydride (18.89 g, 472 mmol) was added thereto under stirring. After stirring for 2.5 hours, sodium hydride (2 g, 50 mmol) was added thereto. The mixture was stirred for 2 hours. The mixture was diluted with water, and heated to room temperature. The aqueous layer was extracted with ethyl acetate. The organic layer was washed by water and brine, and dried over anhydrous magnesium sulfate. The solvent was evaporated under reduced pressure. The obtained solid was washed by a mixed solution of ethyl acetate and hexane, and dried under reduced pressure to give Compound 31 (61.1 g, yield 39%).

Condition [1]: Retention time=2.27 (minutes): [M+H]=365.2

Step 3

Under nitrogen atmosphere, Compound 31 (1 g, 2.74 mmol), 3-chloro-2 methylaniline (776 mg, 5.48 mmol), palladium acetate (61.5 mg, 0.274 mmol), Xantphos (238 mg, 0.411 mmol), and cesium carbonate (2679 mg, 8.22 mmol) were suspended in 1,4-dioxane (10 mL). The mixture was stirred at 110° C. for 1 hour. After cooling, the mixture was diluted with water, and extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give Compound 32 (715.5 mg, yield 56%).

Condition [1]: Retention time=2.33 (minutes): [M+H]=470.2

Step 4

Compound 32 (682 mg, 1.451 mmol) was dissolved in a 4 mol/L hydrochloric acid-dioxane solution (3.5 mL). The mixture was stirred for 20 hours. Water (3.5 mL) was added thereto. After stirring for 2 hours, the saturated aqueous solution of sodium hydrogen carbonate was added thereto. The aqueous layer was extracted with ethyl acetate. The organic layer was washed by water and brine. The organic layer was dried over anhydrous magnesium sulfate. The solvent was evaporated under reduced pressure. The obtained residue was purified by silica-gel column chromatography (chloroform-methanol) to give the crude product of Compound 33 (448.2 mg).

Condition [1]: Retention time=1.09 (minutes): [M+H]=292.0

Step 5

The crude product of Compound 33 (140 mg, 0.48 mmol) obtained in the step 4 was dissolved in tetrahydrofuran (2.8 mL), and cooled to −78° C. A phenylmagnesium bromide-tetrahydrofuran solution (9.6 mL, 9.6 mmol) was added thereto. The mixture was stirred for 9 hours. The mixture was heated to room temperature. The aqueous solution of saturated ammonium chloride was added thereto. The mixture was extracted with ethyl acetate. The organic layer was dried over anhydrous magnesium sulfate. The solvent was evaporated under reduced pressure. The obtained residue was purified by silica-gel column chromatography (chloroform-methanol) to give Compound 34 (124.4 mg, yield 70%).

Condition [1]: Retention time=1.63 (minutes): [M+H]=370.1

Step 6

Compound 34 (50 mg, 0.135 mmol) was dissolved in dichloromethane (1 mL). Triphenylphosphine (78 mg, 0.297 mmol), triethylamine (0.047 mL, 0.338 mmol), and iodine (75 mg, 0.297 mmol) were added thereto. The mixture was stirred for 1 hour. A 10% aqueous solution of sodium thiosulfate was added thereto. The mixture was stirred for a while. The aqueous layer was extracted with chloroform. The solvent was evaporated under reduced pressure. The obtained residue was purified by silica-gel column chromatography (chloroform-methanol) to give Compound I-0007 (7.5 mg, yield 16%).

$^1$H-NMR (CDCl$_3$) δ: 1.69 (s, 3H), 2.12-2.17 (m, 1H), 2.63-2.73 (m, 1H), 2.94 (dd, J=17.2, 8.7 Hz, 1H), 3.05-3.15 (m, 1H), 5.42 (s, 1H), 5.63 (d, J=8.8 Hz, 1H), 6.58 (dd, J=6.7, 2.4 Hz, 1H), 6.98-7.04 (m, 2H), 7.20 (d, J=7.5 Hz, 2H), 7.30 (t, J=7.5 Hz, 2H), 7.37 (t, J=6.8 Hz, 2H).

Example 6

Synthesis of Compound I-0009

[Chemical Formula 48]

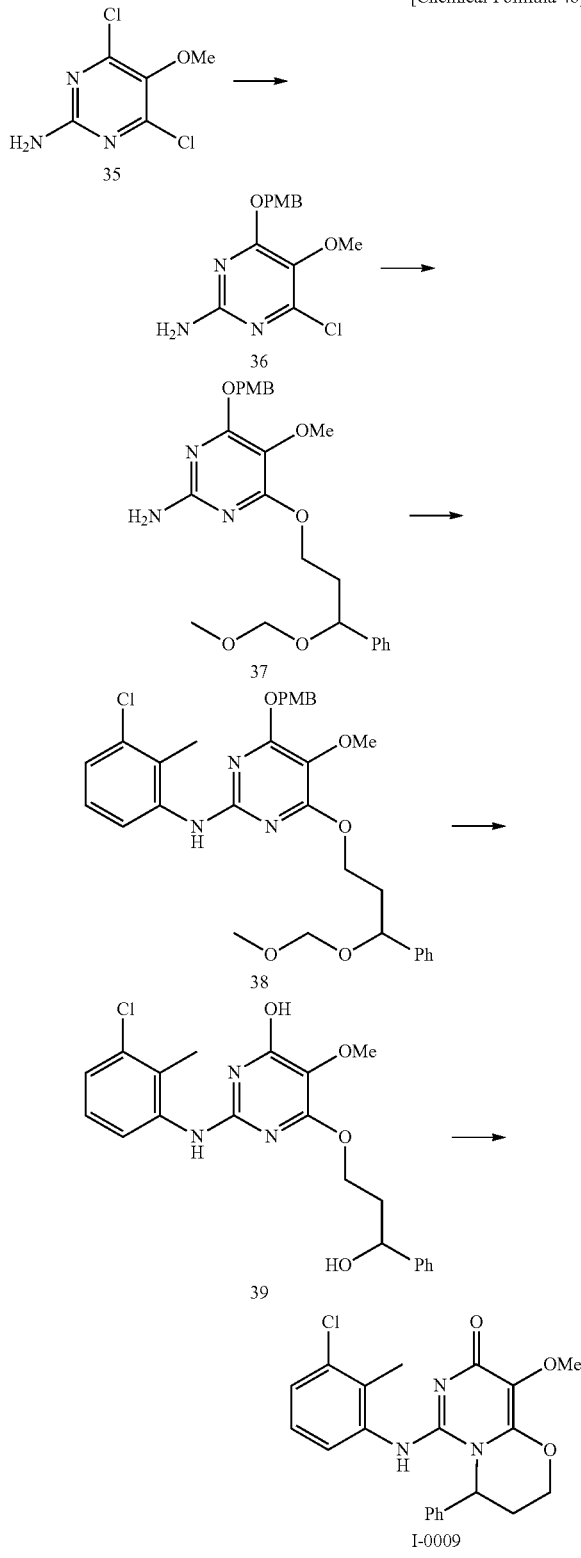

Step 1

Under nitrogen atmosphere, para-methoxybenzyl alcohol (0.400 mL, 3.25 mmol) was dissolved in tetrahydrofuran (2 mL). Under ice cooling, sodium hydride (0.136 mg, 3.40 mmol) was added thereto. The mixture was heated to room temperature, and stirred for 0.5 hours. Under ice cooling, Compound 35 (600 mg, 3.09 mmol) was added thereto. The mixture was heated to room temperature, stirred for 1.5 hours, and cooled to room temperature. The aqueous solution of saturated ammonium chloride was added thereto. The aqueous layer was extracted with chloroform. The organic layer was washed by brine, and dried over anhydrous magnesium sulfate. The solvent was evaporated under reduced pressure. The obtained residue was purified by silica-gel column chromatography (hexane-ethyl acetate), and suspended in diisopropyl ether for washing to give Compound 36 (588.4 mg, yield 64%).

$^1$H-NMR (DMSO-D$_6$) δ: 7.42 (2H, d, J=8.7 Hz), 6.95 (2H, d, J=8.7 Hz), 6.79 (2H, s), 5.29 (2H, s), 3.76 (3H, s), 3.59 (3H, s).

Step 2

Under nitrogen atmosphere, Compound 24 (700 mg, 3.57 mmol) was dissolved in tetrahydrofuran (7 mL). Under ice cooling, sodium hydride (0.157 mg, 3.92 mmol) was added thereto. The mixture was heated to room temperature, and stirred for 0.5 hours. Under ice cooling, Compound 36 (703 mg, 2.378 mmol) was added thereto. After stirring at 60° C. for 1 hour, the mixture was cooled to room temperature. The aqueous solution of saturated ammonium chloride was added thereto. The aqueous layer was extracted with chloroform. The organic layer was washed by brine, and dried over anhydrous magnesium sulfate. The solvent was evaporated under reduced pressure. The obtained residue was purified by silica-gel column chromatography (10% dichloromethane contain hexane-ethyl acetate) to give the crude product of Compound 37.

Condition [1]: Retention time=2.31 (minutes): [M+H]=456.2

Step 3

Under nitrogen atmosphere, the crude product of Compound 37 (300 mg, 0.659 mmol) obtained in the step 2, Pd$_2$(dba)$_3$ (121 mg, 0.132 mmol), BINAP (164 mg, 0.263 mmol), sodium tert-butoxide (0.127 g, 1.317 mmol), and 1-bromo-3-chloro-2-methyl benzene (203 mg, 0.988 mmol) were suspended in toluene (3 mL). The mixture was stirred at 100° C. for 2 hours. After cooling, the mixture was diluted with water. The aqueous layer was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give the crude product of Compound 38 (273.5 mg, yield 49%).

Condition [1]: Retention time=3.04 (minutes): [M+H]=580.2

Step 4

The crude product of Compound 38 (265 mg, 0.457 mmol) obtained in the step 3 was dissolved in a 4 mol/L hydrochloric acid-dioxane solution (2.65 mL). The mixture was stirred for 1 hour. The solvent was evaporated under reduced pressure. The residue was purified by silica-gel column chromatography (hexane-ethyl acetate) to give Compound 39 (106.4 mg, yield 81%).

Condition [1]: Retention time=1.78 (minutes): [M+H]=416.1

Step 5

Compound 39 (92 mg, 0.221 mmol) was dissolved in dichloromethane (1 mL). Triphenylphosphine (128 mg, 0.487 mmol), triethylamine (0.077 mL, 0.553 mmol), and iodine (124 mg, 0.487 mmol) were added thereto. The mixture was stirred for 5 days. A 10% aqueous solution of sodium thiosulfate was added thereto. The mixture was stirred for a while. The aqueous layer was extracted with chloroform. The solvent was evaporated under reduced pressure. The residue was purified by silica-gel column chromatography (chloroform) to give Compound I-0009 (13.7 mg, yield 16%).

$^1$H-NMR (CDCl$_3$) δ: 1.59 (s, 3H), 2.25 (dq, J=14.0, 2.4 Hz, 1H), 2.63-2.73 (m, 1H), 3.79 (s, 3H), 4.18-4.25 (m, 1H), 4.46-4.50 (m, 1H), 6.01 (s, 1H), 6.52 (dd, J=7.3, 2.0 Hz, 1H), 6.98-7.04 (m, 2H), 7.21 (d, J=7.0 Hz, 2H), 7.33 (t, J=7.4 Hz, 1H), 7.41 (t, J=7.3 Hz, 2H).

Example 7

Synthesis of Compound I-0021

[Chemical Formula 49]

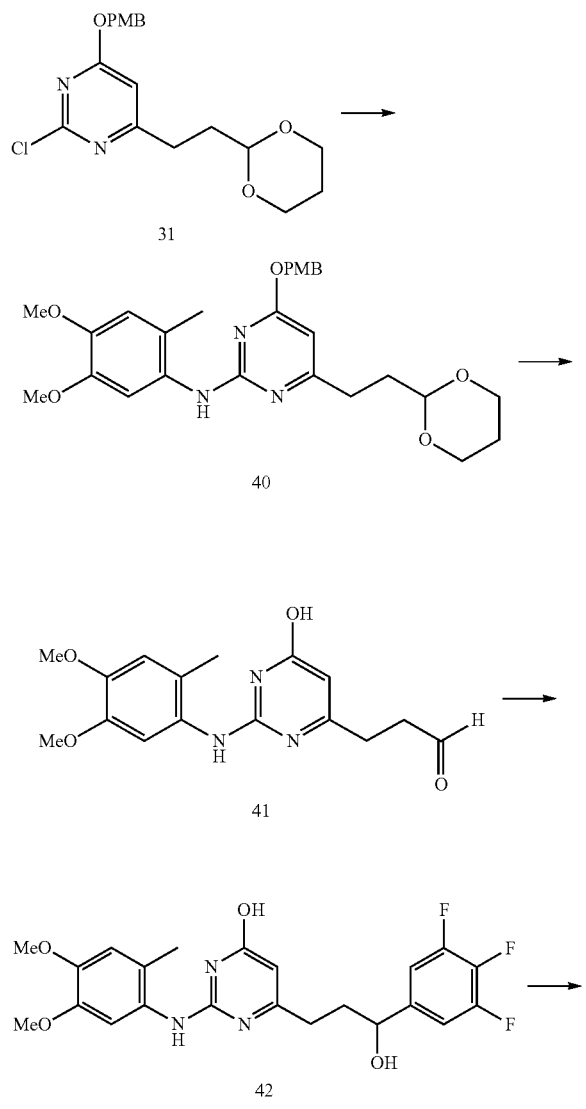

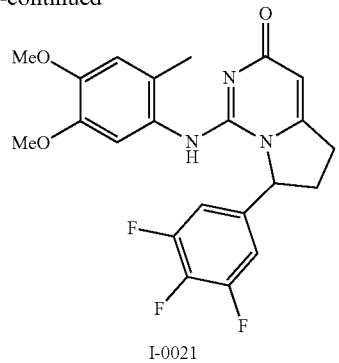

I-0021

Step 1

Under nitrogen atmosphere, Compound 31 (2 g, 5.48 mmol), 4,5-dimethoxy-2-methylaniline (1.375 mg, 8.22 mmol), palladium acetate (123 mg, 0.548 mmol), Xantphos (476 mg, 0.822 mmol), and cesium carbonate (5.36 g, 16.45 mmol) were suspended in 1,4-dioxane (20 mL). The mixture was stirred at 110° C. for 4 hours. After cooling, the mixture was diluted with water, and extracted with chloroform. The organic layer was washed by brine, and dried over anhydrous magnesium sulfate. The solvent was evaporated under reduced pressure. The obtained residue was purified by silica-gel column chromatography (hexane-ethyl acetate) to give Compound 40 (1.69 g, yield 62%).

Condition [1]: Retention time=1.70 (minutes): [M+H]=496.2

Step 2

Compound 40 (1.69 g, 3.41 mmol) was dissolved in a 4 mol/L hydrochloric acid-dioxane solution (17 mL). The mixture was stirred for 0.5 hours. Water (34 mL) was added thereto. The mixture was stirred for 5 hours. The saturated aqueous solution of sodium hydrogen carbonate was added thereto for neutralization. The aqueous layer was extracted with chloroform. The organic layer was dried over anhydrous magnesium sulfate. The solvent was evaporated under reduced pressure to give the crude product of Compound 41 (1.25 g).

Condition [1]: Retention time=0.70 (minutes): [M+H]=318.1

Step 3

The crude product of Compound 41 (150 mg, 0.473 mmol) obtained in the step 2 was dissolved in tetrahydrofuran (1 mL). Under ice cooling, a 3,4,5-trifluorophenylmagnesium bromide-tetrahydrofuran solution (7.88 mL, 2.363 mmol) was added dropwise thereto. The mixture was heated to room temperature, and stirred for 18 hours. A 3,4,5-trifluorophenylmagnesium bromide-tetrahydrofuran solution (2.00 mL, 0.591 mmol) was added dropwise thereto. The mixture was stirred for 2 hours. The aqueous solution of saturated ammonium chloride was added thereto. The mixture was stirred for a while, and extracted with ethyl acetate. The organic layer was washed by brine, and dried over anhydrous sodium sulfate. The obtained residue was purified by silica-gel column chromatography (chloroform-methanol) to give Compound 42 (133 mg, yield 63%).

Condition [1]: Retention time=1.53 (minutes): [M+H]=450.2

Step 4

Compound 42 (133 mg, 0.296 mmol) was dissolved in dichloromethane (2.6 mL). Triphenylphosphine (171 mg, 0.651 mmol), triethylamine (0.103 mL, 0.740 mmol), and iodine (165 mg, 0.651 mmol) were added thereto. The mixture was stirred for 5 days. A 10% aqueous solution of sodium thiosulfate was added thereto. The mixture was stirred for a while. The aqueous layer was extracted with chloroform. The solvent was evaporated under reduced pressure. The obtained residue was purified by silica-gel column chromatography (chloroform). The obtained solid was washed by a mixed solvent of ethyl acetate and diisopropyl ether to give Compound I-0021 (29.0 mg, yield 23%).

$^1$H-NMR (CDCl$_3$) δ: 1.72 (s, 3H), 2.08-2.13 (m, 1H), 2.63-2.74 (m, 1H), 2.92-3.09 (m, 2H), 3.79 (s, 3H), 3.82 (s, 3H), 5.42 (s, 1H), 5.55 (d, J=8.8 Hz, 1H), 6.21 (s, 1H), 6.65 (s, 1H), 6.87 (t, J=7.0 Hz, 2H), 7.37 (s, 1H).

Reference Example 2

Synthesis of Compound 45

[Chemical Formula 50]

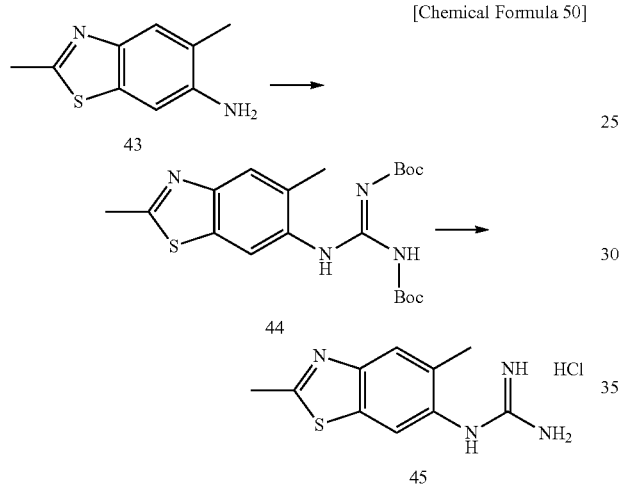

Step 1

Compound 43 (2.2 g, 12.34 mmol) was dissolved in tetrahydrofuran (22 mL). Tert-Butyl((tert-butoxycarbonyl)imino(1H-pyrazol-1-yl)methyl) carbamate (3.48 g, 11.22 mmol) and DIEA (3.92 mL, 22.44 mmol) were added thereto. The mixture was stirred at 50° C. for 24 hours. After cooling, water was added thereto. The mixture was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give Compound 44 (1.97 g, yield 42%).

Condition [1]: Retention time=2.75 (minutes): [M+H]=421.2

Step 2

Compound 44 (1.7 g, 4.04 mmol) was suspended in tert-butanol (136 mL). The mixture was stirred at 80° C. A 4 mol/L hydrochloric acid-dioxane solution (34 mL) was added thereto. The mixture was stirred for 22 hours. Ethanol (17 mL) was added thereto. The mixture was stirred for 24 hours. After cooling, the solvent was evaporated under reduced pressure. The residue was washed by diethylether, and dried under reduced pressure to give Compound 45 (1.21 g, yield 96%).

Condition [1]: Retention time=0.57 (minutes): [M+H]=220.8

Example 8

Synthesis of Compound I-0036

[Chemical Formula 51]

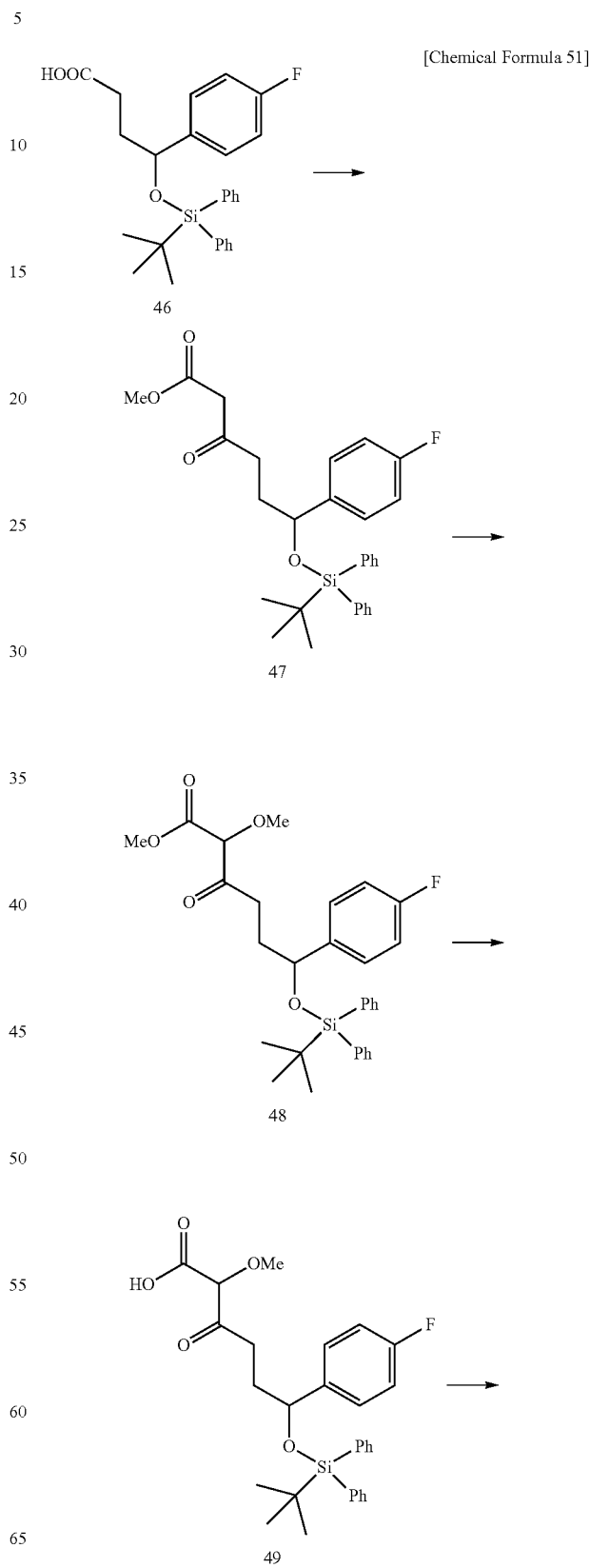

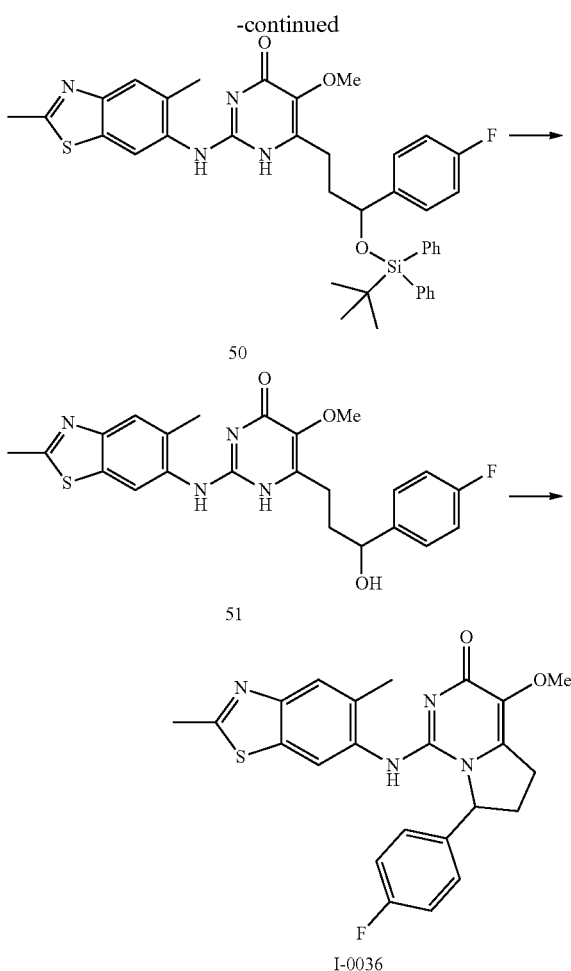

Step 1

Compound 46 derived from 4-(4-fluorophenyl)-4-oxobutanoic acid was reacted with Meldrum's acid according to the condition of the literature (Synlett 1993, 9, 651) to give Compound 47.

Step 2

Iodobenzene diacetate (1.323 g, 4.11 mmol) was dissolved in methanol (10 mL). A boron trifluoride-ethyl ether complex (0.521 mL, 4.11 mmol) was added thereto. The mixture was stirred at room temperature for 10 minutes. A methanol (10 mL) solution of Compound 47 (2 g, 3.73 mmol) was added thereto. The mixture was stirred for 4 hours. The reaction mixture was poured into the saturated aqueous solution of sodium hydrogen carbonate. The aqueous layer was extracted with ethyl acetate. The organic layer was dried over anhydrous magnesium sulfate. The solvent was evaporated under reduced pressure. The obtained residue was purified by silica-gel column chromatography (hexane-ethyl acetate) to give Compound 48 (1.107 g, yield 57%).

Condition [2]: Retention time=3.54 (minutes): [M+H]=522

Step 3

Compound 48 (15.44 g, 34.3 mmol) was suspended in a mixed solvent of methanol (45 mL) and tetrahydrofuran (45 mL). A 2 mol/L aqueous solution of sodium hydroxide (20.56 mL, 41.1 mmol) was added thereto. The mixture was stirred at 60° C. for 1 hour. After cooling, a 2 mol/L hydrochloric acid solution (22 mL) was added thereto, and poured into brine. The aqueous layer was extracted with ethyl acetate. The organic layer was washed by brine, and dried over anhydrous magnesium sulfate. The solvent was evaporated under reduced pressure to give Compound 49 (15.13 g, yield 95%).

Condition [2]: Retention time=3.10 (minutes): [M−H]=435

Step 4

Compound 45 (1.21 g, 4.71 mmol) was suspended in methanol (24 mL). Potassium-tert-butoxide (1.058 g, 9.43 mmol), Compound 49 (2.463 g, 4.71 mmol), and methanol (75 mL) were added thereto. The mixture was stirred at 80° C. for 6 hours, and cooled. The solvent was evaporated under reduced pressure. Methanol (24.6 mL) and potassium-tert-butoxide (0.529 g, 4.712 mmol) were added thereto. The mixture was stirred at 80° C. for 2 hours and 45 minutes. After cooling, Compound 41 (2.463 g, 4.71 mmol) and methanol (3 mL) were added thereto. The mixture was stirred at 80° C. for 3 hours. After cooling, water was added thereto. The aqueous layer was extracted with ethyl acetate. The organic layer was washed by brine, and dried over anhydrous sodium sulfate. The solvent was evaporated under reduced pressure to give the crude product of Compound 50 (5.02 g).

Condition [1]: Retention time=3.05 (minutes): [M+H]=693.3

Step 5

The crude product of Compound 50 (5.02 g) obtained in the step 4 was dissolved in tetrahydrofuran (25 mL). A TBAF-tetrahydrofuran solution (9.438 mL, 9.44 mmol) was added thereto. The mixture was stirred at room temperature for 12 hours. Thereafter, the mixture was stirred at 50° C. for 1 hour. After cooling, water was added thereto. The aqueous layer was extracted with chloroform. The organic layer was washed by brine, and dried over anhydrous sodium sulfate. The solvent was evaporated under reduced pressure. The obtained residue was purified by silica-gel column chromatography (chloroform-methanol) to give Compound 51 (937.4 mg, yield 44%).

Condition [1]: Retention time=1.65 (minutes): [M+H]=455.3

Step 6

Compound 51 (930 mg, 2.046 mmol) was dissolved in dichloromethane (18.6 mL). Triphenylphosphine (1181 mg, 4.50 mmol), triethylamine (1.426 mL, 10.23 mmol), and iodine (1143 mg, 4.50 mmol) were added thereto. The mixture was stirred for 1 hour. A 10% aqueous solution of sodium thiosulfate was added thereto. The mixture was stirred for a while. The aqueous layer was extracted with chloroform. The solvent, was evaporated under reduced pressure. The residue was purified by silica-gel column chromatography (chloroform-methanol). The obtained racemate was subjected to preparative SFC (Preparative condition 1) to separate an optically active form. The obtained amorphous form was dissolved in ethanol. Diisopropyl ether was slowly added thereto. The precipitated solids were filtered, and dried under reduced pressure to give Compound P0036 (117.1 mg, yield 13%).

$^1$H-NMR (CDCl$_3$) δ: 1.77 (s, 3H), 2.12-2.17 (m, 1H), 2.65-2.75 (m, 1H), 2.78 (s, 3H), 3.05-3.19 (m, 2H), 3.82 (s,

3H), 5.63 (d, J=8.6 Hz, 1H), 7.07-7.09 (m, 2H), 7.19-7.22 (m, 2H), 7.43 (brs, 1H), 7.67 (brs, 1H).

Example 9

Synthesis of compound I-0059

[Chemical Formula 52]

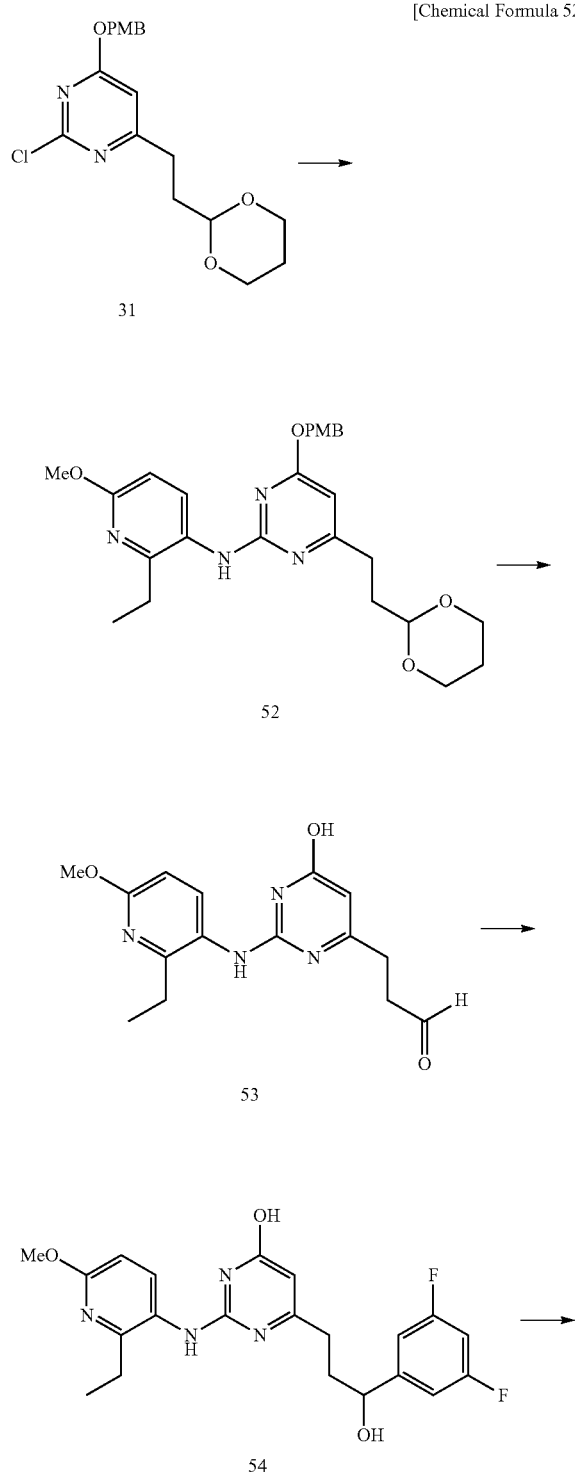

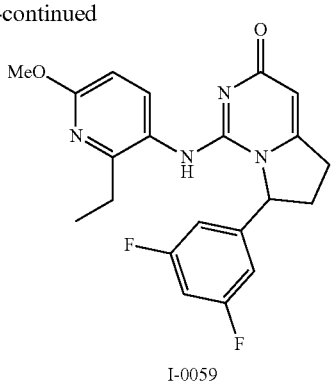

I-0059

Step 1

Under nitrogen atmosphere, Compound 31 (1.918 g, 5.26 mmol), 2-ethyl-6-methoxypyridin-3-amine (400 mg, 2.63 mmol), palladium acetate (59 mg, 0.263 mmol), Xantphos (228 mg, 0.394 mmol), and cesium carbonate (2.569 g, 7.88 mmol) were suspended in 1,4-dioxane (20 mL). The mixture was stirred at 110° C. for 3 hours. After cooling, the mixture was diluted with water, and extracted with chloroform. The organic layer was dried over anhydrous magnesium sulfate. The solvent was evaporated under reduced pressure. The obtained residue was purified by silica-gel column chromatography (hexane-ethyl acetate) to give Compound 52 (685.0 mg, yield 54%).

Condition [1]: Retention time=2.01 (minutes): [M+H]=481.3

Step 2

The compound 52 (680 mg, 1.415 mmol) was suspended in a 4 mol/L hydrochloric acid-dioxane solution (6.8 ml). The mixture was stirred for 20 minutes. Water (6.8 mL) was added thereto. The mixture was stirred for 6 hours. The reaction mixture was washed by ethyl acetate. The saturated aqueous solution of sodium hydrogen carbonate was added to the aqueous layer for neutralization. The mixture was extracted with 10% methanol-containing chloroform. The organic layer was dried over anhydrous sodium sulfate. The solvent was evaporated under reduced pressure to give the crude product of Compound 53 (465 mg).

Condition [1]: Retention time=0.79 (minutes): [M+H]=303.2

Step 3

The crude product of Compound 53 (465 mg) obtained in the step 2 was suspended in tetrahydrofuran (4 mL). Under ice cooling, a 3,5-difluorophenylmagnesium bromide-tetrahydrofuran solution (14.15 mL, 7.07 mmol) was added dropwise thereto. The mixture was heated to room temperature, and stirred for 4 hours. The aqueous solution of saturated ammonium chloride was added thereto. The mixture was stirred for a while, and extracted with ethyl acetate. The organic layer was washed by brine, and dried over anhydrous magnesium sulfate. The obtained residue was purified by silica-gel column chromatography (chloroform-methanol) to give Compound 54 (457.8 mg, yield 78%).

Condition [1]: Retention time=1.62 (minutes): [M+H]=417.2

Step 4

Compound 54 (450 mg, 0.983 mmol) was dissolved in dichloromethane (4.5 mL). Triphenylphosphine (387 mg, 1.475 mmol), triethylamine (0.343 mL, 2.458 mmol), and iodine (374 mg, 1.475 mmol) were added thereto. The mixture was stirred for 15 hours. A 10% aqueous solution of sodium thiosulfate was added thereto. The mixture was stirred for a while. The aqueous layer was extracted with chloroform. The solvent was evaporated under reduced pressure. The obtained residue was purified by silica-gel column chromatography (chloroform-methanol). The obtained racemate was subjected to preparative SFC (Preparative condition 2) to separate an optically active form. The obtained amorphous form was solidified in diisopropyl ether. The precipitated solids were filtered, and dried under reduced pressure to give Compound I-0059 (74.4 g, yield 19%).

$^1$H-NMR (CDCl$_3$) δ: 0.92 (t, J=7.4 Hz, 3H), 2.10-2.18 (m, 3H), 2.64-2.75 (m, 1H), 2.93-3.11 (m, 2H), 3.87 (s, 3H), 5.43 (s, 1H), 5.58 (d, J=8.8 Hz, 1H), 6.51 (d, J=8.8 Hz, 1H), 6.73-6.79 (m, 3H), 6.91 (d, J=8.5 Hz, 1H), 7.30 (brs, 1H).

Example 10

Synthesis of Compound I-0086

[Chemical Formula 53]

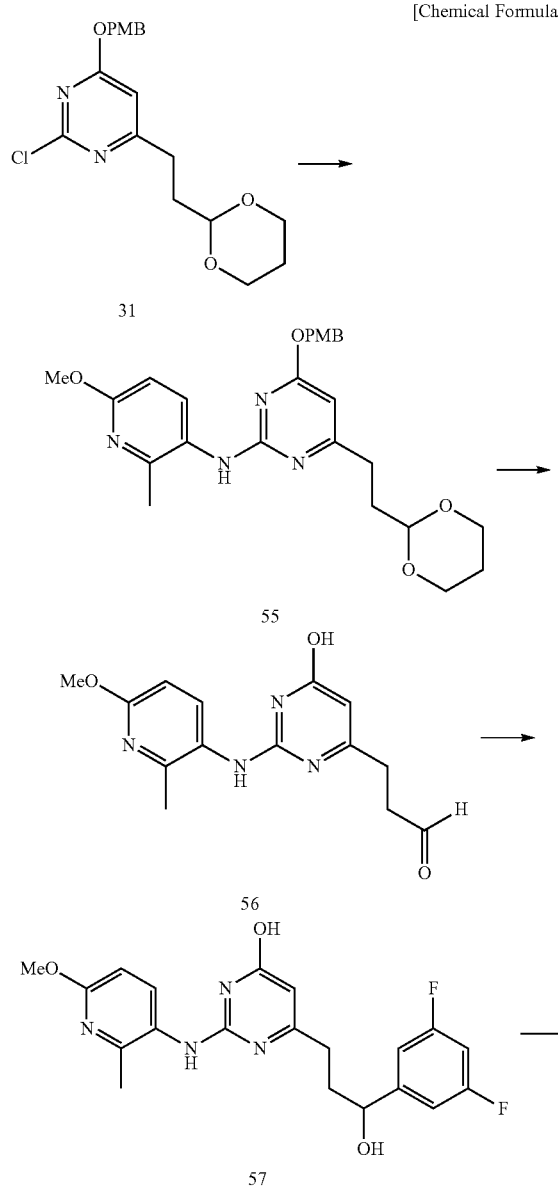

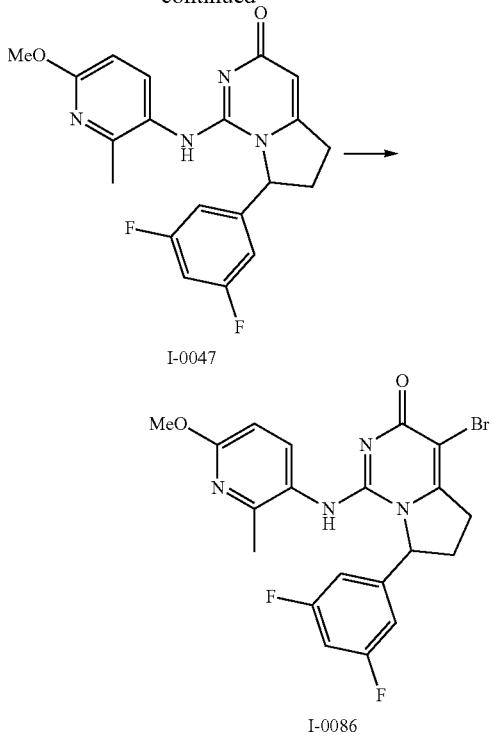

Step 1

Under nitrogen atmosphere, Compound 31 (5.5 g, 15.08 mmol), 6-methoxy-2-methylpyridin-3-amine (2.5 g, 18.09 mmol), palladium acetate (338 mg, 1.508 mmol), Xantphos (1.308 g, 2.261 mmol), and cesium carbonate (14.74 g, 45.2 mmol) were suspended in 1,4-dioxane (55 mL). The mixture was stirred at 110° C. for 1 hour. After cooling, the mixture was diluted with water, and extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give Compound 55 (2.61 g, yield 37%).

Condition [1]: Retention time=1.81 (minutes): [M+H]=467.3

Step 2

Compound 55 (2.61 g, 5.59 mmol) was suspended in a 4 mol/L hydrochloric acid-dioxane solution (26 ml). The mixture was stirred for 30 minutes. Water (26 mL) was added thereto. After stirring for 16 hours, the reaction mixture was washed by ethyl acetate. The saturated aqueous solution of sodium hydrogen carbonate was added to the aqueous layer for neutralization. The mixture was extracted with 10% methanol-containing chloroform. The organic layer was dried over anhydrous sodium sulfate. The solvent was evaporated under reduced pressure to give the crude product of Compound 56 (1.95 g).

Condition [1]: Retention time=0.60 (minutes): [M+H]=289.2

Step 3

The crude product of Compound 56 (1.95 g) obtained in the step 2 was suspended in tetrahydrofuran (4 ml). Under ice cooling, a 3,5-difluorophenylmagnesium bromide-tetrahydrofuran solution (44.9 mL, 22.46 mmol) was added dropwise thereto. The mixture was heated to room temperature, and stirred for 22 hours. The aqueous solution of saturated ammonium chloride was added thereto. The mixture was stirred for a while, and extracted with ethyl acetate. The organic layer was washed by brine, and dried over anhydrous magnesium sulfate. The obtained residue was purified by silica-gel column chromatography (chloroform-methanol) to give Compound 57 (1.73 g, yield 77%).

Condition [1]: Retention time=1.44 (minutes): [M+H]=403.2

Step 4

Compound 57 (1.37 g, 4.3 mmol) was dissolved in dichloromethane (17.3 mL). Triphenylphosphine (2481 mg, 9.46 mmol), triethylamine (1.498 mL, 10.75 mmol), and iodine (2401 mg, 9.46 mmol) were added thereto. The mixture was stirred for 12 hours. A 10% aqueous solution of sodium thiosulfate was added thereto. The mixture was stirred for a while. The aqueous layer was extracted with chloroform. The mixture was dried over anhydrous magnesium sulfate. The solvent was evaporated under reduced pressure. The obtained residue was purified by silica-gel column chromatography (chloroform-methanol). The obtained racemate was subjected to preparative SFC (Preparative condition 3) to separate an optically active form. The obtained amorphous form was solidified in diisopropyl ether. The precipitated solids were filtered, and dried under reduced pressure to give Compound I-0047 (234.5 mg, yield 14%).

$^1$H-NMR (CDCl$_3$) δ: 1.93 (s, 3H), 2.10-2.16 (m, 1H), 2.64-2.75 (m, 1H), 2.92-3.11 (m, 2H), 3.86 (s, 3H), 5.44 (s, 1H), 5.59 (d, J=7.9 Hz, 1H), 6.51 (d, J=8.4 Hz, 1H), 6.74-6.80 (m, 3H), 6.90 (d, J=8.5 Hz, 1H), 7.29 (brs, 1H).

Step 5

Compound I-0047 (1.5 g, 3.90 mmol) was suspended in DMF (30 mL). NBS (0.729 g, 4.10 mmol) was added thereto. The mixture was stirred at 60° C. for 1 hour. After cooling, water was added dropwise thereto. The precipitated solids were filtered, and washed by water and ethyl acetate. The obtained solids were dried under reduced pressure to give Compound I-0086 (1.66 g, yield 92%).

$^1$H-NMR (CDCl$_3$) δ: 1.90 (s, 3H), 2.16-2.21 (m, 1H), 2.71-2.82 (m, 1H), 2.92 (d, J=29.4 Hz, 1H), 3.07-3.21 (m, 2H), 3.86 (s, 3H), 5.69 (d, J=9.3 Hz, 1H), 6.52 (d, J=8.5 Hz, 1H), 6.74-6.80 (m, 3H), 6.87 (d, J=8.5 Hz, 1H), 7.45 (brs, 1H).

Example 11

Synthesis of Compound I-0087

[Chemical Formula 54]

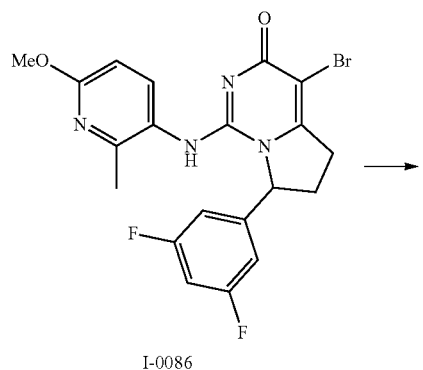

I-0086

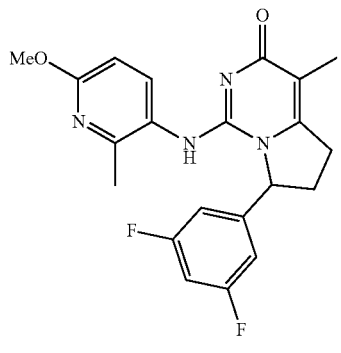

I-0087

Step 1

Under nitrogen atmosphere, Compound I-0086 (200 mg, 0.432 mmol), (1,1'-bis(di-tert-butylphosphino)ferrocene) palladium(II) dichloride (28.1 mg, 0.043 mmol), potassium carbonate (119 mg, 0.863 mmol), and trimethylboroxine (0.302 mL, 2.159 mmol) were suspended in 1,4-dioxane (2 mL). The mixture was stirred at 110° C. for 2 hours. After cooling, the mixture was diluted with water, and extracted with ethyl acetate. The organic layer was washed by brine, and dried over anhydrous magnesium sulfate. The solvent was evaporated under reduced pressure. The obtained residue was purified by amino silica-gel column chromatography (10% dichloromethane containing hexane-ethyl acetate), and solidified in diisopropyl ether. The precipitated solids were filtered, and dried under reduced pressure to give Compound I-0087 (48.2 mg, yield 28%).

$^1$H-NMR (CDCl3) δ: 1.93 (s, 3H), 2.11-2.16 (m, 1H), 2.64-2.75 (m, 1H), 2.93-3.10 (m, 2H), 3.86 (s, 3H), 5.44 (s, 1H), 5.59 (d, J=8.3 Hz, 1H), 6.51 (d, J=8.8 Hz, 1H), 6.74-6.79 (m, 3H), 6.90 (d, J=8.3 Hz, 1H).

Reference Example 3

Synthesis of compound 61

[Chemical Formula 55]

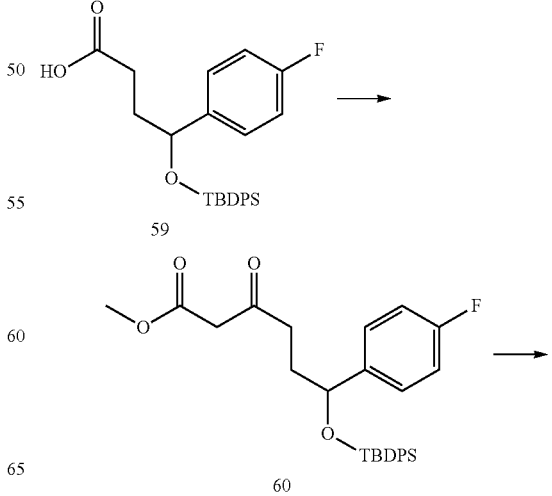

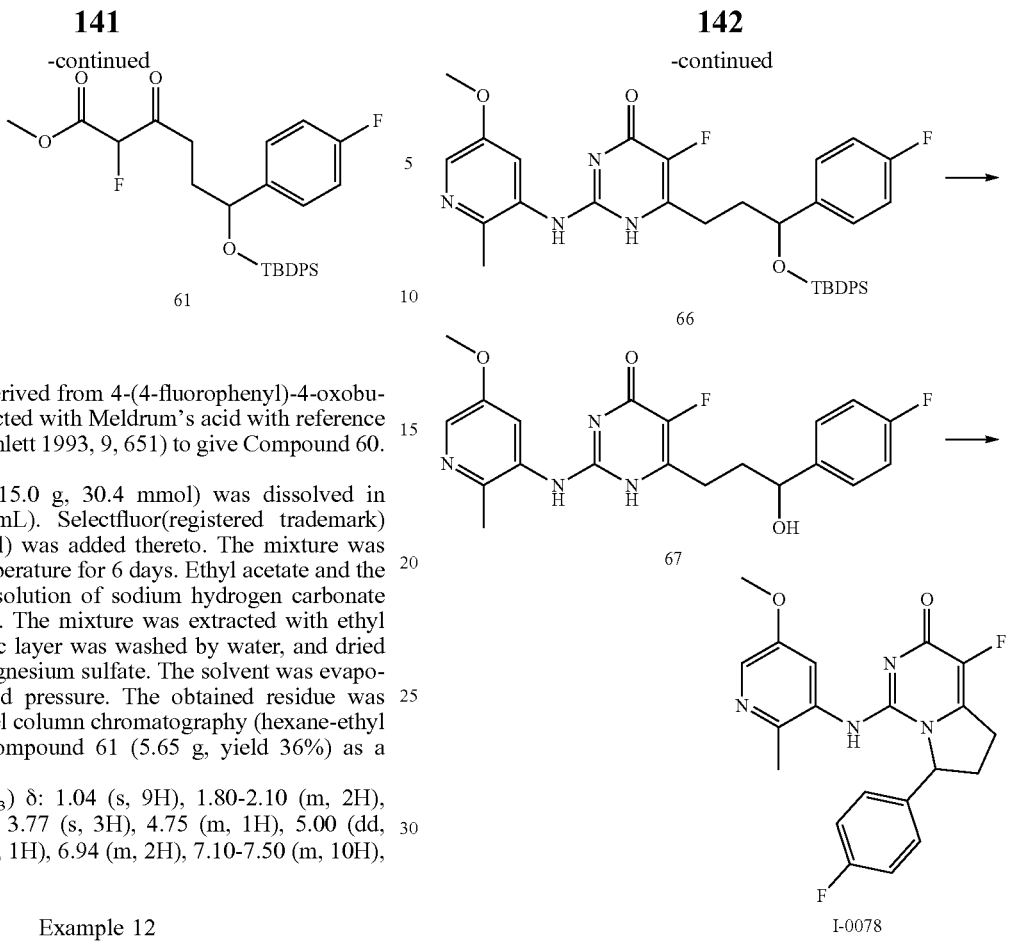

Step 1

Compound 59 derived from 4-(4-fluorophenyl)-4-oxobutanoic acid was reacted with Meldrum's acid with reference to the literature (Synlett 1993, 9, 651) to give Compound 60.

Step 2

Compound 60 (15.0 g, 30.4 mmol) was dissolved in acetonitrile (300 mL). Selectfluor(registered trademark) (20.4 g, 54.8 mmol) was added thereto. The mixture was stirred at room temperature for 6 days. Ethyl acetate and the saturated aqueous solution of sodium hydrogen carbonate were added thereto. The mixture was extracted with ethyl acetate. The organic layer was washed by water, and dried over anhydrous magnesium sulfate. The solvent was evaporated under reduced pressure. The obtained residue was purified by silica-gel column chromatography (hexane-ethyl acetate) to give Compound 61 (5.65 g, yield 36%) as a viscous oil.

$^1$H-NMR (CDCl$_3$) δ: 1.04 (s, 9H), 1.80-2.10 (m, 2H), 2.30-2.70 (m, 2H), 3.77 (s, 3H), 4.75 (m, 1H), 5.00 (dd, J=12.0 Hz, 49.2 Hz, 1H), 6.94 (m, 2H), 7.10-7.50 (m, 10H), 7.65 (m, 2H).

Example 12

Synthesis of Compound P0078

[Chemical Formula 56]

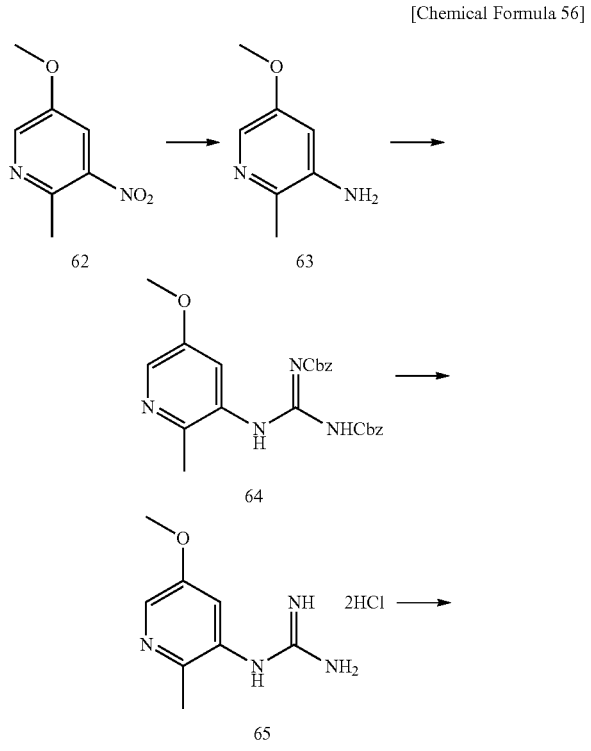

Step 1

5-Methoxy-2-methyl-3-nitropyridine (6.00 g, 17.8 mmol) was dissolved in tetrahydrofuran (60 mL). Pearlman's catalyst (0.60 g) was added thereto. The mixture was subjected to catalytic reduction at room temperature overnight. The reaction mixture was filtered. The solvent was evaporated under reduced pressure to give Compound 63 (2.48 g, quant.) as a solid.

$^1$H-NMR (CDCl$_3$) δ: 2.35 (s, 3H), 3.61 (brs, 2H), 3.80 (s, 3H), 6.51 (d, J=2.4 Hz, 1H), 7.67 (d, J=2.4 Hz, 1H).

Step 2

Compound 63 (1.50 g, 10.9 mmol) and N,N'-bis(carbobenzoxy)-1H-pyrazole-1-carboxamidine (4.52 g, 11.9 mmol) were dissolved in tetrahydrofuran (23 mL). DIEA (1.82 g, 14.1 mmol) was added thereto. The mixture was stirred at room temperature overnight. The solvent was evaporated under reduced pressure. Diethylether was added to the obtained residue. The precipitated solids were filtered to give Compound 64 (4.23 g, yield 87%).

$^1$H-NMR (CDCl$_3$) δ: 2.50 (s, 3H), 3.83 (s, 3H), 5.14 (s, 2H), 5.26 (s, 2H), 7.20-7.40 (m, 10H), 8.02 (s, 1H), 8.07 (s, 1H), 10.24 (s, 1H), 11.88 (s, 1H).

Step 3

Compound 64 (4.00 g, 8.92 mmol) was dissolved in tetrahydrofuran (80 mL). Pearlman's catalyst (0.80 g) was added thereto. The mixture was subjected to catalytic reduction at room temperature for 8 hours. A 2 mol/L hydrochloric acid-methanol solution (13.4 mL, 26.8 mmol) was added thereto. The mixture was filtered. The solvent was evaporated under reduced pressure. Diethylether was added to the obtained residue. The precipitated solids were filtered to give Compound 65 (2.00 g, yield 89%).

$^1$H-NMR (DMSO-d$_6$) δ: 2.49 (s, 3H), 3.91 (s, 3H), 7.71 (brs, 4H), 7.79 (s, 1H), 8.38 (s, 1H), 10.20 (s, 1H).

Step 4

Compound 65 (337 mg, 1.33 mmol) and Compound 61 (400 mg, 0.78 mmol) were dissolved in methanol (8.0 mL). Tert-Butoxy potassium (308 mg, 2.74 mmol) was added thereto. The mixture was stirred at 80° C. for 6 hours. Ethyl acetate and water were added thereto. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give Compound 66 (292 mg, yield 58%) as an amorphous material.

$^1$H-NMR (CDCl$_3$) δ: 1.01 (s, 9H), 2.04 (m, 2H), 2.26 (m, 2H), 2.51 (s, 3H), 3.70 (s, 3H), 4.70 (t, J=5.6 Hz, 1H), 5.60 (s, 1H), 6.91 (t, J=8.8 Hz, 2H), 7.10-7.50 (m, 10H), 7.62 (m, 2H), 8.01 (m, 2H).

Step 5

Compound 66 (290 mg, 0.46 mmol) was dissolved in tetrahydrofuran (3.0 mL). A 1.0 mol/L TBAF-tetrahydrofuran solution (0.684 mL, 0.684 mmol) was added thereto. The mixture was stirred at 50° C. overnight. Ethyl acetate and water were added thereto. The mixture was extracted with ethyl acetate. The organic layer was washed by brine, and dried over anhydrous magnesium sulfate. The solvent was evaporated under reduced pressure. Diethylether was added to the obtained residue. The precipitated solids were filtered to give Compound 67 (180 mg, yield 98%).

[M+H]=385: Condition [2]: Retention time=0.96 (minutes)

Step 6

Compound 67 (180 mg, 0.447 mmol) and triphenylphosphine (176 mg, 0.671 mmol) were dissolved in dichloromethane (3.0 mL). Triethylamine (0.155 mL, 1.12 mmol) and iodine (170 mg, 671 mmol) were added thereto. The mixture was stirred at room temperature overnight. Ethyl acetate and the aqueous solution of sodium thiosulfate were added thereto. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give a racemate (129 mg). The racemate was optically resolved by preparative SFC (Preparative condition 1) to give Compound I-0078 (54.0 mg, yield 31%) as a solid.

$^1$H-NMR (DMSO-d$_6$) δ: 1.84 (s, 3H), 2.08 (m, 1H), 2.77 (m, 1H), 3.00-3.20 (m, 2H), 3.77 (s, 3H), 5.89 (s, 1H), 7.15 (s, 1H), 7.26 (brs, 4H), 8.04 (s, 1H), 8.42 (s, 1H).

Reference Example 4

Synthesis of Compound 71

[Chemical Formula 57]

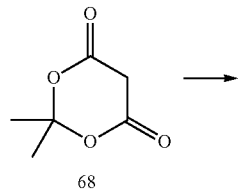

68

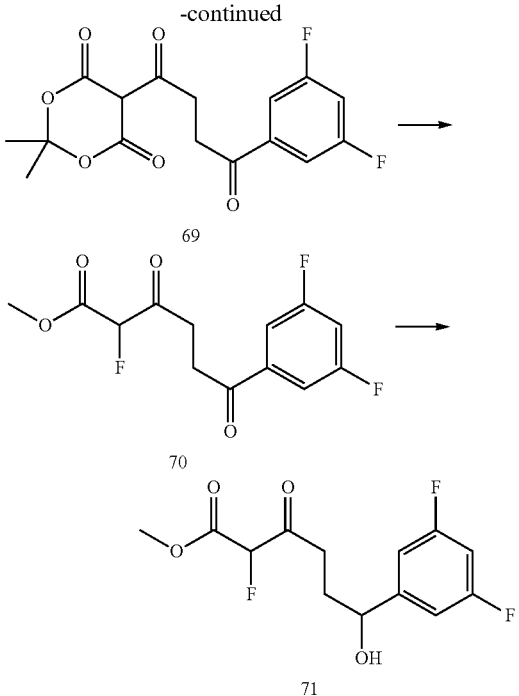

Step 1

Meldrum's acid (7.18 g, 49.8 mmol), 4-(3,5-di fluorophenyl)-4-oxobutanoic acid (9.70 g, 45.3 mmol), and DMAP (0.553 g, 4.53 mmol) were dissolved in dichloromethane (200 mL). EDC hydrochloride (9.55 g, 49.8 mmol) and triethylamine (15.7 mL, 113 mmol) were added thereto. The mixture was stirred at room temperature for 3 hours. The solvent was evaporated under reduced pressure. Ethyl acetate and a 2 mol/L aqueous solution of hydrochloric acid were added to the obtained residue. The mixture was extracted with ethyl acetate. The organic layer was washed by water, and dried over anhydrous magnesium sulfate. The solvent was evaporated under reduced pressure. Ethyl acetate was added to the obtained residue. The precipitated solids were filtered to give Compound 69 (10.2 g, yield 66%).

$^1$H-NMR (CDCl$_3$) δ: 1.78 (s, 6H), 3.38 (t, J=6.4 Hz, 2H), 3.56 (t, J=6.4 Hz, 2H), 7.05 (m, 1H), 7.49 (m, 2H), 15.58 (s, 1H).

Step 2

Compound 69 (2.09 g, 6.14 mmol) was dissolved in acetonitrile (40 mL). Selectfluor(registered trademark) (2.41 g, 6.45 mmol) was added thereto. The mixture was stirred at room temperature overnight. Methanol (100 mL) and water (10 mL) were added thereto. The mixture was stirred at 80° C. for 1.5 hours. The solvent was evaporated under reduced pressure. Water was added to the obtained residue. The mixture was extracted with ethyl acetate. The organic layer was washed by brine, and dried over anhydrous magnesium sulfate. The solvent was evaporated under reduced pressure. The obtained residue was purified by silica-gel column chromatography (hexane-ethyl acetate) to give Compound 70 (572 mg, yield 32%) as an oil.

$^1$H-NMR (CDCl$_3$) δ: 3.08 (m, 2H), 3.31 (m, 2H), 3.91 (s, 3H), 5.39 (d, J=49.2 Hz, 1H), 7.04 (m, 1H), 7.47 (m, 2H).

Step 3

Compound 70 (0.611 g, 2.12 mmol) was dissolved in methanol (12 mL), and 10% palladium carbon (60.0 mg)

145 was added thereto. The mixture was subjected to catalytic reduction at room temperature for 3 hours. The reaction mixture was filtered through Celite. The solvent was evaporated under reduced pressure to give the crude product of Compound 71 (616 mg, quant.) as an oil.

Example 13

Synthesis of Compound I-0099

[Chemical Formula 58]

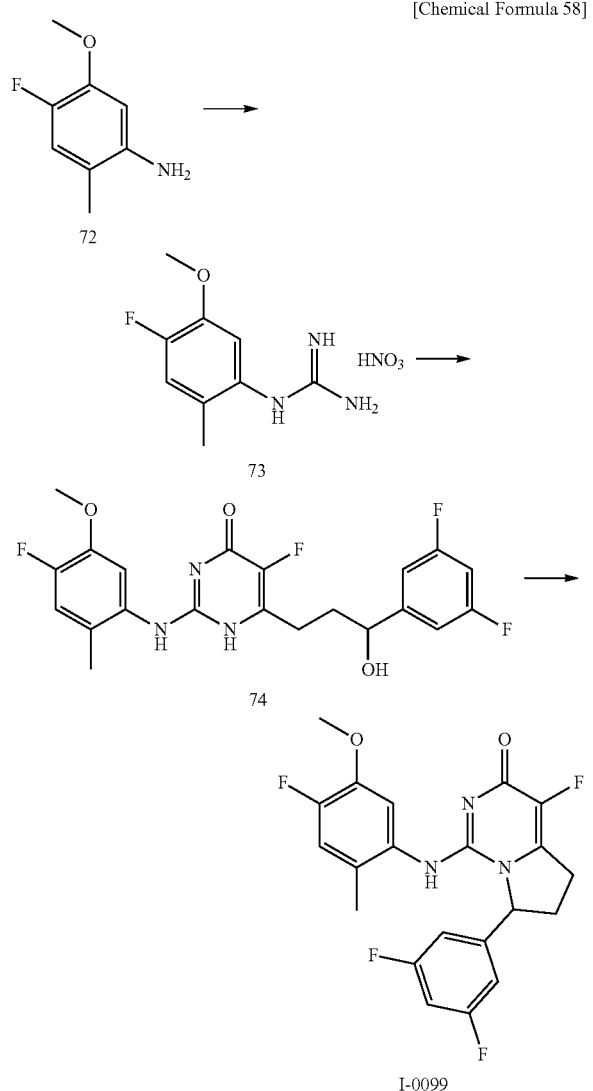

Step 1

1-Fluoro-2-methoxy-5-methyl-aniline (1.67 g, 10.8 mmol) and cyanamide (1.36 g, 32.3 mmol) were dissolved in ethanol (20 mL). A 69% aqueous solution of nitric acid (2.09 mL, 32.3 mmol) was added thereto. The mixture was stirred at 100° C. overnight. The solvent was evaporated under reduced pressure. Ethanol was added to the obtained residue. The precipitated solids were filtered to give Compound 73 (1.31 g, yield 47%).

$^1$H-NMR (DMSO-d6) δ: 2.12 (s, 3H), 3.82 (s, 3H), 7.03 (d, J=8.4 Hz, 1H), 7.17 (brs, 4H), 7.23 (d, J=12.0 Hz, 1H), 9.03 (brs, 1H).

146

Step 2

Compound 73 (0.305 g, 1.17 mmol) and the crude product of Compound 71 (0.200 g, 0.689 mmol) obtained in Reference Example 4 were dissolved in methanol (4.0 mL). Potassium tert-butoxide (0.155 g, 13.8 mmol) was added thereto. The mixture was stirred at 80° C. for 4 hours. Water was added thereto. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give Compound 74 (0.193 g, yield 64%) as an amorphous material.

[M+H]=438: Condition [2]: Retention time=1.88 (minutes)

Step 3

Compound 74 (180 mg, 0.447 mmol) and triphenylphosphine (176 mg, 0.671 mmol) were dissolved in dichloromethane (3.0 mL). Triethylamine (0.155 mL, 1.12 mmol) and iodine (170 mg, 671 mmol) were added thereto. The mixture was stirred at room temperature overnight. Ethyl acetate and the aqueous solution of sodium thiosulfate were added thereto. The mixture was extracted with ethyl acetate. The organic layer was washed by brine, and dried over anhydrous magnesium sulfate. The solvent was evaporated under reduced pressure. The obtained residue was purified by silica-gel column chromatography (chloroform-methanol) to give a racemate (129 mg). The racemate was optically resolved by preparative SFC (Preparative condition 2) to give the compound P0099 (54.0 mg, yield 31%) as a solid.

$^1$H-NMR (DMSO-d$_6$) δ: 1.71 (s, 3H), 2.13 (m, 1H), 2.77 (m, 1H), 3.08 (m, 2H), 3.75 (s, 3H), 5.83 (s, 1H), 6.80-7.10 (m, 4H), 7.23 (t, J=8.8 Hz, 1H), 8.37 (s, 1H).

Example 14

Synthesis of Compound I-Q103

[Chemical Formula 59]

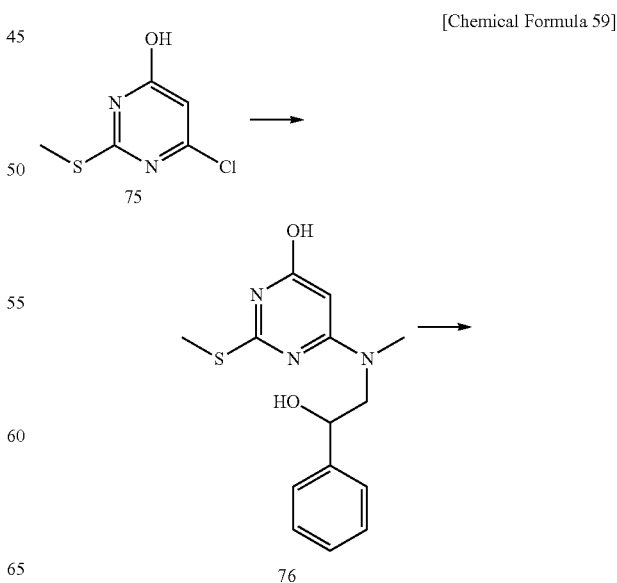

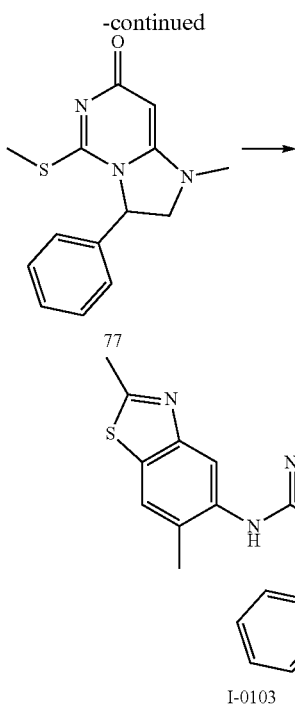

77

I-0103

Step 1

Under nitrogen atmosphere, Compound 75 (500 mg, 2.83 mmol) was dissolved in dioxane (5 mL). 2-Methylamino-1-phenylethan-1-ol (514 mg, 3.40 mmol) was added thereto. The mixture was stirred at 130° C. for 1 hour under microwave irradiation. Water was added thereto. The mixture was extracted with ethyl acetate. The organic layer was washed by brine, and dried over anhydrous sodium sulfate. The solvent was evaporated under reduced pressure. The obtained residue was purified by silica-gel column chromatography (chloroform-methanol) to give Compound 76 (358 mg, yield 43%).

Condition [1]: Retention time=1.38 (minutes): [M+H]=292.2

Step 2

Compound 76 (312 mg, 1.071 mmol) was dissolved in dichloromethane (5 mL). Triphenylphosphine (421 mg, 1.606 mmol), triethylamine (0.371 mL, 2.68 mmol), and iodine (408 mg, 1.606 mmol) were added thereto. The mixture was stirred at room temperature for 4 hours. The solvent was evaporated under reduced pressure. The obtained residue was purified by silica-gel column chromatography (chloroform-methanol) to give Compound 77 (278 mg, yield 95%).

Condition [1]: Retention time=1.27 (minutes): [M+H]=274.1

Step 3

Propionic acid (0.5 mL) and 2,5-dimethyl benzothiazol-6-amine (68.5 mg, 0.384 mmol) were added to Compound 77 (30 mg, 0.22 mmol). The mixture was stirred at 140° C. for 1 hour. The solvent was evaporated under reduced pressure. The residue was purified by reverse-phase column chromatography to give Compound I-0103 (9 mg, yield 20%).

Condition [3]: Retention time=1.40 (minutes): [M+H]=404

Example 15

Synthesis of Compound I-0107

[Chemical Formula 60]

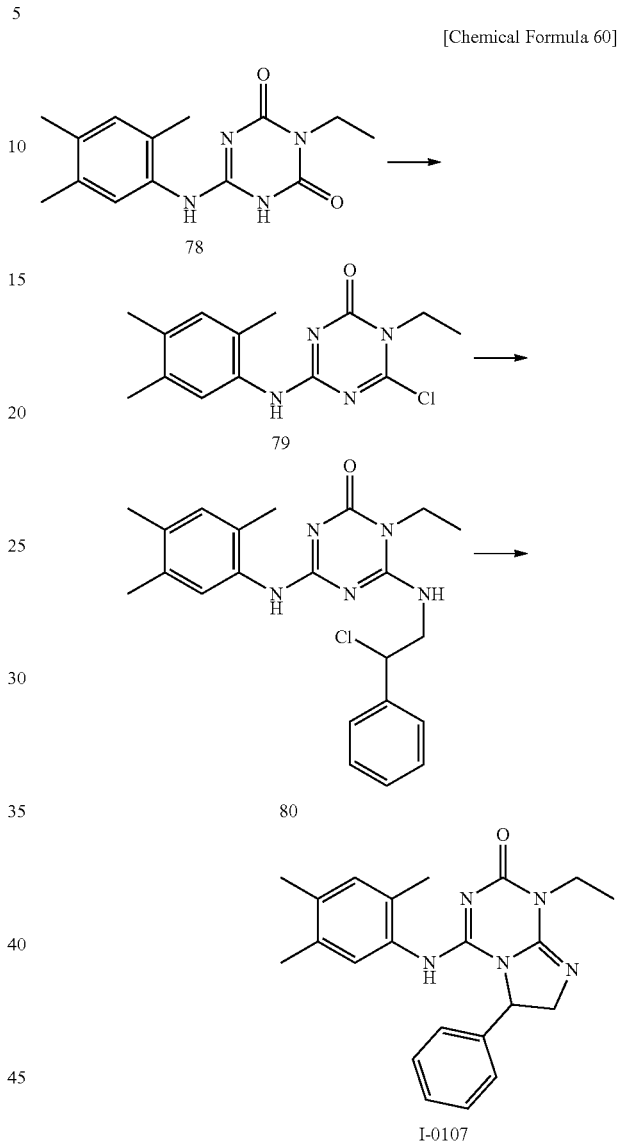

Step 1

Under nitrogen atmosphere, phosphorus oxychloride (0.5 mL) was added to Compound 78 (150 mg, 0.547 mmmol). The mixture was stirred at 80° C. for 30 minutes. The solvent was evaporated under reduced pressure to give the crude product of Compound 79.

Step 2

The crude product of Compound 79 obtained in the step 1 was dissolved in dioxane (1.5 mL). 2-Amino-1-phenylethan-1-ol (90 mg, 0.656 mmol) was added thereto. The mixture was stirred at 130° C. for 30 minutes under microwave irradiation. Water was added thereto. The mixture was extracted with ethyl acetate. The organic layer was washed by brine, and dried over anhydrous sodium sulfate. The solvent was evaporated under reduced pressure to give the crude product of Compound 80.

Step 3

The crude product of Compound 80 obtained in the step 2 was dissolved in DMF (1 mL). Potassium carbonate (92 mg, 0.666 mmol) was added thereto. The mixture was stirred at 50° C. for 30 minutes. Water was added thereto. The mixture was extracted with ethyl acetate. The organic layer was washed by brine, and dried over anhydrous sodium sulfate. The solvent was evaporated under reduced pressure. The obtained residue was purified by reverse-phase column chromatography to give Compound P0107 (23.6 mg, yield 12%).

Condition [1]: Retention time=1.39 (minutes): [M+H]=376

Example 16

Synthesis of Compound I-0145

[Chemical Formula 61]

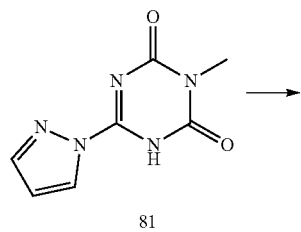

81

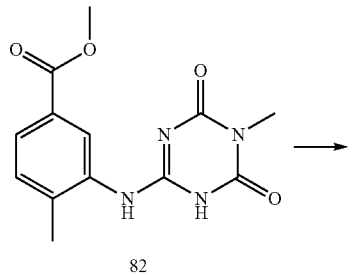

82

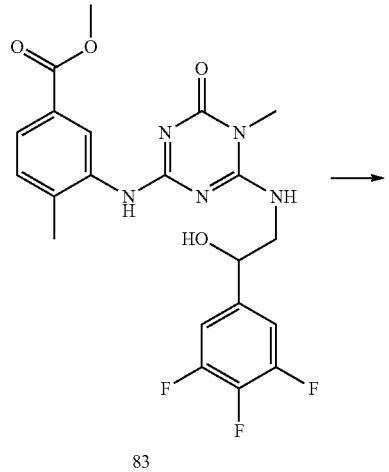

83

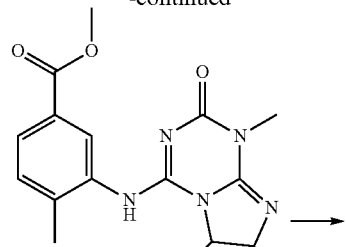

I-0215

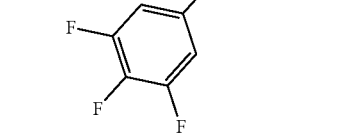

I-0216

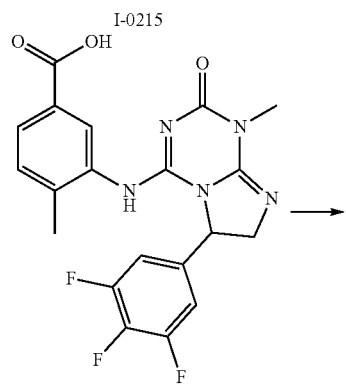

I-0217

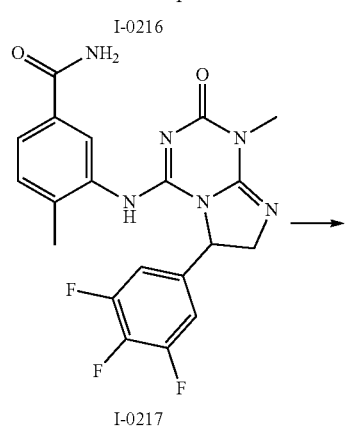

I-0145

Step 1: Synthesis of Compound 82

Methyl 3-amino-4-methylbenzoate (3.85 g, 23.3 mmol) and Compound 81 (3.0 g, 15.5 mmol, refer to International Publication WO 2012/020749A for the synthesis method)

were added to N-methylpyrrolidone (21 mL). The mixture was stirred at 130° C. for 26 hours. The reaction mixture was poured into water (210 mL). Under ice cooling, the mixture was stirred for 30 minutes. The precipitated solids were filtered, washed by water and diisopropyl ether, and dried under reduced pressure to give Compound 82 (4.20 g, yield 93.2%).

$^1$H-NMR (DMSO-$d_6$) δ: 2.28 (s, 3H), 3.08 (s, 3H), 3.85 (s, 3H), 7.41 (d, J=7.8 Hz, 1H), 7.74 (d, J=7.8 Hz, 1H), 8.09 (s, 1H), 8.59-8.68 (br, 1H), 11.28-11.36 (br, 1H).

Step 2: Synthesis of Compound 83

Under nitrogen atmosphere, Compound 82 (4.11 g, 14.2 mmol) was suspended in acetonitrile (41 ml). DIEA (5.44 ml, 31.1 mmol) and a phosphonitrilic chloride trimer (5.17 g, 14.9 mmol) were added thereto. The mixture was stirred at room temperature for 3.5 hours. (±)-2-Amino-1-(3,4,5-trifluorophenyl)ethanol (2.98 g, 15.6 mmol) was added thereto. The mixture was stirred at room temperature for 2 hours. The saturated aqueous solution of sodium hydrogen carbonate was added thereto. The mixture was extracted with ethyl acetate. The organic layer was washed by brine, and dried over anhydrous sodium sulfate. The solvent was evaporated under reduced pressure to give the crude product of Compound 83.

Condition [1]: Retention time=1.44 (minutes): [M+H]=464.2

Step 3: Synthesis of Compound I-0215

Under nitrogen atmosphere, the crude product of Compound 83 obtained in the step 2 was suspended in dichloromethane (120 mL). Triphenylphosphine (6.30 g, 24.0 mmol), triethylamine (7.83 ml, 56.5 mmol), and iodine (6.10 g, 24.0 mmol) were added thereto. The mixture was stirred at room temperature for 45 minutes. The saturated aqueous solution of sodium hydrogen carbonate was added thereto. The mixture was extracted with chloroform. The organic layer was washed by a 10% aqueous solution of sodium thiosulfate and brine, and dried over anhydrous sodium sulfate. The solvent was evaporated under reduced pressure. The obtained residue was purified by silica-gel column chromatography (chloroform-methanol) to give Compound I-0215 (2.70 g, yield 42.9%).

$^1$H-NMR (CDCl$_3$) δ: 1.80 (s, 3H), 3.37 (s, 3H), 3.83 (dd, J=14.3, 5.8 Hz, 1H), 3.87 (s, 3H), 4.44 (dd, J=14.3, 10.5 Hz, 1H), 5.37 (dd, J=10.2, 5.9 Hz, 1H), 7.01 (t, J=7.0 Hz, 2H), 7.10 (s, 1H), 7.20 (d, J=7.8 Hz, 1H), 7.33 (s, 1H), 7.55 (dd, J=7.9, 1.4 Hz, 1H).

Step 4: Synthesis of Compound I-0216

The compound U0215 (2.7 g, 6.06 mmol) was dissolved in a mixed solution of methanol (13.5 ml) and tetrahydrofuran (27 ml). A 1 mol/L aqueous solution of sodium hydroxide (18.2 ml, 18.2 mmol) was added thereto. The mixture was stirred at room temperature for 6.5 hours. The reaction mixture was diluted with water, and washed by diethylether. The aqueous layer was adjusted to pH 4 using a 2 mol/L aqueous solution of hydrochloric acid. The mixture was extracted with ethyl acetate. The organic layer was washed by brine, and dried over anhydrous sodium sulfate. The solvent was evaporated under reduced pressure to give the crude product of Compound I-0216.

Condition [1]: Retention time=1.42 (minutes): [M+H]=432.7

Step 5: Synthesis of Compound I-0217

DMF (28 mL), ammonium chloride (386 mg, 7.22 mmol), HOBt (975 mg, 7.22 mmol), triethylamine (1 0.0 mL, 7.22 mmol), and EDC (1 0.38 g, 7.22 mmol) were added to the crude product of Compound I-0216. The mixture was stirred at room temperature for 2 hours. Water was added to the reaction mixture. The aqueous layer was adjusted to pH 4 using a 2 mol/L aqueous solution of hydrochloric acid. The mixture was extracted with ethyl acetate. The organic layer was washed by the saturated aqueous solution of sodium hydrogen carbonate and brine, and dried over anhydrous sodium sulfate. The solvent was evaporated under reduced pressure. Diethylether was added to the obtained residue. The solids were filtered to give Compound I-0217 (2.11 g, yield 81.5%).

$^1$H-NMR (CDCl$_3$) δ: 1.80 (s, 3H), 3.38 (s, 3H), 3.82 (dd, J=14.4, 5.9 Hz, 1H), 4.44 (dd, J=14.4, 10.4 Hz, 1H), 5.37 (dd, J=10.5, 6.0 Hz, 1H), 5.50-5.75 (br, 1H), 5.86-6.10 (br, 1H), 7.01 (t, J=7.0 Hz, 2H), 7.14 (s, 1H), 7.19 (d, J=8.0 Hz, 1H), 7.32-7.38 (m, 2H).

Step 6: Synthesis of Compound I-0145

Pyridine (17 mL) was added to Compound I-0217 (2.1 g, 4.88 mmol). Under ice cooling, trifluoroacetic acid anhydride (1.72 ml, 12.2 mmol) was added dropwise thereto. The mixture was stirred for 4 hours. Water was added to the reaction mixture. The aqueous layer was adjusted to pH 4 using a 2 mol/L aqueous solution of hydrochloric acid. The mixture was extracted with ethyl acetate. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (chloroform-methanol), and optically resolved by SFC (liquid carbon dioxide-isopropanol) to give Compound I-0145 (725 mg, yield 36.0%).

$^1$H-NMR (CDCl$_3$) δ: 1.79 (s, 3H), 3.36 (s, 3H), 3.84 (dd, J=14.4, 5.9 Hz, 1H), 4.45 (dd, J=14.4, 10.4 Hz, 1H), 5.35 (dd, J=10.3, 5.8 Hz, 1H), 6.92 (s, 1H), 6.99 (t, J=7.0 Hz, 2H), 7.22-7.29 (m, 2H).

Reference Example 5

Synthesis of Compound 88

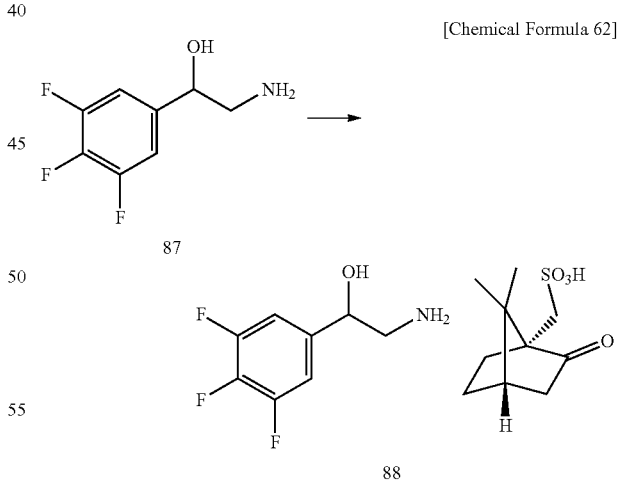

[Chemical Formula 62]

Synthetic Procedures for Seed Crystal (10R)-(−)-Camphorsulfonic acid (1.276 g, 5.49 mmol) was added to a mixed solution of Compound 87 (1.0 g, 5.23 mmol) in ethyl acetate (24.33 mL) and water (0.678 mL) at room temperature under stirring, and dissolved therein. The mixture was stirred at room temperature for 1 hour. The precipitated solids were filtered to give Compound 88 (0.543 g, yield 24.5%, optical purity 91.8% ee).

153

Step 1

(10R)-(-)-Camphorsulfonic acid (96.63 g, 416 mmol) was added to a solution of Compound 87 (75.65 g, 396 mmol) in ethyl acetate (1841 mL) and water (51.3 mL) at room temperature under stirring, and dissolved therein. A small amount of seed crystal was added thereto. The mixture was stirred for 1 hour. The precipitated solids were filtered to give the crude Compound 88 (48.20 g). A small amount of seed crystal was added to a solution of the crude Compound 88 in ethyl acetate (1841 mL) and water (51.3 mL) at room temperature under stirring. The mixture was stirred for 1 hour. The precipitated solids were filtered to give Compound 88 (17.4 g, yield 10%, optical purity 99.5% ee).

$^1$H-NMR (DMSO-d$_6$) δ: 0.75 (s, 3H), 1.05 (s, 3H), 1.29 (m, 2H), 1.80 (d, J=18.0 Hz, 1H), 1.86 (m, 1H), 1.94 (t, J=4.4 Hz, 1H), 2.20-2.30 (m, 1H), 2.38 (d, J=14.8 Hz, 1H), 2.69 (m, 1H), 2.88 (d, J=14.8 Hz, 1H), 2.88 (dd, J=12.8, 8.8 Hz, 1H), 3.10 (dd, J=12.8, 8.8 Hz, 1H), 4.82 (m, 1H), 6.34 (d, J=4.0 Hz, 1H), 7.36 (m, 2H), 7.85 (brs, 3H).

Retention time: 7.1 minutes

Column: CHIRALPAK ID-3, 4.6/SFC (3 μm 150×4.6 mm) (DAICEL)

Flow rate: 0.8 mL/min

UV detection wavelength: 210 nm

Mobile phases: [A] is a 10 mmol/L ammonium bicarbonate buffer (pH9), and [B] is acetonitrile.

Gradient: linear gradient of 10%-90% solvent [B] was performed for 17 minutes, and 90% solvent [B] was maintained for 5 minutes.

Example 17

Synthesis of Compound I-0168

[Chemical Formula 63]

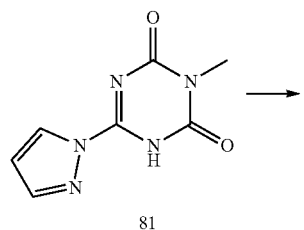
81

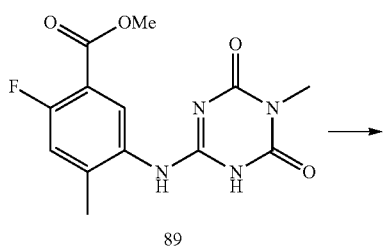
89

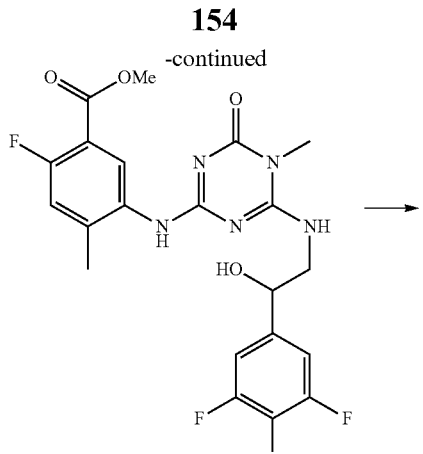
90

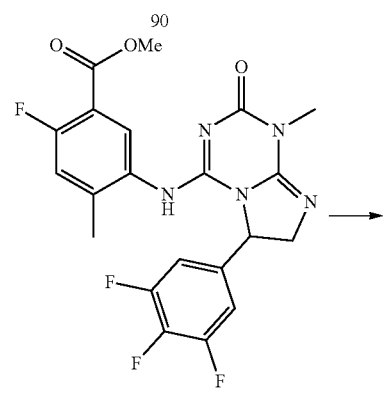
I-0218

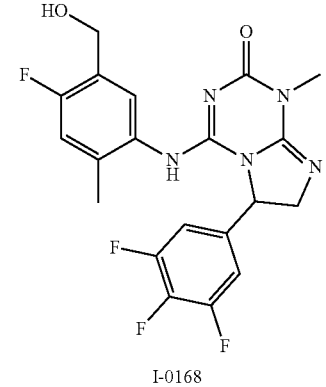
I-0168

Step 1

Methyl 3-amino-4-methyl-6-fluorobenzoate was added to a suspension of Compound 81 (5.00 g, 25.9 mmol) in N-methylpyrrolidone (35 mL) at room temperature. The mixture was stirred at 120° C. for 13 hours. The reaction mixture was added dropwise to water (210 mL). The precipitated solids were filtered, and washed by water and isopropanol. The obtained solids were air-dried to give Compound 89 (6.92 g, yield 87%).

1H-NMR (DMSO-d6) δ: 2.25 (s, 3H), 3.07 (s, 3H), 3.84 (s, 3H), 7.31 (d, J=11.5 Hz, 1H), 7.90 (brs, 1H), 8.64 (brs, 1H), 11.28 (brs, 1H).

Step 2

A phosphonitrilic chloride trimer (2.83 g, 8.14 mmol) was added to a mixed solution of Compound 89 (2.39 g, 7.75 mmol) obtained in the step 1 in acetonitrile (23.9 mL) and N,N-diisopropylethylamine (2.98 mL, 17.06 mmol) at room temperature. The mixture was stirred at room temperature for 90 minutes. Compound 88 (3.61 g, 8.53 mmol) and N,N-diisopropylethylamine (2.98 mL, 17.06 mmol) were added thereto. The mixture was stirred at room temperature for 90 minutes. Saturated sodium hydrogen carbonate was added thereto. The mixture was stirred. The reaction mixture was filtered through Celite. The mixture was extracted with ethyl acetate. The organic layer was washed by water and brine, and dried over anhydrous sodium sulfate. The solvent was evaporated under reduced pressure. The obtained residue (7.36 g) was dissolved in chloroform (66.2 mL) and methanol (7.4 mL). Amino silica-gel (73.6 g) was added thereto. The mixture was stirred at room temperature. Amino silica-gel was washed by chloroform and methanol (9H). The solvent was evaporated under reduced pressure to give the crude product of Compound 90 (3.32 g).

Condition [1]: Retention time=1.33 (minutes): [M+H]=482.15

Step 3

The crude product of Compound 90 (3.32 g, 6.00 mmol) obtained in the step 2 was dissolved in dichloromethane (100 mL). Trimethylamine hydrochloride (1.15 g, 12.00 mmol) was added thereto. Methanesulfonyl chloride (1.40 mL, 18.00 mmol) and triethyl amine (4.16 mL, 30.00 mmol) were added thereto at 0° C. The mixture was stirred at room temperature for 4 hours. The saturated aqueous solution of sodium hydrogen carbonate was added thereto. The mixture was extracted with ethyl acetate. The organic layer was washed by water and brine, and dried over anhydrous sodium sulfate. The solvent was evaporated under reduced pressure. The obtained residue was purified by silica-gel column chromatography (chloroform-methanol) to give Compound I-0218 (1.12 g, yield 40%).

$^1$H-NMR (CDCl$_3$) δ: 1.77 (s, 3H), 3.33 (s, 3H), 3.81 (dd, J=14.3, 6.0 Hz, 1H), 3.88 (s, 3H), 4.43 (dd, J=14.4, 10.4 Hz, 1H), 5.35 (dd, J=10.3, 6.0 Hz, 1H), 7.01-6.92 (m, 3H), 7.23 (d, J=6.7 Hz, 1H), 7.23 (d, J=6.7 Hz, 1H), 7.48 (brs, 1H).

Step 4

Under nitrogen atmosphere, Compound I-0218 (1.12 g, 2.42 mmol) obtained in the step 3 was added to a suspension of lithium borohydride (263 mg, 12.08 mmol) in tetrahydrofuran (13.44 mL) at 0° C. The mixture was refluxed by heating for 6 hours. Methanol and dilute hydrochloric acid were added thereto at 0° C. The mixture was extracted with ethyl acetate. The organic layer was washed by the saturated aqueous solution of sodium hydrogen carbonate and brine, and dried over anhydrous sodium sulfate. The solvent was evaporated under reduced pressure. The obtained residue was purified by silica-gel column chromatography (chloroform-methanol) to give the compound I-0168 (0.88 g, yield 84%).

$^1$H-NMR (CDCl$_3$) δ: 1.72 (s, 3H), 3.39 (s, 3H), 3.82 (dd, J=14.3, 6.0 Hz, 1H), 4.43 (dd, J=14.3, 10.5 Hz, 1H), 4.63 (s, 2H), 5.36 (dd, J=10.3, 6.0 Hz, 1H), 6.68 (d, J=7.0 Hz, 1H), 6.83 (d, J=10.5 Hz, 1H), 6.99 (t, J=7.0 Hz, 2H), 7.24 (brs, 1H).

Example 18

Synthesis of Compound I-0171

[Chemical Formula 64]

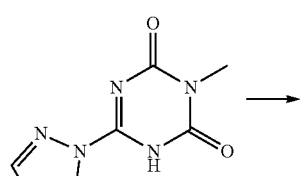

81

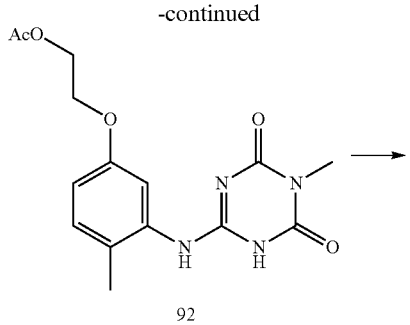

92

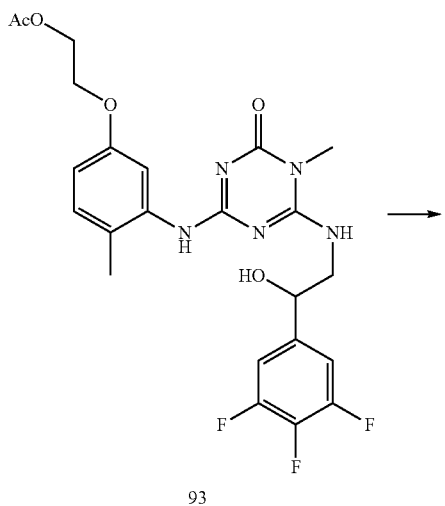

93

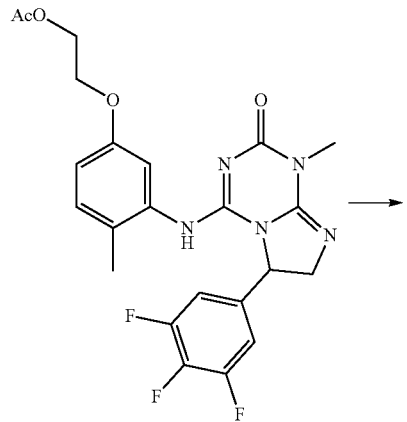

I-0219

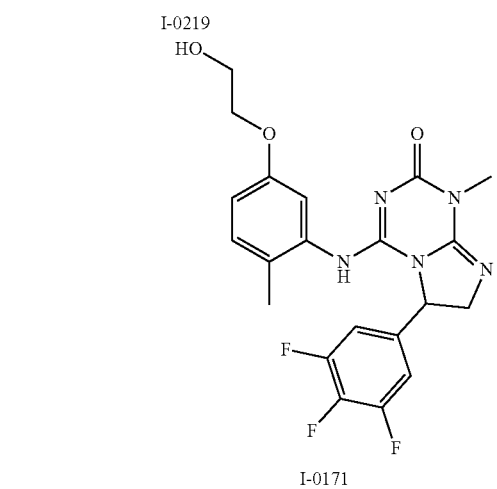

I-0171

Step 1: Synthesis of Compound 92

2-methyl-5-(2-acetoxyethoxy)aniline (23.4 g, 112 mmol, refer to J. Med. Chem. 2015, 58, 8413-8426 for the synthesis method) and Compound 81 (19.6 g, 102 mmol) were added to tert-butanol (234 mL). The mixture was stirred at 110° C. for 56 hours. The reaction mixture was poured into diethylether (234 mL). The mixture was stirred for 5 minutes. The precipitated solids were filtered, washed by diethylether (234 mL), and dried under reduced pressure to give Compound 92 (24.2 g, yield 82.7%).

$^1$H-NMR (DMSO-D$_6$) δ: 2.04 (s, 3H), 2.14 (s, 3H), 3.08 (s, 3H), 4.13 (t, J=4.5 Hz, 2H), 4.31 (t, J=4.5 Hz, 2H), 6.75 (dd, J=8.3, 2.5 Hz, 1H), 7.15 (d, J=8.3 Hz, 1H), 7.28 (d, J=2.5 Hz, 1H), 8.43 (s, 1H), 11.15 (s, 1H).

Step 2: Synthesis of Compound 93

Under nitrogen atmosphere, Compound 92 (11.5 g, 34.4 mmol) was suspended in acetonitrile (115 ml). N,N-Diisopropylethylamine (18.0 ml, 103 mmol) and a phosphonitrilic chloride trimer (12.6 g, 36.1 mmol) were added thereto. The mixture was stirred at room temperature for 1.5 hours. Compound 88 (16.0 g, 37.8 mmol) and N,N-diisopropylethylamine (8.41 ml, 48.2 mmol) were added thereto. The mixture was stirred at room temperature for 1 hour. Water (200 mL) was added thereto. The mixture was extracted three times with ethyl acetate (200 mL). The organic layer was washed by brine (300 mL), and dried over anhydrous sodium sulfate. The solvent was evaporated under reduced pressure. The obtained residue was dissolved in chloroform (332 mL) and methanol (36.8 mL). Amino silica-gel (368 g) was added thereto. The mixture was stirred at room temperature. Amino silica-gel was washed by chloroform and methanol (9H). The solvent was evaporated under reduced pressure to give the crude product of Compound 93 (15.7 g, yield 89.9%).

Condition [1]: Retention time=1.36 (minutes): [M+H]=508.2

Step 3: Synthesis of Compound I-0219

The crude product of Compound 93 (14.1 g, 27.8 mmol) obtained in the step 2 was dissolved in dichloromethane (282 mL). Trimethyl amine hydrochloride (5.31 g, 55.6 mmol) was added thereto. Methanesulfonyl chloride (6.50 ml, 83.0 mmol) and triethylamine (19.3 mL, 139 mmol) were added thereto at 0° C. The mixture was stirred at room temperature for 4 hours. The saturated aqueous solution of sodium hydrogen carbonate was added thereto. The mixture was extracted with ethyl acetate. The organic layer was washed by water and brine, and dried over anhydrous sodium sulfate. The solvent was evaporated under reduced pressure. The obtained residue was purified by silica-gel column chromatography (chloroform-methanol) to give Compound I-0219 (7.18 g, yield 52.8%).

$^1$H-NMR (CDCl$_3$) δ: 1.68 (s, 3H), 2.10 (s, 3H), 3.40 (s, 3H), 3.82 (dd, J=14.4, 5.9 Hz, 1H), 4.09 (t, J=4.8 Hz, 2H), 4.38 (t, J=4.8 Hz, 3H), 4.43 (dd, J=14.4, 10.4 Hz, 3H), 5.37 (dd, J=10.4, 5.9 Hz, 1H), 6.22 (d, J=2.3 Hz, 1H), 6.53-6.55 (m, 1H), 7.01 (dd, J=14.3, 7.8 Hz, 4H).

Step 4: Synthesis of Compound I-0171

Compound I-0219 (7.25 g, 14.8 mmol) was dissolved in a mixed solution of methanol (36.3 ml) and tetrahydrofuran (36.3 ml). A 1 mol/L aqueous solution of sodium hydroxide (22.2 ml, 22.2 mmol) was added thereto. The mixture was stirred at room temperature for 1 hour. Methanol and tetrahydrofuran were evaporated under reduced pressure. The obtained aqueous solution was extracted with ethyl acetate. The organic layer was washed by brine, and dried over anhydrous sodium sulfate. The solvent was evaporated under reduced pressure. The obtained residue was purified by silica-gel chromatography (chloroform-methanol) to give Compound I-0171 (5.51 g, yield 83.1%).

1H-NMR (CDCl3) δ: 1.67 (s, 3H), 2.05 (t, J=5.8 Hz, 1H), 3.39 (s, 3H), 3.82 (dd, J=14.3, 5.8 Hz, 1H), 3.92 (m, 2H), 4.00 (m, 2H), 4.43 (dd, J=14.3, 10.3 Hz, 1H), 5.37 (dd, J=10.3, 5.8 Hz, 1H), 6.23 (d, J=2.3 Hz, 1H), 6.55 (dd, J=8.3, 2.3 Hz, 1H), 7.01 (m, 3H), 7.12 (s, 1H).

The following compounds were synthesized according to the general synthetic procedures and the procedures described in Examples. Their chemical structural formulas and physical properties (LC/MS data or NMR spectrum) are shown below.

In the following tables, the compound expressed as "a" in the column of optical activity is a mixture of an R form and an S form. The compound expressed as "b" in the column of optical activity is either an R form or an S form, through its stereoscopic information is unknown. The compound expressed as "c" in the column of optical activity indicates that its stereoscopy is determined as shown in the chemical structure.

TABLE 1

| Compound No. | Chemical structure | NMR | [M + H] | Retention time (min) | LC/MS condition | Optical activity |
|---|---|---|---|---|---|---|
| I-0001 | 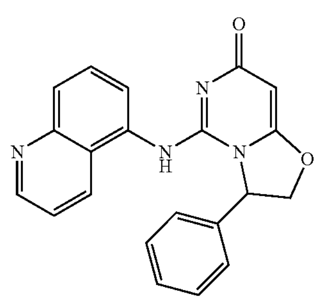 [SMILES: O=c1cc2n(c(Nc3cccc4ncccc34)n1)C(c1ccccc1)CO2] | 1H-NMR (DMSO-d6) δ: 4.65 (dd, J = 8.8, 2.8 Hz, 1H), 4.97 (s, 1H), 5.12 (t, J = 8.6 Hz, 1H), 5.79 (d, J = 6.1 Hz, 1H), 6.87 (br, 1H), 7.10 (dd, J = 8.3, 4.0 Hz, 1H), 7.20 (d, J = 8.3 Hz, 1H), 7.39-7.58 (m, 7H), 8.73 (d, J = 3.6 Hz, 1H), 9.74 (br, 1H). | 357 | 1.29 | [4] | a |

TABLE 1-continued

| Compound No. | Chemical structure | NMR | [M + H] | Retention time (min) | LC/MS condition | Optical activity |
|---|---|---|---|---|---|---|
| I-0002 | 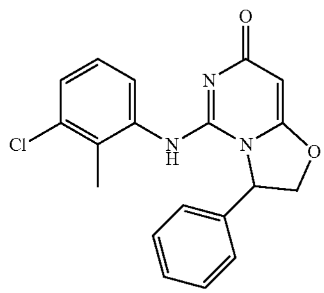 [SMILES: Cc1c(Cl)cccc1Nc1nc(=O)cc2n1C(c1ccccc1)CO2] | 1H-NMR (DMSO-d6) δ: 1.56 (s, 3H), 4.58 (d, J = 8.7 Hz, 1H), 4.93 (s, 1H), 5.06 (t, J = 8.4 Hz, 1H), 5.66 (br, 1H), 6.53 (br, 1H), 6.96-7.04 (m, 2H), 7.30-7.44 (m, 5H), 9.58 (brs, 1H). | 354 | 2.05 | [4] | a |
| I-0003 | 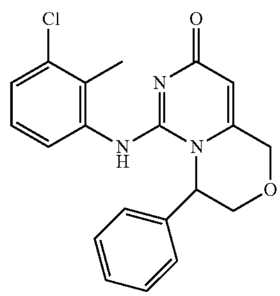 [SMILES: Cc1c(Cl)cccc1Nc1nc(=O)cc2n1C(c1ccccc1)COC2] | 1H-NMR (DMSO-d6) δ: 1.45 (s, 3H), 4.04 (d, J = 12.0 Hz, 1H), 4.23 (d, J = 10.2 Hz, 1H), 4.61 (d, J = 16.2 Hz, 1H), 4.75 (d, J = 16.2 Hz, 1H), 5.33 (s, 1H), 5.47 (s, 1H), 6.47 (br, 1H), 6.95-7.03 (m, 2H), 7.23-7.29 (m, 3H), 7.34-7.38 (m, 2H), 9.74 (br, 1H). | 368 | 2.07 | [4] | b |
| I-0004 | 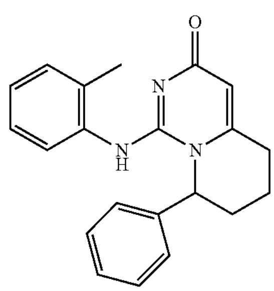 [SMILES: Cc1ccccc1Nc1nc(=O)cc2n1C(c1ccccc1)CCC2] | | 332 | 1.68 | [1] | a |
| I-0005 | 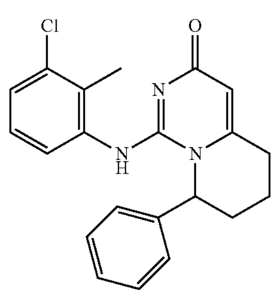 [SMILES: Cc1c(Cl)cccc1Nc1nc(=O)cc2n1C(c1ccccc1)CCC2] | 1H-NMR (CDCl3) δ: 1.53 (s, 3H), 1.65-1.78 (m, 2H), 2.17-2.34 (m, 2H), 2.69-2.84 (m, 2H), 5.34 (s, 1H), 6.00 (dd, J = 5.0, 2.3 Hz, 1H), 6.49 (dd, J = 6.9, 2.6 Hz, 1H), 6.97-7.03 (m, 2H), 7.15 (d, J = 7.3 Hz, 2H), 7.28 (d, J = 7.3 Hz, 1H), 7.35 (t, J = 7.5 Hz, 3H). | 366 | 2.18 | [1] | a |

TABLE 2
| I-0006 | 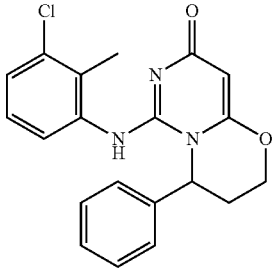 [SMILES: Cc1c(Cl)cccc1Nc1nc(=O)cc2n1C(c1ccccc1)CCO2] | 1H-NMR (CDCl3) δ: 1.60 (s, 3H), 2.24 (dd, J = 14.3, 2.8 Hz, 1H), 2.62-2.71 (m, 1H), 3.72-3.79 (m, 1H), 4.16 (dt, J = 16.6, 6.1 Hz, 1H), 4.32-4.36 (m, 1H), 4.99 (d, J = 2.0 Hz, 1H), 6.00 (d, J = 3.3 Hz, 1H), 6.53 (dd, J = 7.0, 2.3 Hz, 1H), 6.98-7.04 (m, 2H), 7.22 (d, J = 6.3 Hz, 2H), 7.33 (t, J = 7.5 Hz, 1H), 7.41 (t, J = 7.0 Hz, 2H). | 368 | 2.03 | [1] | a |
|---|---|---|---|---|---|---|
| I-0007 | 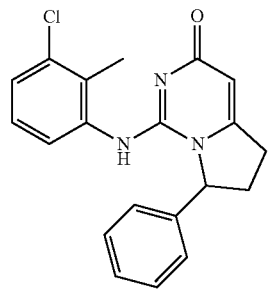 [SMILES: Cc1c(Cl)cccc1Nc1nc(=O)cc2n1C(c1ccccc1)CC2] | 1H-NMR (CDCl3) δ: 1.69 (s, 3H), 2.12-2.17 (m, 1H), 2.63-2.73 (m, 1H), 2.94 (dd, J = 17.2, 8.7 Hz, 1H), 3.05-3.15 (m, 1H), 5.42 (s, 1H), 5.63 (d, J = 8.8 Hz, 1H), 6.58 (dd, J = 6.7, 2.4 Hz, 1H), 6.98-7.04 (m, 2H), 7.20 (d, J = 7.5 Hz, 2H), 7.30 (t, J = 7.5 Hz, 2H), 7.37 (t, J = 6.8 Hz, 2H). | 352 | 1.82 | [1] | a |
| I-0008 | 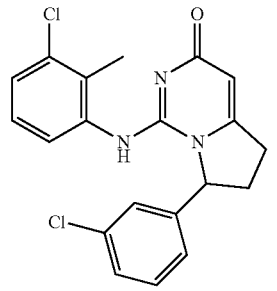 [SMILES: Cc1c(Cl)cccc1Nc1nc(=O)cc2n1C(c1cccc(Cl)c1)CC2] | | 386 | 2.09 | [1] | a |
| I-0009 | 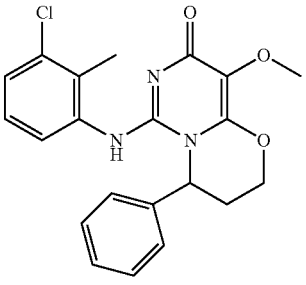 [SMILES: COc1c2n(c(Nc3cccc(Cl)c3C)nc1=O)C(c1ccccc1)CCO2] | 1H-NMR (CDCl3) δ: 1.59 (s, 3H), 2.25 (dq, J = 14.0, 2.4 Hz, 1H), 2.63-2.73 (m, 1H), 3.79 (s, 3H), 4.18-4.25 (m, 1H), 4.46-4.50 (m, 1H), 6.01 (s, 1H), 6.52 (dd, J = 7.3, 2.0 Hz, 1H), 6.98-7.04 (m, 2H), 7.21 (d, J = 7.0 Hz, 2H), 7.33 (t, J = 7.4 Hz, 1H), 7.41 (t, J = 7.3 Hz, 2H). | 398 | 2.02 | [1] | a |
| I-0010 | 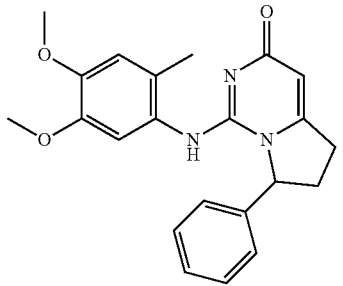 [SMILES: COc1cc(C)c(Nc2nc(=O)cc3n2C(c2ccccc2)CC3)cc1OC] | | 378 | 1.27 | [1] | b |

TABLE 3

| ID | Structure | MW | RT | [M] | Grade |
|---|---|---|---|---|---|
| I-0011 | 5-chloro-2,4-dimethylphenyl-NH / phenyl bicyclic | 366 | 1.85 | [1] | b |
| I-0012 | 5-chloro-2,4-dimethylphenyl-NH / 3-chloro-4-fluorophenyl bicyclic | 418 | 2.18 | [1] | b |
| I-0013 | 4,5-dimethoxy-2-methylphenyl-NH / 3-chloro-4-fluorophenyl bicyclic | 430 | 1.52 | [1] | b |
| I-0014 | 4-methoxy-2-methylphenyl-NH / phenyl bicyclic | 348 | 1.3 | [1] | a |
| I-0015 | 2-methylphenyl-NH / phenyl bicyclic | 318 | 1.37 | [1] | a |
| I-0016 | 5-methoxy-2-methylphenyl-NH / phenyl bicyclic | 348 | 1.46 | [1] | a |

TABLE 4

| ID | Structure | MW | RT | [M] | Grade |
|---|---|---|---|---|---|
| I-0017 | 4,5-dimethoxy-2-methylphenyl-NH / 4-fluorophenyl bicyclic | 396 | 1.32 | [1] | a |
| I-0018 | 4,5-dimethoxy-2-methylphenyl-NH / 3-fluorophenyl bicyclic | 396 | 1.33 | [1] | a |

TABLE 4-continued

| ID | Structure | MS | RT | [method] | ref |
|---|---|---|---|---|---|
| I-0019 | (3,4-dimethoxyphenyl)amino pyrrolo-pyrimidinone, 7-phenyl | 364 | 1.2 | [1] | a |
| I-0020 | (4-methoxy-2,5-dimethylphenyl)amino pyrrolo-pyrimidinone, 7-phenyl | 362 | 1.45 | [1] | a |
| I-0021 | (4,5-dimethoxy-2-methylphenyl)amino pyrrolo-pyrimidinone, 7-(3,4,5-trifluorophenyl); 1H-NMR (CDCl3) δ: 1.72 (s, 3H), 2.08-2.13 (m, 1H), 2.63-2.74 (m, 1H), 2.92-3.09 (m, 2H), 3.79 (s, 3H), 3.82 (s, 3H), 5.42 (s, 1H), 5.55 (d, J = 8.8 Hz, 1H), 6.21 (s, 1H), 6.65 (s, 1H), 6.87 (t, J = 7.0 Hz, 2H), 7.37 (s, 1H). | 432 | 1.55 | [1] | a |

TABLE 5

| ID | Structure | MS | RT | [method] | ref |
|---|---|---|---|---|---|
| I-0022 | (4-fluoro-5-methoxy-2-methylphenyl)amino pyrrolo-pyrimidinone, 7-phenyl | 366 | 1.53 | [1] | a |
| I-0023 | (4-methoxy-2-methylphenyl)amino pyrrolo-pyrimidinone, 7-(4-fluorophenyl) | 366 | 1.4 | [1] | a |
| I-0024 | (5-fluoro-4-methoxy-2-methylphenyl)amino pyrrolo-pyrimidinone, 7-phenyl | 366 | 1.47 | [1] | a |
| I-0025 | (4,5-dimethoxy-2-methylphenyl)amino pyrrolo-pyrimidinone, 7-(3,4-difluorophenyl) | 414 | 1.39 | [1] | b |

TABLE 5-continued
| I-0026 | 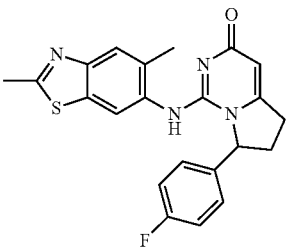 [SMILES: Cc1nc2cc(C)c(Nc3nc(=O)cc4n3C(c3ccc(F)cc3)CC4)cc2s1] | 407 | 1.54 | [1] | a |
TABLE 6
| I-0027 | 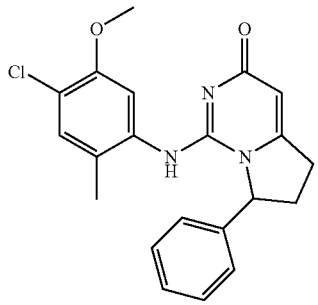 [SMILES: COc1cc(Nc2nc(=O)cc3n2C(c2ccccc2)CC3)c(C)cc1Cl] | 381 | 1.82 | [1] | a |
| I-0028 | 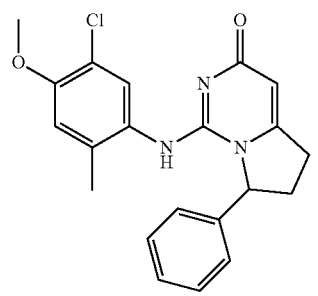 [SMILES: COc1cc(C)c(Nc2nc(=O)cc3n2C(c2ccccc2)CC3)cc1Cl] | 381 | 1.56 | [1] | a |
| I-0029 | 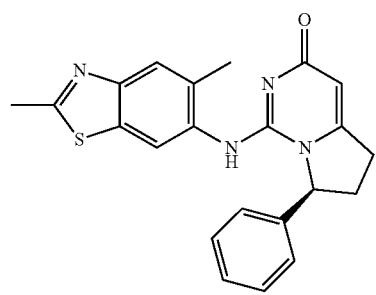 [SMILES: Cc1nc2cc(C)c(Nc3nc(=O)cc4n3[C@H](c3ccccc3)CC4)cc2s1] | 389 | 1.47 | [1] | c |
| I-0030 | 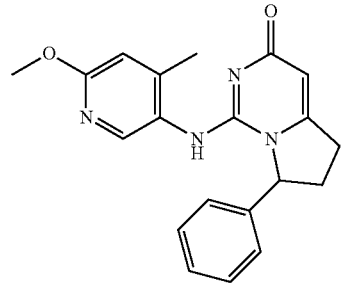 [SMILES: COc1cc(C)c(Nc2nc(=O)cc3n2C(c2ccccc2)CC3)cn1] | 349 | 1.28 | [1] | a |

TABLE 6-continued
| | | | | | |
|---|---|---|---|---|---|
| I-0031 | 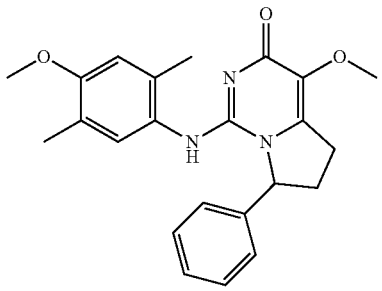 | 392 | 1.56 | [1] | a |
| I-0032 | 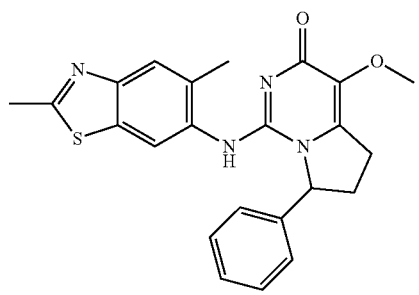 | 419 | 1.47 | [1] | a |
TABLE 7
| | | | | | |
|---|---|---|---|---|---|
| I-0033 | 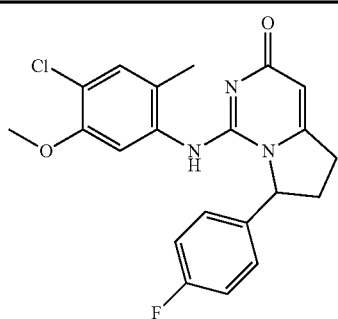 | 400 | 1.83 | [1] | a |
| I-0034 | 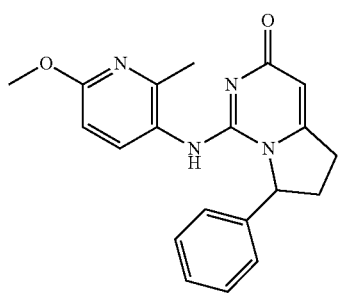 [SMILES: COc1ccc(Nc2nc(=O)cc3n2C(c2ccccc2)CC3)c(C)n1] | 349 | 1.21 | [1] | a |
| I-0035 | 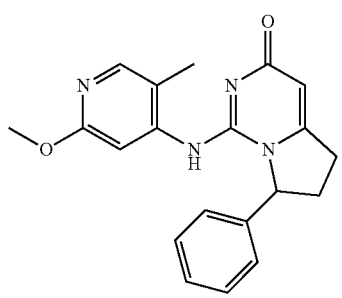 [SMILES: COc1cc(Nc2nc(=O)cc3n2C(c2ccccc2)CC3)c(C)cn1] | 349 | 1.2 | [1] | a |

TABLE 7-continued

| | | | | | | |
|---|---|---|---|---|---|---|
| I-0036 | (structure) | 1H-NMR (CDCl3) δ: 1.77 (s, 3H), 2.12-2.17 (m, 1H), 2.65-2.75 (m, 1H), 2.78 (s, 3H), 3.05-3.19 (m, 2H), 3.82 (s, 3H), 5.63 (d, J = 8.6 Hz, 1H), 7.07-7.09 (m, 2H), 7.19-7.22 (m, 2H), 7.43 (brs, 1H), 7.67 (brs, 1H). | 437 | 1.53 | [1] | b |
| I-0037 | (structure) | | 400 | 1.55 | [1] | b |

TABLE 8

| | | | | | |
|---|---|---|---|---|---|
| I-0038 | (structure) | 384 | 1.45 | [1] | b |
| I-0039 | (structure) | 376 | 1.55 | [1] | a |
| I-0040 | (structure) | 360 | 1.32 | [1] | a |
| I-0041 | (structure) | 384 | 1.48 | [1] | b |
| I-0042 | (structure) | 402 | 1.59 | [1] | b |

TABLE 9

| ID | Structure | m/z | RT | Method | Grp |
|---|---|---|---|---|---|
| I-0043 | 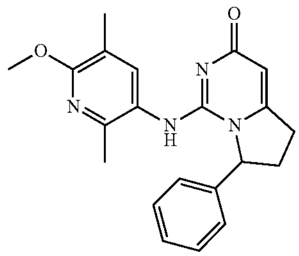 [SMILES: COc1nc(C)c(Nc2nc(=O)cc3n2C(c2ccccc2)CC3)cc1C] | 363 | 1.49 | [1] | a |
| I-0044 | 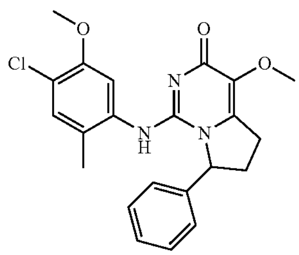 [SMILES: COc1cc(Nc2nc(=O)c(OC)c3n2C(c2ccccc2)CC3)c(C)cc1Cl] | 412 | 1.7 | [1] | a |
| I-0045 | 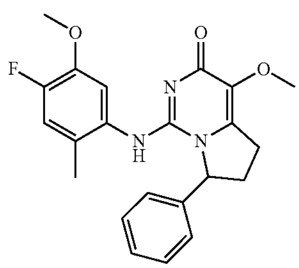 [SMILES: COc1cc(Nc2nc(=O)c(OC)c3n2C(c2ccccc2)CC3)c(C)cc1F] | 396 | 1.52 | [1] | a |
| I-0046 | 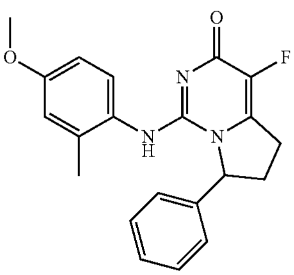 [SMILES: COc1ccc(Nc2nc(=O)c(F)c3n2C(c2ccccc2)CC3)c(C)c1] | 366 | 1.51 | [1] | a |
| I-0047 | 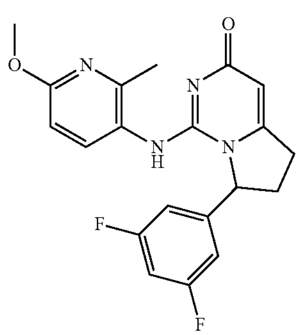 [SMILES: COc1ccc(Nc2nc(=O)cc3n2C(c2cc(F)cc(F)c2)CC3)c(C)n1] | 385 | 1.38 | [1] | b |

TABLE 10

| ID | Structure | m/z | RT | Method | Grp |
|---|---|---|---|---|---|
| I-0048 | 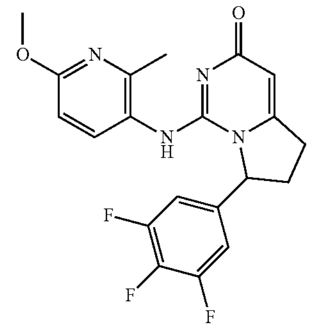 [SMILES: COc1ccc(Nc2nc(=O)cc3n2C(c2cc(F)c(F)c(F)c2)CC3)c(C)n1] | 403 | 1.49 | [1] | b |
| I-0049 | 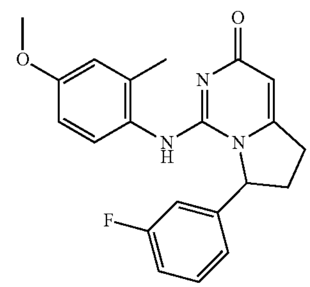 [SMILES: COc1ccc(Nc2nc(=O)cc3n2C(c2cccc(F)c2)CC3)c(C)c1] | 366 | 1.36 | [1] | b |
| I-0050 | 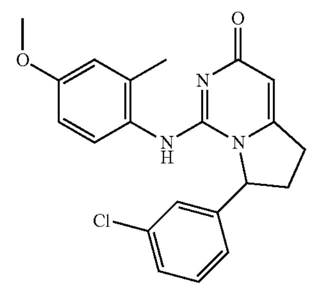 [SMILES: COc1ccc(Nc2nc(=O)cc3n2C(c2cccc(Cl)c2)CC3)c(C)c1] | 382 | 1.5 | [1] | b |
| I-0051 | 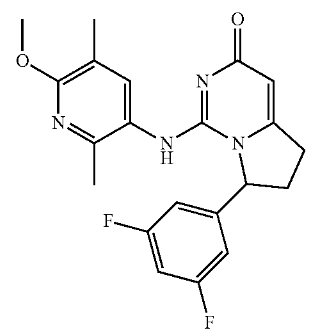 [SMILES: COc1nc(C)c(Nc2nc(=O)cc3n2C(c2cc(F)cc(F)c2)CC3)cc1C] | 399 | 1.64 | [1] | a |
| I-0052 | 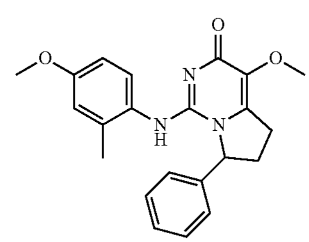 | 378 | 1.43 | [1] | a |

TABLE 11
| | | | | | |
|---|---|---|---|---|---|
| I-0053 | 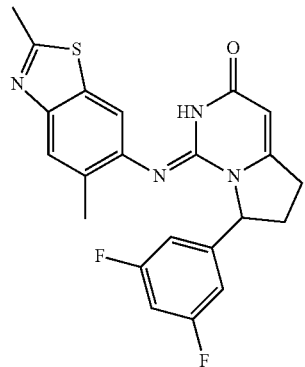 [SMILES: Cc1nc2cc(C)c(/N=c3\[nH]c(=O)cc4n3C(c3cc(F)cc(F)c3)CC4)cc2s1] | 425 | 1.71 | [1] | b |
| I-0054 | 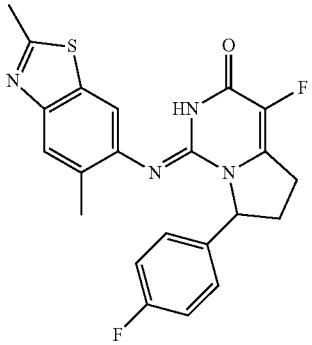 [SMILES: Cc1nc2cc(C)c(/N=c3\[nH]c(=O)c(F)c4n3C(c3ccc(F)cc3)CC4)cc2s1] | 425 | 1.53 | [1] | b |
| I-0055 | 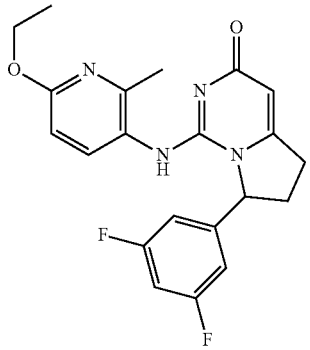 [SMILES: CCOc1ccc(Nc2nc(=O)cc3n2C(c2cc(F)cc(F)c2)CC3)c(C)n1] | 399 | 1.5 | [1] | b |
TABLE 11-continued
| | | | | | |
|---|---|---|---|---|---|
| I-0056 | 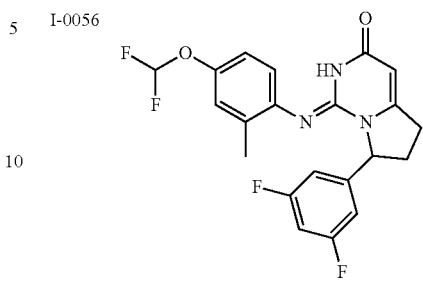 | 420 | 1.86 | [1] | b |
| I-0057 | 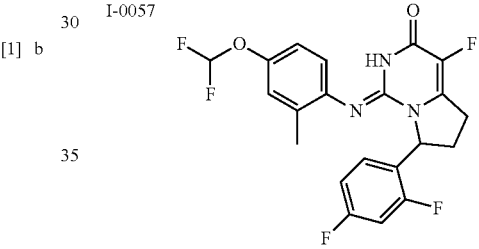 | 438 | 1.78 | [1] | b |
TABLE 12
| | | | | | |
|---|---|---|---|---|---|
| I-0058 | 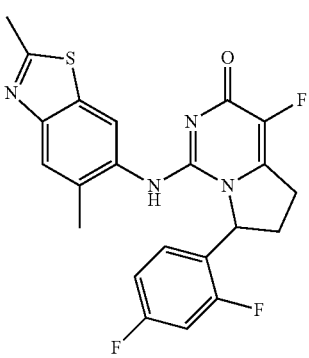 [SMILES: Cc1nc2cc(C)c(Nc3nc(=O)c(F)c4n3C(c3ccc(F)cc3F)CC4)cc2s1] | 443 | 1.57 | [1] | b |

TABLE 12-continued
| I-0059 | 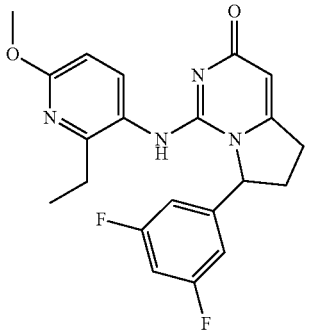 [SMILES: CCc1nc(OC)ccc1Nc1nc(=O)cc2n1C(c1cc(F)cc(F)c1)CC2] | 1H-NMR (CDCl3) δ: 0.92 (t, J = 7.4 Hz, 3H), 2.10-2.18 (m, 3H), 2.64-2.75 (m, 1H), 2.93-3.11 (m, 2H), 3.87 (s, 3H), 5.43 (s, 1H), 5.58 (d, J = 8.8 Hz, 1H), 6.51 (d, J = 8.8 Hz, 1H), 6.73-6.79 (m, 3H), 6.91 (d, J = 8.5 Hz, 1H), 7.30 (brs, 1H). | 399 | 1.56 | [1] | b |
| I-0060 | 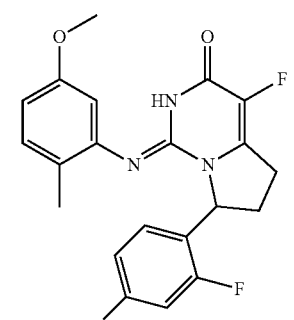 | | 402 | 1.64 | [1] | b |
| I-0061 | 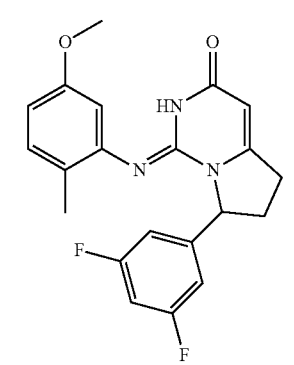 [SMILES: COc1ccc(C)c(/N=c2\[nH]c(=O)cc3n2C(c2cc(F)cc(F)c2)CC3)c1] | | 384 | 1.71 | [1] | b |
| I-0062 | 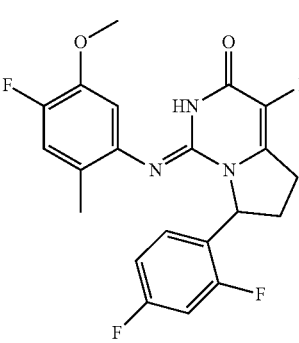 | | 420 | 1.68 | [1] | b |

TABLE 13
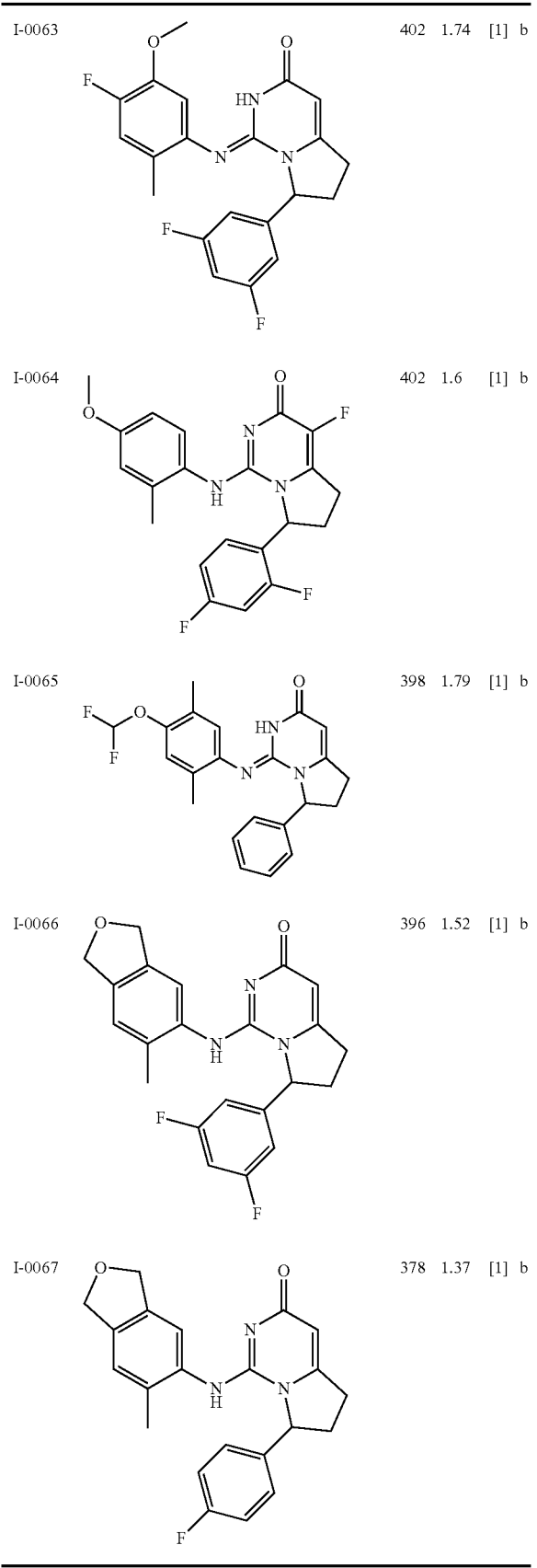
| ID | MW | RT | [M] | b |
|---|---|---|---|---|
| I-0063 | 402 | 1.74 | [1] | b |
| I-0064 | 402 | 1.6 | [1] | b |
| I-0065 | 398 | 1.79 | [1] | b |
| I-0066 | 396 | 1.52 | [1] | b |
| I-0067 | 378 | 1.37 | [1] | b |
TABLE 14
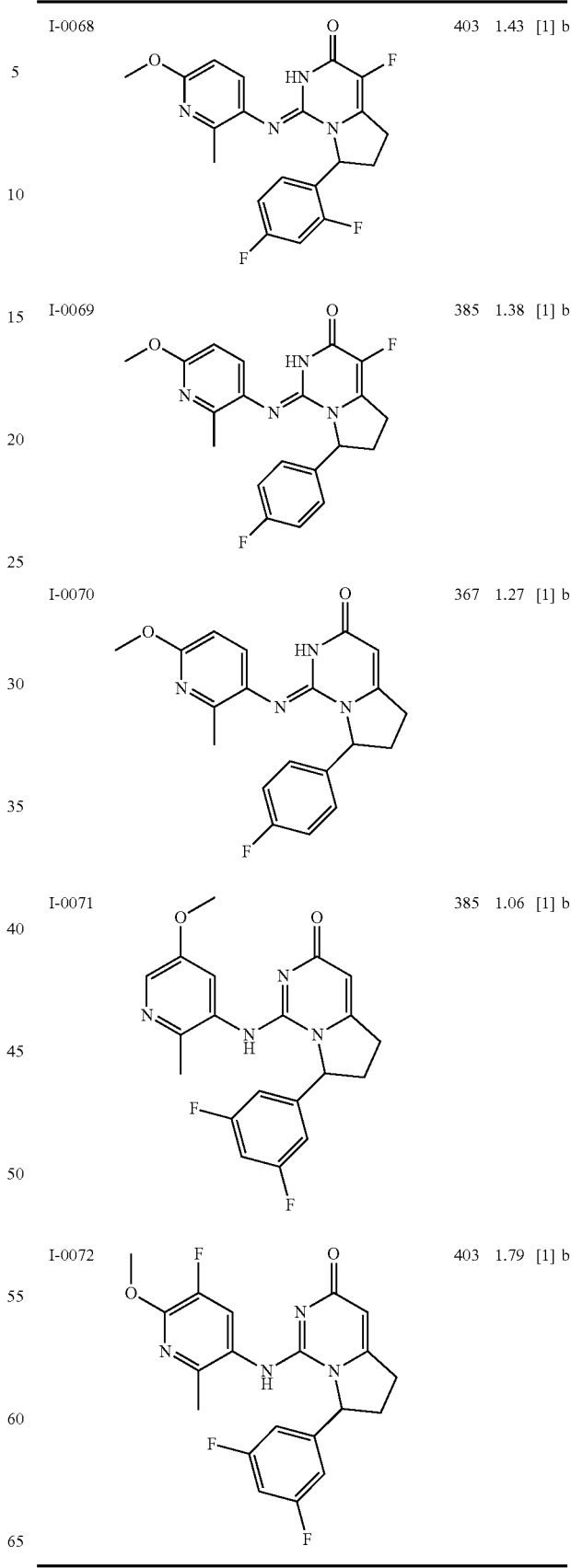
| ID | MW | RT | [M] | b |
|---|---|---|---|---|
| I-0068 | 403 | 1.43 | [1] | b |
| I-0069 | 385 | 1.38 | [1] | b |
| I-0070 | 367 | 1.27 | [1] | b |
| I-0071 | 385 | 1.06 | [1] | b |
| I-0072 | 403 | 1.79 | [1] | b |

TABLE 15

| ID | | | | |
|---|---|---|---|---|
| I-0073 | 414 | 1.51 | [1] | b |
| I-0074 | 396 | 1.46 | [1] | b |
| I-0075 | 413 | 1.71 | [1] | b |
| I-0076 | 431 | 1.75 | [1] | b |
| I-0077 | 402 | 1.7 | [1] | b |

TABLE 16

| ID | | | | |
|---|---|---|---|---|
| I-0078 | 385 | 0.99 | [1] | b |
| I-0079 | 367 | 1.02 | [1] | b |
| I-0080 | 399 | 1.5 | [1] | b |
| I-0081 | 417 | 1.56 | [1] | b |
| I-0082 | 417 | 1.96 | [1] | b |

TABLE 17

| | | | | | |
|---|---|---|---|---|---|
| I-0083 | (structure) | | 435 | 1.79 | [1] b |
| I-0084 | (structure) | | 403 | 1.8 | [1] b |
| I-0085 | (structure) | | 419 | 1.55 | [1] b |
| I-0086 | (structure) | 1H-NMR (CDCl3) δ: 1.90 (s, 3H), 2.16-2.21 (m, 1H), 2.71-2.82 (m, 1H), 2.92 (d, J = 29.4 Hz, 1H), 3.07-3.21 (m, 2H), 3.86 (s, 3H), 5.69 (d, J = 9.3 Hz, 1H), 6.52 (d, J = 8.5 Hz, 1H), 6.74-6.80 (m, 3H), 6.87 (d, J = 8.5 Hz, 1H), 7.45 (brs, 1H). | 463 | 1.59 | [1] b |

TABLE 17-continued

| ID | Structure | NMR | MS | RT | [M] | b/a |
|---|---|---|---|---|---|---|
| I-0087 | (6-methoxy-2-methylpyridin-3-yl)amino / 3,5-difluorophenyl pyrrolo-pyrimidinone | 1H-NMR (CDCl3) δ: 1.93 (s, 3H), 2.11-2.16 (m, 1H), 2.64-2.75 (m, 1H), 2.93-3.10 (m, 2H), 3.86 (s, 3H), 5.44 (s, 1H), 5.59 (d, J = 8.3 Hz, 1H), 6.51 (d, J = 8.8 Hz, 1H), 6.74-6.79 (m, 3H), 6.90 (d, J = 8.3 Hz, 1H). | 399 | 1.41 | [1] | b |

TABLE 18

| ID | Structure | MS | RT | [M] | b/a |
|---|---|---|---|---|---|
| I-0088 | 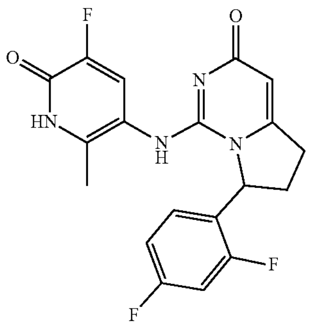 [SMILES: Cc1[nH]c(=O)c(F)cc1Nc1nc(=O)cc2n1C(c1ccc(F)cc1F)CC2] | 389 | 1.16 | [1] | b |
| I-0089 | 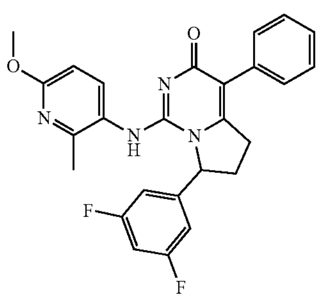 [SMILES: COc1ccc(Nc2nc(=O)c(-c3ccccc3)c3n2C(c2cc(F)cc(F)c2)CC3)c(C)n1] | 461 | 1.88 | [1] | b |
| I-0090 | 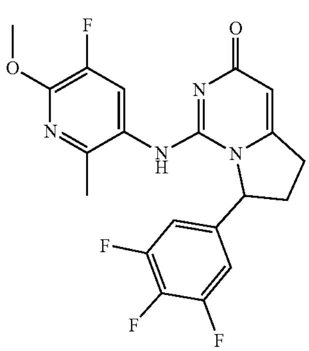 [SMILES: COc1nc(C)c(Nc2nc(=O)cc3n2C(c2cc(F)c(F)c(F)c2)CC3)cc1F] | 421 | 1.89 | [1] | b |
| I-0091 | | 411 | 1.71 | [1] | b |
| I-0092 | | 413 | 1.57 | [1] | b |

TABLE 19

| ID | Structure | MS | RT | [M] | b/a |
|---|---|---|---|---|---|
| I-0093 | 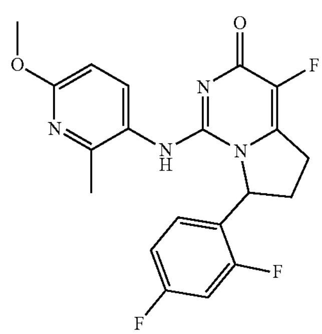 [SMILES: COc1ccc(Nc2nc(=O)c(F)c3n2C(c2ccc(F)cc2F)CC3)c(C)n1] | 403 | 1.43 | [1] | b |

TABLE 19-continued
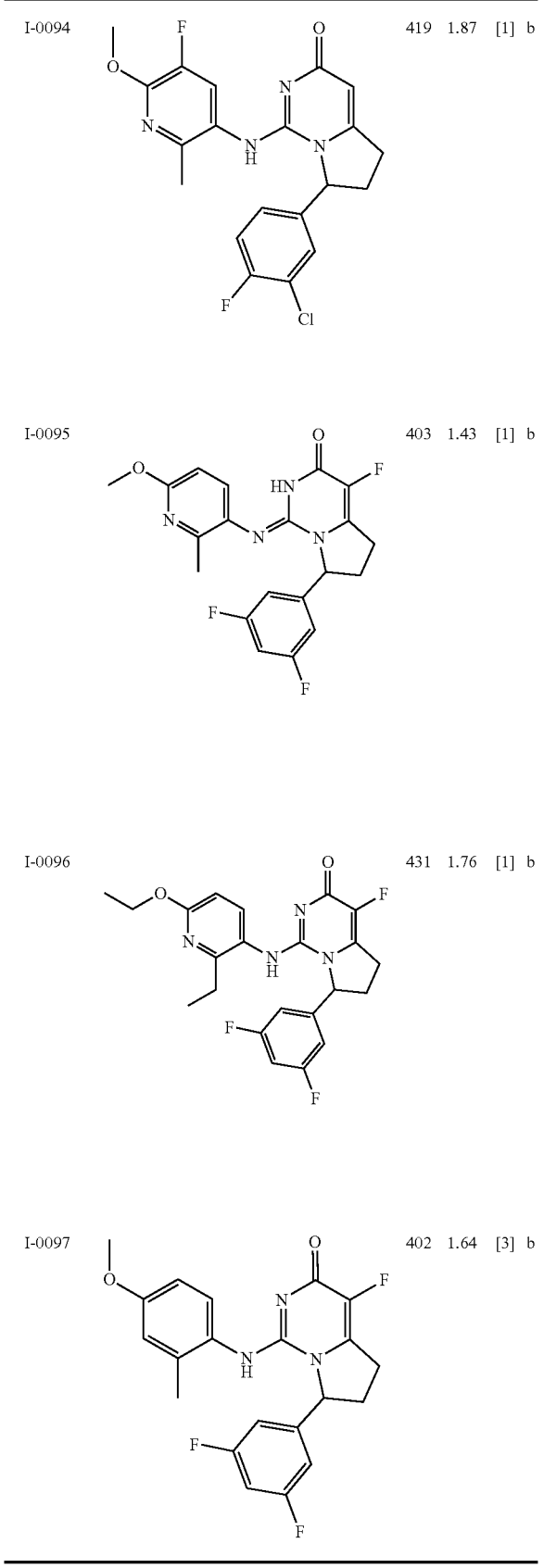
TABLE 20
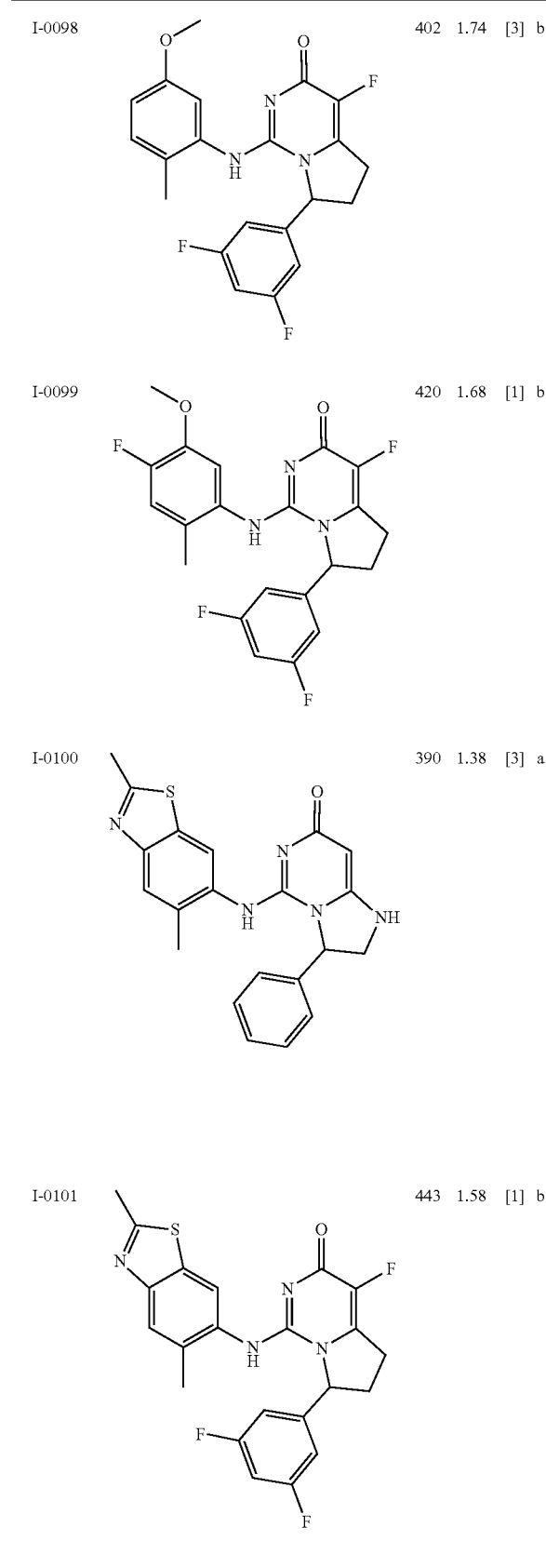

TABLE 20-continued
| I-0102 | 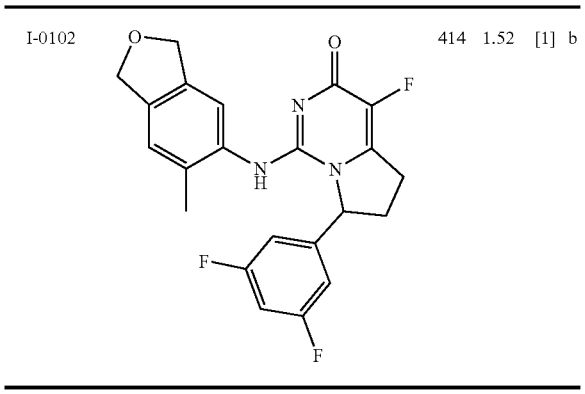 | 414 | 1.52 | [1] | b |
TABLE 21
| I-0103 | 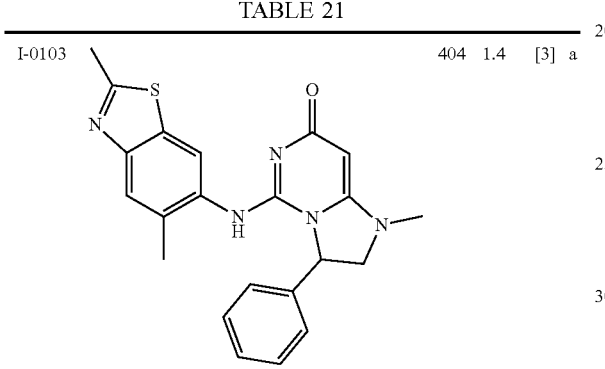 | 404 | 1.4 | [3] | a |
| I-0104 | 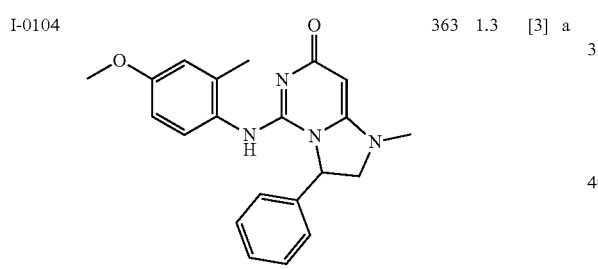 | 363 | 1.3 | [3] | a |
| I-0105 | 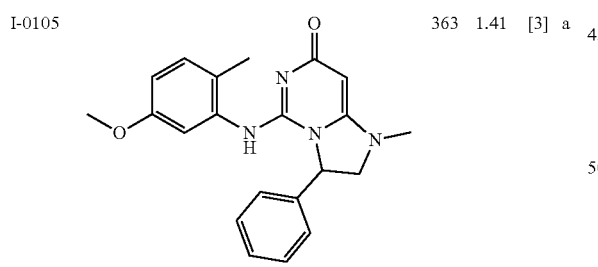 | 363 | 1.41 | [3] | a |
| I-0106 | 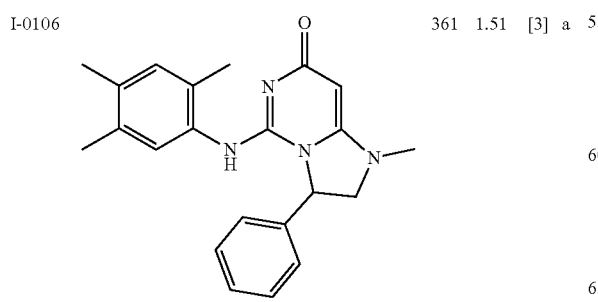 | 361 | 1.51 | [3] | a |
TABLE 21-continued
| I-0107 | 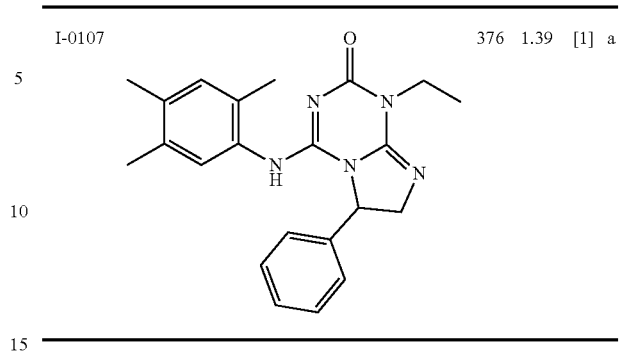 | 376 | 1.39 | [1] | a |
TABLE 22
| I-0108 | 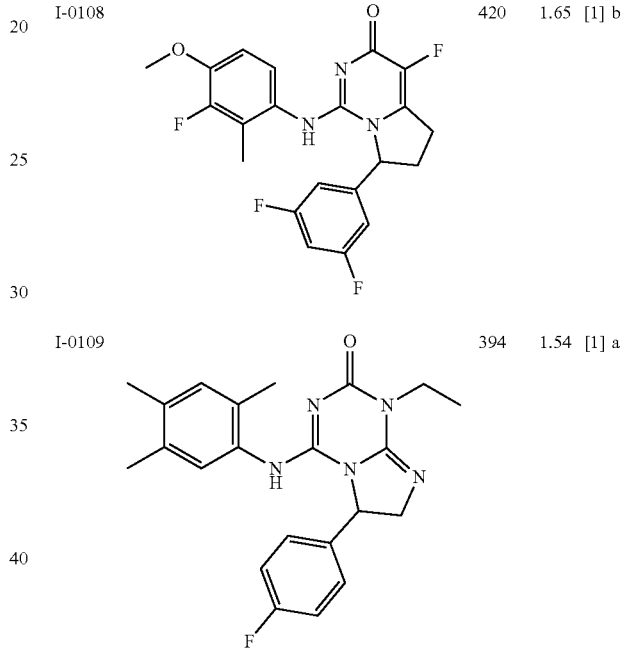 | 420 | 1.65 | [1] | b |
| I-0109 | | 394 | 1.54 | [1] | a |
| I-0110 | 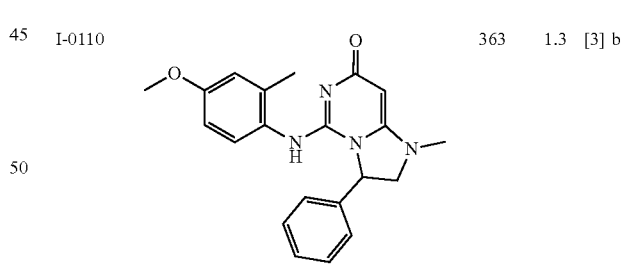 | 363 | 1.3 | [3] | b |
| I-0111 | 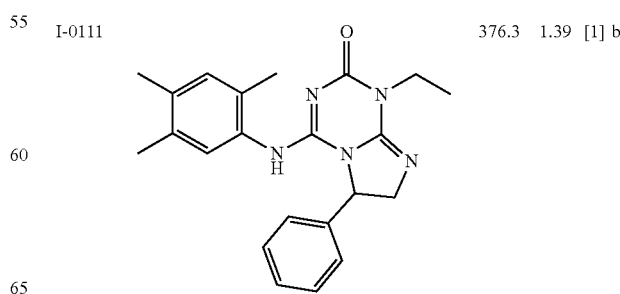 | 376.3 | 1.39 | [1] | b |

TABLE 22-continued
| | | | | | |
|---|---|---|---|---|---|
| I-0112 | | 381 | 1 | [1] | a |
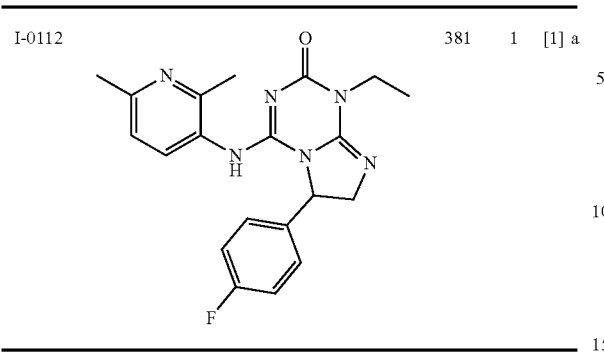
TABLE 23
| | | | | | |
|---|---|---|---|---|---|
| I-0113 | | 382 | 1.36 | [1] | a |
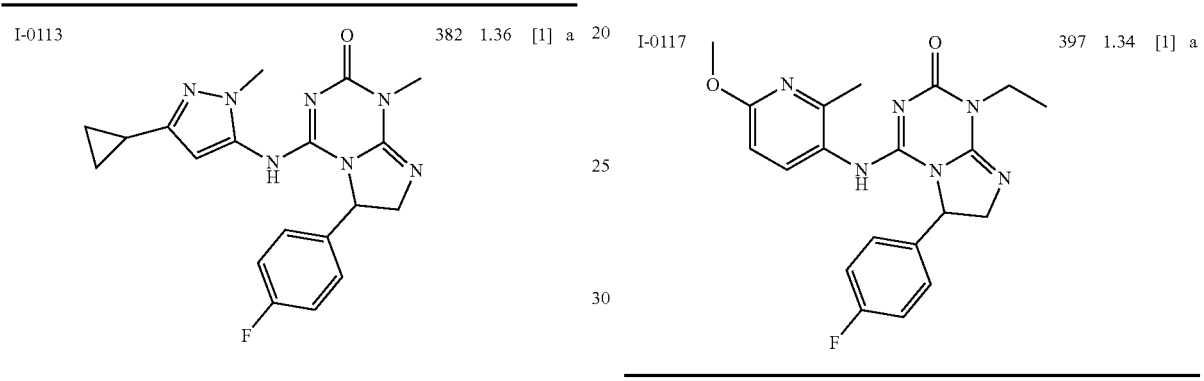
| I-0114 | | 385 | 1.09 | [1] | a |
| I-0115 | | 385 | 1.06 | [1] | a |
TABLE 23-continued
| | | | | | |
|---|---|---|---|---|---|
| I-0116 | | 430 | 1.46 | [1] | a |
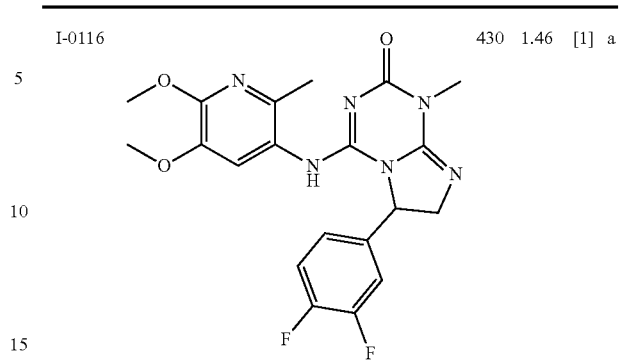
| I-0117 | | 397 | 1.34 | [1] | a |
TABLE 24
| | | | | | |
|---|---|---|---|---|---|
| I-0118 | | 427 | 1.39 | [1] | a |
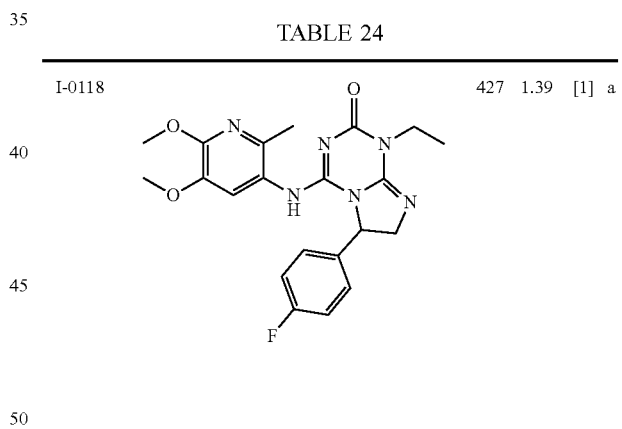
| I-0119 | | 383 | 1.31 | [1] | a |
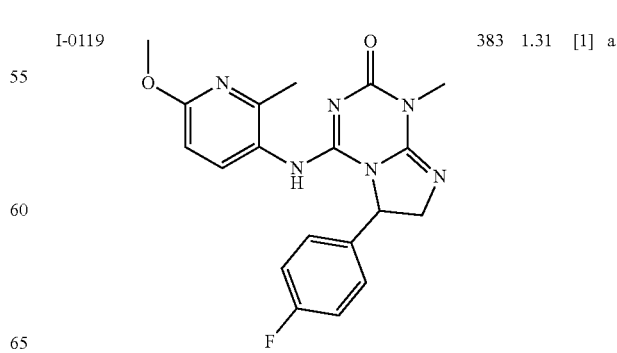

TABLE 24-continued
I-0120 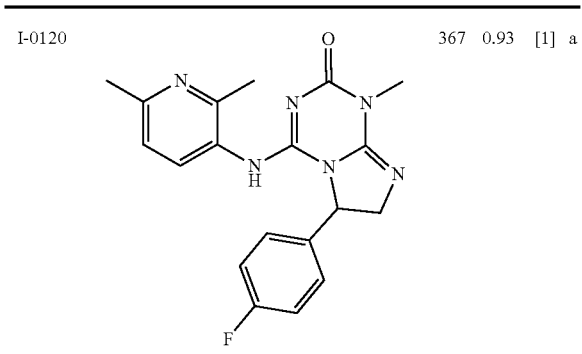 367 0.93 [1] a
I-0121 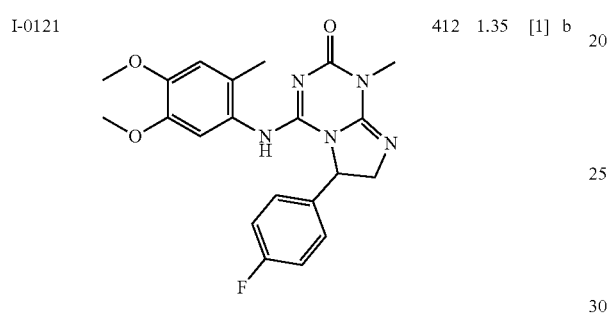 412 1.35 [1] b
I-0122 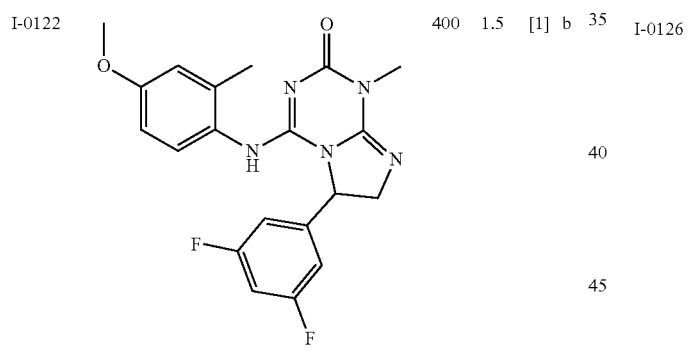 400 1.5 [1] b
TABLE 25
I-0123 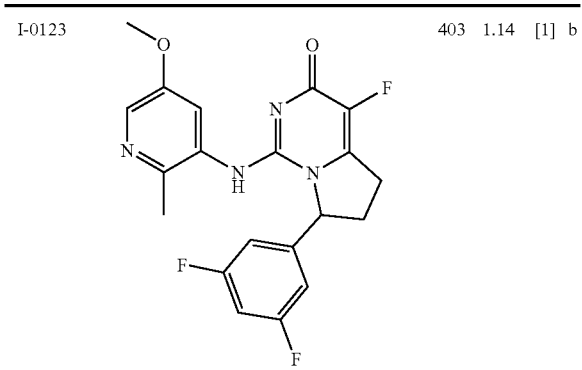 403 1.14 [1] b
TABLE 25-continued
I-0124 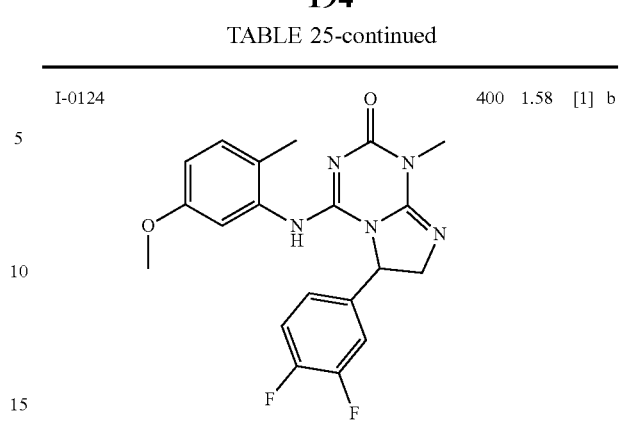 400 1.58 [1] b
I-0125 400 1.52 [1] b
I-0126 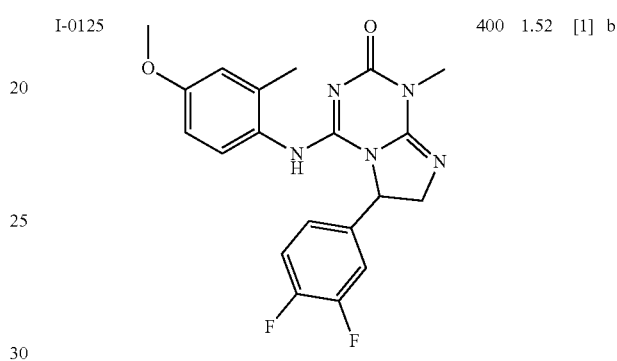 430 1.44 [1] b
I-0127 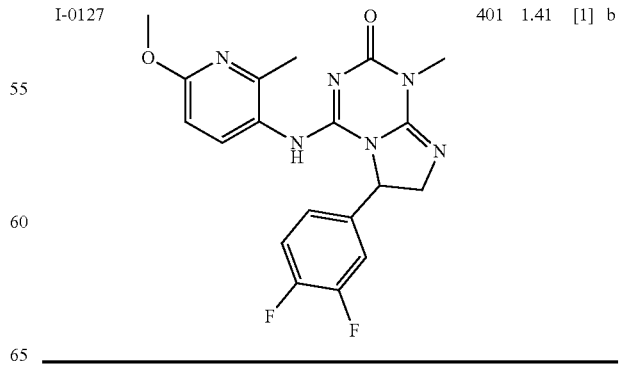 401 1.41 [1] b TABLE 26
I-0128 403 1.51 [1] a
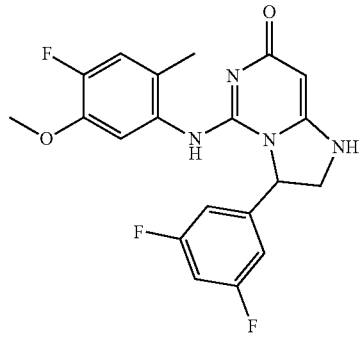 [SMILES: COc1cc(Nc2nc(=O)cc3n2C(c2cc(F)cc(F)c2)CN3)c(C)cc1F]
I-0129 382 1.49 [1] b
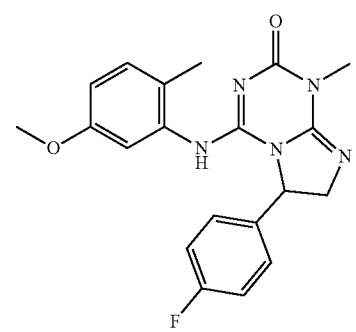
I-0130 382 1.43 [1] b
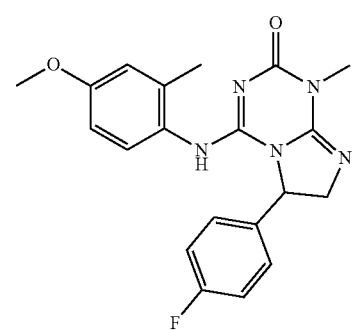
I-0131 400 1.59 [1] b
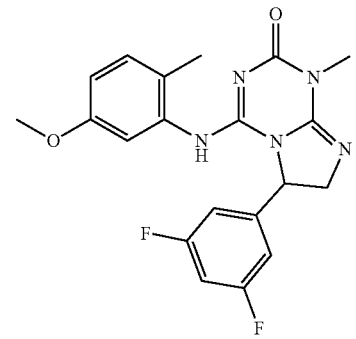
TABLE 26-continued
I-0132 430 1.44 [1] b
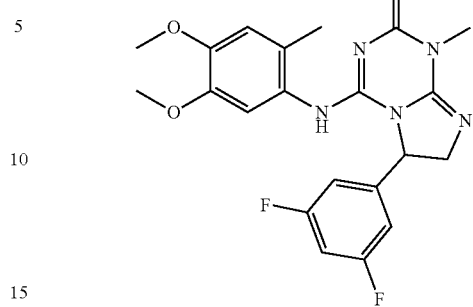
TABLE 27
I-0133 431 1.47 [1] b
I-0134 403 1.67 [1] b
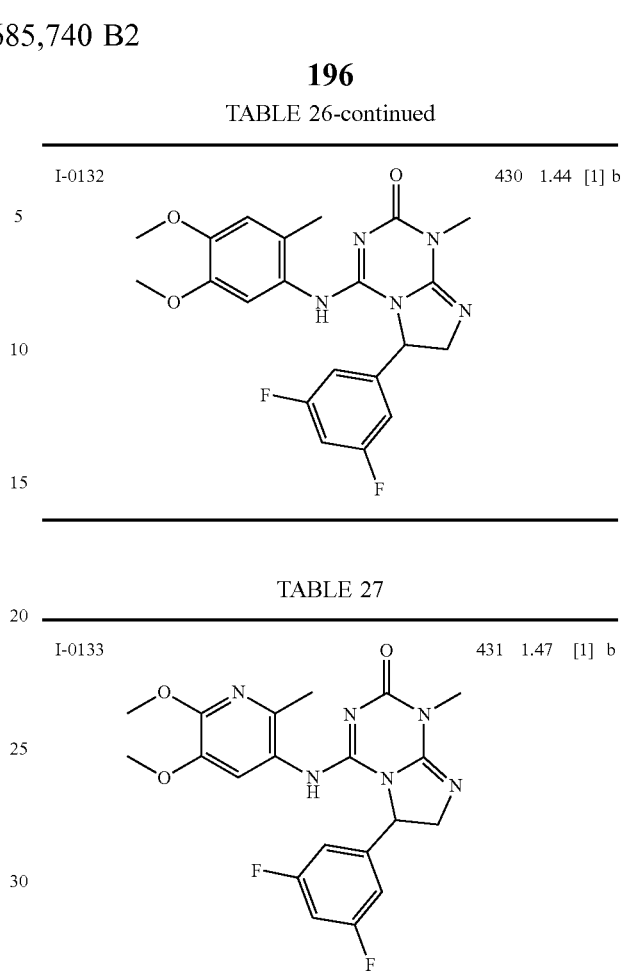
I-0135 418 1.59 [1] b
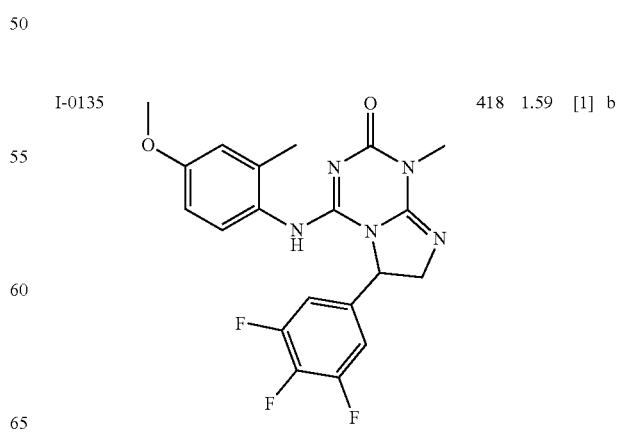

TABLE 27-continued

| ID | Structure | MS | RT | [method] | |
|---|---|---|---|---|---|
| I-0136 | 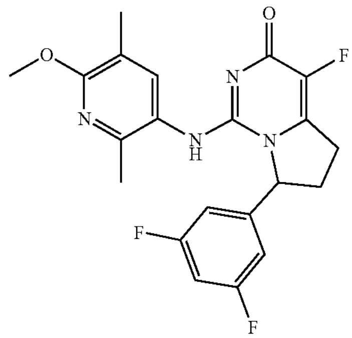 [SMILES: COc1nc(C)c(Nc2nc(=O)c(F)c3n2C(c2cc(F)cc(F)c2)CC3)cc1C] | 417 | 1.67 | [1] | b |
| I-0137 | 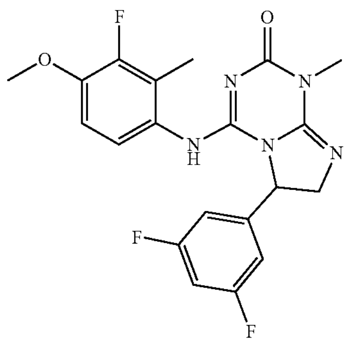 | 418 | 1.59 | [1] | b |

TABLE 28

| ID | Structure | MS | RT | [method] | |
|---|---|---|---|---|---|
| I-0138 | 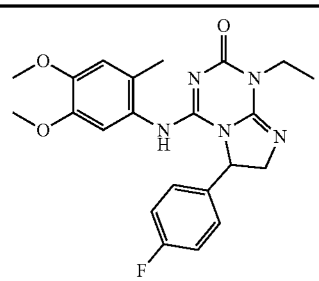 | 426.3 | 1.24 | [1] | b |
| I-0139 | 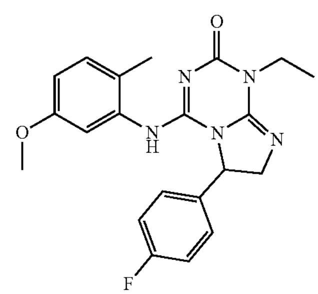 [SMILES: CCN1C(=O)N=C(Nc2cc(OC)ccc2C)N2C1=NCC2c1ccc(F)cc1] | 396 | 1.53 | [1] | b |
| I-0140 | 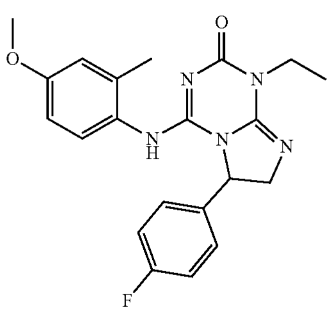 [SMILES: CCN1C(=O)N=C(Nc2ccc(OC)cc2C)N2C1=NCC2c1ccc(F)cc1] | 396 | 1.47 | [1] | b |

TABLE 28-continued

| ID | Structure | MS | RT | [method] | |
|---|---|---|---|---|---|
| I-0141 | 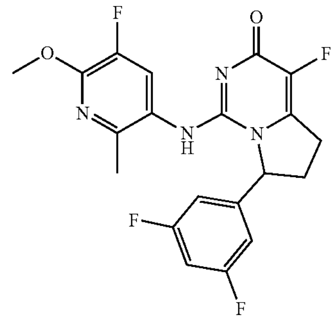 [SMILES: COc1nc(C)c(Nc2nc(=O)c(F)c3n2C(c2cc(F)cc(F)c2)CC3)cc1F] | 421 | 1.63 | [1] | b |
| I-0142 | 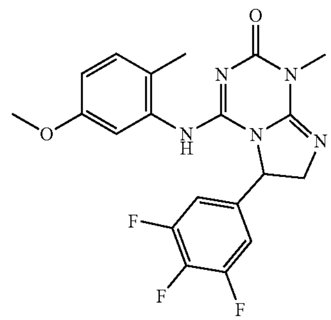 | 418 | 1.56 | [1] | b |

TABLE 29

| ID | Structure | MS | RT | [method] | |
|---|---|---|---|---|---|
| I-0143 | 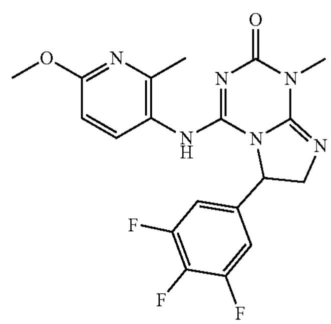 | 419.2 | 1.35 | [1] | b |
| I-0144 | 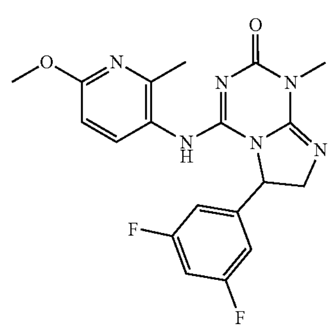 | 401.2 | 1.22 | [1] | b |

TABLE 29-continued
| I-0145 | 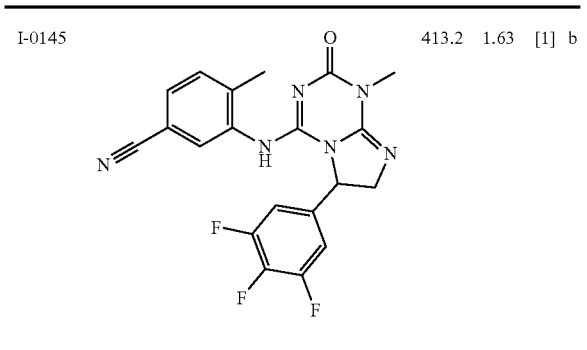 | 413.2 | 1.63 | [1] | b |
| I-0146 |  | 395.3 | 1.51 | [1] | b |
| I-0147 | 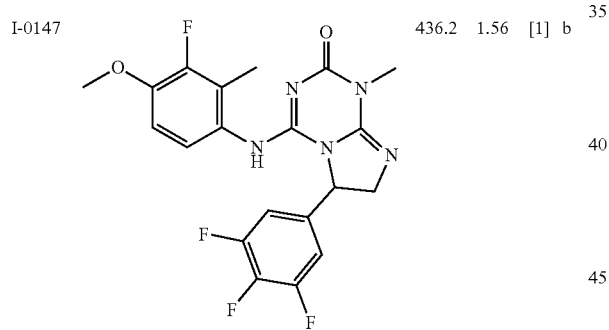 | 436.2 | 1.56 | [1] | b |
TABLE 30
| I-0148 | 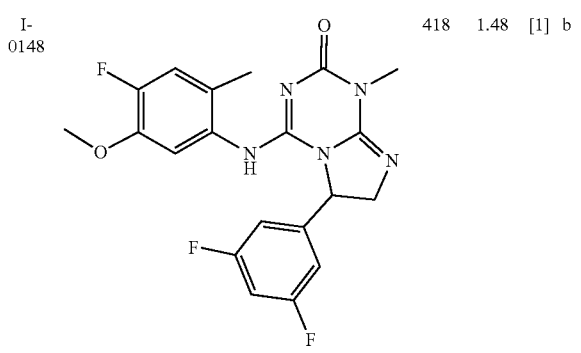 | 418 | 1.48 | [1] | b |
TABLE 30-continued
| I-0149 | 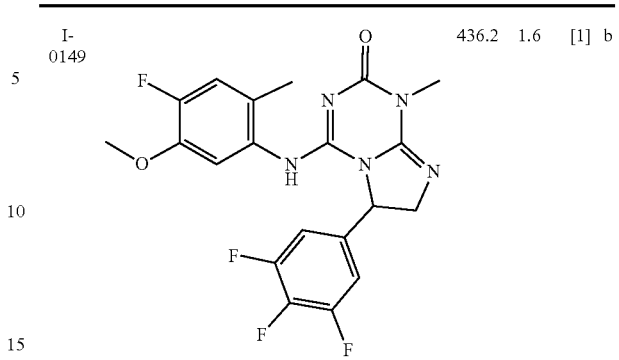 | 436.2 | 1.6 | [1] | b |
| I-0150 | 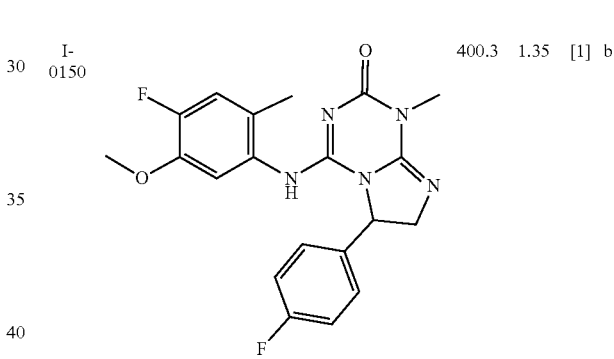 | 400.3 | 1.35 | [1] | b |
| I-0151 | 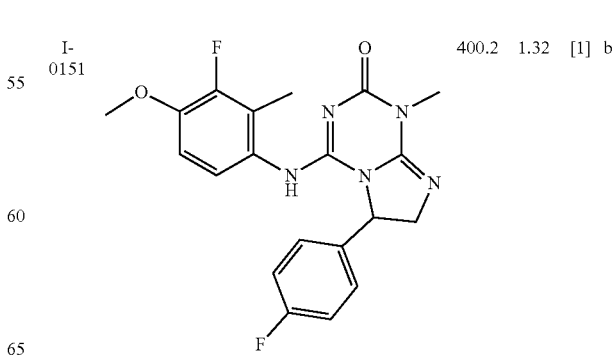 | 400.2 | 1.32 | [1] | b |

TABLE 31
| Compound No. | Chemical Structure | [M + H] | Retention time (min) | LC/MS condition | Optical activity |
|---|---|---|---|---|---|
| I-0152 | 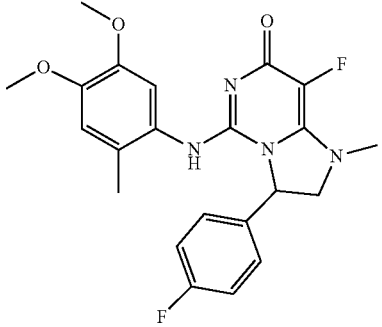 | 429 | 1.55 | [1] | a |
| I-0153 | 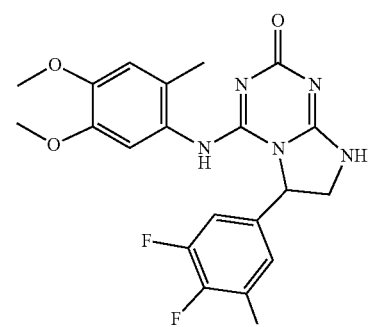 | 434 | 1.71 | [1] | a |
| I-0154 | 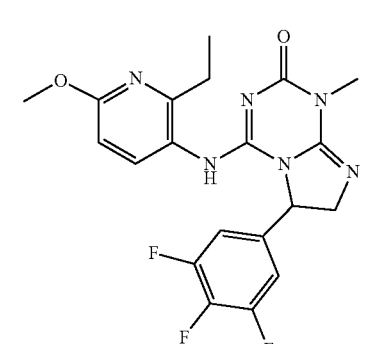 | 433.3 | 1.54 | [1] | b |
| I-0155 | 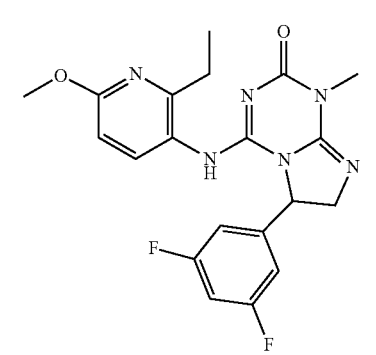 | 415.3 | 1.42 | [1] | b |

TABLE 31-continued

| Compound No. | Chemical Structure | [M + H] | Retention time (min) | LC/MS condition | Optical activity |
|---|---|---|---|---|---|
| I-0156 | 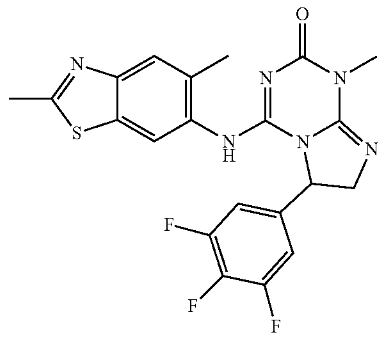 | 459.2 | 1.53 | [1] | b |

TABLE 32

| | | | | | |
|---|---|---|---|---|---|
| I-0157 | | 450.2 | 1.73 | [1] | b |
| I-0158 | | 462.2 | 1.55 | [1] | b |
| I-0159 | | 433 | 1.57 | [1] | b |

TABLE 32-continued

| | | | | | |
|---|---|---|---|---|---|
| I-0160 | | 400 | 1.33 | [3] | b |
| I-0161 | | 418 | 1.39 | [3] | b |

TABLE 33

| | | | | | |
|---|---|---|---|---|---|
| I-0162 | | 437 | 1.63 | [1] | b |

TABLE 33-continued
| I-0163 | 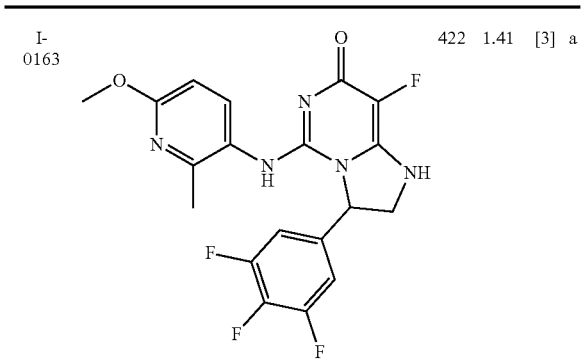 | 422 | 1.41 | [3] | a |
| I-0164 | 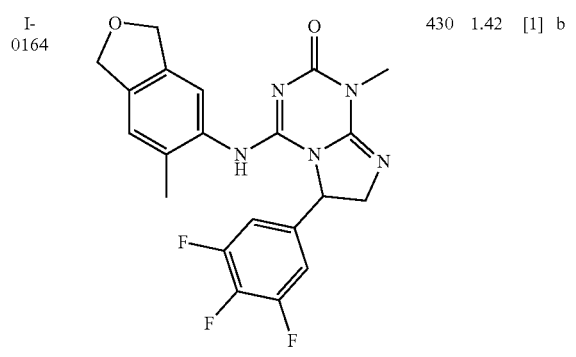 | 430 | 1.42 | [1] | b |
| I-0165 | 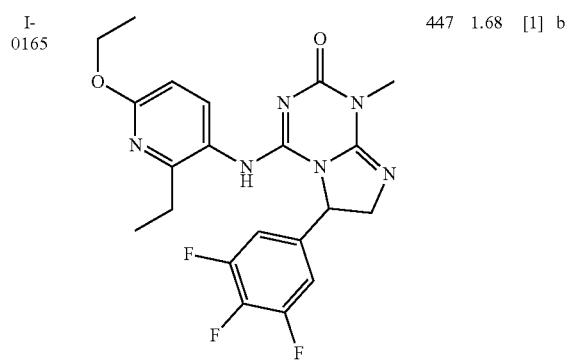 | 447 | 1.68 | [1] | b |
| I-0166 | 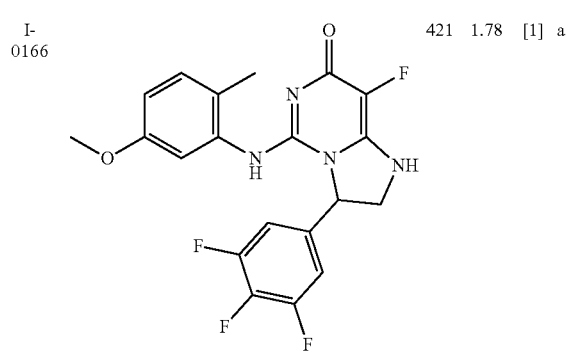 | 421 | 1.78 | [1] | a |
TABLE 34
| I-0167 | 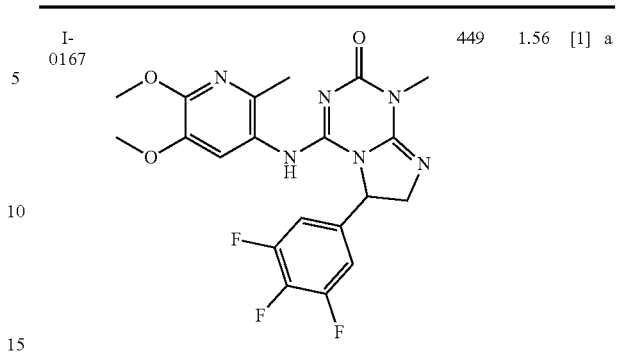 | 449 | 1.56 | [1] | a |
| I-0168 | 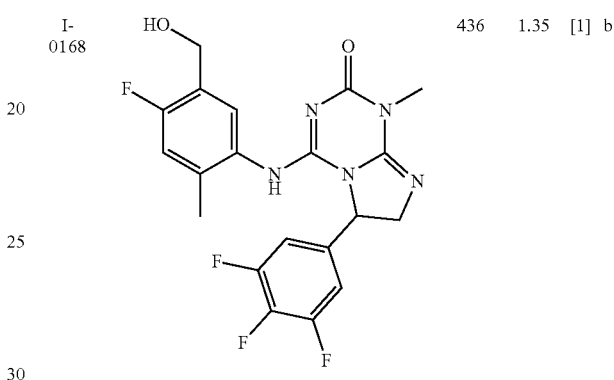 | 436 | 1.35 | [1] | b |
| I-0169 | 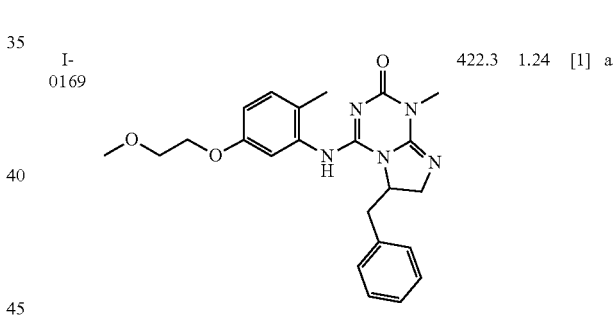 | 422.3 | 1.24 | [1] | a |
| I-0170 | 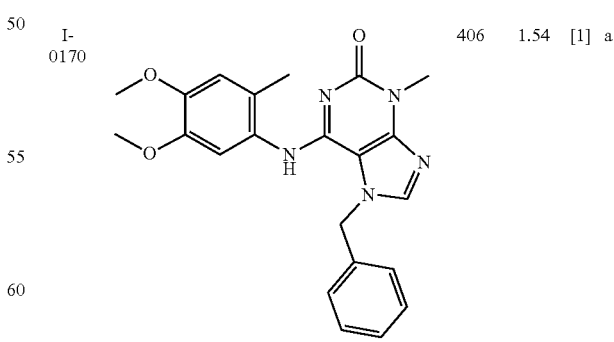 | 406 | 1.54 | [1] | a |

TABLE 34-continued
I-0171 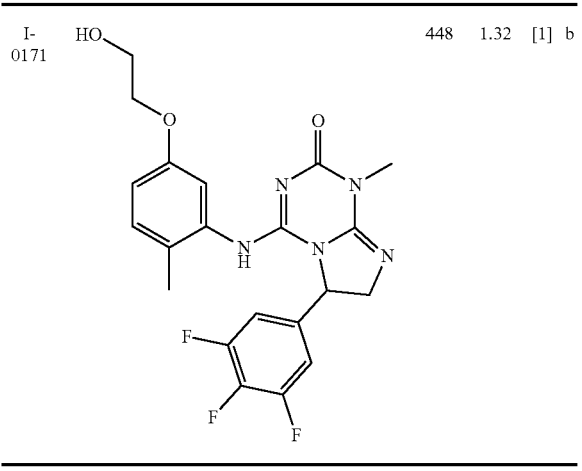 448 1.32 [1] b
TABLE 35
I-0172 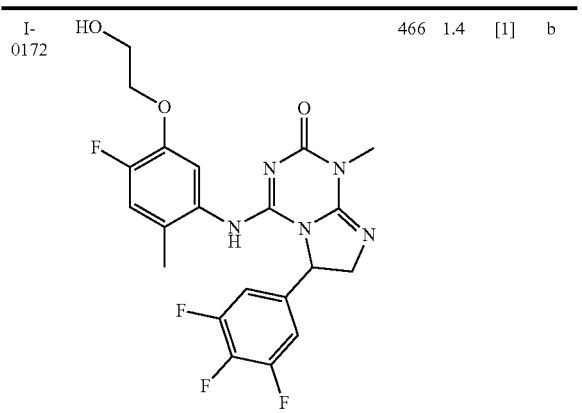 466 1.4 [1] b
I-0173 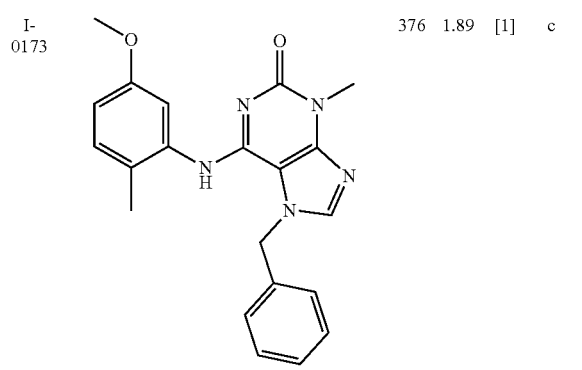 376 1.89 [1] c
I-0174 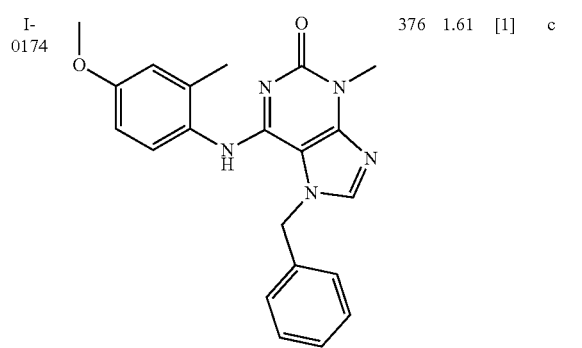 376 1.61 [1] c
TABLE 35-continued
I-0175 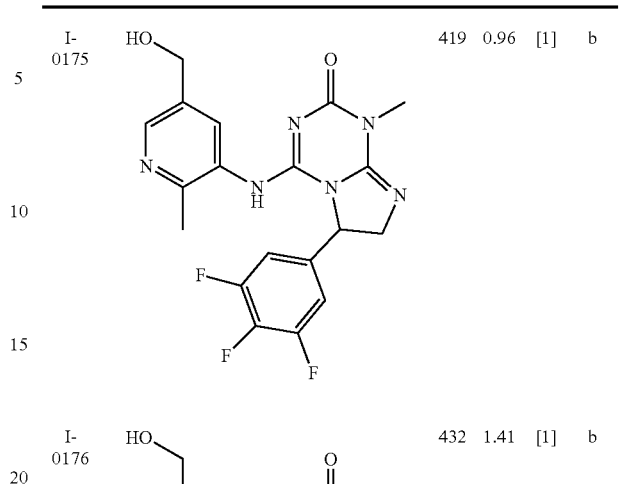 419 0.96 [1] b
I-0176 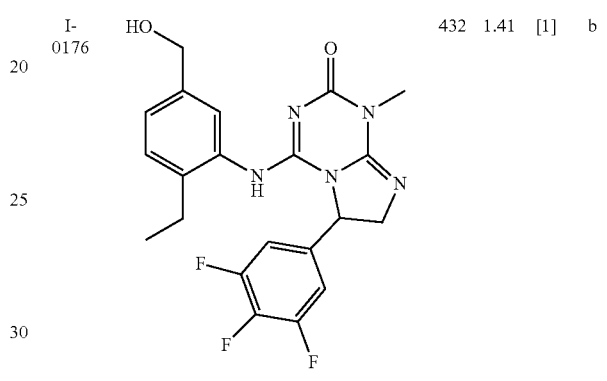 432 1.41 [1] b
TABLE 36
I-0177 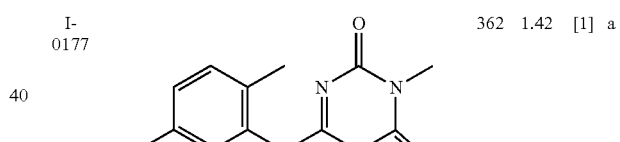 362 1.42 [1] a
I-0178 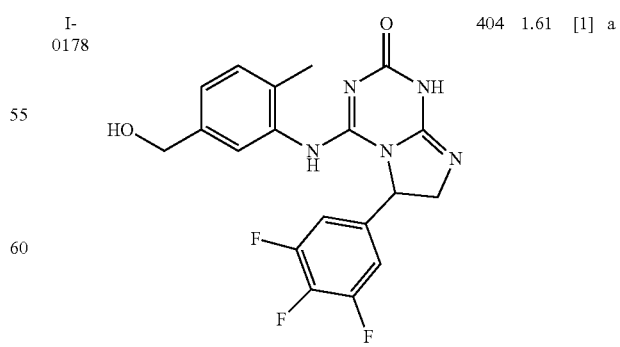 404 1.61 [1] a TABLE 36-continued
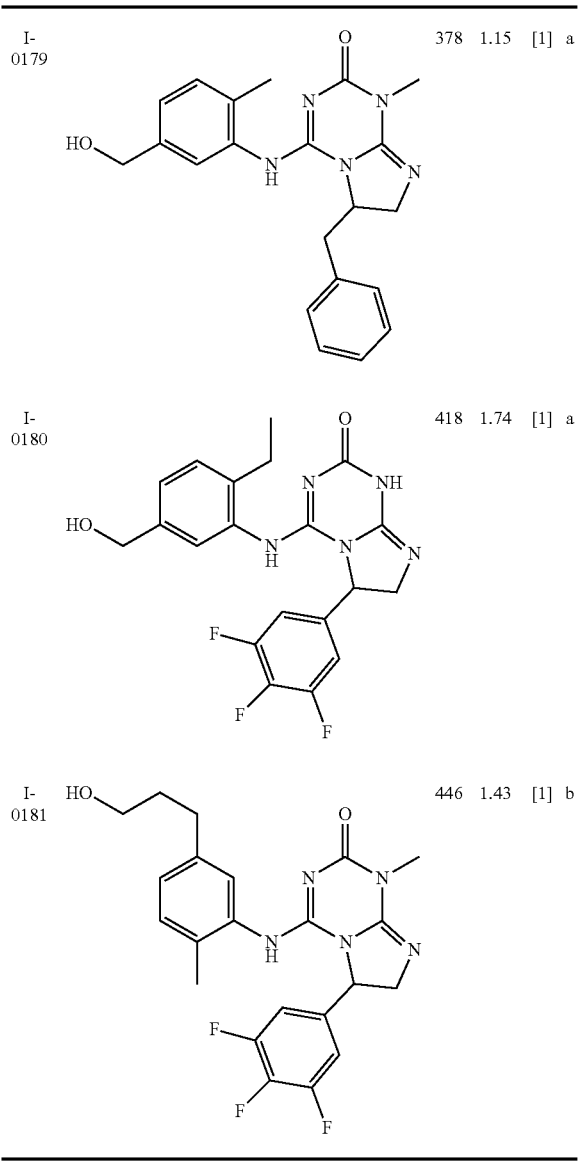
TABLE 37
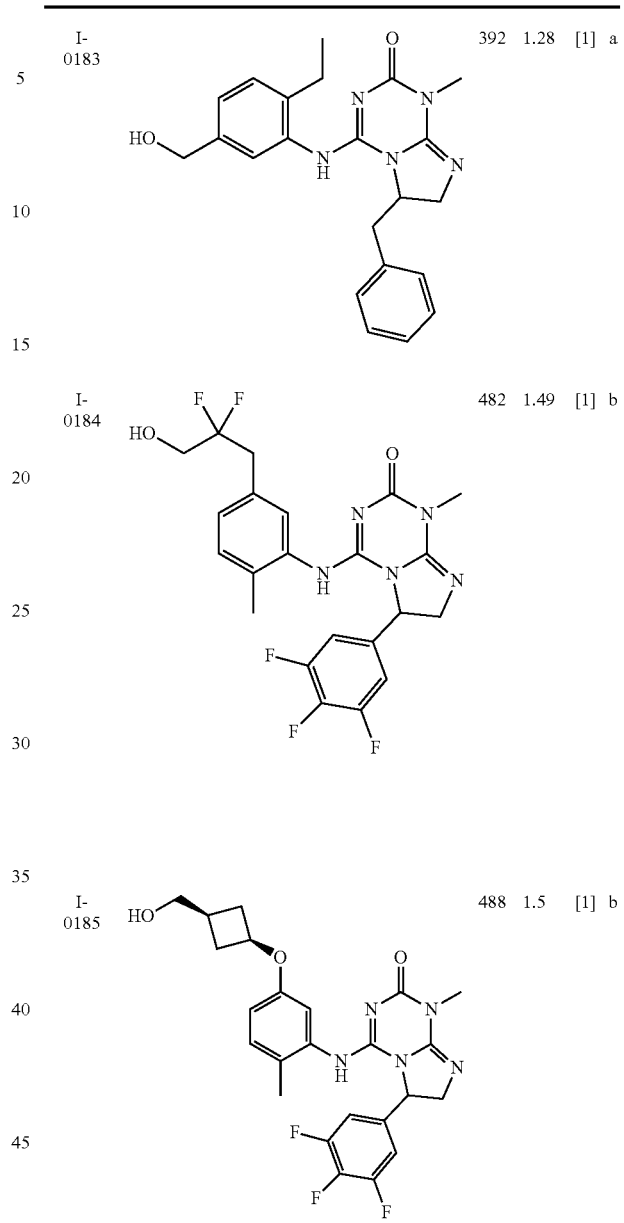
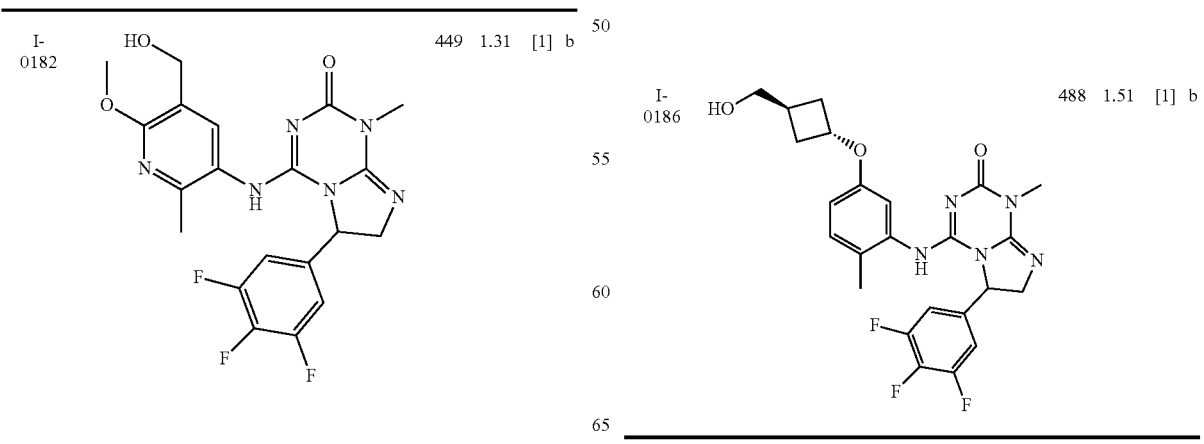

TABLE 38
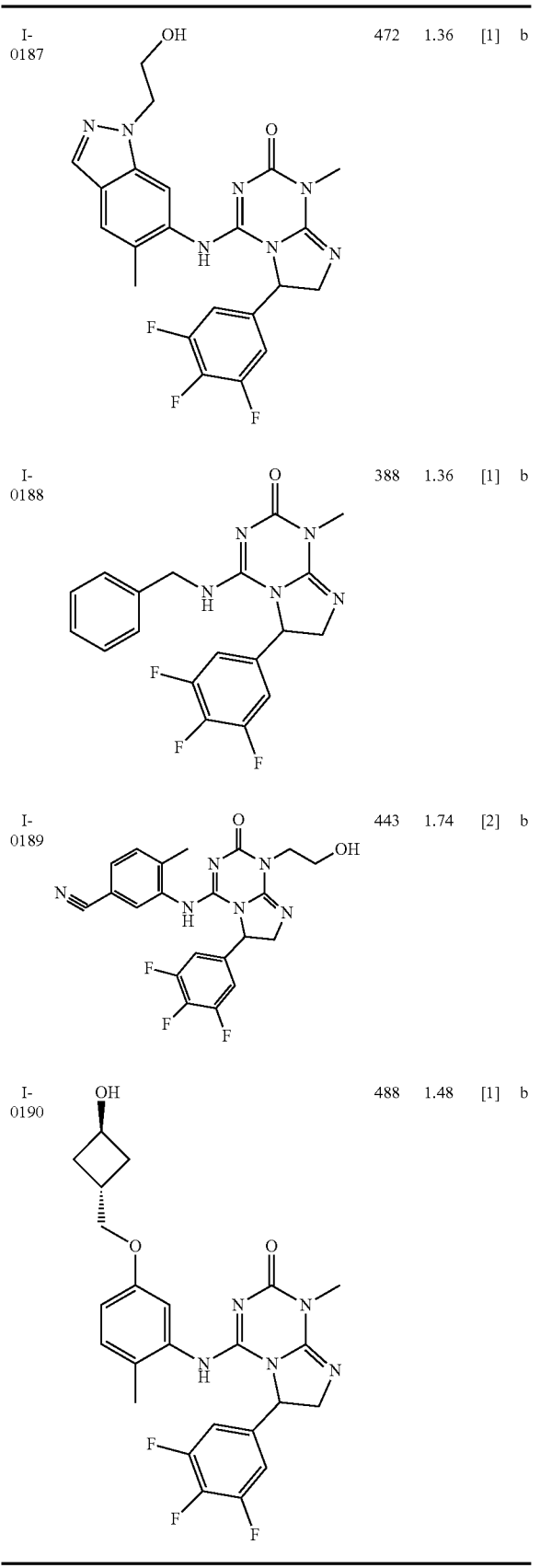
TABLE 39
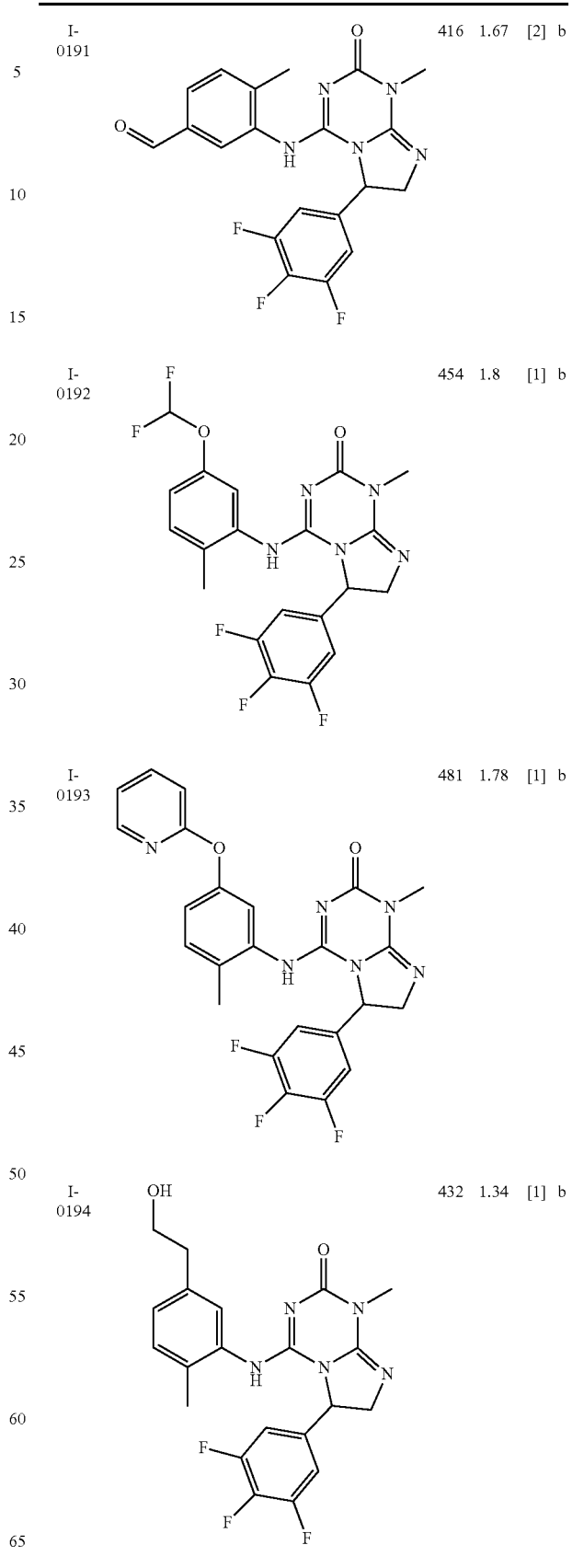

TABLE 39-continued
I-0195 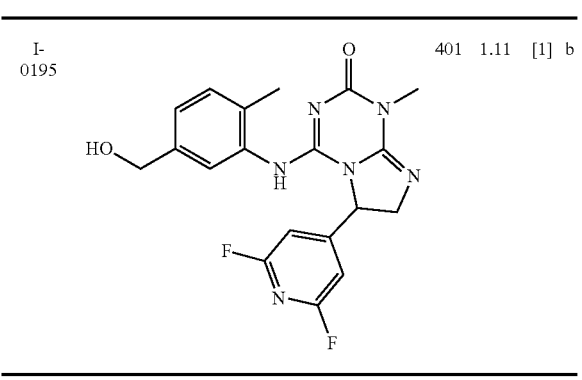 401 1.11 [1] b
TABLE 40
I-0196 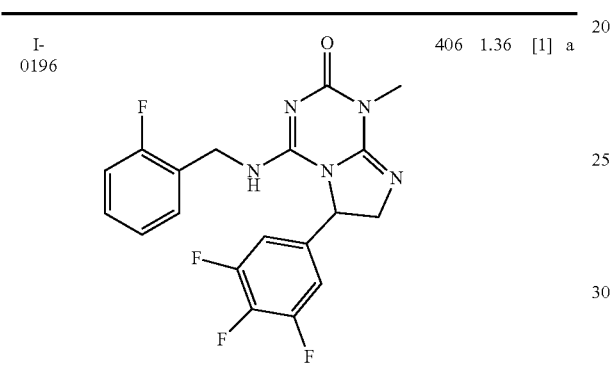 406 1.36 [1] a
I-0197 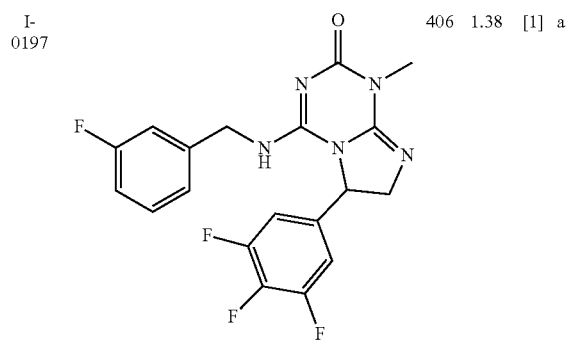 406 1.38 [1] a
I-0198 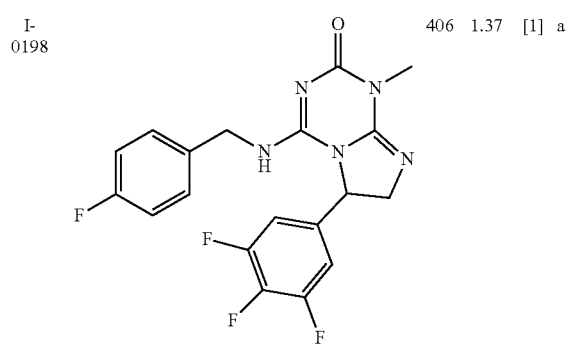 406 1.37 [1] a
TABLE 40-continued
I-0199 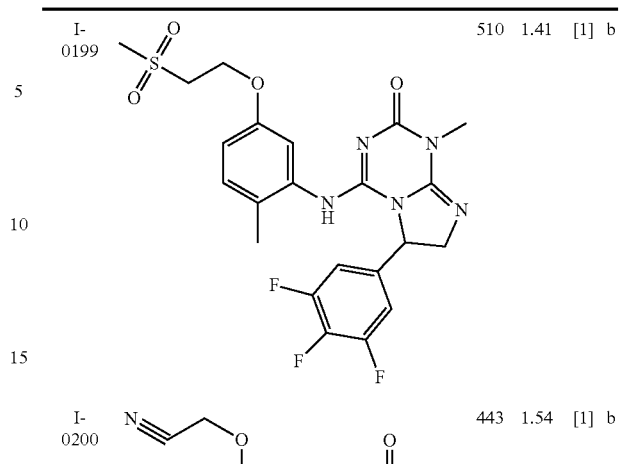 510 1.41 [1] b
I-0200 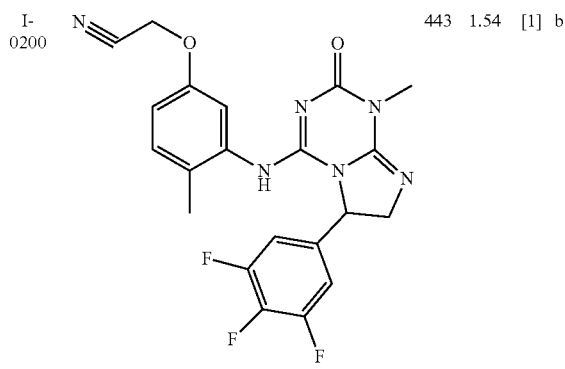 443 1.54 [1] b
TABLE 41
I-0201 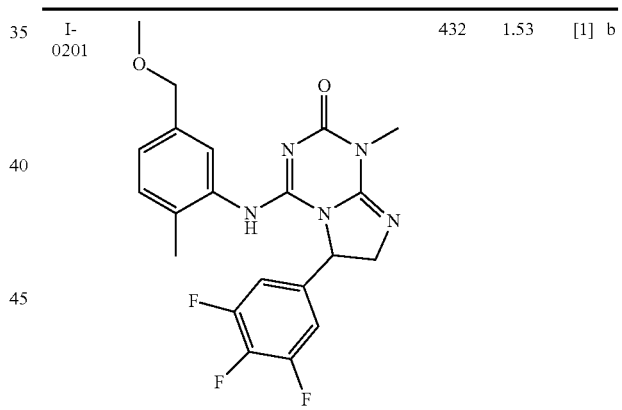 432 1.53 [1] b
I-0202 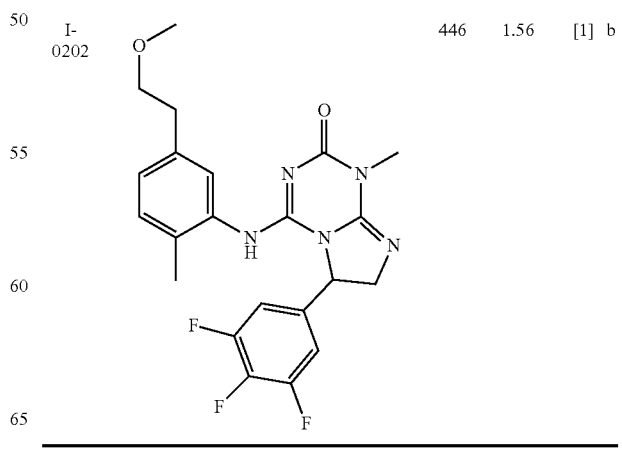 446 1.56 [1] b TABLE 42
| Compound No. | Chemical structure | [M + H] | Retention time (min) | LC/MS condition | Optical activity |
|---|---|---|---|---|---|
| I-0203 | 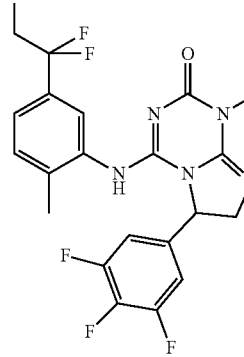 | 498 | 1.79 | [1] | b |
| I-0204 | 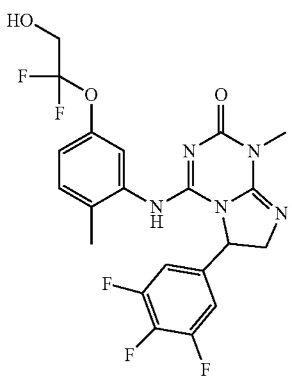 [SMILES: Cc1ccc(OC(F)(F)CO)cc1NC1=NC(=O)N(C)C2=NCC(c3cc(F)c(F)c(F)c3)N12] | 484 | 1.52 | [1] | b |
| I-0205 | 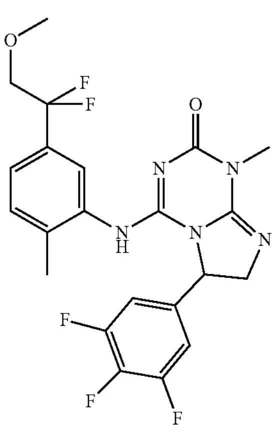 [SMILES: COCC(F)(F)c1ccc(C)c(NC2=NC(=O)N(C)C3=NCC(c4cc(F)c(F)c(F)c4)N23)c1] | 482 | 1.73 | [1] | b |
TABLE 42-continued
| Compound No. | Chemical structure | [M + H] | Retention time (min) | LC/MS condition | Optical activity |
|---|---|---|---|---|---|
| I-0206 | 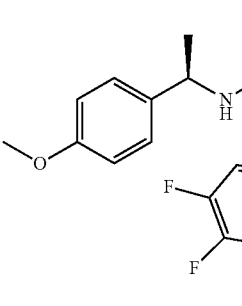 | 468 | 1.48 | [1] | b |
TABLE 43
| Compound No. | Chemical structure | [M + H] | Retention time (min) | LC/MS condition | Optical activity |
|---|---|---|---|---|---|
| I-0207 | 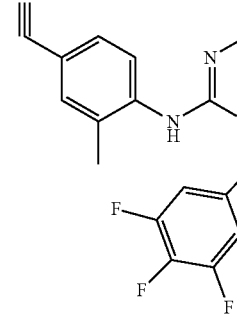 | 432 | 1.45 | [1] | c |
| I-0208 | 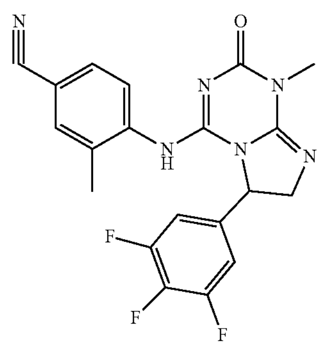 [SMILES: Cc1cc(C#N)ccc1NC1=NC(=O)N(C)C2=NCC(c3cc(F)c(F)c(F)c3)N12] | 413 | 1.67 | [1] | b |
| I-0209 | 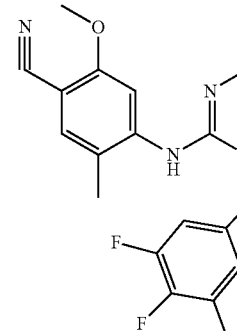 | 443 | 1.75 | [1] | b |

TABLE 43-continued
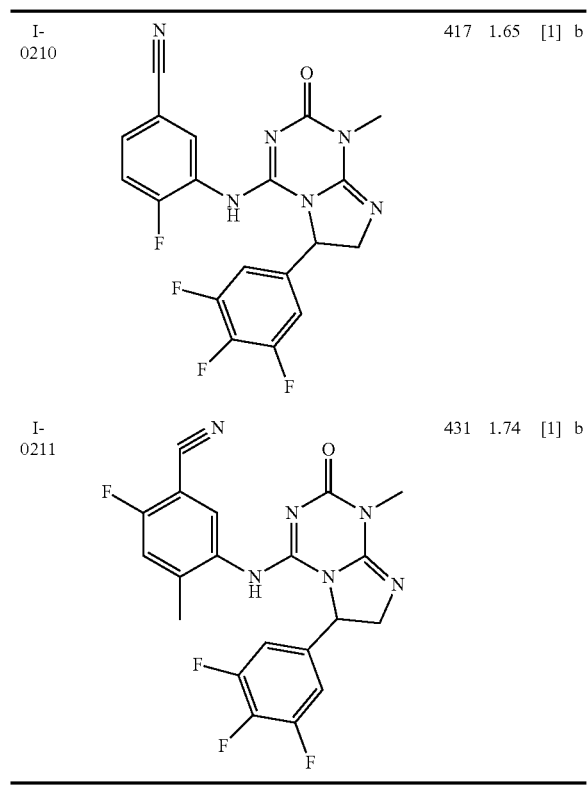
TABLE 44
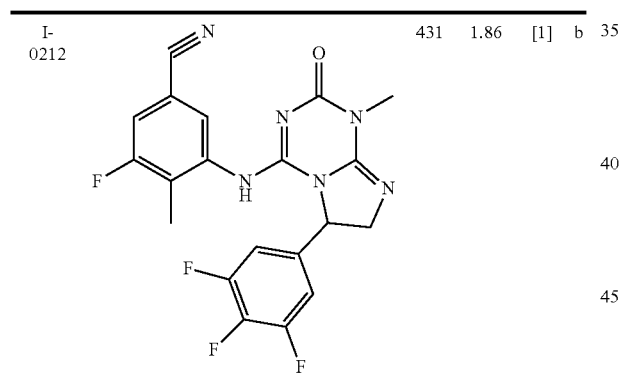
TABLE 44-continued
| I-0213 | | 457 | 1.25 | [1] | b |
| I-0214 | | 475 | 1.66 | [2] | b |
TABLE 45
| Compound No. | NMR |
|---|---|
| I-0059 | 1H-NMR (CDCl3) δ: 0.92 (t, J = 7.4 Hz, 3H), 2.10-2.18 (m, 3H), 2.64-2.75 (m, 1H), 2.93-3.11 (m, 2H), 3.87 (s, 3H), 5.43 (s, 1H), 5.58 (d, J = 8.8 Hz, 1H), 6.51 (d, J = 8.8 Hz, 1H), 6.73-6.79 (m, 3H), 6.91 (d, J = 8.5 Hz, 1H), 7.30 (brs, 1H). |
| I-0102 | 1H-NMR (DMSO-d6) δ: 1.79 (s, 3H), 2.13 (m, 1H), 2.79 (m, 1H), 3.08 (m, 2H), 4.94 (s, 4H), 5.85 (d, J = 7.2 Hz, 1H), 6.95 (d, J = 7.6 Hz, 2H), 7.00 (s, 1H), 7.11 (s, 1H), 7.25 (t, J = 9.2 Hz, 1H), 8.35 (s, 1H). |
| I-0145 | 1H-NMR (CDCl3) δ: 1.79 (s, 3H), 3.36 (s, 3H), 3.84 (dd, J = 14.4, 5.9 Hz, 1H), 4.45 (dd, J = 14.4, 10.4 Hz, 1H), 5.35 (dd, J = 10.3, 5.8 Hz, 1H), 6.92 (s, 1H), 6.99 (t, J = 7.0 Hz, 2H), 7.22-7.29 (m, 2H). |
| I-0147 | 1H-NMR (DMSO-d6) δ: 1.65 (s, 3H), 3.01 (m, 1H), 3.16 (s, 3H), 3.77(s, 3H), 4.24-4.36 (m, 2H), 5.51 (bs, 1H), 6.83-6.98 (m, 1H), 7.33-7.45 (m, 3H) |
| I-0161 | 1H-NMR (CDCl3) δ: 1.74 (s, 3H), 3.39 (s, 3H), 3.82 (dd, J = 14.2, 5.8 Hz, 1H), 4.43 (dd, J = 14.2, 10.4 Hz, 1H), 4.57 (s, 2H), 5.37 (dd, J = 10.2, 5.8 Hz, 1H), 6.65 (s, 1H), 6.94-7.02 (m, 3H), 7.11(d, J = 7.8 Hz, 1H) |

TABLE 45-continued

| Compound No. | NMR |
|---|---|
| I-0162 | 1H-NMR (CDCl3) δ: 1.87 (s, 3H), 3.33 (s, 3H), 3.82 (dd, J = 14.4, 5.6 Hz, 1H), 3.95 (s, 3H), 4.42 (dd, J = 14.4, 10.4 Hz, 1H), 5.34 (dd, J = 10.3, 5.8 Hz, 1H), 6.71 (d, J = 10.3 Hz, 1H), 6.98 (t, J = 7.0 Hz, 2H). |
| I-0164 | 1H-NMR (CDCl3) δ: 1.74 (s, 3H), 3.40 (s, 3H), 3.83 (dd, J = 14.3, 5.8 Hz, 1H), 4.44 (dd, J = 14.3, 10.3 Hz, 1H), 5.01 (s, 4H), 5.38 (dd, J = 10.0, 5.8 Hz, 1H), 6.50 (s, 1H), 6.99-7.02 (m, 3H). |
| I-0168 | 1H-NMR (CDCl3) δ: 1.72 (s, 3H), 3.39 (s, 3H), 3.82 (dd, J = 14.3, 6.0 Hz, 1H), 4.43 (dd, J = 14.3, 10.5 Hz, 1H), 4.63 (s, 2H), 5.36 (dd, J = 10.3, 6.0 Hz, 1H), 6.68 (d, J = 7.0 Hz, 1H), 6.83 (d, J = 10.5 Hz, 1H), 6.99 (t, J = 7.0 Hz, 2H), 7.24 (brs, 1H) |
| I-0171 | 1H-NMR (CDCl3) δ: 1.67 (s, 3H), 2.05 (t, J = 5.8 Hz, 1H), 3.39 (s, 3H), 3.82 (dd, J = 14.3, 5.8 Hz, 1H), 3.92 (m, 2H), 4.00 (m, 2H), 4.43 (dd, J = 14.3, 10.3 Hz, 1H), 5.37 (dd, J = 10.3, 5.8 Hz, 1H), 6.23 (d, J = 2.3 Hz, 1H), 6.55 (dd, J = 8.3, 2.3 Hz, 1H), 7.01 (m, 3H), 7.12 (s, 1H). |
| I-0176 | 1H-NMR (CDCl3) δ: 0.83 (t, J = 7.5 Hz, 3H), 2.04 (q, J = 7.5 Hz, 2H), 3.40 (s, 3H), 3.81 (dd, J = 14.3, 6.0 Hz, 1H), 4.43 (dd, J = 14.3, 10.3 Hz, 1H), 4.58 (s, 2H), 5.36 (dd, J = 10.3, 6.0 Hz, 1H), 6.67 (s, 1H), 6.98-7.02 (m, 3H), 7.12 (d, J = 7.8 Hz, 1H). |
| I-0188 | 1H-NMR (CDCl3) δ: 3.37 (s, 3H), 3.73 (dd, J = 13.9, 5.8 Hz, 1H), 4.37-4.44 (m, 2H), 4.55-4.62 (m, 2H), 5.14 (dd, J = 10.2, 5.8 Hz, 1H), 6.91-7.00 (m, 4H), 7.24-7.28 (m, 3H). |

TABLE 46

| | |
|---|---|
| I-0192 | 1H-NMR (CDCl3) δ: 1.71 (s, 3H), 3.39 (s, 3H), 3.83 (dd, J = 14.4, 5.8 Hz, 1H), 4.44 (dd, J = 14.4, 10.4 Hz, 1H), 5.36 (dd, J = 10.4, 5.8 Hz, 1H), 6.44 (t, J = 74.0 Hz, 2H), 6.75 (dd, J = 8.2, 2.2 Hz, 1H), 6.95-7.03 (m, 3H), 7.10 (d, J = 8.4 Hz, 1H). |
| I-0201 | 1H-NMR (CDCl3) δ: 1.74 (s, 3H), 3.36 (s, 3H), 3.40 (s, 3H), 3.82 (dd, J = 14.3, 5.8 Hz, 1H), 4.35 (s, 2H), 4.43 (dd, J = 14.3, 10.5 Hz, 1H), 5.37 (dd, J = 10.4, 5.9 Hz, 1H), 6.62 (s, 1H), 6.95-7.00 (m, 3H), 7.11(d, J = 7.8 Hz, 1H) |

Biological test examples for the compounds of the present invention are described below.

The compounds represented by Formula (I) according to the present invention needs only to have an antagonistic activity for the P2X$_7$ receptor so as to inhibit the human P2X$_7$ receptor.

Specifically, in the evaluation methods described below, IC50 is preferably 5000 nM or less, more preferably 1000 nM or less, further preferably 100 nM or less.

Evaluation of a human P2X$_7$ receptor inhibitory activity Stably expressing cell line (1321N1 cell transfected with the human P2X$_7$ receptor gene (GenBank accession number NM_002562.5 including T606C and G952A SNP)) was used. The cells were seeded in a 384-well microtiter plate at a concentration of 8000 cells/well and cultured in the medium (10% fetal bovine serum, 25 mM HEPES, 1% penicillin and streptomycin in DMEM) for one day at 37° C. under 5% carbon dioxide atmosphere. After replacing with 20 µL of the HBSS buffer (20 mM HEPES, 55.6 mM D-glucose, 1×HBSS(−), pH7.4-7.5), 15 µL of 17.3 µM Yo-Pro solution in the HBSS buffer was added. The plate was placed in high-throughput cellular screening system FLIPR TETRA (Molecullar Devices, LLC.) and 15 µL of 130 µM BzATP solution in the HBSS buffer was added. Measurement of fluorescence intensity by FLIPR TETRA was started. After eight minutes, 15 µL of DMSO solutions containing different concentrations of the compound of the present invention as prepared by dilution with the HBSS buffer were dispensed to each well through the built-in automatic dispenser, and the measurement of fluorescence intensity was continued for 20 minutes. The maximum fluorescence intensity without the compound of the present invention is calculated as 0% inhibition and the maximum fluorescence intensity when the reference compound was added is calculated as 100% inhibition. Changing values of fluorescence intensity by the compound of the present invention were calculated by difference between maximum and minimum fluorescence intensity for 20 minutes. Inhibition ratios (%) were calculated from the following equation:

Inhibition Ratio:

$$\left[1 - \frac{\text{changing values by a compound of the present invention} - \text{changing values by reference compound}}{\text{changing values without a compound of the present invention} - \text{changing values by reference compound}}\right] \times 100 \ (\%)$$

IC$_{50}$ was calculated using logistic approximation.

The antagonistic activity for the human P2X$_7$ receptor of the compounds of the present invention is shown in the following table.

TABLE 47

| Compound No. | IC50 (nM) |
|---|---|
| I-0001 | 16 |
| I-0003 | 1.8 |
| I-0004 | 37 |
| I-0009 | 22 |
| I-0032 | 16 |
| I-0059 | 11 |
| I-0069 | 10 |

TABLE 47-continued

| Compound No. | IC50 (nM) |
| --- | --- |
| I-0091 | 17 |
| I-0100 | 12 |
| I-0102 | 11 |
| I-0106 | 11 |
| I-0107 | 25 |
| I-0145 | 19 |
| I-0147 | 24 |
| I-0149 | 21 |
| I-0150 | 18 |
| I-0151 | 14 |

TABLE 48

| Compound No. | IC50 (nM) |
| --- | --- |
| I-0154 | 17 |
| I-0158 | 27 |
| I-0161 | 19 |
| I-0162 | 19 |
| I-0164 | 28 |
| I-0168 | 23 |
| I-0171 | 19 |
| I-0176 | 20 |
| I-0188 | 7.6 |
| I-0192 | 18 |
| I-0201 | 26 |

The antagonistic activity for the human P2X$_7$ receptor of the other compounds of the present invention is shown in the following table. As for IC50 value, value to below 10 nmol/L is represented as "A", value from 10 nmol/L to below 100 nmol/L is represented as "B", value from 100 nmol/L to below 500 nmol/L is represented as "C", and value from 500 nmol/L to below 1 μmol/L is represented as "D".

TABLE 49

| Compound No. | IC50 |
| --- | --- |
| I-0002 | A |
| I-0005 | B |
| I-0006 | B |
| I-0007 | A |
| I-0008 | A |
| I-0010 | A |
| I-0011 | A |
| I-0012 | A |
| I-0013 | A |
| I-0014 | A |
| I-0015 | B |
| I-0016 | B |
| I-0017 | B |
| I-0018 | B |
| I-0019 | A |
| I-0020 | A |
| I-0021 | B |
| I-0022 | A |
| I-0023 | A |
| I-0024 | B |
| I-0025 | B |
| I-0026 | A |
| I-0027 | A |
| I-0028 | A |
| I-0029 | A |
| I-0030 | C |
| I-0031 | B |
| I-0033 | B |
| I-0034 | B |
| I-0035 | C |
| I-0036 | B |
| I-0037 | A |
| I-0038 | A |
| I-0039 | A |
| I-0040 | B |
| I-0041 | A |
| I-0042 | A |
| I-0043 | A |
| I-0044 | B |
| I-0045 | B |
| I-0046 | B |
| I-0047 | B |
| I-0048 | B |
| I-0049 | A |
| I-0050 | A |
| I-0051 | B |
| I-0052 | B |
| I-0053 | B |
| I-0054 | A |
| I-0055 | B |
| I-0056 | B |
| I-0057 | B |
| I-0058 | A |
| I-0059 | B |
| I-0060 | B |
| I-0061 | B |
| I-0062 | B |
| I-0063 | B |
| I-0064 | B |
| I-0065 | A |
| I-0066 | A |
| I-0067 | A |
| I-0068 | B |
| I-0070 | B |
| I-0071 | B |
| I-0072 | B |
| I-0073 | B |
| I-0074 | A |
| I-0075 | B |
| I-0076 | B |
| I-0077 | A |
| I-0078 | B |
| I-0079 | B |
| I-0080 | A |
| I-0081 | B |
| I-0082 | B |
| I-0083 | B |
| I-0084 | B |
| I-0085 | B |
| I-0086 | B |
| I-0087 | B |
| I-0088 | D |
| I-0089 | B |
| I-0090 | B |
| I-0092 | B |
| I-0093 | C |
| I-0094 | B |
| I-0095 | B |
| I-0096 | B |
| I-0097 | A |
| I-0098 | A |
| I-0099 | A |
| I-0101 | B |
| I-0103 | B |
| I-0104 | B |
| I-0105 | B |
| I-0108 | B |
| I-0109 | B |
| I-0110 | A |
| I-0111 | A |
| I-0112 | D |
| I-0113 | D |
| I-0114 | C |
| I-0115 | C |
| I-0116 | C |
| I-0117 | C |
| I-0118 | C |
| I-0119 | B |
| I-0120 | C |
| I-0121 | B |
| I-0122 | B |

TABLE 49-continued

| Compound No. | IC50 |
|---|---|
| I-0123 | B |
| I-0124 | B |
| I-0125 | B |
| I-0126 | B |
| I-0127 | B |
| I-0128 | B |
| I-0129 | B |
| I-0130 | B |
| I-0131 | B |
| I-0132 | B |
| I-0133 | B |
| I-0134 | A |
| I-0135 | B |
| I-0136 | B |
| I-0137 | B |
| I-0138 | B |
| I-0139 | B |
| I-0140 | B |
| I-0141 | B |
| I-0142 | B |
| I-0143 | B |
| I-0144 | B |
| I-0145 | B |
| I-0146 | B |
| I-0147 | B |
| I-0148 | B |

TABLE 50

| Compound No. | IC50 |
|---|---|
| I-0152 | B |
| I-0153 | B |
| I-0155 | B |
| I-0156 | B |
| I-0157 | B |
| I-0159 | B |
| I-0160 | B |
| I-0163 | B |
| I-0165 | B |
| I-0166 | B |
| I-0167 | C |
| I-0169 | B |
| I-0170 | B |
| I-0172 | B |
| I-0173 | D |
| I-0174 | C |
| I-0175 | B |
| I-0177 | C |
| I-0178 | B |
| I-0179 | C |
| I-0180 | B |
| I-0181 | B |
| I-0182 | B |
| I-0183 | C |
| I-0184 | B |
| I-0185 | B |
| I-0186 | B |
| I-0187 | B |
| I-0189 | B |
| I-0190 | B |
| I-0191 | B |
| I-0193 | B |
| I-0194 | B |

TABLE 50-continued

| Compound No. | IC50 |
|---|---|
| I-0195 | B |
| I-0196 | B |
| I-0197 | B |
| I-0198 | B |
| I-0199 | B |
| I-0200 | B |
| I-0202 | B |

TABLE 51

| Compound No. | IC50 |
|---|---|
| I-0203 | B |
| I-0204 | B |
| I-0205 | B |
| I-0206 | B |
| I-0207 | C |
| I-0208 | B |
| I-0209 | B |
| I-0210 | B |
| I-0211 | B |
| I-0212 | B |
| I-0213 | B |
| I-0214 | B |

Test Example 2 Evaluation of the Rat $P2X_7$ Receptor Inhibitory Activity

Stably expressing cell line (1321N1 cell transfected with the rat $P2X_7$ receptor gene (GenBank accession number NM_019256.1 including C586T and C652A SNP)) is used. The cells are seeded in a 384-well microtiter plate at a concentration of 10000 cells/well and cultured in the medium (10% fetal bovine serum, 2 mM ClutaMax-1, 1% penicillin and streptomycin in DMEM) for one day at 37° C. under 5% carbon dioxide atmosphere. After replacing with 20 μL of the HBSS buffer (20 mM HEPES, 55.6 mM D-glucose, lx HBSS(+), pH7.4), 15 μL of 17.3 μM Yo-Pro solution in the HBSS buffer is added. The plate is placed in high-throughput cellular screening system FLIPR TETRA (Molecullar Devices, LLC.) and 15 μL of 1083 μM BzATP solution in the HBSS buffer is added. Measurement of fluorescence intensity by FLIPR TETRA is started. Eight minutes after, 15 μL of DMSO solutions containing different concentrations of the compound of the present invention as prepared by dilution with the HBSS buffer are dispensed to each well through the built-in automatic dispenser, and the measurement of fluorescence intensity is continued for 20 minutes. The maximum fluorescence intensity without the compound of the present invention is calculated as 0% inhibition and the maximum fluorescence intensity when the reference compound is added is calculated as 100% inhibition, Changing values of fluorescence intensity by the compound of the present invention are calculated by difference between maximum and minimum fluorescence intensity for 20 minutes. Inhibition ratios (%) are calculated from the following equation:

Inhibition Ratio:

$$\left[1 - \frac{\text{changing values by a compound of the present invention} - \text{changing values by reference compound}}{\text{changing values without a compound of the present invention} - \text{changing values by reference compound}}\right] \times 100 \; (\%)$$

$IC_{50}$ is calculated using logistic approximation.

Test Example 3-1: Analgesic Effect in a Seltzer Model

Preparation of Partial Sciatic Nerve Ligation model in Rats Rats were anaesthetized using isoflurane/O2 inhalation anaesthesia. After induction of anesthesia, the left thigh was shaved. An incision was made in the skin just below the hip bone. The muscle was bluntly dissected to expose the sciatic nerve. About one half (½) of the sciatic nerve thickness was tightly ligated with a nylon thread and the wound was closed. The right thigh was used as a sham-operated control. The right thigh underwent an identical procedure with the left hind limb, however, the sciatic nerve was not manipulated or ligated.

Evaluation (1)

Two weeks after nerve ligation, the effect on mechanical allodynia was assessed using a series of von Frey filaments. For habituation, the rats were placed into a plastic cage on a wire mesh bottom. Von Frey filaments (0.4 to 26 g) were applied to the plantar surface of the rat hind paws from the wire mesh side, and the value of the filament pressure at which the paw was withdrawn was used as a pain threshold. The measurement of mechanical sensitivity of the right and left hind paws was performed to obtain predose mechanical sensitivity. The rats showing the threshold change from 0.6 to 2 g (in nerve ligated side) and 8 to 15 g (in sham operated side) were used in the experiments. On the day before the experiment, the rats were evaluated with a series of von Frey filaments to familiarize them with the test procedure. The adopted animal was administrated with the compounds of the present invention. The compounds of the present invention were homogenized with mortar and pestle and suspended or diluted in 0.5% Methyl Cellulose to prepare 0.03-100 mg/2 mL/kg suspension and orally administered to rat using a syringe attached with a sonde. Post-dose mechanical sensitivities of the right and left hind paws were measured at approximately 1 to 5 hours after drug administration. Percent reversal of mechanical allodynia for each rat was calculated using the following formula. The analgesic effects of the compounds were compared.

% Reversal =

$$100 \times \frac{\text{Log}_{10}(\text{Postdose mechanical sensitivity in nerve ligated side}) - \text{Log}_{10}(\text{Predose mechanical sensitivity in nerve ligated side})}{\text{Log}_{10}(\text{Predose mechanical sensitivity in sham operated side}) - \text{Log}_{10}(\text{Predose mechanical sensitivity in nerve ligated side})}$$

Results

TABLE 52

| Compound No. | % reversal |
|---|---|
| I-0102 | 55% (3 mg/kg) |
| I-0135 | 52% (3 mg/kg) |

TABLE 52-continued

| Compound No. | % reversal |
|---|---|
| I-0145 | 58% (1 mg/kg) |
| I-0147 | 33% (1 mg/kg) |
| I-0149 | 41% (1 mg/kg) |
| I-0154 | 44% (1 mg/kg) |
| I-0158 | 47% (1 mg/kg) |
| I-0161 | 51% (1 mg/kg) |
| I-0164 | 47% (1 mg/kg) |
| I-0168 | 53% (1 mg/kg) |
| I-0171 | 52% (1 mg/kg) |
| I-0192 | 50% (1 mg/kg) |
| I-0201 | 51% (1 mg/kg) |

Evaluation (2)

Mechanical hyperalgesia is evaluated using an analgesy meter (Randall Selitto). Two weeks after nerve ligation, the paw pressure test is performed using an analgesy meter (stimulus pressure increased 16 g per second) to obtain paw withdrawal thresholds (PWT). Measurements are made on both sides of the hind paw and to obtain pre-dose PWT. The rats showing the threshold change from 60 to 90 g (in nerve ligated side) and 100 to 175 g (in sham operated side) are used in the experiments. On the day before the experiment, the rats have their hind paws set on the apparatus to familiarize them with the test procedure. The adopted animal is administrated with the compound of the present invention. The compounds of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose PWT of the right and left hind paws are measured at approximately 1 to 5 hours after drug administration. Percent reversal of mechanical hyperalgesia for each rat is calculated using the following formula. The analgesic effects of the compounds are compared.

$$\% \text{ Reversal} = 100 \times \frac{\text{Postdose } PWT \text{ in nerve ligated side} - \text{Predose } PWT \text{ in nerve ligated side}}{\text{Predose } PWT \text{ in sham operated side} - \text{Predose } PWT \text{ in nerve ligated side}}$$

Test Example 9-2: Analgesic Effect in a Cauda Equina Nerve Compression Model Preparation of Animal Model In order to prepare animal models, an incision is made in the lumbar portions of the back of rats under anesthesia to expose the fourth, fifth, and sixth lumbar vertebras. An incision is made in the 4-5 and 5-6 lumbar vertebral joints. Silicon rubber is inserted into the fourth and sixth lumbar vertebral canals from the wounds of the vertebral joints, and indwelled. The wounds are closed.

In order to sham-operated animals, rats are operated by the above procedures except for the insertion and indwelling of silicon rubber.

Evaluation of Analgesic Effect

Two weeks after operation, the effect on mechanical allodynia is assessed using a series of von Frey filaments. For habituation, the rats are placed into a plastic cage on a wire mesh bottom. Von Frey filaments (0.4 to 26 g) were applied to the plantar surface of the rat hind paws from the wire mesh side, and the value of the filament pressure at which the paw was withdrawn was used as a pain threshold. The measurement of mechanical sensitivity of the right and left hind paws is performed to obtain predose mechanical sensitivity. The mechanical sensitivity of both hind paws is evaluated to obtain predose mechanical sensitivity in the animal models showing the threshold change from 0.4 to 1 g and a higher pain threshold. The rats showing the threshold change from 8 to 15 g (in sham-operated group) are used in the experiments. On the day before the experiment, the rats are evaluated with a series of von Frey filaments to familiarize them with the test procedure. The adopted animal is administrated with the compounds of the present invention. The compounds of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose mechanical sensitivities of the right and left hind paws are measured at approximately 1 to 5 hours after drug administration. Percent reversal of mechanical allodynia for each rat is calculated using the following formula. The analgesic effects of the compounds are compared.

Test Example 3-3: Analgesic Effect in an EAE Model

Preparation of Rat Experimental Autoimmune Encephalomyelitis Model

Rats (Lewis rats, female) are anaesthetized using isoflurane. The backs at the tail bases are shaved. 1 g/L of an emulsion containing CFA (complete Freund's adjuvant) and the saline solution of MBP (myelin basic protein) mixed at 1:1 is prepared, and subcutaneously administered at 100 uL/animal to the backs at the rat tail bases for immunization. This is used as an operated group. An emulsion with CFA is prepared using MBP-free saline, and similar treatment is performed. This is used as a sham-operated group.

Evaluation

Three weeks after immunization, the effect on mechanical allodynia is assessed using a series of von Frey filaments. For habituation, the rats are placed into a plastic cage on a wire mesh bottom. Von Frey filaments (0.4 to 26 g) were applied to the plantar surface of the rat hind paws from the wire mesh side, and the value of the filament pressure at which the paw was withdrawn was used as a pain threshold. The mechanical sensitivity of both hind paws is evaluated to obtain predose mechanical sensitivity in the animal models showing the threshold change from 4 g or less and a higher pain threshold from 0.6 to 2 g. The rats showing the threshold change from 6 to 15 g (in sham-operated group) are used in the experiments. On the day before the experiment, the rats are evaluated with a series of von Frey filaments to familiarize them with the test procedure. The adopted animal is administrated with the compounds of the present invention. The compounds of the present invention are homogenized with mortar and pestle and suspended or diluted in 0.5% Methyl Cellulose to prepare 0.03-100 mg/2 mL/kg suspension and orally administered to rat using a syringe attached with a sonde. Post-dose mechanical sensitivities of the hind paws are measured at approximately 1 to 5 hours after drug administration. Percent reversal of mechanical allodynia for each rat is calculated using the following formula. The analgesic effects of the compounds are compared. % Reversal=$\text{Log}_{10}$ (Postdose mechanical sensitivity in the operated group)–$\text{Log}_{10}$ (Predose mechanical sensitivity in the operated group)/$\text{Log}_{10}$ (Predose mechanical sensitivity in the sham-operated group)–$\text{Log}_{10}$ (Predose mechanical sensitivity in the operated group)

The antagonistic activity for the $P2X_7$ receptor of the compounds of the present invention can be also evaluated by using the method described in British Journal of Pharmacology (2013) 170 624-640.

Test Example 4: CYP Inhibition Test

Using commercially available pooled human liver microsomes, an inhibitory degree of each metabolite production amount by the compound of the present invention is assessed as marker reactions of human main five CYP isoforms (CYP1A2, 2C9, 2C19, 2D6, and 3A4), 7-ethoxyresorufin O-deethylation (CYP1A2), tolbutamide methylhydroxylation (CYP2C9), mephenytoin 4'-hydroxylation (CYP2C19), dextromethorphan O-demethylation (CYP2D6), and terfenedine hydroxylation (CYP3A4).

The reaction conditions are as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenedine (CYP3A4); reaction time, 15 minutes; reaction temperature, 37° C.; enzyme, pooled human liver microsomes 0.2 mg protein/mL; concentration of the compound of the present invention, 1.0, 5.0, 10, 20 μmol/L (four points).

Each five kinds of substrates, human liver microsomes, or the compound of the present invention in 50 mmol/L Hepes buffer are added to a 96-well plate at the composition as described above, and NADPH, as a cofactor is added to initiate metabolism reactions. After the incubation at 37° C. for 15 minutes, a methanol/acetonitrile=1/1 (V/V) solution is added to stop the reaction. After the centrifugation at 3000 rpm for 15 minutes, resorufin (CYP1A2 metabolite) in the supernatant is quantified by a fluorescent multilabel counter or LC/MS/MS and hydroxytolbutamide (CYP2C9 metabolite), 4-hydroxymephenytoin (CYP2C19 metabolite), doxtrorphan (CYP2D6 metabolite), and terfenadine alcohol metabolite (CYP3A4 metabolite) are quantified by LC/MS/MS.

The sample obtained by adding only DMSO that is a solvent dissolving a compound instead of the compound of the present invention to a reaction mixture is adopted as a control (100%). Remaining activity (%) is calculated at each concentration of the compound of the present invention compared to control, and $IC_{50}$ is calculated by reverse presumption by a logistic model using a concentration and an inhibition rate.

Test Example 5: CYP3A4 (MDZ) MBI Test

The CYP3A4(MDZ) MBI test is a test of investigating Mechanism based inhibition (MBI) potential on CYP3A4 inhibition of the compound of the present invention by the enhancement of the inhibitory effect caused by a metabolic reaction of the compound of the present invention. CYP3A4 inhibition is evaluated using pooled human liver microsomes by 1-hydroxylation reaction of midazolam (MDZ) as a marker reaction.

The reaction conditions are as follows: substrate, 10 μmol/L MDZ; pre-reaction time, 0 or 30 minutes; substrate metabolic reaction time, 2 minutes; reaction temperature, 37° C.; protein content of pooled human liver microsomes, at pre-reaction 0.5 mg/mL, at reaction 0.05 mg/mL (at 10-fold dilution); concentrations of the compound of the present invention, 1, 5, 10, 20 μmol/L (four points).

Pooled human liver microsomes and a solution of the compound of the present invention in K-Pi buffer (pH 7.4) as a pre-reaction solution are added to a 96-well plate at the composition of the pre-reaction. A part of pre-reaction solution is transferred to another 96-well plate, and 1/10 diluted by K-Pi buffer containing a substrate. NADPH as a cofactor is added to initiate a reaction as a marker reaction (Preincubation 0 min). After a predetermined time of a marker reaction, a solution of methanol/acetonitrile=1/1 (V/V) is added to stop the reaction. In addition, NADPH is added to a remaining pre-reaction solution to initiate a pre-reaction (Preincubation 30 min). After a predetermined time of a pre-reaction, a part is transferred to another 96-well plate, and 1/10 diluted by K-Pi buffer containing a substrate to initiate a reaction as a marker reaction. After a predetermined time of a marker reaction, a solution of methanol/acetonitrile=1/1 (V/V) is added to stop the reaction. After centrifuged at 3000 rpm for 15 minutes, 1-hydroxymidazolam in the supernatant is quantified by LC/MS/MS.

The sample obtained by adding only DMSO that is a solvent dissolving a compound instead of the compound of the present invention to a reaction mixture is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation 0 min/IC of preincubation 30 min". When a shifted IC is 1.5 or more, this is defined as positive. When a shifted IC is 1.0 or less, this is defined as negative.

Test Example 6: BA Test

Materials and Methods for experiments to evaluate oral absorption
(1) Animals: The mice or rats are used
(2) Breeding conditions: The mice or rats are allowed to freely take solid food and sterilized tap water.
(3) Dose and grouping: orally or intravenously administered at a predetermined dose; grouping is as follows (Dose depends on the compound)
Oral administration: 2 to 60 μmol/kg or 1 to 30 mg/kg (n=2 to 3)
Intravenous administration: 1 to 30 μmol/kg or 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein with a needle-equipped syringe
(6) Evaluation items: blood is collected over time, and the plasma concentration of drug is measured by LC/MS/MS
(7) Statistical analysis: regarding the transition of the plasma concentration of the compound of the present invention, the area under the plasma concentration-time curve (AUC) is calculated by non-linear least squares program WinNonlin (Registered trade name), and the bioavailability (BA) is calculated from the AUCs of the oral administration group and intravenous administration group.

Test Example 7: Fluctuation Ames Test

Mutagenicity of the compound of the present invention is evaluated.

A 20 μL of freezing-stored *Salmonella typhimurium* (TA98 strain, TA100 strain) is inoculated on 10 ml of a liquid nutrient medium (2.5% Oxoid nutrient broth No. 2), and this is incubated at 37° C. for 10 hours under shaking. The 7.70 to 8.00 ml of TA98 culture medium is centrifuged (2000× g; 10 minutes) Bacteria are suspended in a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4.7H_2O$: 0.1 g/L) with the same volume as that, of the culture medium used for centrifugation. The suspension is added to 120 ml of Exposure medium (Micro F buffer containing biotin: 8 μg/mL, histidine: 0.2 μg/mL, and glucose: 8 mg/mL). The 3.10 to 3.42 mL of TA100 culture medium strain is mixed with 120 to 130 mL Exposure medium. Each 12 μL of DMSO solution of the compound of the present invention (several stage dilution from maximum dose 50 mg/mL at 2 to 3 fold ratio), DMSO as a negative control, and 50 μg/mL of 4-nitroquinoline 1-oxide DMSO solution for the TA98 strain and 0.25 μg/mL of 2-(2-furyl)-3-(5-nitro-2-furyl)acrylamide DMSO solution for the TA100 strain in the assay without metabolic activation, 40 μg/mL of 2-aminoanthracene DMSO solution for the TA98 strain and 20 μg/mL of 2-aminoanthracene DMSO solution for the TA100 strain in the assay with metabolic activation as a positive control, and 588 μL of the test bacterial suspension (498 μL and 90 μL of S9 mixture in the case of metabolic activation assay) are mixed, and this is incubated at 37° C. for 90 minutes under shaking. A 460 μL of the mixture is mixed with 2300 μL of Indicator medium (Micro E buffer containing 8 μg/mL biotin, 0.2 μg/mL histidine, 8 mg/mL glucose, 37.5 μg/mL bromocresol purple), each 50 μL is dispensed to microplate 48 wells/dose, and this is incubated at 37° C. for 3 days. Since the wells containing the bacteria which gained growth ability by point mutation in amino acid (histidine) synthesizing enzyme gene turns from purple to yellow due to a pH change, the number of yellow wells in 48 wells is counted per dose, and is compared with the negative control group. (−) and (+) means negative and positive in mutagenicity respectively.

Test, Example 8: hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, is studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and gave a leak potential of −50 mV, $I_{Kr}$ induced by depolarization pulse stimulation at +20 mV for 2 seconds and, further, repolarization pulse stimulation at −50 mV for 2 seconds, is recorded. Extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid, 4-(2-hydroxyethyl)-1-piperazineethanesulfonic acid): 10 mmol/L, pH=7.4) adjusted to contain 0.1% dimethylsulfoxide is used as a medium. The extracellular solution in which the medium and the compound of the present invention had been dissolved at each objective concentration is applied to the cell for 7 minutes or more at room temperature. From the recording Im, an absolute value of the tail peak current is measured based on the current value at the resting membrane potential using analysis software (QPatch Assay software; Sophion Bioscience A/S). Further, the tail peak current after application of the compound of the present invention relative to the tail peak current after application of the medium is calculated as a % inhibition to assess the influence of the compound of the present invention on Im.

Test Example 9: Solubility Test

The solubility of the compound of the present invention is determined under 1% DMSO addition conditions. 10 mmol/L solution of the compound is prepared with DMSO. 2 µL of the solution of the compound of the present, invention is respectively added to 198 µL of JP-1 fluid or JP-2 fluid. The mixture is left shaking at room temperature for 1 hour, and the mixture is vacuum-filtered. The filtrate is 10- or 100-fold diluted with methanol/water=1/1 (v/v) or acetonitrile/methanol/water=1/1/2 (v/v/v), and the compound concentration in the filtrate is measured with LC/MS or Solid-Phase Extraction (SPE)/MS by the absolute calibration method.

The composition of the JP-1 fluid is as below.
Water is added to 2.0 g of sodium chloride and 7.0 mL of hydrochloric acid to reach 1000 mL.

The composition of the JP-2 fluid is as below.
1 volume of water is added to 1 volume of the solution in which 3.40 g of potassium dihydrogen phosphate and 3.55 g of anhydrous disodium hydrogen phosphate are dissolved in water to reach 1000 mL.

Test Example 10: Metabolism Stability Test

Using commercially available pooled human liver microsomes, the compound of the present invention is reacted for a constant time, a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution is added to 100 µL of a methanol/acetonitrile=1/1 (v/v), mixed and centrifuged at 3000 rpm for 15 minutes. The compound of the present invention in the supernatant is quantified by LC/MS/MS or Solid-Phase Extraction (SPE)/MS, and a remaining amount of the compound of the present invention after the reaction is calculated, letting a compound amount at 0 minute reaction time to be 100%.

Test Example 11: Powder Solubility Test

Appropriate quantity of the compound of the present invention is put in suitable containers. 200 µL of JP-1 fluid (water is added to 2.0 g of sodium chloride and 7.0 mL of hydrochloric acid to reach 1000 mL), 200 µL of JP-2 fluid (1 volume of water is added to 1 volume of the solution which 3.40 g of potassium dihydrogen phosphate and 3.55 g of anhydrous disodium hydrogen phosphate dissolve in water to reach 1000 mL) or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. After sealing and shaking at 37° C. for 1 hour, solution is filtrated and 100 µL of methanol is added to 100 µL of each filtrate to dilute two-fold. The dilution rate is changed as necessary. After checking that there is no bubble and precipitate, the container is sealed and shaken. The compound of the present invention is measured using HPLC by absolute calibration curve method.

Test Example 12: Brain Distribution Test

The compound of the present invention is intravenously administered at a dose of 1 µmol/mL/kg or 0.5 mg/mL/kg to rats. After 30 minutes, the rats are killed by exsanguination through whole blood collection from the inferior vena cava under isoflurane anesthesia.

Then, the brain is excised, and 20 to 25% homogenate is prepared with distilled water.

The obtained blood is centrifuged, and plasma is then obtained. Then, control plasma and control brain are added to the brain sample and the plasma sample, respectively, at 1:1, and each sample is assayed using LC/MS/MS. The measured area ratio (brain/plasma) obtained is used as a brain Kp value.

Test Example 13: P-gp Substrate Test

The compound of the present invention is added to one side of Transwell (registered trademark, CORNING) where human MDR1-expressing cells or parent cells have been monolayer-cultured. The cells are reacted for a constant time. The membrane permeability coefficients from the apical side toward the basolateral side (A→B) and from the basolateral side toward the apical side (B→A) are calculated for the MDR1-expressing cells or the parent cells, and the efflux ratio (ER; ratio of the membrane permeability coefficients of B→A and A→B) values of the MDR1-expressing cells and the parent cells are calculated. The efflux ratio (ER) values of the MDR1-expressing cells and the parent cells are compared to confirm whether or not the compound of the present invention would be a P-gp substrate.

Test Example 14: mdr1a (−/−) B6 Mouse P-gp Substrate Test

Animal Used
mdr1a (−/−) B6 Mice (Knockout Mice) or C57BL/6J Mice (Wild Mice)
Method
1. The mice are allowed to freely take solid food and sterilized tap water.
2. The compound of the present invention is administered to 3 animals at each point in time. Blood and brain samples are collected at a predetermined point in time (e.g., 15 minutes, 30 minutes, 1 hour, 2 hours, 4 hours, 0 hours, 8 hours or 24 hours) after administration. The blood (0.3-0.7 mL) is collected with a syringe containing anticoagulants (EDTA and heparin). The blood and brain samples are immediately cooled in ice.
3. The blood sample is centrifugated (1780×g, 10 minutes) for removal of cells to obtain plasma. Then, the plasma sample is transferred to a tube, and stored at −70° C.

4. The brain sample is homogenized at a tissue weight: distilled water weight ratio=1:3, transferred to a tube, and stored at −70° C.
5. The plasma and brain samples are deproteinized, and analyzed by LC/MS/MS. A calibration curve prepared from blank plasma or blank brain is used in measurement. A sample for quality control is used to confirm measurement trueness and accuracy.
6. Concentrations (ng/mL and ng/g) in the plasma and the brain are analyzed by an appropriate method for determining pharmacokinetic parameters, for example, WinNonlin (registered trademark) pharmacokinetic analysis software program.

Analysis

Kp5 brain/plasma concentration ratio
Kp ratio=knockout mouse (KO) Kp value/wild mouse (Wild) Kp value
KO/Wild ratio of brain AUC/plasma AUC={brain AUC/plasma AUC (KO)}/{brain AUC/plasma AUC (Wild)}

Test Example 15: Evaluation of Activation of Human Pregnane X Receptor (PXR)

A Human PXR activation (Puracyp, Inc.) kit was used for evaluation.

DPX2 cells expressing human PXR were seeded in a 96-well plate at a concentration of 40000 cells/well and cultured at 37° C. under 5% carbon dioxide for 24 hours (medium: culture medium for DPX2 cells containing 10% fetal bovine serum, antibiotics, sodium pyruvate, D-glucose, and phenol red). After culture for 24 hours, a DMSO solution of the compound of the present invention was diluted with a medium (dosing medium for DPX2 cells containing 10% fetal bovine serum, D-glucose, antibiotics, sodium pyruvate, and L-glutamine) so that the final concentration was 10 and 50 μM, and a rifampicin DMSO solution as a positive control drug was 0.2, 1, 2, and 20 μM. The medium was removed from the 96-well plate after culture for 24 hours. 100 μL of the solution of the compound of the present invention and 100 μL of the rifampicin solution prepared were added to each well, and cultured for 48 hours. The medium was removed from the 96-well plate after culture for 48 hours. 100 μL of each reaction mixture obtained by adding 5.25 μL of CellTiter-Fluor to 10.5 mL of TubeE was filled therein. The plate was set in a plate reader (PerkinElmer, Inc.) after culture for 1 hour to measure the fluorescence intensity at an interval of 0.1 seconds per well. The plate was taken out. 100 μL of a solution obtained by adding ONE-Glo Assay Substrate to ONE-Glo Assaybuffer was added to each well. After 2 minutes from the addition of the solution, the plate was set in the plate reader to measure the fluorescence intensity at an interval of 2 seconds per well. The PXR activity of the product of the present invention was a value obtained by dividing the emission intensity by the fluorescence intensity.
(Results)

TABLE 53

| Compound No. | PXR 10 μM | PXR 50 μM |
| --- | --- | --- |
| I-0135 | 3 | 9 |
| I-0142 | 5.8 | 13 |
| I-0145 | 1.9 | 6.2 |
| I-0154 | 7.9 | 15.8 |
| I-0158 | 1.2 | 4.7 |
| I-0161 | 1.2 | 2.5 |
| I-0162 | 6.7 | 20 |

TABLE 53-continued

| Compound No. | PXR 10 μM | PXR 50 μM |
| --- | --- | --- |
| I-0164 | 10.6 | 25 |
| I-0168 | 0.9 | 1.7 |
| I-0171 | 1.2 | 2.5 |
| I-0176 | 1.1 | 2 |
| I-0188 | 1.3 | 3.5 |
| I-0192 | 7.9 | 15 |
| I-0201 | 4 | 13.5 |

FORMULATION EXAMPLE

The following Formulation Example s are only exemplified and not intended to limit the scope of the invention.

Formulation Example

Formulation Example 1: Tablets

The compounds of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2: Capsules

The compounds of the present invention, lactose and calcium stearate are mixed uniformly to obtain powder medicines in the form of powders or fine granules. The powder medicines are filled into capsule containers to give capsules.

Formulation Example 3: Granules

The compounds of the present invention, lactose and calcium stearate are mixed uniformly and the mixture is compressed and molded. Then, it is crushed, granulated and sieved to give suitable sizes of granules.

Formulation Example 4: Orally Dispersing Tablets

The compounds of the present invention and crystalline cellulose are mixed, granulated and tablets are made to give orally dispersing tablets.

Formulation Example 5: Dry Syrups

The compounds of the present invention and lactose are mixed, crushed, granulated and sieved to give suitable sizes of dry syrups.

Formulation Example 6: Injections

The compounds of the present invention and phosphate buffer are mixed to give injections.

Formulation Example 7: Infusions

The compounds of the present invention and phosphate buffer are mixed to give infusions.

Formulation Example 8: Inhalations

The compound of the present invention and lactose are mixed and crushed finely to give inhalations.

Formulation Example 9: Ointments

The compounds of the present invention and petrolatum are mixed to give ointments.

Formulation Example 10: Patches

The compounds of the present invention and base such as adhesive plaster or the like are mixed to give patches.

INDUSTRIAL APPLICABILITY

The compounds of the present invention have an antagonistic activity for the $P2X_7$ receptor and are considered to be useful as a therapeutic and/or preventive agent for diseases or conditions associated with the $P2X_7$ receptor.

The invention claimed is:

1. A method for treating stroke or depression, comprising administering an effective amount of a compound represented by Formula (I):

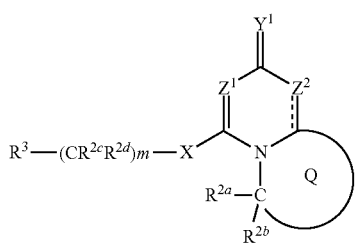

wherein
$Z^1$ is N;
$Z^2$ is $C(R^{5a})(R^{5a'})$ or $N(R^{5b})$;
the dashed line represents the presence or absence of a bond;
when the dashed line represents the presence of a bond, then $R^{5a'}$ and $R^{5b}$ are absent;
$R^{5a}$ is a hydrogen atom, halogen, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylamino, substituted or unsubstituted alkenylamino, substituted or unsubstituted alkynylamino, substituted or unsubstituted aromatic carbocyclyl, or substituted or unsubstituted aromatic heterocyclyl;
$R^{5a'}$ is a hydrogen atom;
$R^{5b}$ is a hydrogen atom, substituted or unsubstituted alkyl, substituted or unsubstituted alkenyl, or substituted or unsubstituted alkynyl;
Ring Q is a substituted or unsubstituted 5-membered non-aromatic heterocycle or a substituted or unsubstituted 6-membered non-aromatic heterocycle;
$Y^1$ is O;
$R^{2a}$ is a represented by the formula: $-C(R^{2a'})(R^{2b'})(R^{2b'})_n-R^1$;
$R^{2b}$ is a hydrogen atom, halogen, hydroxy, substituted or unsubstituted alkyl, or substituted or unsubstituted alkyloxy;
$R^{2a'}$ is each independently a hydrogen atom, halogen, hydroxy, substituted or unsubstituted alkyl, or substituted or unsubstituted alkyloxy;
$R^{2b'}$ is each independently a hydrogen atom, halogen, hydroxy, substituted or unsubstituted alkyl, or substituted or unsubstituted alkyloxy;
$R^{2a'}$ and $R^{2b'}$ which are attached to the same carbon atom may be taken together to form oxo;
$R^1$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl;
X is $N(R^{7a})$;
$R^{7a}$ is a hydrogen atom, substituted or unsubstituted alkyl, or substituted or unsubstituted alkylcarbonyl;
$R^{2c}$ is each independently a hydrogen atom, halogen, hydroxy, substituted or unsubstituted alkyl, or substituted or unsubstituted alkyloxy;
$R^{2d}$ is each independently a hydrogen atom, halogen, hydroxy, substituted or unsubstituted alkyl, or substituted or unsubstituted alkyloxy;
$R^{2c}$ and $R^{2d}$ which are attached to the same carbon atom may be taken together to form a substituted or unsubstituted non-aromatic carbocycle, or two of $R^{2c}$ may be taken together to form a substituted or unsubstituted non-aromatic carbocycle;
$R^3$ is substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl;
n is an integer from 0 to 4; and
m is an integer from 0 to 4,
or a pharmaceutically acceptable salt thereof, to a patient in need thereof.

2. The method according to claim 1, wherein the method is for treating stroke.

3. The method according to claim 1, wherein the method is for treating depression.

4. The method according to claim 1, wherein the compound is:

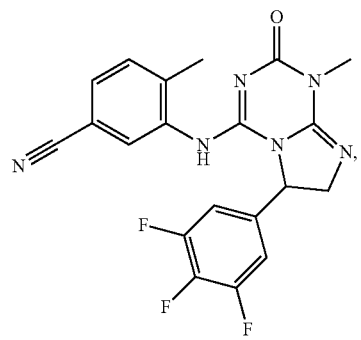 [SMILES: Cc1ccc(C#N)cc1NC1=NC(=O)N(C)C2=NCC(c3cc(F)c(F)c(F)c3)N12]

or a pharmaceutically acceptable salt thereof.

5. The method according to claim 1, wherein the compound is:

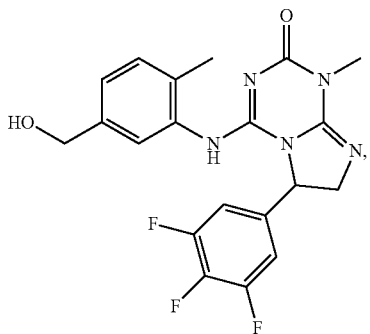 [SMILES: Cc1ccc(CO)cc1NC1=NC(=O)N(C)C2=NCC(c3cc(F)c(F)c(F)c3)N12]

or a pharmaceutically acceptable salt thereof.

6. The method according to claim 1, wherein the compound is:

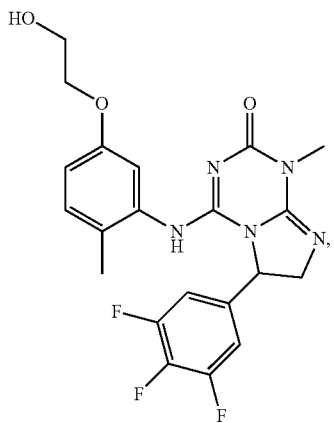 [SMILES: Cc1ccc(OCCO)cc1NC1=NC(=O)N(C)C2=NCC(c3cc(F)c(F)c(F)c3)N12]

or a pharmaceutically acceptable salt thereof.

7. The method according to claim 1, wherein the compound is:

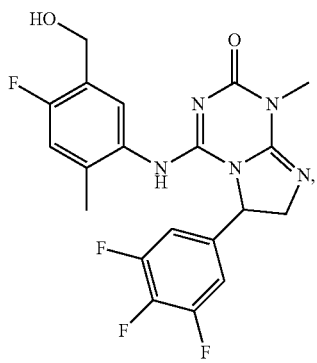 [SMILES: Cc1cc(F)c(CO)cc1NC1=NC(=O)N(C)C2=NCC(c3cc(F)c(F)c(F)c3)N12]

or a pharmaceutically acceptable salt thereof.

8. The method according to claim 1, wherein the compound is:

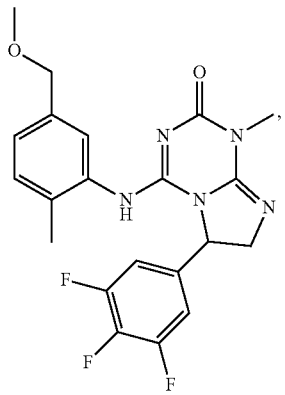 [SMILES: COCc1ccc(C)c(NC2=NC(=O)N(C)C3=NCC(c4cc(F)c(F)c(F)c4)N23)c1]

or a pharmaceutically acceptable salt thereof.

* * * * *